US006852731B2

(12) United States Patent
Larsen et al.

(10) Patent No.: US 6,852,731 B2
(45) Date of Patent: Feb. 8, 2005

(54) ANTIVIRAL COMPOUNDS

(75) Inventors: Scott D. Larsen, Kalamazoo, MI (US); Paul May, Richland, MI (US); Karen Romines, Durham, NC (US); Mark E. Schnute, Kalamazoo, MI (US); Steven P. Tanis, Kalamazoo, MI (US); James A. Nieman, Galesburg, MI (US); David John Anderson, Kalamazoo, MI (US); Euibong J. Kim, Kalamazoo, MI (US); Steven R. Turner, Kalamazoo, MI (US)

(73) Assignee: Pfizer, Bridgewater, NJ (US)

( * ) Notice: Subject to any disclaimer, the term of this patent is extended or adjusted under 35 U.S.C. 154(b) by 0 days.

(21) Appl. No.: 10/345,061

(22) Filed: Jan. 14, 2003

(65) Prior Publication Data

US 2004/0242884 A1 Dec. 2, 2004

Related U.S. Application Data

(60) Provisional application No. 60/348,866, filed on Jan. 14, 2002.

(51) Int. Cl.$^7$ ..................... C07D 495/04; A61K 31/435
(52) U.S. Cl. ...................................... 514/301; 546/114
(58) Field of Search .......................... 546/114; 514/301

(56) References Cited

U.S. PATENT DOCUMENTS

| | | | |
|---|---|---|---|
| 4,125,611 A | 11/1978 | Yamade et al. ............. | 424/246 |
| 4,145,418 A | 3/1979 | Kuwada et al. ............. | 424/246 |
| 4,767,766 A | 8/1988 | Baker et al. ................ | 514/301 |
| 4,877,793 A | * 10/1989 | Davies ........................ | 514/301 |
| 4,959,363 A | 9/1990 | Wentland .................. | 514/235.2 |
| 5,155,115 A | 10/1992 | Suzuki et al. ............... | 514/301 |
| 5,219,864 A | 6/1993 | Suzuki et al. ............... | 514/301 |
| 5,352,685 A | 10/1994 | Maruyama et al. ......... | 514/301 |
| 5,593,943 A | 1/1997 | Nuebling et al. ........... | 504/221 |
| 5,817,819 A | 10/1998 | Furuya et al. .............. | 546/114 |
| 6,239,142 B1 | 5/2001 | Schnute et al. ............. | 514/301 |
| 6,620,810 B2 | 9/2003 | Thorarensen ............ | 514/233.8 |

FOREIGN PATENT DOCUMENTS

| | | | | |
|---|---|---|---|---|
| DE | 4227747 | 2/1994 | ......... | C07D/487/04 |
| EP | 0046990 | 3/1982 | ......... | C07D/495/04 |
| EP | 0269295 | 6/1988 | ......... | C07D/495/04 |
| EP | 0443568 | 2/1991 | | |
| EP | 0505058 | 9/1992 | ......... | C07D/495/04 |
| EP | 0560348 | 9/1993 | ......... | C07D/519/00 |
| GB | 2289276 | 11/1995 | ....... | C07D/491/048 |
| JP | 46-032198 | 9/1970 | | |
| JP | 57116077 | 7/1982 | ......... | C07D/495/04 |
| JP | 57142985 | 9/1982 | ......... | C07D/495/04 |
| JP | 07076586 | 3/1995 | ....... | C07D/491/048 |
| JP | 8143573 | 6/1996 | ......... | C07D/519/00 |
| JP | 08301849 | 11/1996 | ......... | C07D/217/26 |
| JP | 9208496 | 8/1997 | .......... | A61K/47/40 |
| WO | WO-92/03427 | 3/1992 | ......... | C07D/307/82 |
| WO | WO-95/28405 | 10/1995 | ......... | C07D/495/04 |
| WO | WO-96/18616 | 6/1996 | ......... | C07D/213/75 |
| WO | WO-96/18617 | 6/1996 | ......... | C07D/213/75 |
| WO | WO-97/40846 | 11/1997 | .......... | A61K/38/09 |
| WO | WO-98/11073 | 3/1998 | ......... | C07D/215/48 |
| WO | WO-99/32450 | 7/1999 | | |
| WO | WO-99/62908 | 12/1999 | ......... | C07D/495/04 |
| WO | WO-00/07595 | 2/2000 | .......... | A61K/31/47 |
| WO | WO-00/40561 | 7/2000 | ......... | C07D/215/16 |
| WO | WO-00/40563 | 7/2000 | ......... | C07D/215/56 |
| WO | WO-00/53610 | 9/2000 | ......... | C07D/513/04 |
| WO | WO-00/76990 | 12/2000 | ......... | C07D/307/78 |
| WO | WO-01/58898 | 8/2001 | ......... | C07D/453/02 |
| WO | WO-03/020729 | 3/2003 | ......... | C07D/495/04 |

OTHER PUBLICATIONS

*Database Crossfire Beilstein,* vol. 26, No. 1, Beilstein Institut zur Foerderung der chemischen Wissenschaften,Frankfurt am Main, DE Database Accession No. 4321837, (1991).

*Database Crossfire Beilstein,* vol. 21, Beilstein Institut zur Foerderung der chemischen Wissenschaften,Frankfurt am Main, DE Database Accession No. 4381517, (1984).

Blaskiewicz, Peter, "Thienopyridinonecarboxylic Acid Derivatives", *Chemical Abstracts,* Abstract of German Patent No. 2,447,477, Abstract No. 85:46627, (Apr. 15, 1976), 1 page.

El–Abadelah, Mustafa M., "Synthesis and Chiroptical Properties of Some N–(2–Chloro–7–cyclopropyl–4.7–dihydro–4–oxo–thieno [2,3–b]pyridine–5–carbonyl) L–α–Amino Esters", *Zeitschrift fur Naturforschung B, A Journal of Chemical Sciences,* 52 (3), (1997), pp. 419–426.

Elliott, Richard L., et al., "The Preparation of 2–(Heterocyclyl)thieno[3,2–b]pyridine Derivatives", *Tetrahedron,* vol. 43, No. 14, (1987), 3295–3302.

(List continued on next page.)

*Primary Examiner*—Bruck Kifle
(74) *Attorney, Agent, or Firm*—Schwegman, Lundberg, Woessner & Kluth, P.A.

(57) ABSTRACT

The invention provides a compound of formula I:

wherein G, $R^2$, $R^3$, and $R^4$ have any of the values defined in the specification, or a pharmaceutically acceptable salt thereof, as well as processes and intermediates useful for preparing such compounds or salts, and methods of preventing or treating a herpesvirus infection using such compounds or salts.

64 Claims, No Drawings

OTHER PUBLICATIONS

Goerlitzer, K., et al., "Gyrase inhibitors; Parts 3.: Synthesis and reactions of ethyl 1,4–dihydro–4–oxo[1]benzothieno[3, 2–b]pyridine–3–carboxylate", *Pharmazie,* vol. 55, No. 8, (2000), 595–600.

Nishikawa, Yoshinori, et al., "Synthesis and Antiallergic Activity of N–[4–(4–Diphenylmethyl–1–piperazinyl)butyl]–1,4–dihydro–4–oxopyridine–3–carboxamides", *Chem. Pharm. Bull.,* vol. 37, No. 5, (1989), 1256–1259.

Patani, G. A., et al., "Bioisosterism: A Rational Approach in Drug Design", *Chemical Reviews,* 96(8), (1996), 3147–3176.

Revel, L., et al., "MKC–733", *Drugs of the Future,* vol. 24, No. 9, (1999), 966–968.

Thornber, C. W., "Isosterism and Molecular Modification in Drug Design", *Chemical Society Reviews,* 8(4), (1979), 563–580.

Vaillancourt, V. A., et al., "Naphthalene carboxamides as inhibitors of human cytomegalovirus DNA polymerase", *Bioorganic & Medicinal Chemistry Letters,* vol. 10, No. 18, (Sep. 2000), 2079–2081.

* cited by examiner

ANTIVIRAL COMPOUNDS

RELATED APPLICATIONS

This application claims priority to U.S. Provisional Patent Application Ser. No. 60/348,866, filed Jan. 14, 2002.

FIELD OF THE INVENTION

The present invention provides 3-substituted-7-oxo-4,7-dihydro-thieno[3,2-b]pyridine-6-carboxylic acid benzylamide derivatives that are useful as antivirals, or example, as agents against viruses of the herpes family.

BACKGROUND OF THE INVENTION

The herpesviruses comprise a large family of double stranded DNA viruses. They are also a source of the most common viral illnesses in man. Eight of the herpes viruses, herpes simplex virus types 1 and 2 (HSV-1 and HSV-2), varicella zoster virus (VZV), human cytomegalovirus (HCMV), Epstein-Barr virus (EBV), and human herpes viruses 6, 7, and 8 (HHV-6, HHV-7, and HHV-8), have been shown to infect humans.

HSV-1 and HSV-2 cause herpetic lesions on the lips and genitals, respectively. They also occasionally cause infections of the eye and encephalitis. HCMV causes birth defects in infants and a variety of diseases in immuno-compromised patients such as retinitis, pneumonia, and gastrointestinal disease. VZV is the causative agent of chicken pox and shingles. EBV causes infectious mononucleosis. It can also cause lymphomas in immuno-compromised patients and has been associated with Burkitt's lymphoma, nasopharyngeal carcinoma, post-transplant lymphoproliferative disease (PTLD), and Hodgkins disease. HHV-6 is the causative agent of roseola and may be associated with multiple sclerosis and chronic fatigue syndrome. HHV-7 disease association is unclear, but it may be involved in some cases of roseola. HHV-8 has been associated with Karposi's sarcoma, body cavity based lymphomas, and multiple myeloma.

Infection by or reactivation of herpesviruses is associated with several cardiovascular diseases or conditions in the host such as atherosclerosis and restenosis resulting in inflammation of coronary vessel walls. It is thought that in many patients suffering from restenosis following coronary atherectomy viral infection particularly by CMV plays an important role in the proliferation of the disease. Atherosclerosis is believed to be associated with the overall infectious disease burden in the host and particularly by the herpesviruses such as HSV, CMV, and EBV.

Infection in the animal population (livestock and companion) by strains of herpesviruses is endemic including cattle (Bovine herpesvirus 1-5, BHV), sheep (Ovine herpesvirus 1 and 2), dog (Canine herpesvirus 1), horse (Equine herpesvirus 1-8, EHV), cat (Feline herpesvirus 1, FHV), swine (pseudorabies virus, PRV), and many species of fowl. In the case of bovine herpesvirus infection, animals may suffer from ocular, respiratory, or digestive disorders. Pseudorabies is an extremely contagious viral pathogen infecting several species such as cattle, horses, dogs, cats, sheep, and goats leading to rapid death. The virus is benign in adult swine, however, it remains contagious and leads to high mortality in pigs under three weeks. Infection of horses by equine herpesvirus may lead to neurological syndromes, respiratory disease, and neonatal disease. Herpesvirus infection in cats leads to the disease known as feline viral rhinotracheitis (FVR) which is characterized by rhinitis, tracheitis, laryngitis, and conjunctivitis.

Information Disclosure

JP 08301849 discloses heterocyclic carboxamide compounds which are reported to be useful as tachykinin receptor antagonists.

U.S. Pat. No. 6,239,142 discloses compounds having a thieno[2,3-b]pyridine core which are reported to be useful for the treatment of herpesvirus infections.

U.S. Pat. No. 5,352,685 discloses thieno[3,2-b]pyridine derivatives reported to be useful for the treatment of gastrointestinal disorders. The compounds are also reported to be useful for the treatment of anxiety and neuroses, and arrhythmia.

EP 269295 discloses thieno[3,2-b]pyridine compounds which are reported to be useful as cardiovascular agents.

EP 46990 discloses thieno[3,2-b]pyridine compounds which are reported to be useful as broad-spectrum antibacterials.

JP 57116077 discloses thieno[3,2-b]pyridine compounds which are reported to be useful as antibiotics.

JP 57142985 discloses thieno[3,2-b]pyridine compounds which are reported to be useful as antimicrobial agents.

In *Drugs Future*, 1999, 24, 966, there is disclosed a thieno[3,2-b]pyridine compound MKC-733 which is reported to be useful as a 5-$HT_3$ receptor agonist for the treatment of constipation and GERD.

In *Chem. Pharm. Bull.* 1989, 37, 1256, there is disclosed a thieno[3,2-b]pyridine compound (7) prepared and evaluated for anti-allergic activity. Compound 7 was reported to be inactive.

JP 08143573 A2 discloses thieno[3,2-b]pyridine compounds which are reported to be useful for treatment of intestinal dysfunction.

U.S. Pat. No. 5,155,115 discloses compounds including certain thieno[3,2-b]pyridine compounds which are reported to be useful as S3 antagonists for use as anti-emetics and anti-migraine agents.

U.S. Pat. No. 5,219,864 discloses compounds including certain thienopyridine compounds which are reported to be useful as immunoregulators and antiosteoporosis drugs.

In *Pharmazie* 2000, 55, 595, there is disclosed the preparation of certain thienopyridine compounds which are reported to be useful as gyrase inhibitors for the inhibition of growth of bacteria.

In *Tetrahedron* 1987, 43, 3295, there is disclosed the preparation of certain thienopyridine compounds as potential antibacterials.

WO 00/07595 discloses certain thienopyridine compounds which are reported to be useful to treat sexual dysfunction.

WO 97/40846 discloses a pharmaceutical comprising an LH releasing hormone agonist and an LH releasing hormone antagonist. The disclosed LH releasing hormone antagonists include an array of bicyclic compounds that include thienopyridines. The LH releasing hormone antagonists are not reported to possess any antiviral activity.

EP 505058 discloses thienopyridone compounds that are reported to possess immunoregulating and bone absorption inhibiting activity.

Despite the above teachings, there still exists a need for compounds with desirable antiviral activity.

SUMMARY OF THE INVENTION

The present invention provides compound of formula I:

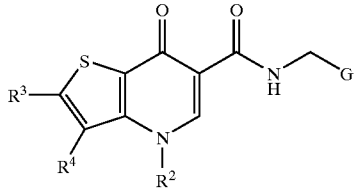

wherein

G is phenyl substituted with from one to five $R^1$ substituents, where each $R^1$ is independently
- (a) Cl,
- (b) Br,
- (c) F,
- (b) cyano,
- (c) $C_{1-7}$alkyl, or
- (a) $NO_2$;

$R^2$ is
- (a) H,
- (b) $R^5$,
- (c) $NR^7R^8$,
- (d) $SO_2R^9$, or
- (e) $OR^6$;

$R^3$ is
- (a) H,
- (b) halo,
- (c) aryl,
- (d) $S(O)_mR^6$,
- (e) $(C=O)R^6$,
- (f) $(C=O)OH$,
- (g) $(C=O)OR^9$,
- (h) cyano,
- (i) het, wherein the het is bound via a carbon atom,
- (j) $OR^{14}$,
- (k) $NR^7R^8$
- (l) $SR^{14}$,
- (m) $NHSO_2R^{12}$,
- (n) $C_{1-7}$alkyl which is optionally partially unsaturated and optionally substituted by one or more $R^{11}$ substituents, or
- (o) $C_{3-8}$cycloalkyl which is optionally partially unsaturated and optionally substituted by one or more $R^{11}$, or substituted by one or more $C_{1-7}$alkyl which $C_{1-7}$alkyl is optionally substituted by one or more $R^{11}$;

$R^4$ is
- (a) halo,
- (b) $C_{1-7}$alkyl which is optionally partially unsaturated and optionally substituted by one or more $R^{11}$ substituents,
- (c) $NR^7R^8$, or
- (d) $S(O)_mR^9$;

or $R^4$ together with $R^3$ may form a saturated carbocyclic or heterocyclic ring which is optionally substituted by $OR^{14}$, $SR^{14}$, $NR^7R^8$, or substituted by one or more $C_{1-7}$alkyl which $C_{1-7}$alkyl is optionally substituted by one or more $R^{11}$;

$R^5$ is
- (a) $(CH_2CH_2O)_rR^{10}$,
- (b) het, wherein the het is bound via a carbon atom,
- (c) aryl,
- (d) $C_{1-7}$alkyl which is optionally partially unsaturated and is optionally substituted with one or more $R^{11}$ substituents, or
- (e) $C_{3-8}$cycloalkyl which is optionally partially unsaturated and optionally substituted with one or more $R^{11}$, or substituted by one or more $C_{1-7}$alkyl which $C_{1-7}$alkyl is optionally substituted by one or more $R^{11}$;

$R^6$ is
- (a) $C_{1-7}$alkyl optionally substituted by aryl, het, $OR^{13}$, $SR^{13}$, $NR^{13}R^{13}$, halo, or $C_{3-8}$cycloalkyl, which $C_{3-8}$cycloalkyl is optionally substituted by $OR^{13}$,
- (b) $C_{3-8}$cycloalkyl which is optionally partially unsaturated and is optionally substituted by one or more halo, $OR^{13}$, $SR^{13}$, or $NR^{13}R^{13}$ substituents,
- (c) $NR^7R^8$,
- (d) aryl, or
- (e) het, wherein the het is bound via a carbon atom;

$R^7$ and $R^8$ are independently
- (a) H,
- (b) aryl,
- (c) $C_{1-7}$alkyl which is optionally partially unsaturated and is optionally substituted by one or more $NR^{13}R^{13}$, $OR^{14}$, $SR^{14}$, $S(O)_mR^9$, $P(=O)(OR^{14})(R^{14})$, $CONR^{14}R^{14}$, $CO_2R^{13}$, $(C=O)R^9$, het, aryl, cyano, or halo substituents,
- (d) $C_{3-8}$cycloalkyl which is optionally partially unsaturated and is optionally substituted by one or more halo, $OR^{13}$, $SR^{13}$, oxo, or $NR^{13}R^{13}$,
- (e) $(C=O)R^9$, or
- (f) $R^7$ and $R^8$ together with the nitrogen to which they are attached form a het;

$R^9$ is
- (a) aryl,
- (b) het,
- (c) $C_{3-8}$cycloalkyl, or
- (d) $C_{1-7}$alkyl which is optionally unsaturated and is optionally substituted with one or more $NR^{13}R^{13}$, $OR^{14}$, $SR^{14}$, halo, $CONR^{13}R^{13}$, $CO_2R^{13}$, het, or aryl substituents;

$R^{10}$ is
- (a) H, or
- (b) $C_{1-7}$alkyl optionally substituted with OH;

$R^{11}$ is
- (a) $OR^{14}$,
- (b) $SR^{14}$,
- (c) $NR^7R^8$,
- (d) halo,
- (e) $CONH_2$,
- (f) $CONHR^9$,
- (g) $CONR^9R^9$,
- (h) $CO_2H$,
- (i) $CO_2R^9$,
- (j) het,
- (k) aryl,
- (l) cyano,
- (m) oxo, or
- (n) $SO_mR^6$, or
- (o) $P(=O)(OR^{14})(R^{14})$;
- (p) $NHSO_mR^6$;
- (q) $N_3$;

$R^{12}$ is
- (a) H,
- (b) het,
- (c) aryl, (d) $C_{3-8}$cycloalkyl optionally substituted with $R^{11}$, or (e) $C_{1-7}$alkyl optionally substituted with $R^{11}$;

$R^{13}$ is (a) H, or (b) $C_{1-7}$alkyl;

$R^{14}$ is (a) H, (b) aryl, (c) het, (d) $C_{1-7}$alkyl which is optionally partially unsaturated and optionally substituted by aryl, het, $OR^{13}$, $Si(R^{13})_3$, $SR^{13}$, $NR^{13}R^{13}$, halo, or $C_{3-8}$cycloalkyl which $C_{3-8}$cycloalkyl is optionally substituted by one or more $OR^{13}$, or (e) $C_{3-8}$cycloalkyl which is optionally partially unsaturated and optionally substituted with one or more substituents halo, $OR^{13}$, $SR^{13}$, or $NR^{13}R^{13}$;

$R^{15}$ is (a) H, (b) halo, (c) $OR^{13}$, (d) $SR^{13}$, (e) $NR^{13}R^{13}$, (f) $O(CH_2CH_2O)_nR^{10}$, (g) phenyl, (h) cyano, (i) nitro, (j) $CONR^{13}R^{13}$, (k) $CO_2R^{13}$, (l) $S(O)_mNR^{13}R^{13}$, (m) $C_{1-7}$alkyl which is optionally partially unsaturated and optionally substituted with one or more oxo, phenyl, 4-morpholine, $OR^{13}$, $SR^{13}$, $NR^{13}R^{13}$, halo, $CO_2R^{13}$, $CONR^{13}R^{13}$, or $C_{3-8}$cycloalkyl which $C_{3-8}$cycloalkyl is optionally substituted by one or more $OR^{13}$, (n) $C_{3-8}$cycloalkyl which is optionally partially unsaturated and optionally substituted by one or more oxo, halo, $OR^{13}$, $SR^{13}$, $C_{1-7}$alkyl, or $NR^{13}R^{13}$ substituents, (o) pyrimidinyl, pyridyl, pyrrolyl, pyrazinyl, pyridazinyl, imidazolyl, or pyrazolyl;

(p) morpholino, or (q) $NR^{13}COR^{13}$, each i is independently 2, 3, or 4;

each n is independently 1, 2, 3, 4 or 5;

each m is independently 1 or 2;

wherein any aryl other than G is optionally substituted with one or more $R^{15}$ substituents; and wherein any het is optionally substituted with one or more =O, =N—$OR^{13}$, or $R^{15}$ substituents;

or a pharmaceutically acceptable salt thereof.

In another aspect, the present invention also provides:

a pharmaceutical composition comprising a compound of formula I, or a pharmaceutically acceptable salt thereof, and a pharmaceutically acceptable excipient (the composition preferably comprises an effective antiviral amount of the compound or salt);

a method of treating a herpesviral infection, comprising administering to a mammal (e.g. a human) in need of such treatment, a compound of formula I or a pharmaceutically acceptable salt thereof;

a method of treating atherosclerosis or restenosis comprising administering to a mammal (e.g. a human) in need of such treatment, a compound of formula I or a pharmaceutically acceptable salt thereof;

a method for inhibiting a viral DNA polymerase, comprising contacting (in vitro or in vivo) the polymerase with an effective inhibitory amount of a compound of formula I, or a pharmaceutically acceptable salt thereof.

a compound of formula I or a pharmaceutically acceptable salt thereof for use in medical treatment (e.g. the treatment of a herpesviral infection or the treatment of atherosclerosis or restenosis);

the use of a compound of formula I or a pharmaceutically acceptable salt thereof to prepare a medicament for treating a herpesviral infection in a mammal (e.g. a human);

the use of a compound of formula I or a pharmaceutically acceptable salt thereof to prepare a medicament for treating atherosclerosis or restenosis in a mammal (e.g. a human); and the use of a compound of formula I or a pharmaceutically acceptable salt thereof to prepare a medicament for inhibiting a viral DNA polymerase in a mammal (e.g. a human).

The invention also provides novel intermediates and processes disclosed herein that are useful for preparing compounds of formula I, including the generic and specific intermediates as well as the synthetic processes described in the Charts and Examples herein.

DETAILED DESCRIPTION OF THE INVENTION

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl can be partially unsaturated, the alkyl chain may comprise one or more (e.g. 1, 2, 3, or 4) double or triple bonds in the chain.

"Aryl" denotes a phenyl radical or an ortho-fused bicyclic carbocyclic radical having about nine to ten ring atoms in which at least one ring is aromatic.

"Het" is a 4–16 membered saturated or unsaturated monocyclic, bicyclic, or tricyclic ring system having 1, 2, 3, or 4 heteroatoms, such as oxygen (—O—), sulfur (—S—), oxygenated sulfur such as sulfinyl (S=O) and sulfonyl (S(=O)$_2$), or nitrogen, or an N-oxide thereof. Het includes "heteroaryl", which encompasses a radical attached via a ring carbon of a monocyclic aromatic ring containing five or six ring atoms consisting of carbon and 1, 2, 3, or 4 heteroatoms, such as non-peroxide oxygen (—O—), sulfur (—S—), oxygenated sulfur such as sulfinyl (S=O) and sulfonyl (S(=O)$_2$), or nitrogen N(X) wherein X is absent or is H, O, $C_{1-4}$alkyl, phenyl or benzyl, as well as a radical of an ortho-fused bicyclic heterocycle of about eight to ten ring atoms derived there from, particularly a benz-derivative or one derived by fusing a propylene, trimethylene, or tetramethylene diradical thereto. When heteroaryl is an ortho-fused benz-derivative it can be attached via any atom in an aromatic ring (e.g. an atom of the benz-ring).

"Partially unsaturated", for example, a $C_{1-7}$alkyl which is optionally partially unsaturated, means the named substituent has one or more unsaturations, such as one or more double bonds, one or more triple bonds, or both.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

"Optional" or "optionally" mean that the subsequently described event or condition may but need not occur, and that the description includes instances where the event or condition occurs and instances in which it does not. For example, "optionally substituted" means that the named substituent may be present but need not be present, and the description includes situations where the named substituent is included and situations where the named substituent is not included.

"Mammal" denotes humans and animals. Animals specifically refer to, for example, food animals or companion animals.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine antiviral activity using the standard tests described herein, or using other similar tests which are well known in the art. In particular, it is understood that compounds of formula I wherein $R^2$ is hydrogen can exist in the corresponding tautomeric "enol" form as illustrated in the following formula

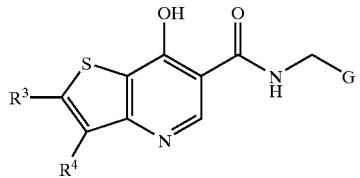

and that such tautomers are included as compounds of the invention.

The carbon atom content of various hydrocarbon-containing moieties is indicated by a prefix designating a lower and upper number of carbon atoms in the moiety, i.e., the prefix $C_{i-j}$ indicates a moiety of the integer 'i' to the integer "j" carbon atoms, inclusive. Thus, for example, $C_{1-7}$alkyl refers to alkyl of one to seven carbon atoms, inclusive.

The compounds of the present invention are generally named according to the IUPAC or CAS nomenclature system. Abbreviations which are well known to one of ordinary skill in the art may be used (e.g. "Ph" for phenyl, 'Me" for methyl, "Et" for ethyl, "h" for hour or hours and "rt" for room temperature).

Specific and preferred values listed below for radicals, substituents, and ranges, are for illustration only; they do not exclude other defined values or other values within defined ranges for the radicals and substituents. The compounds of the invention include compounds of formula I having any combination of the values, specific values, more specific values, and preferred values described herein.

Specifically, $C_{1-7}$alkyl can be methyl, ethyl, propyl, isopropyl, butyl, isobutyl, sec-butyl, pentyl, 3-pentyl, hexyl, or heptyl; $C_{3-8}$cycloalkyl can be cyclopropyl, cyclobutyl, cyclopentyl, cyclohexyl, cycloheptyl, or cyclooctyl; $C_{1-7}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; $C_{1-7}$alkanoyl can be acetyl, propanoyl, butanoyl, pentanoyl, 4-methylpentanoyl, hexanoyl, or heptanoyl; aryl can be phenyl, indenyl, or naphthyl.

"Heteroaryl" can be pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxalinyl, 1-phthalazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 4,5,-dihydrooxazole, 1,2,3-oxathiole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-indolyl, 3-indolyl, 3-indazolyl, 2-benzoxazolyl, 2-benzothiazolyl, 2-benzimidazolyl, 2-benzofuranyl, 3-benzofuranyl, benzoisothiazole, benzisoxazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-yl, 1-tetrazolyl, 1-indolyl, 1-indazolyl, 2-isoindolyl, 7-oxo-2-isoindolyl, 1-purinyl, 3-isothiazolyl, 4-isothiazolyl and 5-isothiazolyl, 1,3,4,-oxadiazole, 4-oxo-2-thiazolinyl, or 5-methyl-1,3,4-thiadiazol-2-yl, thiazoledione, 1,2,3,4-thiatriazole, 1,2,4-dithiazolone. Each of these moieties may be substituted as appropriate or can include and their corresponding N-oxides as appropriate.

When $C_{1-7}$alkyl is partially unsaturated, it can specifically be vinyl, allyl, 1-propenyl, 2-propenyl, 1-butenyl, 2-butenyl, 3-butenyl, 1,3-butadienyl, 1-pentenyl, 2-pentenyl, 3-pentenyl, 4-pentenyl, 1-hexenyl, 2-hexenyl, 3-hexenyl, 4-hexenyl, 5-hexenyl, ethynyl, 1-propynyl, 2-propynyl, 1-butynyl, 2-butynyl, 3-butynyl, 1-pentynyl, 2-pentynyl, 3-pentynyl, 4-pentynyl, 5-hexene-1-ynyl, 2-hexynyl, 3-hexynyl, 4-hexynyl, or 5-hexynyl.

A specific value for Het is a four—(4), five—(5), six—(6), or seven—(7) membered saturated or unsaturated monocyclic, bicyclic, or tricyclic ring system having 1, 2, 3, or 4 heteroatoms, such as oxygen (—O—), sulfur (—S—), oxygenated sulfur such as sulfinyl (S═O) and sulfonyl (S(═O)$_2$), or nitrogen, and which ring system is optionally fused to a benzene ring or an N-oxide thereof.

Another specific value for Het is a five—(5), six—(6), or seven—(7) membered saturated or unsaturated ring containing 1, 2, 3, or 4 heteroatoms, for example, non-peroxide oxy, thio, sulfinyl, sulfonyl, and nitrogen; as well as a radical of an ortho-fused bicyclic heterocycle of about eight to twelve ring atoms derived therefrom, particularly a benz-derivative or one derived by fusing a propylene, trimethylene, tetramethylene or another monocyclic het diradical thereto.

Specific values of "het" are, but not limited to, pyridine, thiophene, furan, pyrazoline, pyrimidine, 2-pyridyl, 3-pyridyl, 4-pyridyl, 2-pyrimidinyl, 4-pyrimidinyl, 5-pyrimidinyl, 3-pyridazinyl, 4-pyridazinyl, 3-pyrazinyl, 4-oxo-2-imidazolyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 4-oxo-2-oxazolyl, 5-oxazolyl, 1,2,3-oxathiazole, 1,2,3-oxadiazole, 1,2,4-oxadiazole, 1,2,5-oxadiazole, 1,3,4-oxadiazole, 2-thiazolyl, 4-thiazolyl, 5-thiazolyl, 3-isothiazole, 4-isothiazole, 5-isothiazole, 2-furanyl, 3-furanyl, 2-thienyl, 3-thienyl, 2-pyrrolyl, 3-pyrrolyl, 3-isopyrrolyl, 4-isopyrrolyl, 5-isopyrrolyl, 1,2,3,-oxathiazole-1-oxide, 1,2,4-oxadiazol-3-yl, 1,2,4-oxadiazol-5-yl, 5-oxo-1,2,4-oxadiazol-3-yl, 1,2,4-thiadiazol-3-yl, 1,2,4-thiadiazol-5-yl, 3-oxo-1,2,4-thiadiazol-5-yl, 1,3,4-thiadiazol-5-yl, 2-oxo-1,3,4-thiadiazol-5-yl, 1,2,4-triazol-3-yl, 1,2,4-triazol-5-yl, 1,2,3,4-tetrazol-5-yl, 5-oxazolyl, 3-isothiazolyl, 4-isothiazolyl, 5-isothiazolyl, 1,3,4,-oxadiazole, 4-oxo-2-thiazolinyl, 5-methyl-1,3,4-thiadiazol-2-yl, thiazoledione, 1,2,3,4-thiatriazole, 1,2,4-dithiazolone, phthalimide, quinolinyl, morpholinyl, benzoxazoyl, diazinyl, triazinyl, quinolinyl, quinoxalinyl, naphthyridinyl, azetidinyl, pyrrolidinyl, hydantoinyl, oxathiolanyl, dioxolanyl, imidazolidinyl, azabicyclo[2.2.1]heptyl, and optionally their corresponding N-oxides.

Another specific value for het is pyridyl, thiazolyl, pyrazinyl, thienyl, pyrimidinyl, furanyl, pyrazolyl, pyrrolyl), pyrazinyl, 3,4-dihydro-2H-benzo[1,4]oxazinyl, pyridyl-N-oxide, quinolyl, or imidazolyl.

A specific value for G is phenyl substituted with one $R^1$.

A more specific value for G is phenyl substituted with two $R^1$.

Another specific value for G is phenyl substituted with three $R^1$.

Another specific value for G is 4-chlorophenyl.
Another specific value for G is 4-fluorophenyl.
Another specific value for G is 3,4-dichlorophenyl.
Another specific value for G is 3,4-difluorophenyl.
Another specific value for G is 2,4-dichlorophenyl.
Another specific value for G is 2,4-difluorophenyl.
Another specific value for G is 4-chloro-2-fluorophenyl.
Another specific value for G is 2-chloro-4-fluorophenyl.
Another specific value for G is 3,4,5-trifluorophenyl.
Another specific value for G is 4-bromophenyl.
Another specific value for G is 4-methylphenyl.
Another specific value for G is 4-cyanophenyl.
Another specific value for G is 4-nitrophenyl.
A specific value for $R^1$ is F, Cl, or Br.
A more specific value for $R^1$ is Cl.
Another specific value for $R^1$ is methyl.
Another specific value for $R^1$ is methyl.
A specific value for $R^2$ is cyano.
Another specific value for $R^2$ is $C_{1-7}$alkyl which is optionally partially unsaturated and is optionally substituted with one or more $R^{11}$ substituents.
Another specific value for $R^2$ is methyl.
Another specific value for $R^2$ is ethyl.
A specific value for $R^3$ is H, halo, aryl, $S(O)_mR^6$, (C=O)$R^6$, (C=O)OH, (C=O)$OR^9$, cyano, $OR^{14}$, $NR^7R^8SR^{14}$, or $NHSO_2R^{12}$.
Another specific value for $R^3$ is Cl, F, or cyano.
Another specific value for $R^3$ is $C_{1-7}$alkyl which is optionally partially unsaturated and optionally substituted with one or more $R^{11}$, $OR^{13}$, $SR^{10}$, $SR^{13}$, $NR^7R^8$, halo, $C_{1-7}$alkanoyl, and $SO_mR^9$ substituents.
A specific value for $R^3$ is $C_{1-7}$alkyl which is optionally partially unsaturated and optionally substituted with one or more $R^{11}$ substituents, or $C_{3-8}$cycloalkyl which is optionally partially unsaturated and optionally substituted by one or more $R^{11}$ or $C_{1-7}$alkyl substituents.
Another specific value for $R^3$ is $C_{1-7}$alkyl which is optionally partially unsaturated and optionally substituted with one or more $R^{11}$ substituents, or $C_{3-8}$cycloalkyl which $C_{3-8}$cycloalkyl is optionally partially unsaturated and optionally substituted by one or more $R^{11}$ or $C_{1-7}$alkyl substituents.

Another specific value for $R^3$ is (Z or E) —CH=CH(CH$_2$)$_n$R$_a$ or —C≡C(CH$_2$)$_n$R$_a$ wherein R$_a$ is $R^{11}$, $OR^{13}$, $SR^{10}$, $SR^{13}$, $NR^7R^8$, halo, $C_{1-7}$alkanoyl, or $SO_mR^9$.

Another specific value for $R^3$ is $CH_2NR^7R^8$.

A more specific value for $R^3$ is $CH_2NR^7R^8$ where $R^7$ is $C_{1-7}$alkyl, and $R^8$ is $C_{1-7}$alkyl which is optionally partially unsaturated and is optionally substituted by one or more $NR^{13}R^{13}$, $OR^{14}$, $SR^{14}$, $S(O)_mR^9$, $CONR^{13}R^{13}$, $CO_2R^{13}$, (C=O)$R^9$, het, aryl, cyano, or halo substituents.

Another specific value for $R^3$ is $CH_2NR^7R^8$ where $R^7$ is methyl, and $R^8$ is ethyl substituted with aryl or het, and an $OR^{14}$.

Another specific value for $R^3$ is $C_{1-7}$alkyl which comprise one double bond and is optionally substituted by one or more $R^{11}$ substituents.

Another specific value for $R^3$ is $C_{1-7}$alkyl which comprise one triple bond and is optionally substituted by one or more $R^{11}$ substituents.

Another specific value for $R^3$ is het, wherein the het is bound to the thieno ring via a carbon atom.

Another specific value for $R^3$ is het, wherein the het is bound to the thieno ring via a nitrogen atom.

Another specific value for $R^3$ is H.

Another specific value for $R^3$ is hydroxymethyl.

Another specific value for $R^3$ is N-methyl-N-{2-(4-hydroxyphenyl)-2-hydroxy-ethyl}aminomethyl.

Another specific value for $R^3$ is morpholinomethyl.

Another specific value for $R^3$ is N-methyl-N-{2-phenyl-2-hydroxy-ethyl}aminomethyl.

Another specific value for $R^3$ is N-methyl-N-(2-furan-2-yl-2-hydroxy-ethyl)aminomethyl.

Another specific value for $R^3$ is N-methyl-N-{2-(3-methoxyphenyl)-2-hydroxy-ethyl}aminomethyl.

Another specific value for $R^3$ is N-{2-phenyl-2-hydroxy-ethyl}aminomethyl.

Another specific value for $R^3$ is N-{2-hydroxy-1-benzylethyl)aminomethyl.

Another specific value for $R^3$ is N-{phenylphosphinylmethyl)-N-(methyl)aminomethyl.

Another specific value for $R^3$ is N-methyl-N-{2-(pyridin-2-yl)-2-hydroxy-ethyl}aminomethyl.

A specific value for $R^4$ is halo.

Another specific value for $R^4$ is $C_{1-7}$alkyl which is optionally partially unsaturated and optionally substituted by one or more $R^{11}$ substituents.

Another specific value for $R^4$ is methyl.

Another specific value for $R^4$ is $NR^7R^8$.

Another specific value for $R^4$ is $S(O)_mR^9$.

Another specific value for $R^4$ is propylsulfonyl.

Another specific value for $R^4$ is where $R^4$ together with $R^3$ forms a saturated carbocyclic or heterocyclic ring which is optionally substituted by $OR^{14}$, $SR^{14}$, $NR^7R^8$, or $C_{1-7}$alkyl which $C_{1-7}$alkyl is optionally substituted by one or more $R^{11}$ substituents. When $R^4$ together with $R^3$ form a carbocyclic, $R^4$ and $R^3$ together can be a 2, 3, 4, 5, or 6 membered saturated or unsaturated carbon chain, which chain can optionally be fused to a benzene ring.

A specific value for $R^5$ is $(CH_2CH_2O)_xR^{10}$.

A specific value for $R^5$ is $C_{1-7}$alkyl which is optionally partially unsaturated and is optionally substituted by one or more $R^1$ substituents, or $C_{3-8}$cycloalkyl which is optionally partially unsaturated and optionally substituted by one or more $R^{11}$ or $C_{1-7}$alkyl substituents and optionally substituted with $R^{11}$.

A specific group of compounds are compounds of formula I wherein G is phenyl substituted with one or two $R^1$ groups when $R^2$, $R^3$, and $R^4$ are $C_{1-7}$alkyl which $C_{1-7}$alkyl substituents are optionally partially unsaturated and optionally substituted with one or more $R^{11}$ substituents.

Another specific group of compounds are compounds of formula I wherein G is phenyl substituted at the 4-position with $R^1$ and $R^3$ and $R^4$ are $C_{1-7}$alkyl which $C_{1-7}$alkyl groups are optionally partially unsaturated and optionally substituted by one or more $R^{11}$ substituents or which $C_{1-7}$alkyl is optionally substituted by $NR^7R^8$; and $R^2$ is $CH_3$.

Another specific value for G is 4-chlorophenyl when $R^3$ is $CH_2N(CH_3)CH_2CH(OH)$aryl or $CH_2N(CH_3)CH_2CH(OH)$het, and $R^2$ is $CH_3$.

A specific compound of the present invention is N-(4-chlorobenzyl)-2-(hydroxymethyl)-3,4-dimethyl-7-oxo-4,7-dihydrothieno[3,2-b]pyridine-6-carboxamide.

Another specific compound of the present invention is N-(4-chlorobenzyl)-2-{[[2-hydroxy-2-(4-hydroxyphenyl)ethyl](methyl)amino]methyl}-3,4-dimethyl-7-oxo-4,7-dihydrothieno[3,2-b]pyridine-6-carboxamide.

Another specific compound of the present invention is N-(4-chlorobenzyl)-2-{[(2-hydroxy-2-phenylethyl)(methyl)amino]methyl}-3,4-dimethyl-7-oxo-4,7-dihydrothieno[3,2-b]pyridine-6-carboxamide.

Another specific compound of the present invention is N-(4-chlorobenzyl)-2-{[[2-hydroxy-2-(3-methoxyphenyl)ethyl](methyl)amino]methyl}-3,4-dimethyl-7-oxo-4,7-dihydrothieno[3,2-b]pyridine-6-carboxamide.

Another specific compound of the present invention is N-(4-chlorobenzyl)-2-{[[2-(2-furyl)-2-hydroxyethyl](methyl)amino]methyl}-3,4-dimethyl-7-oxo-4,7-dihydrothieno[3,2-b]pyridine-6-carboxamide.

Another specific compound of the present invention is N-(4-chlorobenzyl)-2-{[(2-hydroxy-2-pyridin-2-ylethyl)(methyl)amino]methyl}-3,4-dimethyl-7-oxo-4,7-dihydrothieno[3,2-b]pyridine-6-carboxamide.

Another specific compound of the present invention is N-(4-chlorobenzyl)-2-{[(2-hydroxy-2-phenylethyl)amino]methyl}-3,4-dimethyl-7-oxo-4,7-dihydrothieno[3,2-b]pyridine-6-carboxamide.

Another specific compound of the present invention is N-(4-chlorobenzyl)-3,4-dimethyl-2-(morpholin-4-ylmethyl)-7-oxo-4,7-dihydrothieno[3,2-b]pyridine-6-carboxamide.

Another specific compound of the present invention is 2-({[(1S)-1-benzyl-2-hydroxyethyl]amino}methyl)-N-(4-chlorobenzyl)-3,4-dimethyl-7-oxo-4,7-dihydrothieno[3,2-b]pyridine-6-carboxamide.

Another specific compound of the present invention is [[(6-{[(4-chlorobenzyl)amino]carbonyl}-3,4-dimethyl-7-oxo-4,7-dihydrothieno[3,2-b]pyridin-2-yl)methyl](methyl)amino]methyl(phenyl)phosphinic acid.

Another specific compound of the present invention is N-(4-chlorobenzyl)-7-oxo-3-(propylsulfonyl)-4,7-dihydrothieno[3,2-b]pyridine-6-carboxamide.

The present invention includes a pharmaceutically acceptable salt of any of the above mentioned compounds.

Another specific compound of the invention is a compound of formula I wherein: G is phenyl substituted with from one to five $R^1$ substituents, where each $R^1$ is independently
  (a) Cl,
  (b) Br,
  (c) F,
  (d) cyano,
  (e) $C_{1-7}$alkyl, or $R^2$ is
  (a) H,
  (b) $R^5$,
  (c) $NR^7R^8$,
  (d) $SO_2R^9$, or
  (e) $OR^5$;

$R^3$ is
  (a) H,
  (b) halo,
  (c) aryl,
  (d) $S(O)_mR^6$,
  (e) $(C=O)R^6$,
  (f) $(C=O)OH$
  (g) $(C=O)OR^9$,
  (h) cyano,
  (i) het, wherein the het is bound via a carbon atom,
  (j) $OR^{14}$,
  (k) $NR^7R^8$
  (l) $SR^{14}$,
  (m) $NHSO_2R^{12}$,
  (n) $C_{1-7}$alkyl which is optionally partially unsaturated and optionally substituted by one or more $R^{11}$ substituents, or
  (o) $C_{3-8}$cycloalkyl which is optionally partially unsaturated and optionally substituted by one or more $R^{11}$, or substituted by one or more $C_{1-7}$alkyl which $C_{1-7}$alkyl is optionally substituted by one or more $R^{11}$;

$R^4$ is
  (a) halo,
  (b) $C_{1-7}$alkyl which is optionally partially unsaturated and optionally substituted by one or more $R^{11}$ substituents,
  (c) $NR^7R^8$, or
  (d) $S(O)_mR^9$;

or $R^4$ together with $R^3$ may form a saturated carbocyclic or heterocyclic ring which is optionally substituted by $OR^{14}$, $SR^{14}$, $NR^7R^8$, or substituted by one or more $C_{1-7}$alkyl which $C_{1-7}$alkyl is optionally substituted by one or more $R^{11}$;

$R^5$ is
  (a) $(CH_2CH_2O)_iR^{10}$,
  (b) het, wherein the het is bound via a carbon atom,
  (c) aryl,
  (d) $C_{1-7}$alkyl which is optionally partially unsaturated and is optionally substituted with one or more $R^1$ substituents, or
  (e) $C_{3-8}$cycloalkyl which is optionally partially unsaturated and optionally substituted with one or more $R^{11}$, or substituted by one or more $C_{1-7}$alkyl which $C_{1-7}$alkyl is optionally substituted by one or more $R^{11}$;

$R^6$ is
  (a) $C_{1-7}$alkyl optionally substituted by aryl, het, $OR^{13}$, $SR^{13}$, $NR^{13}R^{13}$, halo, or $C_{3-8}$cycloalkyl, which $C_{3-8}$cycloalkyl is optionally substituted by $OR^{13}$,
  (b) $C_{3-8}$cycloalkyl which is optionally partially unsaturated and is optionally substituted by one or more halo, $OR^{13}$, $SR^{13}$, or $NR^{13}R^{13}$ substituents,
  (c) $NR^7R^8$,
  (d) aryl, or
  (e) het, wherein the het is bound via a carbon atom;

$R^7$ and $R^8$ are independently
  (a) H,
  (b) aryl,
  (c) $C_{1-7}$alkyl which is optionally partially unsaturated and is optionally substituted by one or more $NR^{13}R^{13}$, $OR^{14}$, $SR^{14}$, $S(O)_mR^9$, $P(=O)(OR^{14})(R^{14})$, $CONR^{13}R^{13}$, $CO_2R^{13}$, $(C=O)R^9$, het, aryl, cyano, or halo substituents, (d) $C_{3-8}$cycloalkyl which is optionally partially unsaturated and is optionally substituted by one or more halo, $OR^{13}$, $SR^{13}$, oxo, or $NR^{13}R^{13}$,
(e) (C=O)$R^9$, or
(f) $R^7$ and $R^8$ together with the nitrogen to which they are attached form a het;

$R^9$ is
(a) aryl,
(b) het,
(c) $C_{3-8}$cycloalkyl, or
(d) $C_{1-7}$alkyl which is optionally unsaturated and is optionally substituted with one or more $NR^{13}R^{13}$, $OR^{14}$, $SR^{14}$, halo, $CONR^{13}R^{13}$, $CO_2R^{13}$, het, or aryl substituents;

$R^{10}$ is
(a) H, or
(b) $C_{1-7}$alkyl optionally substituted with OH;

$R^{11}$ is
(a) $OR^{14}$,
(b) $SR^{14}$,
(c) $NR^7R^8$,
(d) halo,
(e) $CONH_2$,
(f) $CONHR^9$,
(g) $CONR^9R^9$,
(h) $CO_2H$,
(i) $CO_2R^9$,
(j) het,
(k) aryl,
(l) cyano,
(m) oxo, or
(n) $SO_mR^6$, or
(o) P(=O)($OR^{14}$)($R^{14}$);

$R^{12}$ is
(a) H,
(b) het,
(c) aryl,
(d) $C_{3-8}$cycloalkyl optionally substituted with $R^{11}$, or
(e) $C_{1-7}$alkyl optionally substituted with $R^{11}$;

$R^{13}$ is
(a) H, or
(a) $C_{1-7}$alkyl;

$R^{14}$ is
(a) H,
(b) aryl,
(c) het, wherein the het is bound through a carbon atom,
(d) $C_{1-7}$alkyl which is optionally partially unsaturated and optionally substituted by aryl, het, $OR^{13}$, $SR^{13}$, $NR^{13}R^{13}$, halo, or $C_{3-8}$cycloalkyl which $C_{3-8}$cycloalkyl is optionally substituted by one or more $OR^{13}$, or
(e) $C_{3-8}$cycloalkyl which is optionally partially unsaturated and optionally substituted with one or more substituents halo, $OR^{13}$, $SR^{13}$, or $NR^{13}R^{13}$;

$R^{15}$ is
(a) H,
(b) halo,
(c) $OR^{13}$,
(d) $SR^{13}$,
(e) $NR^{13}R^{13}$,
(f) $O(CH_2CH_2O)_nR^{10}$,
(g) phenyl,
(h) cyano,
(i) nitro,
(j) $CONR^{13}R^{13}$,
(k) $CO_2R^{13}$, (l) $S(O)_mNR^{13}R^{13}$,
(m) $C_{1-7}$alkyl which is optionally partially unsaturated and optionally substituted with oxo, phenyl, 4-morpholine, $OR^{13}$, $SR^{13}$, $NR^{13}R^{13}$, halo, $CO_2R^{13}$, $CONR^{13}R^{13}$, or $C_{3-8}$cycloalkyl which $C_{3-8}$cycloalkyl is optionally substituted by one or more $OR^{13}$, or
(n) $C_{3-8}$cycloalkyl which is optionally partially unsaturated and optionally substituted by one or more oxo, halo, $OR^{13}$, $SR^{13}$, $C_{1-7}$alkyl or $NR^{13}R^{13}$ substituents;

each i is independently 2, 3, or 4;
each n is independently 1, 2, 3, 4 or 5;
each m is independently 1 or 2;
wherein any aryl other than G is optionally substituted with one or more $R^{15}$ substituents; and
wherein any het is optionally substituted with one or more oxo (=O), oxime (=N—$OR^{13}$), or $R^{15}$ substituents;
or a pharmaceutically acceptable salt thereof.

Specifically, the invention provides a compound of formula IV:

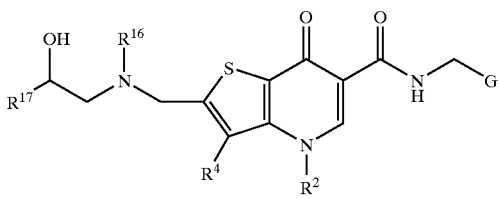

IV wherein:
G, $R^2$, and $R^4$, have any of the values or specific values described herein;

$R^6$ is
(a) H,
(b) aryl,
(c) $C_{1-7}$alkyl which is optionally partially unsaturated and is optionally substituted by one or more $NR^{13}R^{13}$, $OR^{14}$, or $SR^{14}$, $S(O)_mR^9$, $CONR^{14}R^{14}$, $CO_2R^{13}$, (C=O)$R^9$, het, aryl, cyano, or halo substituents,
(d) $C_{3-8}$cycloalkyl which is optionally partially unsaturated and is optionally substituted by one or more halo, $OR^{13}$, $SR^{13}$, oxo, or $NR^{13}R^{13}$ substituents, or
(e) (C=O)$R^9$;

$R^{17}$ is
(a) aryl, or
(b) het, $R^9$ is
(a) aryl,
(a) het,
(b) $C_{3-8}$cycloalkyl, or
(c) $C_{1-7}$alkyl which is optionally unsaturated and is optionally substituted with one or more $NR^{13}R^{13}$, $OR^{14}$, $SR^{14}$, halo, $CONR^{13}R^{13}$, $CO_2R^{13}$, het, or aryl substituents;

$R^{10}$ is
(c) H, or
(d) $C_{1-7}$alkyl optionally substituted with OH;

$R^{13}$ is
(a) H, or
(b) $C_{1-7}$alkyl;

$R^{14}$ is
(a) H, (b) aryl, (c) het, (d) $C_{1-7}$alkyl which is optionally partially unsaturated and optionally substituted by aryl, het, $OR^{13}$, $Si(R^{13})_3$, $SR^{13}$, $NR^{13}R^{13}$, halo, or $C_{3-8}$cycloalkyl which $C_{3-8}$cycloalkyl is optionally substituted by one or more $OR^{13}$, or (e) $C_{3-8}$cycloalkyl which is optionally partially unsaturated and optionally substituted with one or more substituents halo, $OR^{13}$, $SR^{13}$, or $NR^{13}R^{13}$;

$R^5$ is (a) H, (b) halo, (c) $OR^{13}$, (d) $SR^{13}$, (e) $NR^{13}R^{13}$, (f) $O(CH_2CH_2O)_nR^{10}$, (g) phenyl, (h) cyano, (i) nitro, (j) $CONR^{13}R^{13}$, (k) $CO_2R^{13}$, (l) $S(O)_mNR^{13}R^{13}$, (m) $C_{1-7}$alkyl which is optionally partially unsaturated and optionally substituted with one or more oxo, phenyl, 4-morpholine, $OR^{13}$, $SR^{13}$, $NR^{13}R^{13}$, halo, $CO_2R^{13}$, $CONR^{13}R^{13}$, or $C_{3-8}$cycloalkyl which $C_{3-8}$cycloalkyl is optionally substituted by one or more $OR^{13}$, (n) $C_{3-8}$cycloalkyl which is optionally partially unsaturated and optionally substituted by one or more oxo, halo, $OR^{13}$, $SR^{13}$, $C_{1-7}$alkyl, or $NR^{13}R^{13}$ substituents, (o) pyrimidinyl, pyridyl, pyrrolyl, pyrazinyl, pyridazinyl, imidazolyl, or pyrazolyl;

(p) morpholino, or (q) $NR^{13}COR^{13}$, each m is independently 1 or 2;

each n is independently 1, 2, 3, 4, or 5;

wherein any aryl other than G is optionally substituted with one or more $R^{15}$ substituents; and wherein any het is optionally substituted with one or more =O, =N—$OR^{13}$, or $R^{15}$ substituents;

or a pharmaceutically acceptable salt thereof.

The invention also specifically provides a compound of formula IV which is a compound of formula V:

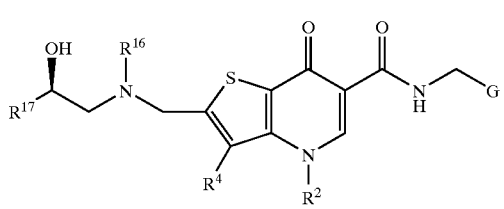

V or a pharmaceutically acceptable salt thereof.

The invention also specifically provides a compound of formula IV which is a compound of formula VI:

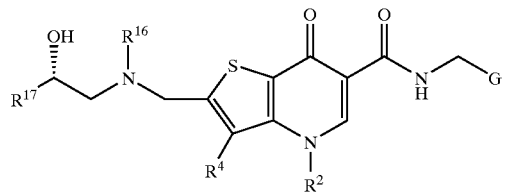

VI or a pharmaceutically acceptable salt thereof.

Specifically, the invention provides the synthetic processes and intermediates described in Preparations and Examples hereinbelow (e.g. Preparations 6, 10, 11, 12, 15, 16, 17, 20, 21, 22, 23, 24, 25, 26, 27, 28, 29, 30, 31, 32, 33, 34, 35, 36, 38, 39, 40, and 41).

The following Charts A–K describe the preparation of the compounds of the present invention. All of the starting materials are prepared by procedures described in these charts or by procedures analogous thereto, which would be well known to one of ordinary skill in organic chemistry. All of the final compounds of the present invention are prepared by procedures described in these charts, by procedures analogous thereto, or by procedures which are known to one of ordinary skill in organic chemistry. All of the variables used in the charts are as defined below or as in the claims.

Optionally substituted 3-aminothiophene-2-carboxylate esters of formula A-1 (Morris et al, *J. Het. Chem.* 1999, 36, 423–7; Jourdan et al, *J. Het. Chem.* 1994, 33, 436–40; Kirsch et al, *J. Het. Chem.* 1982, 19, 443; Saito et al, *Synthesis* 1982, 1056–59; Stephens et al, *J. Het. Chem.* 1999, 36, 659–65; Sauter et al, *Helv. Chim. Acta,* 1998, 81, 14–34; Jourdan et al, *J. Het. Chem.* 1994, 31, 305–12) can be saponified with aqueous sodium hydroxide and then acidified with acetic acid. The resulting 3-aminothiophenes can be reacted with diethyl ethoxymethylenemalonate (DEEM) to afford aminomethylene malonates of the formula A-2. Refluxing in diphenyl ether induces cyclization to compounds of formula A-3. Reaction with excess strong base, such as lithium diisopropylamide (LDA), followed by quenching with a suitable polar solvent and a source of the formyl group, such as dimethylformamide (DMF), provides the carboxaldehyde of formula A-4. N-Alkylation with optionally substituted alkyl halides occurs in DMF in the presence of potassium carbonate to afford compounds of formula A-5. Reduction with sodium triacetoxyborohydride produces alcohols of the formula A-6, which are reacted with substituted benzylamines to afford amides of formula A-7. The alcohols are converted to chlorides of formula A-8 by reaction with methanesulfonyl chloride (MsCl) in the presence of dimethylaminopyridine (DMAP). Displacement of the chloride with optionally substituted nucleophiles NuH, for example Nu=$R^{14}O$, $R^{14}S$ or $R^7R^8N$, in the presence of a suitable base then yields compounds of the formula A-9.

Chart A.

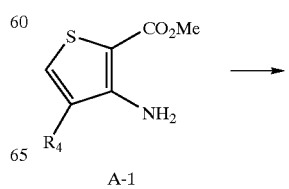

A-1

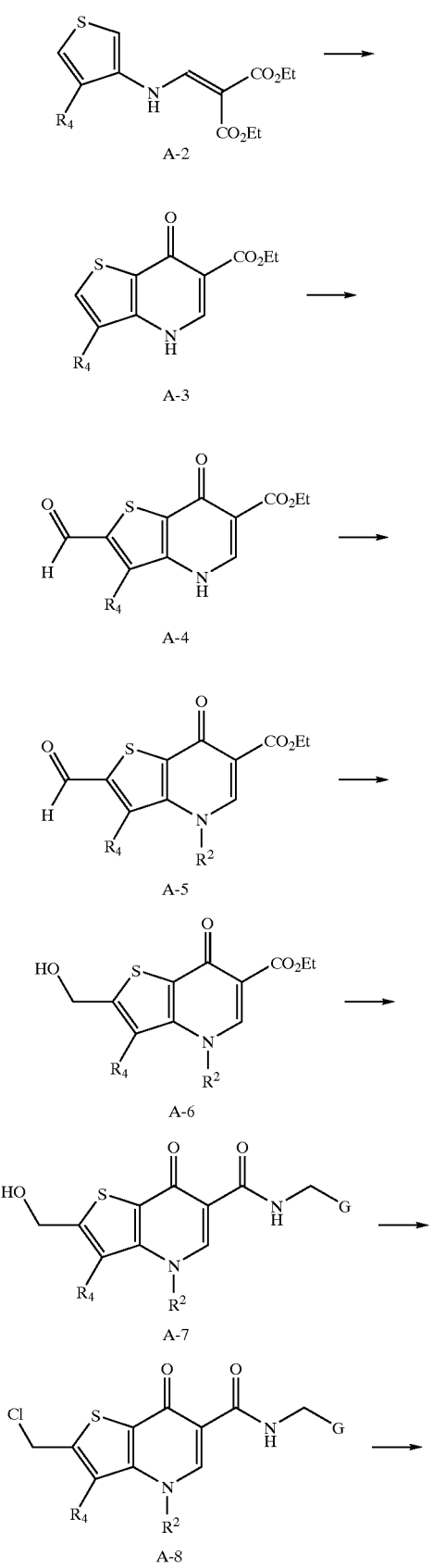

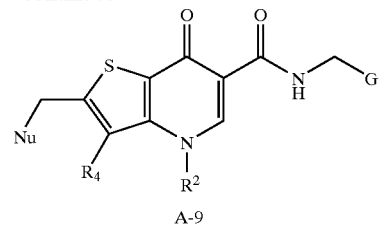

Specific compounds of the invention wherein $R^3$ is H can be prepared as depicted in Chart B. Ester A-3 (Chart A) is condensed with a benzylamine (e.g. 4-chloro-benzylamine, 4-bromobenzylamine, or 4-fluorobenzylamine) at high temperature, for example greater than about 50° C., to afford the corresponding amides of the general formula B-2. Alternatively, ester A-3 is saponified to afford the corresponding acid which can be coupled with a benzylamine mediated by 1,1'-carbonyldiimidazole (or other suitable carboxylic acid activating agents) to likewise provide amides of the general formula B-2. Amides of the formula B-2 can be alkylated at the ring nitrogen by treatment with an optionally substituted alkyl halide or alkyl mesylate in the presence of a base (e.g. potassium carbonate) or by reaction with an optionally substituted alkanol under Mitsunobu conditions to afford compounds of the general formula B-3 where R is a subset of $R^2$.

Chart B.

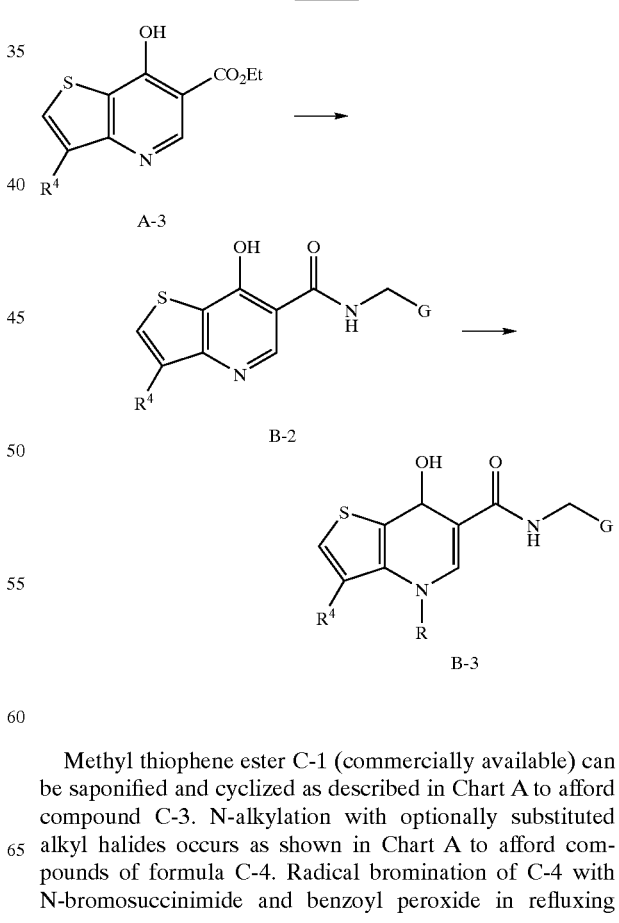

Methyl thiophene ester C-1 (commercially available) can be saponified and cyclized as described in Chart A to afford compound C-3. N-alkylation with optionally substituted alkyl halides occurs as shown in Chart A to afford compounds of formula C-4. Radical bromination of C-4 with N-bromosuccinimide and benzoyl peroxide in refluxing dichloroethane, followed by reaction with an optionally substituted nucleophile NuH, for example, Nu=$R^{14}O$, $R^{14}S$ or $R^7R^8N$, in the presence of a suitable base provides compounds of formula C-5. Reaction with benzylamines as described in Chart A then affords compounds of formula C-6.

An alternative preparation of alcohols of the formula A-7 is presented in Chart E. Aldehyde A-4 is reduced with sodium borohydride to afford alcohol E-1. Reaction with substituted benzylamines affords amides of the formula E-2. N-Alkylation with optionally substituted alkyl halides occurs in DMF in the presence of potassium carbonate to afford compounds of the formula A-7.

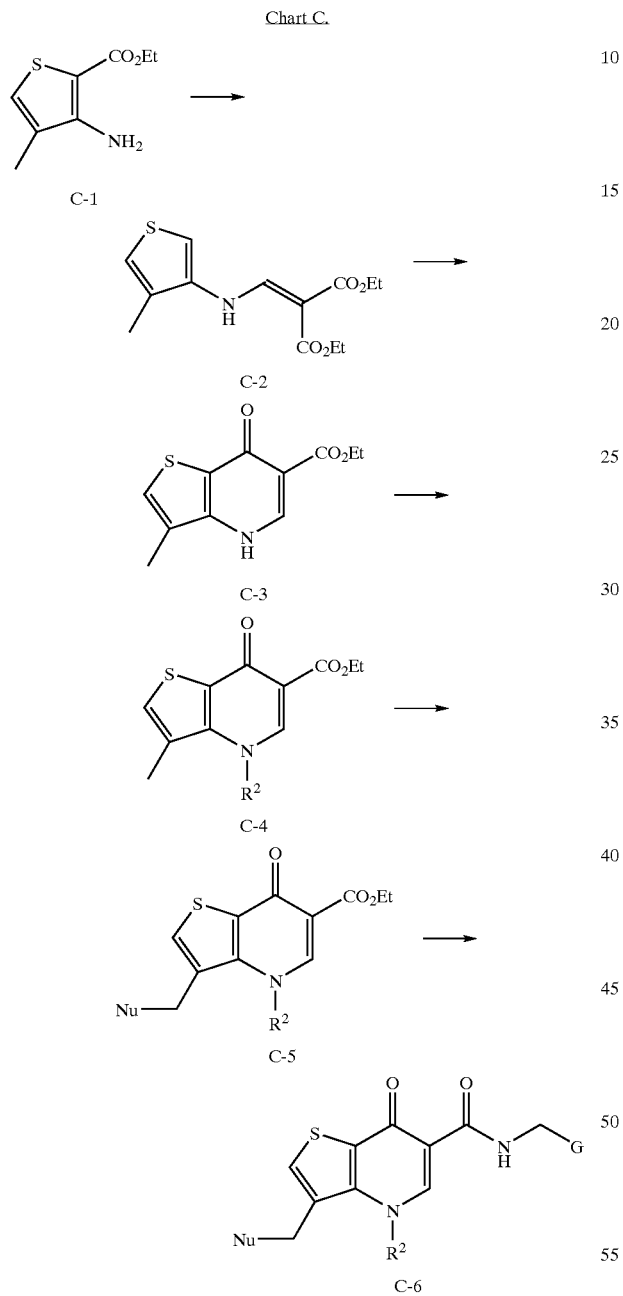

Amines of the formula D-3 can be prepared, for example, by bromination of ketones D-1 to form the corresponding bromoketones D-2, followed by reaction with a primary amine of the formula $R^7NH_2$, for example methylamine, and reduction with a suitable reducing agent, such as sodium borohydride to afford compounds of the formula D-3 wherein Y is aryl or het (Chart D).

Alkylation of C-3 with iodomethane and potassium carbonate affords F-1 (Chart F). Radical bromination of F-1 with NBS produces F-2, which is reacted with the lithium salt of 2-methoxyethanol followed by amidation with variously substituted benzylamines to produce ethers of formula F-3. Formylation of F-3 is accomplished by deprotonation with lithium diisopropylamide followed by the addition of DMF, giving aldehydes of formula F-4. The aldehydes can be reduced with sodium triacetoxyborohydride to afford alcohols of formula F-5, which are subsequently converted to chlorides of formula F-6 by reaction with methanesulfonyl chloride. Addition of variously substituted amines can then generate compounds of the formula F-7, wherein Y is aryl or het.

Chart F.

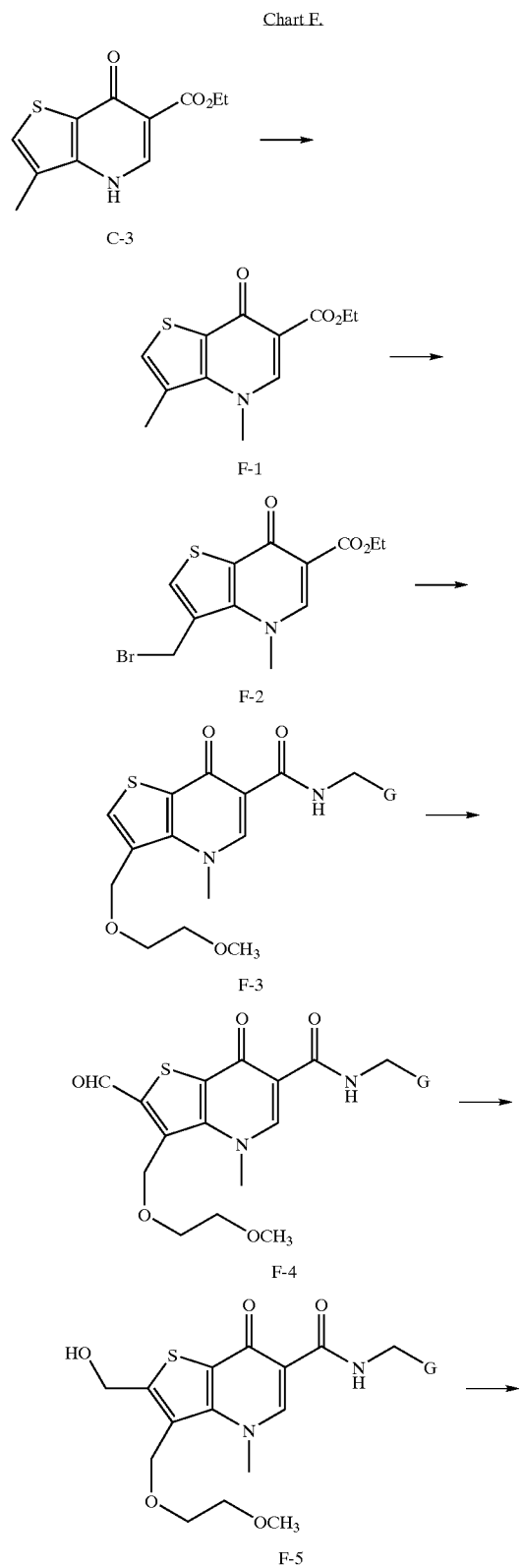

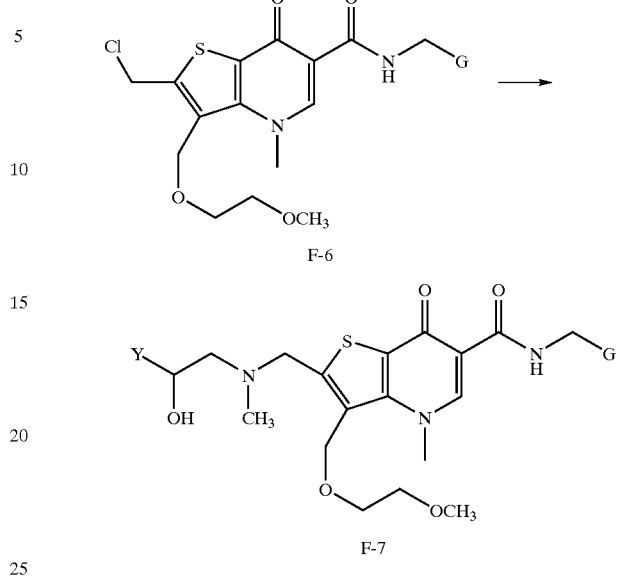

Bromide F-2 can also be reacted with the lithium salts of variously substituted alcohols ROH, wherein R is, for example, Me$_3$SiCH$_2$CH$_2$ or CH=CHCH$_2$, followed by amidation with variously substituted benzylamines to afford ethers of the formula G-1 (Chart G). Formylation as described in Chart F followed by reduction of the resulting aldehyde with sodium triacetoxyborohydride can then generate alcohols of the formula G-3. These alcohols can be converted to the corresponding chlorides of formula G-4 with methanesulfonyl chloride and reacted with variously substituted amines to produce amines of the formula G-5. Cleavage of the ethers under standard conditions known to one skilled in the art can then provide diols of the formula G-6, wherein Y is aryl or het.

Chart G.

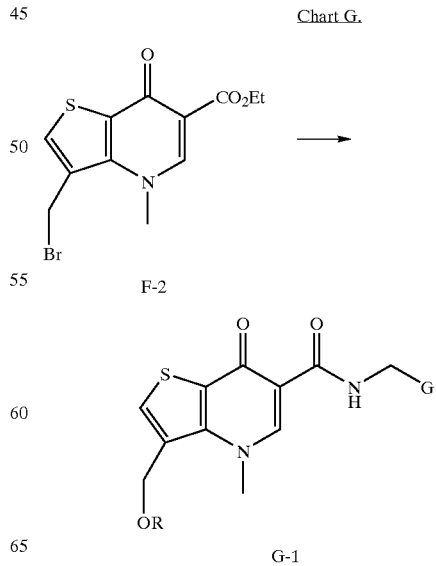

-continued

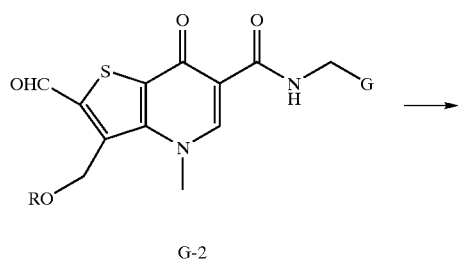

G-2

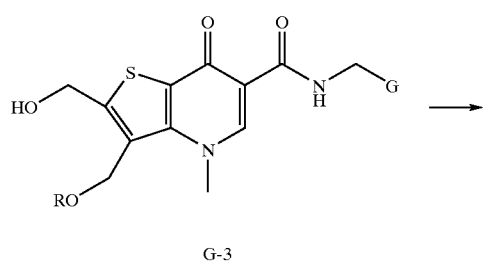

G-3

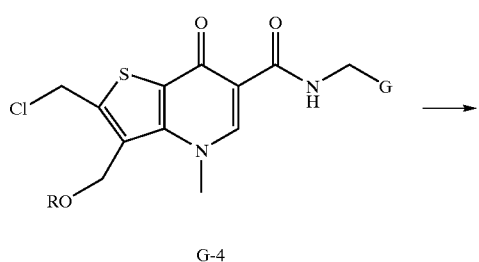

G-4

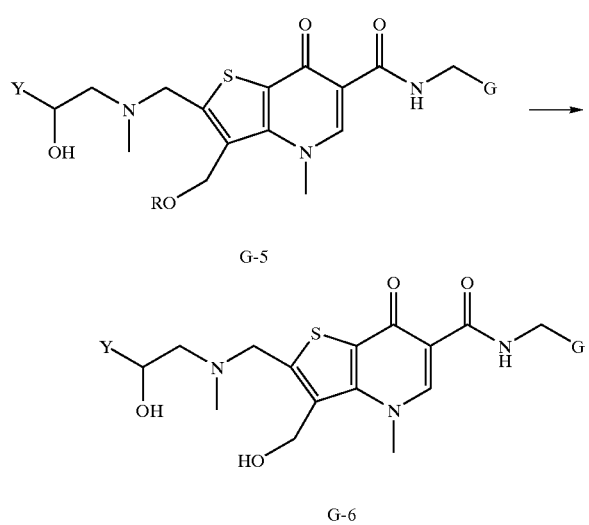

G-5

G-6

Bromide F-2 can be reacted with sodium azide to afford azide H-1 (Chart H). The ester can be converted to the corresponding amides of formula H-2 by reaction with variously substituted benzylamines. Formylation with LDA/DMF can then produce aldehydes of formula H-3, which can be reduced with sodium triacetoxyborohydride to alcohols of formula H-4. Conversion to chlorides H-5 followed by addition of variously substituted amines then generates amines of formula H-6. Reduction of the azides to the corresponding primary amines H-7 can be accomplished with triphenylphosphine. Sulfonylation of the amines with, for example, methanesulfonyl chloride then can afford sulfonamides of the formula H-8, wherein Y is aryl or het.

Chart H.

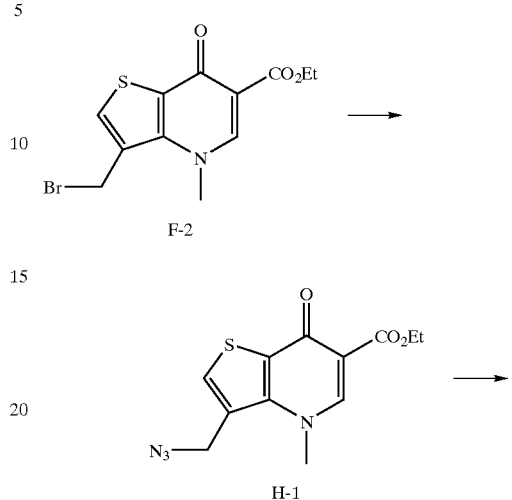

F-2

H-1

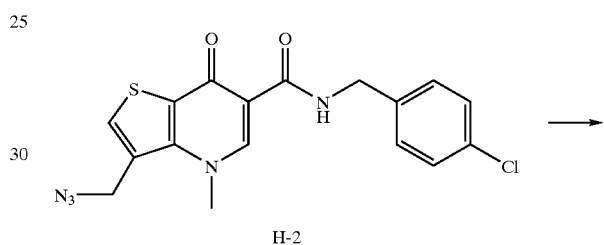

H-2

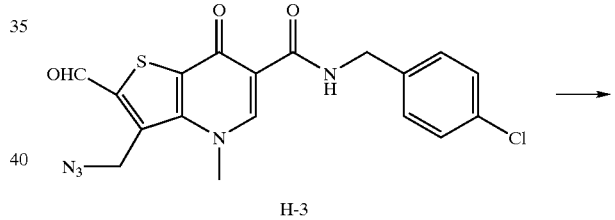

H-3

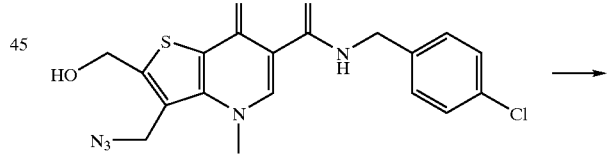

H-4

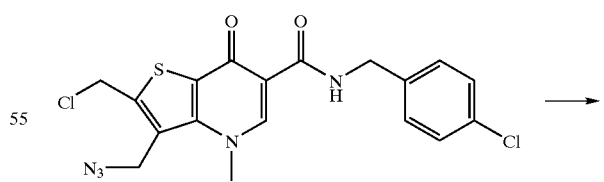

H-5

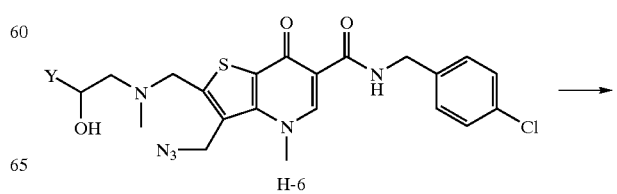

H-6

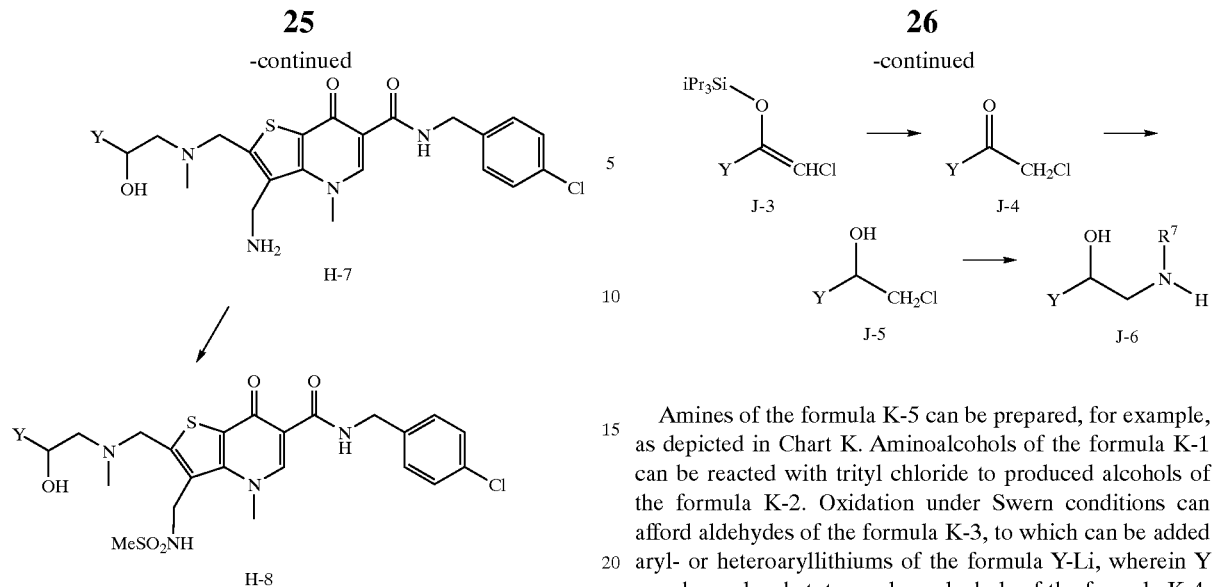

Amines of the formula I-3 can be prepared by, for example, epoxidation of aldehydes of formula I-1 with demethylsulfoxonium ylide to form the corresponding epoxides of formula I-2, followed by addition of variously substituted amines, for example methylamine, to afford amines of the formula I-3, wherein Y is het or aryl and $R^7$ is as defined herein.

Chart I.

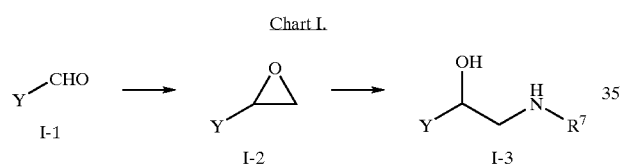

Amines of the formula J-6 can be prepared, for example, by conversion of ketones J-1 to enol silyl ethers of formula J-2 with triisopropylsilyl triflate and diisopropylethylamine (Chart J). Chlorination with N-chlorosuccinimide, followed by hydrolysis with aqueous HF then can afford alpha-chloroketones of formula J-4. Reduction of the ketones can be accomplished with sodium borohydride and cerium trichloride to afforded racemic alcohols of the formula J-5. Alternatively, the ketones J-4 can be reduced in an asymmetric fashion by, for example, hydrogenation with formic acid and the catalyst prepared from $[RuCl_2(\eta^6\text{-p-cymene})]_2$, $Et_3N$ and (1R,2R)-N-p-toluenesulfonyl-1,2-diphenylethylenediamine to provide optically active alcohols of the formula J-5. Reaction of alcohols J-5 with variously substituted amines, for example methylamine, then affords amines of formula J-6 wherein Y is aryl or het, and $R^7$ is as defined herein.

Chart J.

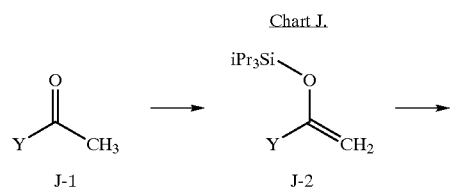

Amines of the formula K-5 can be prepared, for example, as depicted in Chart K. Aminoalcohols of the formula K-1 can be reacted with trityl chloride to produced alcohols of the formula K-2. Oxidation under Swern conditions can afford aldehydes of the formula K-3, to which can be added aryl- or heteroaryllithiums of the formula Y-Li, wherein Y may be aryl or het, to produce alcohols of the formula K-4. Cleavage of the trityl group with HCl in dioxane can then afford amines of the formula K-5, wherein $R^7$ is as defined herein.

Chart K.

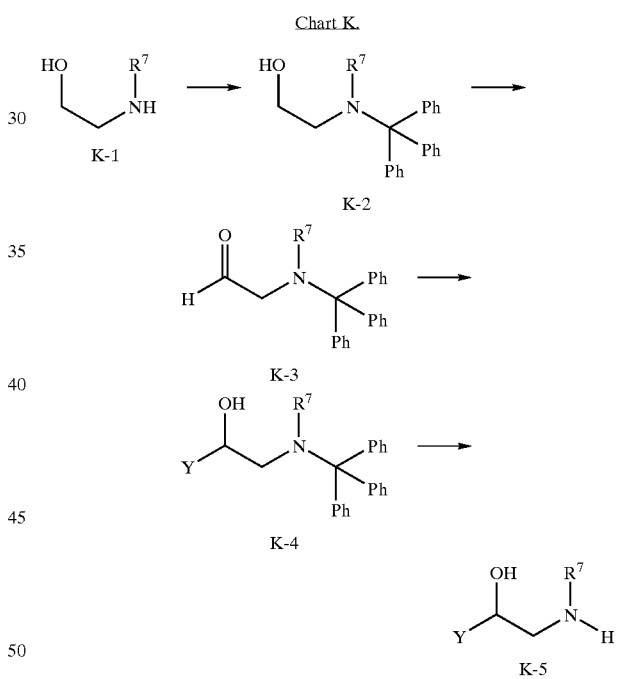

The invention also provides processes and intermediates described herein that are useful for preparing compounds of the invention. For example, compounds of the formula I wherein $R^2$ is other than H can be prepared from a corresponding compound of formula I wherein $R^2$ is H by, for example, alkylation. Accordingly, the present invention provides a method for preparing compounds of the formula I wherein $R^2$ is other than H, comprising alkylating a corresponding compound of the formula I wherein $R^2$ is hydrogen with a compound of the formula $R^2$—Z wherein Z is a suitable leaving group to provide the compound wherein $R^2$ is not H. Suitable Z leaving groups are known to those skilled in the art.

The invention also provides a method for preparing a compound of formula I:

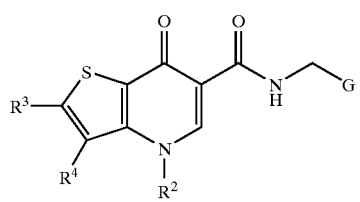

wherein G, $R^2$ and $R^4$ have the values described herein and $R^3$ is of the formula —$CH^2R^a$ where $R^a$ is, for example, $OR^{14}$, $SR^{14}$, $NR^7R^8$, N-linked Het, or CN, comprising: reacting a corresponding nucleophile with a compound of the formula III:

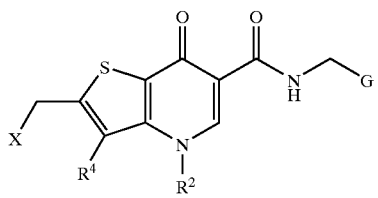

X is a leaving group, for example, Cl, Br, alkyl ester, anhydride, tosyl, mesyl, or like groups, under conditions suitable to provide the compound of formula I. Accordingly, the present invention provides a method for preparing compounds of the formula I wherein $R^3$ is $CH_2$-Nu where Nu is a nucleophile.

The invention also provides processes and intermediates described herein that are useful for preparing compounds of the invention. For example, the invention provides a method for preparing a compound of formula I wherein $R^2$ and $R^3$ have the values described herein comprising: reacting a nucleophile, for example, of the formula $NH_2$—$CH_2$—G with a compound of the formula II:

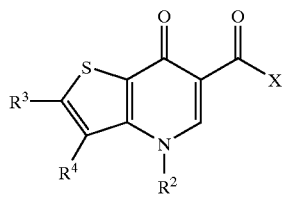

where X is a leaving group, for example, Cl, Br, alkyl ester, anhydride, tosyl, mesyl, or like groups, under conditions suitable to provide the compound of formula I. Suitable conditions for preparing an amide from a corresponding carboxylic acid are well known in the art. The reaction can be carried out under any suitable conditions. For example, the reaction can conveniently be carried out by activating a carboxylic acid of the formula C(=O)—OH with a suitable activating agent, and treating the activated acid of the formula C(=O)—X with, for example, a substituted benzyl amine or like reactants, to provide the compound of formula I. Suitable amines include, for example, 4-chlorobenzylamine, 4-fluorobenzylamine, 4-bromobenzylamine, 4-cyanobenzylamine, 4-nitrobenzylamine, and like amines. Accordingly, the present invention also provides intermediate compounds of the formula II wherein X is an activating leaving group.

The invention also provides a method for preparing a compound of formula A-4:

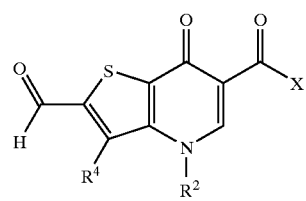

wherein $R^2$ is H, $R^4$ is as defined herein, and X is a leaving group or blocking group, comprising: treating a compound of formula A-3:

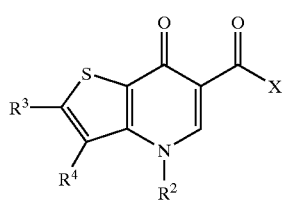

wherein $R^3$ is H, with a strong aprotic base and then reacting the resulting intermediate with a formylating agent.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate.

Suitable inorganic salts may also be formed, including hydrochloride, hydrobromide, sulfate, nitrate, bicarbonate, and carbonate salts.

Pharmaceutically acceptable salts may be obtained using standard procedures well known in the art, for example, by reacting a sufficiently basic compound such as an amine with a suitable acid affording a physiologically acceptable anion. Alkali metals, for example, sodium, potassium or lithium, or alkaline earth metal salts, for example calcium, of carboxylic acids can also be made.

Compounds of the present invention can conveniently be administered in a pharmaceutical composition containing the compound in combination with a suitable excipient, the composition being useful in combating viral infections. Pharmaceutical compositions containing a compound appropriate for antiviral use are prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally, for example, by intravenous, intraperitoneal or intramuscular injection, topically, orally, or rectally, depending on whether the preparation is used to treat internal or external viral infections.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohoUglycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing 5 to 1,000 mg, conveniently 10 to 750 mg, most conveniently, 50 to 500 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

For internal infections, the compositions can be administered orally or parenterally at dose levels, calculated as the free base, of about 0.1 to 300 mg/kg, preferably 1.0 to 30 mg/kg of mammal body weight, and can be used in man in a unit dosage form, administered one to four times daily in the amount of 1 to 1,000 mg per unit dose.

For parenteral administration or for administration as drops, as for eye infections, the compounds are presented in aqueous solution in a concentration of from about 0.1 to about 10%, more preferably about 0.1 to about 7%. The solution may contain other ingredients, such as emulsifiers, antioxidants or buffers.

Generally, the concentration of the compound(s) of formula I in a liquid composition, such as a lotion, will be from about 0.1–25 wt-%, preferably from about 0.5–10 weight percent. The concentration in a semi-solid or solid composition such as a gel or a powder will be about 0.1–5 weight percent, preferably about 0.5–2.5 weight percent.

The exact regimen for administration of the compounds and compositions disclosed herein will necessarily be dependent upon the needs of the individual subject being treated, the type of treatment and, of course, the judgment of the attending practitioner.

The antiviral activity of a compound of the invention can be determined using pharmacological models which are well known to the art, or using Test A described below.

The compounds of formula (I) and pharmaceutically acceptable salts thereof are useful as antiviral agents. Thus, they are useful to combat viral infections in animals, including man. The compounds are generally active against herpes viruses, and are particularly useful against the varicella zoster virus, the Epstein-Barr virus, the herpes simplex virus, the human herpes virus type 8 (HHV-8) and the cytomegalovirus (CMV). The compounds of the present invention may also be useful for the treatment of herpesvirus infections in animals, for example, illnesses caused by bovine herpesvirus 1-5 (BHV), ovine herpesvirus 1 and 2, Canine herpesvirus 1, equine herpesvirus 1-8 (EHV), feline herpesvirus 1 (FHV), and pseudorabies virus (PRV).

While many of the compounds of the present invention have shown activity against the CMV polymerase, these compounds may be active against the cytomegalovirus by this or other mechanisms of action. Thus, the description below of these compounds' activity against the CMV polymerase is not meant to limit the present invention to a specific mechanism of action.

Test A

The HCMV polymerase assay is performed using a scintillation proximity assay (SPA) as described in several references, such as N. D. Cook, et al., Pharmaceutical Manufacturing International, pages 49–53 (1992); K. Takeuchi, Laboratory Practice, September issue (1992); U.S. Pat. No. 4,568,649 (1986); which are incorporated by reference herein. Reactions are performed in 96-well plates. The assay is conducted in 100 μl volume with 5.4 mM HEPES (pH 7.5), 11.7 mM KCl, 4.5 mM $MgCl_2$, 0.36 mg/mL BSA, and 90 nM $^3$H-dTTP. Assays are run with and without CHAPS, (3-[(3-cholamidopropyl)dimethylammonio]-1-propane-sulfonate) at a final concentration of 2 mM. HCMV polymerase is diluted in enzyme dilution buffer containing 50% glycerol, 250 mM NaCl, 10 mM HEPES (pH 7.5), 100 μg/mL BSA, and 0.01% sodium azide. The HCMV polymerase, which is expressed in recombinant baculovirus-infected SF-9 cells and purified according to literature procedures, is added at 10% (or 10 μl) of the final reaction volume, i.e., 100 μl. Compounds are diluted in 50% DMSO and 10 μl are added to each well. Control wells contain an equivalent concentration of DMSO. Unless noted otherwise, reactions are initiated via the addition of 6 nM biotinylated poly (dA)-oligo (dT) template/primer to reaction mixtures containing the enzyme, substrate, and compounds of interest. Plates are incubated in a 25 C or 37° C. $H_2O$ bath and terminated via the addition of 40 μL/reaction of 0.5 M EDTA (pH 8) per well. Reactions are terminated within the time-frame during which substrate incorporation is linear and varied depending upon the enzyme and conditions used, i.e., 30 min. for HCMV polymerase. Ten μl of streptavidin-SPA beads (20 mg/mL in PBS/10% glycerol) are added following termination of the reaction. Plates are incubated 10 min. at 37° C., then equilibrated to room temperature, and counted on a Packard Topcount. Linear regressions are performed and $IC_{50}$'s are calculated using computer software.

A modified version of the above HCMV polymerase assay is performed as described above, but with the following changes: Compounds are diluted in 100% DMSO until final dilution into assay buffer. In the previous assay, compounds are diluted in 50% DMSO. 4.5 mM dithiotherotol (DTT) is added to the polymerase buffer. Also, a different lot of CMV polymerase is used, which appears to be more active resulting in a more rapid polymerase reaction. Representative compounds of formula I that were tested were found to be active in this assay. Unexpectedly, the compounds of formula I were typically found to have greater activity than the corresponding compounds wherein $R^4$ is hydrogen.

DESCRIPTION OF THE PREFERRED EMBODIMENTS

Preparation 1

Diethyl 2-{[(4-methylthien-3-yl)amino]methylene}malonate

To a solution of methyl 3-amino-4-methylthiophene-2-carboxylate (commercially available from Avocado, catalog number 10115, 5.00 g, 29.2 mmol) in 95% ethanol (25 mL) was added 1.0 N NaOH (35 mL). The mixture was heated to reflux and stirred for 2.5 hrs. The resulting solution was cooled to room temperature before the addition of glacial acetic acid (2.05 mL, 35.8 mmol). After stirring for 5 minutes at room temperature, diethyl ethoxymethylenemalonate (DEEM, 6.5 mL, 32.2 mmol) was added. The mixture was stirred vigorously until it nearly solidified (ca. 5 min), and then it was left standing at room temp for 3 hours. 95% ethanol (60 mL) was added, and the mixture was warmed on a steam bath until solution was achieved. Water (50 mL) was added with continued heating on the steam bath, resulting in a slightly cloudy solution. The flask was removed from the steam bath and allowed to cool to room temp and then placed in a 0° C. refrigerator, at which point crystallization of the product as fine white filaments was rapid. After standing at 0° C. for. 2 hours, the mixture was filtered. The collected solid was washed with 50% ethanol/water and dried, affording a white solid (5.79 g). The filtrate was diluted with water to a total volume of 500 mL, left overnight at 0° C., and filtered to afford a second crop (0.96 g) that was of equal purity to the first crop by HPLC analysis.

Physical characteristics are as follows:

$^1$H NMR (DMSO-$d_6$) δ 10.67 (1 H), 8.32 (1 H), 7.46 (1 H), 7.27 (1 H), 4.18 (2 H), 4.11 (2 H), 2.16 (3 H), 1.26 (3 H), 1.23 (3 H); Anal. Found: C, 55.05; H, 6.05; N, 4.93. MS (ESI−) for $C_{13}H_{17}NO_4S$ m/z 282 (M−H)$^-$.

Preparation 2

Ethyl 7-hydroxy-3-methylthieno[3,2-b]pyridine-6-carboxylate

A solution of diethyl 2-{[(4-methylthien-3-yl)amino]methylene}malonate (5.79 g) in diphenyl ether (200 mL) in a 500 mL round bottom (RB) flask was degassed by three cycles of evacuation and nitrogen purge. The solution was then heated rapidly with a heating mantle to reflux and stirred at that temperature for 10 minutes. The heating mantle was removed and the golden yellow solution was then stirred for 3 hours, during which time a copious precipitate appeared. The mixture was diluted with diethyl ether (300 mL) before collecting the solid by vacuum filtration. The collected solid was washed thoroughly with ether and dried in vacuo, leaving a white solid (3.94 g).

Physical characteristics are as follows:

$^1$H NMR (400 MHz, DMSO-$d_6$) δ 12.6 (1 H), 8.33 (1 H), 7.69 (1 H), 4.22 (2 H), 2.35 (3 H), 1.28 (3 H); Anal Found: C, 55.61; H, 4.71; N, 5.92. MS (ESI+) for $C_{11}H_{11}NO_3S$ m/z 238 (M+H)$^+$.

Preparation 3

Ethyl 2-formyl-3-methyl-7-oxo-4,7-dihydrothieno[3,2-b]pyridine-6-carboxylate A fresh solution of LDA was prepared by adding n-BuLi (1.6 M in hexanes, 7.94 mL, 12.7 mmol) to a 0° C. solution of diisopropylamine (1.95 mL, 13.9 mmol) in anhydrous THF (20 mL). The LDA solution was then added via syringe drop-wise to a suspension of ethyl 7-hydroxy-3-methylthieno[3,2-b]pyridine-6-carboxylate (1.00 g, 4.22 mmol) in THF (30 mL) at −78° C. over a period of about 10 minutes. After addition of the LDA, the solution was stirred at −78° C. for 1 hr 15 min before the drop-wise addition of dry DMF (1.63 mL, 21.1 mmol). The reaction was stirred at −78° C. for 20 minutes and then the dry ice bath was removed. The temperature was allowed to rise to over 0° C. before the reaction was quenched by the addition of sat. aqueous ammonium chloride (25 mL). Water (20 mL) and ethyl acetate (25 mL) were added, and the mixture was stirred vigorously for one hour. After standing overnight at 0° C., the solid precipitate was collected by vacuum filtration, and the solid was washed with ethyl acetate and water. Drying in vacuo left a yellow solid (1.04 g).

Physical characteristics are as follows:

$^1$H NMR (400 MHz, DMSO-d$_6$) δ 10.25 (1 H), 8.66 (1 H), 4.22 (2 H), 2.68 (3 H), 1.29 (3 H); ES MS (ES+): 266. MS (ESI+) for $C_{12}H_{11}NO_4S$ m/z 266 (M+H)$^+$.

Preparation 4

Ethyl 2-formyl-3,4-dimethyl-7-oxo-4,7-dihydrothieno[3,2-b]pyridine-6-carboxylate A mixture of ethyl 2-formyl-3-methyl-7-oxo-4,7-dihydrothieno[3,2-b]pyridine-6-carboxylate (1.06 g, 3.99 mmol), potassium carbonate (826 mg, 5.98 mmol) and methyl iodide (1.24 mL, 19.9 mmol) in DMF (30 mL) was stirred at 50° C. for 24 hours. The mixture was diluted with water (60 mL), stirred with ice bath cooling for 5 minutes, and then filtered. The collected solid was washed with water and dried in vacuo, leaving a pale tan solid (764 mg, 69%).

Physical characteristics are as follows:

$^1$H NMR (400 MHz, DMSO-d$_6$) δ 10.31 (1 H), 8.58 (1 H), 4.23 (2 H), 4.20 (3 H), 2.95 (3 H), 1.28 (3 H); Anal Found: C, 55.49; H, 4.81; N, 4.89.

Preparation 5

Ethyl 2-(hydroxymethyl)-3,4-dimethyl-7-oxo-4,7-dihydrothieno[3,2-b]pyridine-6-carboxylate To a 0° C. mixture of ethyl 2-formyl-3,4-dimethyl-7-oxo-4,7-dihydrothieno[3,2-b]pyridine-6-carboxylate (695 mg, 2.49 mmol) and glacial acetic acid (0.71 mL, 12.5 mmol) in 1,2-dichloroethane (23 mL) was added sodium triacetoxyborohydride (1.06 g, 4.98 mmol). After stirring for 5 min at 0° C., the reaction was stirred at room temperature for 3.5 hours. The reaction was poured into sat. aqueous. sodium bicarbonate (50 mL) and methylene chloride (30 mL), stirred vigorously for 5 minutes, and filtered. The collected solid was washed with water and methylene chloride, then dried in vacuo, leaving an off-white solid (665 mg, 93%).

Physical characteristics are as follows:

$^1$H NMR (400 MHz, DMSO-d$_6$) δ 8.41 (1 H), 5.82 (1 H), 4.69 (2 H), 4.21 (2 H), 4.12 (3 H), 2.44 (3 H), 1.27 (3 H); Anal Found: C, 54.13; H, 5.34; N, 4.82.

EXAMPLE 1

N-(4-chlorobenzyl)-2-(hydroxymethyl)-3,4-dimethyl-7-oxo-4,7-dihydrothieno[3,2-b]pyridine-6-carboxamide

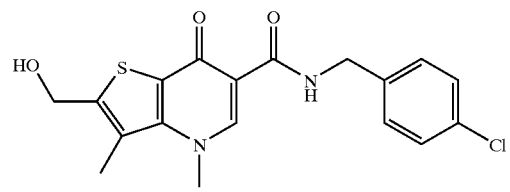

A solution of ethyl 2-(hydroxymethyl)-3,4-dimethyl-7-oxo-4,7-dihydrothieno[3,2-b]pyridine-6-carboxylate (627 mg, 2.23 mmol), 4-chlorobenzylamine (2.0 mL, 16.4 mmol), 0.5 M sodium methoxide in methanol (25 mL, 8.92 mmol) and methanol (10 mL) was stirred under nitrogen in a tightly capped 250 mL round bottom flask at 50° C. for 24 hours. The initial solution slowly dropped a thick white precipitate during the reaction. After cooling to room temperature, the mixture was filtered, and the collected solid was washed with methanol and dried in vacuo, leaving a white solid. The crude solid was suspended in boiling methanol (200 mL), cooled to room temperature, and filtered, to give the title compound as a white powder (585 mg).

Physical characteristics are as follows:

$^1$H NMR (400 MHz, DMSO-d$_6$) δ 10.42 (1 H), 8.58 (1 H), 7.40, 7.34 (4 H), 5.88 (1 H), 4.72 (2 H), 4.53 (2 H), 4.21 (3 H), 2.47 (3 H); $^{13}$C NMR (DMSO-d6) δ 171.1, 164.2, 150.5, 147.6, 143.8, 138.5, 131.3, 129.5, 129.1, 128.2, 122.4, 110.6, 57.8, 43.4, 41.3, 14.0; Anal Found: C, 55.17; H, 4.44; N, 7.09.

Preparation 6

N-(4-chlorobenzyl)-2-(chloromethyl)-3,4-dimethyl-7-oxo-4,7-dihydrothieno[3,2-b]pyridine-6-carboxamide Methanesulfonyl chloride (0.23 mL, 3.0 mmol) was added to a mixture of N-(4-chlorobenzyl)-2-(hydroxymethyl)-3,4-dimethyl-7-oxo-4,7-dihydrothieno[3,2-b]pyridine-6-carboxamide (446 mg, 1.19 mmol), collidine (0.39 mL, 3.0 mmol) and DMAP (22 mg, 0.18 mmol) in DMF (21 mL). The reaction was stirred at room temperature for 1 hour 15 minutes, going to an orange/amber solution. The reaction was cooled in an ice bath before diluting with water to a total volume of 100 mL. The mixture was stirred vigorously for 5 minutes before the solid precipitate was collected by filtration, washed with water and dried in vacuo, leaving the title compound as a white solid (460 mg).

Physical characteristics are as follows:

$^1$H NMR (400 MHz, DMSO-d$_6$) δ 10.3 (1 H), 8.65 (1 H), 7.39, 7.34 (4 H), 5.13 (2 H), 4.54 (2 H), 4.25 (3 H), 2.60 (3 H); MS (ESI+) m/z 395, 397 (M+H)$^+$.

EXAMPLE 2

N-(4-chlorobenzyl)-2-{[[2-hydroxy-2-(4-hydroxyphenyl)ethyl](methyl)amino]methyl}-3,4-dimethyl-7-oxo-4,7-dihydrothieno[3,2-b]pyridine-6-carboxamide

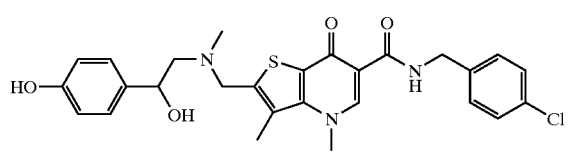

A mixture of N-(4-chlorobenzyl)-2-(chloromethyl)-3,4-dimethyl-7-oxo-4,7-dihydrothieno[3,2-b]pyridine-6-carboxamide (48 mg, 0.12 mmol), synephrine (Aldrich, 30 mg, 0.18 mmol) and diisopropylethylamine (31 μL, 0.18 mmol) in dry DMF (2.0 mL) was heated to 60° C., becoming a solution. The reaction was stirred for 3 hours at that temperature. After cooling to room temperature, the solution was diluted with water (5 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (49 mg) as a white solid.

Physical characteristics are as follows:

$^1$H NMR (400 MHz, DMSO-$d_6$) δ 10.42 (1 H), 9.2 (1 H), 8.57 (1 H), 7.40, 7.34 (4 H), 7.10 (2 H), 6.66 (2 H), 4.92 (1 H), 4.65 (1 H), 4.53 (2 H), 4.20 (3 H), 3.85, 3.78 (2 H), 2.6 (2 H), 2.46 (3 H), 2.30 (3 H); Anal. Found: C, 59.17; H, 5.34; N, 8.36. MS (ESI+) for $C_{27}H_{28}ClN_3O_4S$ m/Z 526, 528 (M+H)$^+$.

EXAMPLE 3

N-(4-chlorobenzyl)-2-{[(2-hydroxy-2-phenylethyl)(methyl)amino]methyl}-3,4-dimethyl-7-oxo-4,7-dihydrothieno[3,2-b]pyridine-6-carboxamide

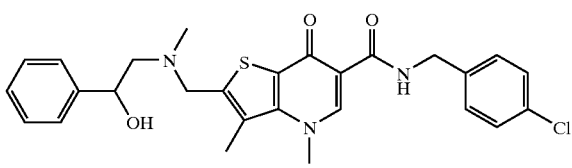

Prepared from 2-(methylamino)-1-phenylethanol (Aldrich) by the procedure described for Example 2. Recrystallization afforded 41 mg of the title compound as a white solid.

Physical characteristics are as follows:

$^1$H NMR (400 MHz, DMSO-$d_6$) δ 10.42 (1 H), 8.57 (1 H), 7.2–7.45 (9 H), 5.15 (1 H), 4.76 (1 H), 4.53 (2 H), 4.20 (3 H), 3.85, 3.80 (2 H), 2.68, 2.60 (2 H), 2.46 (3 H), 2.32 (3 H); Anal Found: C, 59.92; H, 5.15; N, 7.74. MS (ESI+) for $C_{27}H_{28}ClN_3O_3S$ m/z 510, 512 (M+H)$^+$.

EXAMPLE 4

N-(4-chlorobenzyl)-2-{[[2-hydroxy-2-(3-methoxyphenyl)ethyl](methyl)amino]methyl}-3,4-dimethyl-7-oxo-4,7-dihydrothieno[3,2-b]pyridine-6-carboxamide

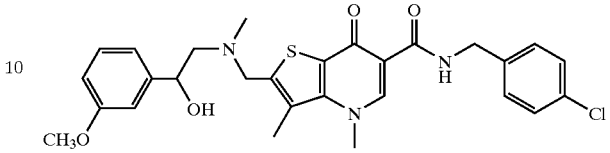

Prepared from 1-(3-methoxyphenyl)-2-(methylamino)ethanol (*Chem. Abstr.;* 1957; 6548) by the procedure described for Example 2. Recrystallization afforded 50 mg of the title compound as a white solid.

Physical characteristics are as follows:

$^1$H NMR (400 MHz, DMSOd$_6$) δ 8.58 (1 H), 7.40, 7.34 (4 H), 7.20 (1 H), 6.89 (1 H), 6.88 (1 H), 6.78 (1 H), 5.15 (1 H), 4.72 (1 H), 4.54 (2 H), 4.20 (3 H), 3.87, 3.79 (2 H), 3.71 (3 H), 2.63 (2 H), 2.46 (3 H), 2.33 (3 H); Anal Found: C, 62.16; H, 5.59; N, 7.79. MS (ESI+) for $C_{28}H_{30}ClN_3O_4S$ m/z 540, 542 (M+H)$^+$.

Preparation 7

2-bromo-1-(2-furyl)ethanone

Bromine (6.5 mL, 127 mmol) was added dropwise over 1 hour to a solution of 2-acetylfuran (11.0 g, 100 mmol) in dioxane/Et$_2$O (1/2, 60 mL) at 0° C. After addition was complete, the reaction was warmed to room temperature and stirred for 2 hours. A saturated ammonium chloride solution (70 mL) was then added. The organic layer was removed and the aqueous layer was extracted with Et$_2$O (2×50 mL). The combined organic layers were dried over MgSO$_4$, filtered, and concentrated. The resulting brown solid was purified using a Biotage 40 M column (hexanes/CH$_2$Cl$_2$, 70/30) to yield the bromoketone as a yellow oil that solidified upon standing (4.40 g).

Physical characteristics are as follows:

$^1$H NMR (DMSO-d$_6$) δ 4.66 (2 H), 6.78 (1 H), 7.66 (1 H), 8.09 (1 H).

Preparation 8

1-(2-furyl)-2-(methylamino)ethanol

A solution of 2-bromo-1-(2-furyl)ethanone (3.0 g, 15.88 mmol) in methanol (16 mL) was added dropwise to a 2.0 M solution of methylamine in methanol (79.4 mL, 158.8 mmol) at 0° C. The reaction stirred at 0° C. for 30 minutes. A solution of sodium borohydride (0.90 g, 23.82 mmol) in H$_2$O (16 mL) was then added dropwise. The reaction mixture was stirred at 0° C. for 30 minutes and then quenched with 2 N HCl (to pH 3–4). The reaction mixture was concentrated in vacuo to remove methanol and then poured into a cold mixture of EtOAc (80 mL) and 2 N HCl (40 mL). The organic layer was removed. The aqueous layer was adjusted to pH 12 with 2 N NaOH and extracted with EtOAc (3×80 mL). The combined extracts were dried over MgSO$_4$, filtered, and concentrated in vacuo. The resulting brown oil was purified using a Biotage 40 M column (CHCl$_3$/methanol, 95/5; CHCl$_3$/methanol/NH$_4$OH, 90/10/1) to yield the aminoalcohol as a brown oil (0.86 g).

Physical characteristics are as follows:

$^1$H NMR (DMSO-$d_6$) δ 2.33 (3 H), 2.77–2.66 (2 H), 4.61 (1 H), 6.26 (1 H), 6.38 (1 H), 7.56 (1 H). OAMS (ES+) m/z 141.9 (M+H)$^+$.

EXAMPLE 5

N-(4-chlorobenzyl)-2-{[[2-(2-furyl)-2-hydroxyethyl](methyl)amino]methyl}-3,4-dimethyl-7-oxo-4,7-dihydrothieno[3,2-b]pyridine-6-carboxamide

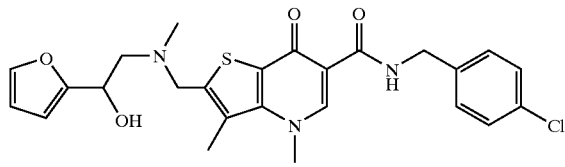

Prepared from 1-(2-furyl)-2-(methylamino)ethanol (Preparation 8) by the procedure described for Example 2. Recrystallization afforded 43 mg of the title compound as a white solid.

Physical characteristics are as follows:

$^1$H NMR (400 MHz, DMSO-$d_6$) δ 10.42 (1 H), 8.57 (1 H), 7.55 (1 H), 7.39, 7.34 (4 H), 6.38 (1 H), 6.28 (1 H), 5.30 (1 H), 4.75 (1 H), 4.53 (2 H), 4.21 (3 H), 3.83, 3.77 (2 H), 2.79 (2 H), 2.48 (3 H), 2.28 (3 H); Anal Found: C, 55.72; H, 5.06; N, 7.80. MS (ESI+) for $C_{25}H_{26}ClN_3O_4S$ m/z 500, 502 (M+H)$^+$.

EXAMPLE 6

N-(4-chlorobenzyl)-2-{[(2-hydroxy-2-pyridin-2-ylethyl)(methyl)amino]methyl}-3,4-dimethyl-7-oxo-4,7-dihydrothieno[3,2b]pyridine-6-carboxamide

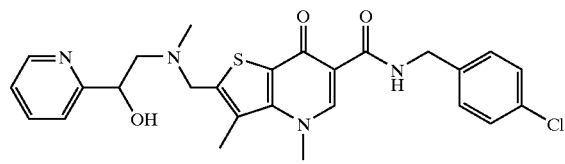

Prepared from 1-(2-pyridyl)-2-methylamino)ethanol (prepared from 2-acetylpyridine by the procedure outlined in Preparations 7 and 8) by the procedure described for Example 2. Dilution of the reaction mixture with water and filtration afforded 30 mg of the title compound as a white solid.

Physical characteristics are as follows:

$^1$H NMR (400 MHz, DMSO-$d_6$) δ 10.42 (1 H), 8.57 (1 H), 8.45 (1 H), 7.76 (1 H), 7.48 (1 H), 7.39, 7.34 (4 H), 7.24 (1 H), 5.36 (1 H), 4.82 (1 H), 4.53 (2 H), 4.20 (3 H), 3.84 (2 H), 2.85, 2.70 (2 H), 2.46 (3 H), 2.33 (3 H); Anal Found: C, 57.10; H, 4.99; N, 10.19. MS (ESI+) for $C_{26}H_{27}ClN_4O_3S$ m/z 511, 513 (M+H)$^+$.

EXAMPLE 7

N-(4-chlorobenzyl)-3,4-dimethyl-2-(morpholin-4-ylmethyl)-7-oxo-4,7-dihydrothieno[3,2-b]pyridine-6-carboxamide

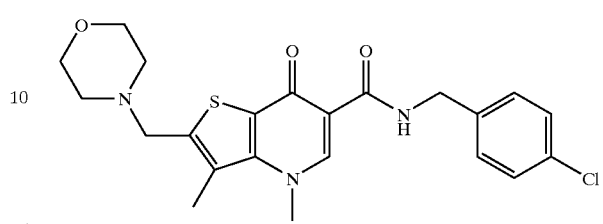

Prepared from morpholine by the procedure described for Example 2. Recrystallization afforded 41 mg of the title compound as a white solid.

Physical characteristics are as follows:

$^1$H NMR (400 MHz, DMSO-$d_6$) δ 10.42 (1 H), 8.59 (1 H), 7.39, 7.34 (4 H), 4.53 (2 H), 4.22 (3 H), 3.74 (2 H), 3.60 (4 H), 2.54 (3 H), 2.50 (4 H); Anal Found: C, 56.64; H, 5.61; N, 9.00. MS (ESI+) for $C_{22}H_{24}ClN_3O_3S$ m/z 446, 448 (M+H)$^+$.

EXAMPLE 8

[[(6-{[(4-chlorobenzyl)amino]carbonyl}-3,4-dimethyl-7-oxo-4,7-dihydrothieno[3,2-b]pyridin-2-yl)methyl](methyl)amino]methyl(phenyl)phosphinic acid

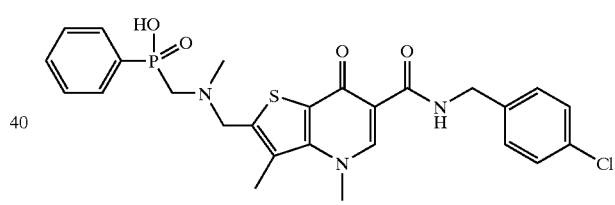

A mixture of N-(4-chlorobenzyl)-2-(chloromethyl)-3,4-dimethyl-7-oxo-4,7-dihydrothieno[3,2-b]pyridine-6-carboxamide (25 mg, 0.063 mmol), 1-(methylamino)methyl(phenyl)phosphinic acid (R. Tyka, *Synthesis* 1984, 218) (24 mg, 0.0.13 mmol) and potassium carbonate (35 mg, 0.25 mmol) in dry DMF (1.0 mL) and water (0.25 mL) was stirred at 60° C. for 30 minutes, going to a solution. HPLC analysis indicated reaction was complete. The solvent was removed in vacuo, and the resulting white solid was washed with methylene chloride. The solid was dissolved in water (5 mL) and brought to pH 7 with 1.0 M aqueous HCl. After standing in a 0° C. refrigerator overnight, the mixture was filtered, and the collected solid was washed with cold water. Drying in vacuo left the title compound as a white powder (23 mg).

Physical characteristics are as follows:

$^1$H NMR (400 MHz, DMSO-$d_6$) δ 10.38 (1 H), 8.57 (1 H), 7.72 (2 H), 7.54 (1 H), 7.44 (2 H), 7.40, 7.34 (4 H), 4.53 (2 H), 4.17 (3 H), 3.89 (2 H), 2.97 (2 H), 2.37 (3 H), 2.33 (3 H); Anal Found: C, 55.30; H, 5.11; N, 7.38. MS (ESI−) for $C_{26}H_{27}ClN_3O_4PS$ m/z 542, 544 (M−H)$^−$.

EXAMPLE 9

N-(4-chlorobenzyl)-2-{[[2-hydroxy-2-(1,3-thiazol-2-yl)ethyl](methyl)amino]methyl}-3,4-dimethyl-7-oxo-4,7-dihydrothieno[3,2-b]pyridine-6-carboxamide

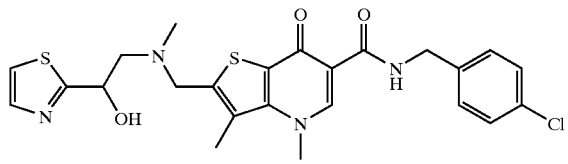

Prepared from 2-(methylamino)-1-(1,3-thiazol-2-yl) ethanol (prepared from 2-acetyl-1,3-thiazole by a procedure analogous to that described in Preparations 7 and 8) by the procedure described for Example 2. Recrystallization afforded 59 mg of the title compound.

Physical characteristics are as follows:
$^1$H NMR (400 MHz, DMSO-d$_6$) δ 10.43, 8.58, 7.72, 7.62, 7.39, 7.34, 6.22, 5.06, 4.54, 4.21, 3.88, 2.95, 2.79, 2.49, 2.36; Anal. Found: C, 53.92; H, 5.02; N, 10.35; OAMS (ESI+) m/z 517, 519 (M+H)$^+$.

EXAMPLE 10

N-(4-chlorobenzyl)-2-{[[2-(5-cyanothien-2-yl)-2-hydroxyethyl](methyl)amino]methyl}-3,4-dimethyl-7-oxo-4,7-dihydrothieno[3,2-b]pyridine-6-carboxamide

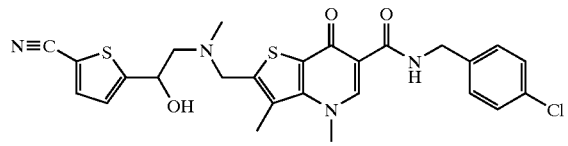

Prepared from 5-[1-hydroxy-2-(methylamino)ethyl] thiophene-2-carbonitrile (prepared from 5-acetylthiophene-2-carbonitrile by a procedure analogous to that described in Preparations 7 and 8) by the procedure described for Example 2. Recrystallization afforded the title compound (37 mg).

Physical characteristics are as follows:
HPLC retention time: 2.65 min; OAMS (ESI+) m/z 541 (M+H)$^+$.

EXAMPLE 11

N-(4-chlorobenzyl)-2-{[(2-hydroxy-2-pyrazin-2-ylethyl)(methyl)amino]methyl}-3,4-dimethyl-7-oxo-4,7-dihydrothieno[3,2-b]pyridine-6-carboxamide

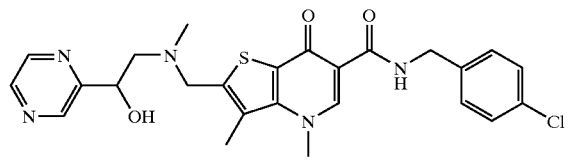

Prepared from 2-(methylamino)-1-pyrazin-2-ylethanol (prepared from 2-acetylpyrazine by a procedure analogous to that described in Preparations 7 and 8) by the procedure described for Example 2. Recrystallization afforded 31 mg of the title compound.

Physical characteristics are as follows:
HPLC retention time: 2.25 min.; OAMS (ESI+) m/z 512 (M+H)$^+$.

EXAMPLE 12

N-(4-chlorobenzyl)-2-{[{2-hydroxy-2-[4-(methylsulfonyl)phenyl]ethyl}(methyl)amino] methyl}-3,4-dimethyl-7-oxo-4,7-dihydrothieno[3,2-b]pyridine-6-carboxamide

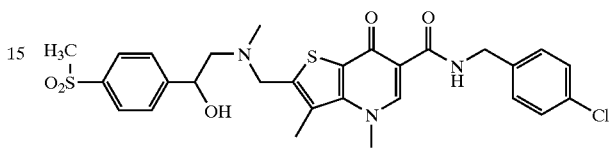

Prepared from 2-(methylamino)-1-[4-(methylsulfonyl) phenyl]ethanol (prepared from 4-methylsulphonylacetophenone by a procedure analogous to that described in Preparations 7 and 8) by the procedure described for Example 2. Recrystallization afforded 71 mg of the title compound.

Physical characteristics are as follows:
$^1$H NMR (400 MHz, DMSO-d$_6$) δ) 10.4, 8.56, 7.85, 7.59, 7.40, 7.34, 5.46, 4.90, 4.52, 4.19, 3.82, 3.20, 2.67, 2.44, 2.34; Anal Found: C, 56.66; H, 5.30; N, 7.13; OAMS (ESI+) m/z 588, 590 (M+H)$^+$.

EXAMPLE 13

N-(4-chlorobenzyl)-2-{[[2-hydroxy-1-(3-oxo-3,4-dihydro-2H-1,4-benzoxazin-6-yl)ethyl](methyl) amino]methyl}-3,4-dimethyl-7-oxo-4,7-dihydrothieno[3,2-b]pyridine-6-carboxamide

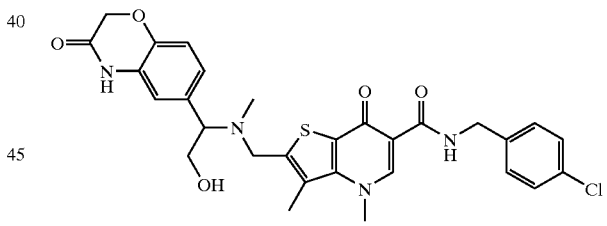

Prepared from 6-[2-hydroxy-1-(methylamino)ethyl]-2H-1,4-benzoxazin-3(4H)-one (prepared from 6-acetyl-2H-1,4-benzoxazin-3(4H)-one by a procedure analogous to that described in Preparations 7 and 8) by the procedure described for Example 2. Recrystallization afforded 56 mg of the title compound.

Physical characteristics are as follows:
$^1$H NMR (400 MHz, DMSO-d$_6$) δ) 10.7, 10.4, 8.57, 7.40, 7.34, 6.92, 4.66, 4.55, 4.54, 4.21, 3.76, 3.59, 2.48, 2.21; Anal Found: C, 59.20; H, 5.08; N, 9.58; OAMS (ESI+) m/z 581, 583 (M+H)$^+$.

Preparation 9

Ethyl 7-hydroxy-2-(hydroxymethyl)-3-methylthieno [3,2-b]pyridine-6-carboxylate

A suspension of ethyl 2-formyl-3-methyl-7-oxo-4,7-dihydrothieno[3,2-b]pyridine-6-carboxylate (Preparation 3)(1.50 g, 5.66 mmol) in 1:1 CH$_2$Cl$_2$:MeOH (15 mL) was chilled in an ice bath before the addition of sodium borohydride (0.214 g, 5.66 mmol). The reaction was stirred at 0° C. for one hour and then quenched by the addition of water (30 mL). While continuing to chill in an ice bath, the mixture was adjusted to pH 4 by the careful addition of 1 N HCl. The resulting thick mixture was stirred at 0° C. for one hour before filtering. The collected solid was washed with water and dried in vacuo, affording the title compound (0.90 g) as an off-white solid. The filtrate was concentrated in vacuo to a volume of about 50 mL, more water was added, and the mixture was again filtered after chilling in ice, giving an additional 0.29 g of the title product.

Physical characteristics are as follows:

$^1$H NMR (400 MHz, DMSO-d$_6$) δ 8.36 (1 H), 4.69 (2H), 4.22 (2H), 2.24 (3H), 1.28 (3H); HPLC ret time=1.57 min; MS (ES+) m/z 268.

Preparation 10

N-(4-chlorobenzyl)-7-hydroxy-2-(hydroxymethyl)-3-methylthieno[3,2-b]pyridine-6-carboxamide Ethyl 7-hydroxy-2-(hydroxymethyl)-3-methylthieno[3,2-b]pyridine-6-carboxylate (1.27 g, 4.77 mmol) was dissolved in 4-chlorobenzylamine (11.6 mL, 95.4 mmol) and heated to 80° C. for 18 hours. After cooling to room temperature, the mixture was treated with 1 N HCl (100 mL). After chilling in the refrigerator for 2 hrs, the resulting thick precipitate was collected and washed with copious amounts of 1 N HCl until all unreacted 4-chlorobenzylamine had been washed away. The resulting off-white solid was dried in vacuo to give the title compound (1.60 g). $^1$H NMR (DMSO-d$_6$) δ 2.27 (3 H), 4.53 (2 H), 4.72 (2 H), 5.06 (1 H), 7.38 (4 H), 8.52 (1 H), 10.49 (1 H), 12.95 (1 H). HPLC retention time: 2.73 minutes; MS (ESI–) for C$_{17}$H$_{15}$ClN$_2$O$_3$S m/z 361, 363.

Preparation 11

4-(2-amino-2-oxoethyl)-N-(4-chlorobenzyl)-2-(hydroxymethyl)-3-methyl-7-oxo-4,7-dihydrothieno[3,2-b]pyridine-6-carboxamide A mixture of N-(4-chlorobenzyl)-7-hydroxy-2-(hydroxymethyl)-3-methylthieno[3,2-b]pyridine-6-carboxamide (100 mg, 0.276 mmol), potassium carbonate (57 mg, 0.41 mmol) and iodoacetamide (255 mg, 1.38 mmol) in DMF (1.5 mL) was stirred at 50° C. for 18 hrs. Additional iodoacetamide (255 mg) and potassium carbonate (57 mg) were added, and the reaction was stirred at the same temperature for another 12 hrs. After cooling, cold water was added, and the resulting ppt was collected by filtration after chilling in an ice bath. The collected crude solid was recrystallized from aq. ethanol to give the title compound (65 mg) as a lt. brown solid.

Physical characteristics are as follows:

$^1$H NMR (400 MHz, DMSO-d$_6$) δ 10.4 (1H), 8.58 (1H), 7.82 (1H), 7.49 (1H), 7.37 (4H), 5.87 (1H), 5.25 (2H), 4.71 (2H), 4.54 (2H), 2.31 (3H); HPLC ret time=2.51 minutes; MS (ES+) m/z 420, 422.

Preparation 12

4-(2-amino-2-oxoethyl)-N-(4-chlorobenzyl)-2-(chloromethyl)-3-methyl-7-oxo-4,7-dihydrothieno[3,2-b]pyridine-6-carboxamide To a mixture of 4-(2-amino-2-oxoethyl)-N-(4-chlorobenzyl)-2-(hydroxymethyl)-3-methyl-7-oxo-4,7-dihydrothieno[3,2-b]pyridine-6-carboxamide (58 mg, 0.13 mmol), collidine (44 μL, 0.33 mmol) and DMAP (2.4 mg) in DMF (2.25 mL) was added methanesulfonyl chloride (26 μL, 0.33 mmol). The mixture was stirred at room temperature for 48 hrs. Additional reagents (half original amounts) were added and the reaction was stirred another 4 hrs. The reaction was chilled in ice before the addition of water (8 mL). The ppt was collected by filtration, washed with water and dried in vacuo, giving the title compound as a white solid (58 mg).

Physical characteristics are as follows:

HPLC ret time=3.23 minutes; MS (ES+) m/z 438, 440.

EXAMPLE 14

4-(2-amino-2-oxoethyl)-N-(4-chlorobenzyl)-2-{[[2-(2-furyl)-2-hydroxyethyl](methyl)amino]methyl}-3-methyl-7-oxo-4,7-dihydrothieno[3,2-b]pyridine-6-carboxamide

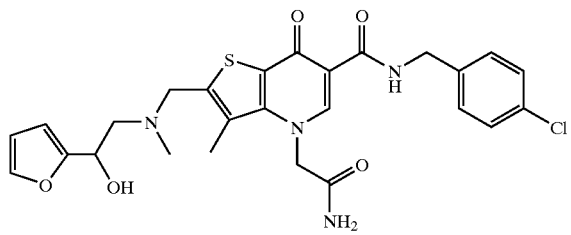

Prepared from 1-(2-furyl)-2-(methylamino)ethanol (Preparation 8) and 4-(2-amino-2-oxoethyl)-N-(4-chlorobenzyl)-2-(chloromethyl)-3-methyl-7-oxo-4,7-dihydrothieno[3,2-b]pyridine-6-carboxamide by the procedure described for Example 2. Recrystallization from acetonitrile afforded 17 mg of the title compound as a white solid.

Physical characteristics are as follows:

$^1$H NMR (400 MHz, DMSO-d$_6$) δ 10.4 (1 H), 8.56 (1H), 7.82 (1 H), 7.54 (1H), 7.48 (1H), 7.37 (4H), 6.38 (1H), 6.28 (1H), 5.30 (1H), 5.24 (2H), 4.75 (1H), 4.54 (2H), 3.79 (2H), 2.79 (2H), 2.32 (3H), 2.27 (3H); HPLC ret time=2.30 minutes; MS (ES+) m/z 543, 545.

EXAMPLE 15

N-(4-chlorobenzyl)-4-(cyanomethyl)-2-{[[2-(2-furyl)-2-hydroxyethyl](methyl)amino]methyl}-3-methyl-7-oxo-4,7-dihydrothieno[3,2-b]pyridine-6-carboxamide

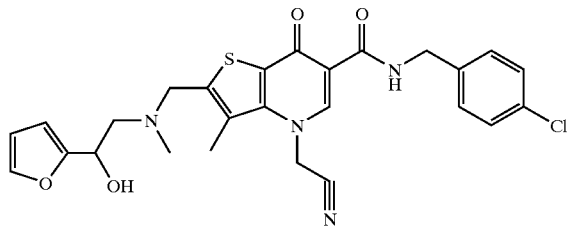

Prepared by the procedures described in Preparations 11–12 and Example 14 employing bromoacetonitrile instead of iodoacetamide, affording the title compound as a white amorphous solid (25 mg) after recrystallization from acetonitrile.

Physical characteristics are as follows:

$^{1}$H NMR (400 MHz, DMSO-$d_6$) δ 10.25 (1H), 8.80 (1H), 7.55 (1H), 7.37 (4H), 6.38 (1H), 6.29 (1H), 5.84 (2H), 5.32 (1H), 4.75 (1H), 4.54 (2H), 3.85 (2H), 2.81 (2H), 2.54 (3H), 2.30 (3H); HPLC ret time=2.58 minutes; MS (ES+) m/z 525, 527.

EXAMPLE 16

N-(4-fluorobenzyl)-2-{[(2-hydroxy-2-pyridin-2-ylethyl)(methyl)amino]methyl}-3,4-dimethyl-7-oxo-4,7-dihydrothieno[3,2-b]pyridine-6-carboxamide

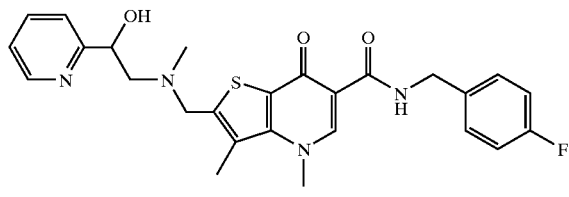

Prepared by the procedures described in Example 1, Preparation 6 and Example 6, employing 4-fluorobenzylamine instead of 4-chlorobenzylamine. The crude solid (119 mg) was dissolved in boiling acetonitrile, left at room temperature overnight, filtered, and the filtrate was concentrated in vacuo to afford the title compound (69 mg) as an off-white solid.

Physical characteristics are as follows:

$^{1}$H NMR (400 MHz, DMSO-$d_6$) δ 10.4 (1H), 8.57 (1H), 8.45 (1H), 7.76 (1H), 7.47 (1H), 7.37 (2H), 7.24 (1H), 7.16 (2H), 5.36 (1H), 4.81 (1H), 4.52 (2H), 4.20 (3H), 3.84 (2H), 2.8 (2H), 2.46 (3H), 2.33 (1H); HPLC ret time=2.06 minutes; MS (ES+) m/z 495.

EXAMPLE 17

N-(4-chlorobenzyl)-2-{[[(2R)-2-hydroxy-2-pyrimidin-2-ylethyl](methyl)amino]methyl}-3,4-dimethyl-7-oxo-4,7-dihydrothieno[3,2-b]pyridine-6-carboxamide

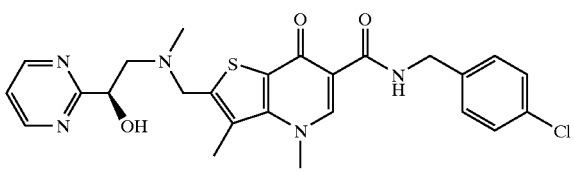

A mixture of N-(4-chlorobenzyl)-2-(chloromethyl)-3,4-dimethyl-7-oxo-4,7-dihydrothieno[3,2-b]pyridine-6-carboxamide (195 mg, 0.49 mmol), (1R)-2-(methylamino)-1-pyrimidin-2-ylethanol (Preparation 104, 168 mg, 0.74 mmol) and diisopropylethylamine (430 μL, 2.5 mmol) in dry DME (10 mL) was heated to 60° C., becoming a solution. The reaction was stirred overnight at that temperature. After cooling to room temperature, the solution was diluted with ice water (30 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (30 mL, dissolved with warming and then cooled to 0° C. overnight) gave the title compound (105 mg) as a white solid.

Physical characteristics are as follows:

$^{1}$H NMR (400 MHz, DMSO-$d_6$) δ 10.43 (1 H), 8.77 (2 H), 8.56 (1 H), 7.42, 7.34 (5 H), 5.35 (1 H), 4.85 (1 H), 4.53 (2 H), 4.19 (3 H), 3.79 (2 H), 3.01 (1 H), 2.82 (1 H), 2.42 (3 H), 2.29 (3 H); Anal. Found: C, 58.38; H, 5.03; N, 13.59.

EXAMPLE 18

2-{[[(2-hydroxy-2-pyridin-2-ylethyl)(methyl)amino]methyl}-3,4-dimethyl-7-oxo-N-(3,4,5-trifluorobenzyl)-4,7-dihydrothieno[3,2-b]pyridine-6-carboxamide

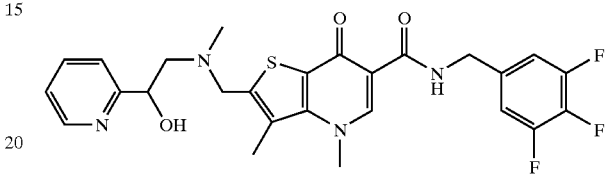

Prepared by the procedures described in Example 1, Preparation 6 and Example 6, employing 3,4,5-trifluorobenzylamine instead of 4-chlorobenzylamine. The crude solid was dissolved in acetonitrile and filtered to remove insolubles. The filtrate was concentrated in vacuo and the resulting residue triturated with ether (30 mL) and dried in vacuo to afford the title compound (101 mg).

Physical characteristics are as follows:

$^{1}$H NMR (400 MHz, DMSO-$d_6$) δ 10.45 (1 H), 8.57 (1H), 8.45 (1H), 7.76 (1H), 7.48 (1H), 7.27 (3H), 5.38 (1H), 4.83 (1H), 4.52 (2H), 4.20 (3H), 3.85 (2H), 2.8 (2H), 2.47 (3H), 2.34 (3H); HPLC ret time=2.27 minutes; MS (ES+) m/z 531.

EXAMPLE 19

N-(4-fluorobenzyl)-2-{[[(2R)-2-hydroxy-2-pyridin-2-ylethyl](methyl)amino]methyl}-3,4-dimethyl-7-oxo-4,7-dihydrothieno[3,2-b]pyridine-6-carboxamide

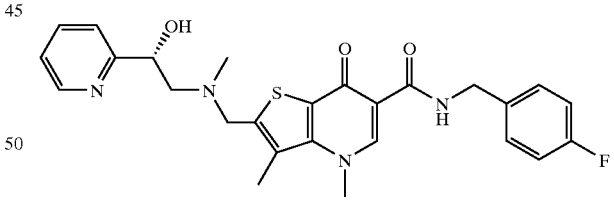

Prepared by the procedure described in Example 16, using (1R)-2-(methylamino)-1-pyridin-2-ylethanol (Preparation 69) instead of racemic 2-(methylamino)-1-pyridin-2-ylethanol. The crude solid was taken up in hot acetonitrile, cooled in a refrigerator overnight, filtered, and the filtrate concentrated in vacuo. The resulting oil was triturated with water, affording the title compound as a pale yellow solid (82 mg).

Physical characteristics are as follows:

$^{1}$H NMR (400 MHz, DMSO-$d_6$) data same as Example 16; HPLC ret time=2.03 minutes; MS (ES+) m/z 495; Anal. Found: C, 59.97; H, 5.46; N, 10.36.

EXAMPLE 20

N-(4-chlorobenzyl)-2-{[[(2R)-2-hydroxy-2-pyridin-2-ylethyl](methyl)amino]methyl}-3,4-dimethyl-7-oxo-4,7-dihydrothieno[3,2-b]pyridine-6-carboxamide

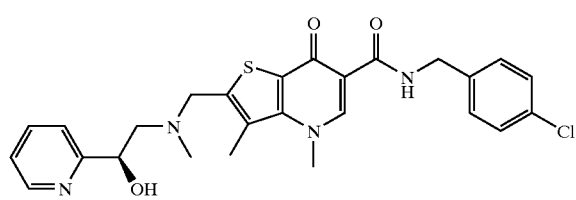

Prepared by the procedure described in Example 6, using (1R)-2-(methylamino)-1-pyridin-2-ylethanol (Preparation 69) instead of racemic 2-(methylamino)-1-pyridin-2-ylethanol. The crude solid was recrystallized from acetonitrile to give the title compound as white needles (656 mg).

Physical characteristics are as follows:

$^1$H NMR (400 MHz, DMSO-$d_6$) data same as Example 6; HPLC ret time=2.26 minutes; Anal. Found: C, 60.92; H, 5.37; N, 10.94.

EXAMPLE 21

N-(4-chlorobenzyl)-2-{[[(2S)-2-hydroxy-2-pyridin-2-ylethyl](methyl)amino]methyl}-3,4-dimethyl-7-oxo-4,7-dihydrothieno[3,2-b]pyridine-6-carboxamide

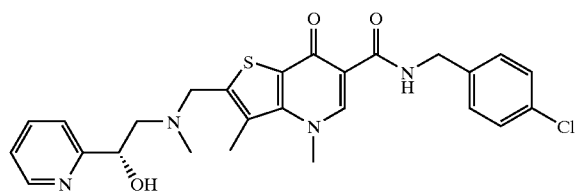

Prepared by the procedure described in Example 6, using (1S)-2-(methylamino)-1-pyridin-2-ylethanol (Preparation 70) instead of racemic 2-(methylamino)-1-pyridin-2-ylethanol. The crude solid was recrystallized from acetonitrile to give the title compound as white needles (39 mg).

Physical characteristics are as follows:

$^1$H NMR (400 MHz, DMSO-$d_6$) data same as Example 6; HPLC ret time=2.25 minutes; Anal. Found: C, 60.62; H, 5.32; N, 10.78.

EXAMPLE 22

N-(4-chlorobenzyl)-2-{[(2-hydroxy-2-pyrazin-2-ylethyl)(methyl)amino]methyl}-3,4-dimethyl-7-oxo-4,7-dihydrothieno[3,2-b]pyridine-6-carboxamide

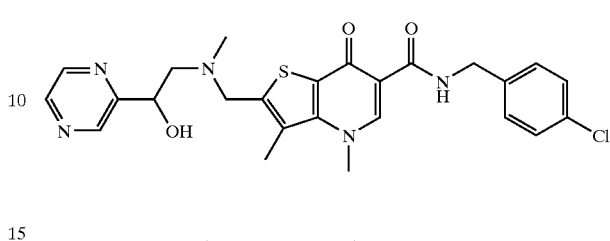

Racemic 2-(methylamino)-1-pyrazin-2-ylethanol (prepared from 2-acetylpyrazine by the procedure outlined in Preparations 7 and 8) was separated into individual enantiomers via chiral HPLC (5×50 cm Chiralpak AD column, 0.1% diethylamine/ethanol eluant, 70 mL/min flow rate, 310 mg sample loading). The slower eluting enantiomer (−optical rotation, 89% ee) was used to prepare the title compound (as described in Example 11). The crude product was recrystallized from acetonitrile/water to afford the title compound (57 mg) as a white solid.

Physical characteristics are as follows:

$^1$H NMR (400 MHz, DMSO-$d_6$) δ 10.4 (1H), 8.71 (1H), 8.56 (1H), 8.52 (2H), 7.37 (4H), 5.64 (1H), 4.88 (1H), 4.53 (2H), 4.19 (3H), 3.81 (2H), 2.91, 2.8 (2H), 2.42 (3H), 2.31 (3H); HPLC ret time=2.25 minutes; MS (ES+) m/z 512, 514; Anal. Found=58.50; H, 5.09; N, 13.31.

EXAMPLE 23

N-(4-chlorobenzyl)-2-{[(2-hydroxy-2-pyrazin-2-ylethyl)(methyl)amino]methyl}-3,4-dimethyl-7-oxo-4,7-dihydrothieno[3,2-b]pyridine-6-carboxamide

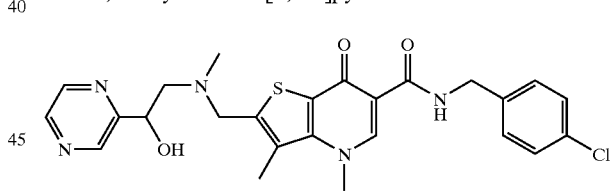

Racemic 2-(methylamino)-1-pyrazin-2-ylethanol (prepared from 2-acetylpyrazine by the procedure outlined in Preparations 7 and 8) was separated into individual enantiomers via chiral HPLC (5×50 cm Chiralpak AD column, 0.1% diethylamine/ethanol eluant, 70 mL/min flow rate, 310 mg sample loading). The faster eluting enantiomer (+optical rotation, 95% ee) was used to prepare the title compound (as described in Example 11). The crude product was recrystallized from acetonitrile/water to afford the title compound (57 mg) as a white solid.

Physical characteristics are as follows:

$^1$H NMR (400 MHz, DMSO-$d_6$) δ 10.4 (1H), 8.71 (1H), 8.56 (1H), 8.52 (2H), 7.37 (4H), 5.64 (1H), 4.88 (1H), 4.53 (2H), 4.19 (3H), 3.81 (2H), 2.91, 2.8 (2H), 2.42 (3H), 2.31 (3H); HPLC ret time=2.24 minutes; MS (ES+) m/z 512, 514; Anal. Found=57.59; H, 5.24; N, 13.01.

EXAMPLE 24

N-(4-chlorobenzyl)-2-{[[2-hydroxy-2-(1-oxidopyridin-3-yl)ethyl](methyl)amino]methyl}-3,4-dimethyl-7-oxo-4,7-dihydrothieno[3,2-b]pyridine-6-carboxamide

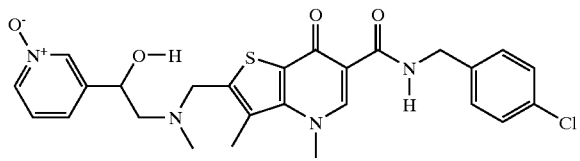

A mixture of N-(4-chlorobenzyl)-2-(chloromethyl)-3,4-dimethyl-7-oxo-4,7-dihydrothieno[3,2-b]pyridine-6-carboxamide (135 mg, 0.342 mmol), 2-(methylamino)-1-(1-oxidopyridin-3-yl)ethanol (Preparation 86, 69 mg, 0.50 mmol) and diisopropylethylamine (89 μL, 0.51 mmol) in dry DMF (5.0 mL) was stirred for 20 hours at room temperature. The solution was then diluted with water (20 mL). The resulting precipitate was collected by filtration and the collected solid was dried in vacuo, providing 107 mg of the titled compound as a white solid.

Physical characteristics are as follows:

$^1$H NMR (400 MHz, DMSO-d$_6$) δ 10.40 (1H), 8.56 (1H), 8.18 (1H), 7.56 (1H), 7.36 (4H), 5.74 (1H), 5.29 (1H), 4.53 (1H), 4.20 (3H), 3.88 (2H), 3.17 (1H), 2.85 (1H), 2.77 (1H), 2.48 (3H), 2.35 (3H). HRMS calc'd for $C_{26}H_{27}Cl_1N_4O_4S_1$+$H_1$=527.1520. Found 527.1506.

EXAMPLE 25

N-(4-chlorobenzyl)-2-{[hydroxy(2-hydroxy-2-phenylethyl)amino]methyl}-3,4-dimethyl-7-oxo-4,7-dihydrothieno[3,2-b]pyridine-6-carboxamide

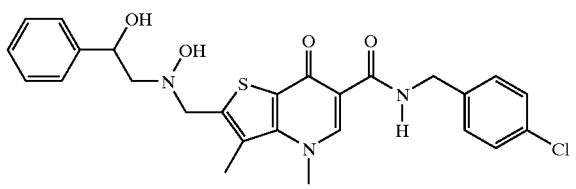

A mixture of N-(4-chlorobenzyl)-2-(chloromethyl)-3,4-dimethyl-7-oxo-4,7-dihydrothieno[3,2-b]pyridine-6-carboxamide (220 mg, 0.557 mmol), 3-hydroxy-3-phenylpropylhydroxylamine hemioxalate (Aldrich S662003, 204 mg, 0.839 mmol) and diisopropylethylamine (389 μL, 2.23 mmol) in dry DMF (10 mL) was heated to 60° C. for 18 hours. The solution was then diluted with water (75 mL). The resulting precipitate was collected by filtration and the collected solid was dried in vacuo. Recrystallization from acetonitrile three times gave the title compound (41 mg) as a white solid.

Physical characteristics are as follows:

$^1$H NMR (400 MHz, DMSO-d$_6$) δ 10.40 (1H), 8.58 (1H), 8.33 (1H), 7.36 (8H), 7.23 (1H), 5.09 (1H), 4.84 (1H), 4.53 (2H), 4.20 (3H), 4.05 (2H), 2.96 (1H), 2.82 (1H), 2.48 (3H).

EXAMPLE 26

N-(4-chlorobenzyl)-2-{[(2-hydroxyethyl)(2-hydroxy-2-phenylethyl)amino]methyl}-3,4-dimethyl-7-oxo-4,7-dihydrothieno[3,2-b]pyridine-6-carboxamide A mixture of N-(4-chlorobenzyl)-2-(chloromethyl)-3,4-dimethyl-7-oxo-4,7-dihydrothieno[3,2-b]pyridine-6-carboxamide (75 mg, 0.190 mmol), α-2-hydroxyethylaminomethyl-benzyl alcohol (Bulletin of the Chemical Society of Japan, 56(1), 212–18; 1983)(51 mg, 0.28 mmol) and diisopropylethylamine (50 μL, 0.29 mmol) in dry DMF (4.0 mL) was heated to 60° C. for 18 hours. The solution was then diluted with water (20 mL). The resulting precipitate was collected by filtration and the collected solid was dried in vacuo at 60° C. to provide the titled compound (92 mg) as a white solid.

Physical characteristics are as follows:

$^1$H NMR (400 MHz, DMSO-d$_6$) δ 10.45 (1H), 8.57 (1H), 7.31 (9H), 5.17 (1H), 4.74 (1H), 4.54 (2H), 4.46 (1H), 4.20 (3H), 4.00 (2H), 3.47 (2H), 2.74 (2H), 2.67 (2H), 2.46 (3H). Anal. Calc'd for $C_{28}H_{30}Cl_1N_3O_4S_1$ C,62.27; H,5.60; N, 7.78. Found: C,62.05; H,5.68; N,7.74. HR MS calc'd for $C_{28}H_{30}Cl_1N_3O_4S_1$+$H_1$=540.1724. Found 540.1744.

Preparation 13

1-(1,4-benzodioxan-6-yl)-2-(methylamino)ethanol

To a slurry of 6-chloroacetyl-1,4-benzodioxane (Aldrich, 53258-4, 3.03 g, 14.3 mmol) in 45 mL methanol cooled in a sodium chloride/ice bath, was added in portions a solution of sodium borohydride (855 mg, 22.6 mmol) in 10 mL water keeping the temperature below 5° C. The mixture was stirred until complete consumption of starting material observed by thin layer chromatography. To the mixture then, 7 mL of concentrated HCl was added in 0.5 mL portions. The mixture became cloudy and 75 mL of saturated aqueous sodium bicarbonate was added. The mixture was extracted with ethyl acetate (2x) and the combined organic layers were dried (MgSO$_4$) and concentrated to provide 2.96 g of the halohydrin intermediate. In a resealable tube, halohydrin intermediate (2.26 g, 10.6 mmol) was combined with methyl amine (52 mL of 2 M in methanol) and sodium iodide (188 mg, 1.25 mmol) and the tube was sealed. The mixture was heated behind a shield at 60° C. for 24 hours and then concentrated to a tacky oil. The oil was purified by silica gel chromatography on a Biotage column (40 M, eluting with DCM:MeOH:NH$_4$OH; 94:5:1) to provide the titled compound (620 mg) as a white solid.

Physical characteristics are as follows:

$^1$H NMR (400 MHz, DMSO-d$_6$) δ 6.78 (4H), 5.13 (1H), 4.20 (5H), 2.51 (2H under DMSO), 2.28 (3H). OAMS (ES+, m/z) calc'd for $C_{11}H_{15}N_1O_3$+$H_1$:210. Found: 210.

EXAMPLE 27

N-(4-chlorobenzyl)-2-{[[2-(2,3-dihydro-1,4-benzodioxin-6-yl)-2-hydroxyethyl](methyl)amino]methyl}-3,4-dimethyl-7-oxo-4,7-dihydrothieno[3,2-b]pyridine-6-carboxamide

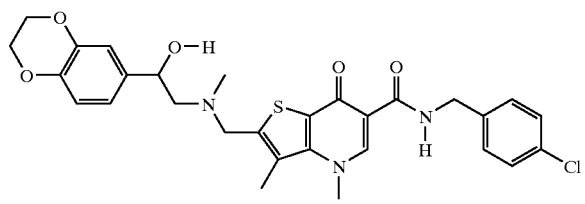

A mixture of N-(4-chlorobenzyl)-2-(chloromethyl)-3,4-dimethyl-7-oxo-4,7-dihydrothieno[3,2-b]pyridine-6-carboxamide (100 mg, 0.253 mmol), 1-(1,4-benzodioxan-6-yl)-2-(methylamino)ethanol (Preparation 13, 79 mg, 0.38 mmol), and diisopropylethylamine (66 µL, 0.38 mmol) in dry DMF (5.5 mL) was stirred at room temperature for 18 hours. The solution was then diluted with water (20 mL). The resulting precipitate was collected by filtration and the collected solid was dried in vacuo at 60° C. to provide the titled compound (105 mg) as an off white solid.

Physical characteristics are as follows:
$^1$H NMR (400 MHz, DMSO-d$_6$) δ 10.40 (1H), 8.75 (1H), 7.38 (4H), 6.78 (3H), 5.03 (1H), 4.65 (1H), 4.54 (2H), 4.20 (7H), 3.81 (2H), 2.57 (2H), 2.47 (3H), 2.31 (3H). HR MS calc'd for $C_{29}H_{30}Cl_1N_3O_5S_1+H_1$=568.1673. Found 568.1671.

Preparation 14

6-(1-(2-methylamino)ethanol)-2H-1,4-benzoxazin-3(4H)-one

To a slurry of 6-(chloroacetyl)-2H-1,4-benzoxazin-3(4H)-one (Aldrich, 47548-3, 2.57 g, 11.4 mmol) in 50 mL methanol cooled in a sodium chloride/ice bath, was added in portions a solution of sodium borohydride (648 mg, 17.1 mmol) in 10 mL water keeping the temperature below 5° C. The mixture was stirred until complete consumption of starting material observed by HPLC. To the mixture then, 5 mL of concentrated HCl was added in 1.0 mL portions. The mixture became cloudy and 125 mL of saturated aqueous sodium bicarbonate was added. The mixture was extracted with ethyl acetate (3×) and the combined organic layers were dried (MgSO$_4$) and concentrated to provide 2.77 g of the halohydrin intermediate. In a resealable tube, all of the halohydrine intermediate was combined with methyl amine (50 mL of 2 M in methanol) and sodium iodide (166 mg, 1.11 mmol) was combined and the tube was sealed. The mixture was heated behind a shield at 60° C. for 24 hours and then concentrated to a dark brown oil. The oil was purified by silica gel chromatography on a Biotage column (40 M) to provide the titled compound (870 mg) as a tan solid.

Physical characteristics are as follows:
$^1$H NMR (400 MHz, DMSO-d$_6$) δ 6.86 (3H), 4.53 (3H), 2.55 (2H), 2.308 (3H). OAMS (ES+, m/z) calc'd for $C_{11}H_{14}N_2O_3+H_1$:223. Found: 223.

EXAMPLE 28

N-(4-chlorobenzyl)-2-{[[2-hydroxy-2-(3-oxo-3,4-dihydro-2H-1,4-benzoxazin-6-yl)ethyl](methyl)amino]methyl}-3,4-dimethyl-7-oxo-4,7-dihydrothieno[3,2-b]pyridine-6-carboxamide

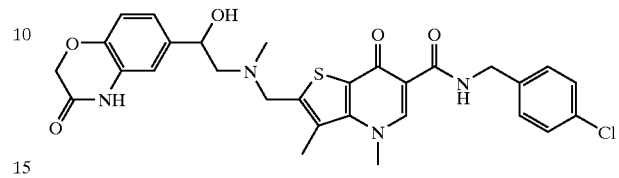

A mixture of N-(4-chlorobenzyl)-2-(chloromethyl)-3,4-dimethyl-7-oxo-4,7-dihydrothieno[3,2-b]pyridine-6-carboxamide (102 mg, 0.258 mmol), 6-(1-(2-methylamino)ethanol)-2H-1,4-benzoxazin-3(4H)-one (Preparation 14, 89 mg, 0.40 mmol), and diisopropylethylamine (68 µL, 0.39 mmol) in dry DMF (5.0 mL) was stirred at room temperature for 18 hours. The solution was then diluted with water (20 mL). The resulting precipitate was collected by filtration resulting in a gummy residue. The residue was taken up into methanol and dichloromethane and then reconcentrated to a tan solid. The solid was then radial chromatagraphed on silica to provide the title compound as a foamy solid (84 mg).

Physical characteristics are as follows:
$^1$H NMR (400 MHz, DMSO-d$_6$) δ 10.66 (1H), 10.40 (1H), 8.56 (1H), 7.38 (4H), 6.85 (3H), 5.15 (1H), 4.67 (1H), 4.54 (4H), 4.20 (3H), 3.80 (2H), 2.57 (2H), 2.46 (3H), 2.33 (3H). HR MS calc'd for $C_{29}H_{29}Cl_1N_4O_5S_1+H_1$=581.1625. Found 581.1619.

EXAMPLES 29–51

General Procedure for the Multiple Parallel Synthesis of Examples 29–51

In a capped 8 mL vial, a mixture of 0.02 mmol selected amine (obtained as indicated in Table 3), 1.0 mL of 0.037 M solution of N-(4-chlorobenzyl)-2-(chloromethyl)-3,4-dimethyl-7-oxo-4,7-dihydrothieno[3,2-b]pyridine-6-carboxamide in DMF, and 20 uL (0.115 mmol) diisopropyl ethyl amine was heated to 60° C. over night using a J-chem heating block on an orbital shaker. The reaction mixtures were then transferred to a Robbins block pre loaded with 84 mg (0.30 mmol) trisamine resin (Argonaut, #800230, 3.58 mmol/g) per well and heated to 60° C. over night. The wells of the block were then filtered into individual 2 mL tubes. The contents were analyzed and concentrated under reduced pressure, affording the title compounds as amorphous solids (Table 2). HPLC Rt is HPLC retention time under the following conditions: Instrument: Hewlett Packard HP1100; Column: Zorbax SB-C18 (4.6×75 mm, 3.5 micron); Detector: UV @210 nm, 254 nm; Flow Rate: 2.0 mL/min; Method hydro2: Gradient: 25:75 to 90:10 acetonitrile:0.07% aq. H$_3$PO$_4$ over 4.5 minutes; then 90:10 acetonitrile:0.07% aq. H$_3$PO$_4$ for 1.5 minutes.

TABLE 2

Examples 29–51.

| Ex # | Compound Structure, Name | Observed Ion (M + H) | HPLC Rt (min) |
|---|---|---|---|
| 29 | 2-[(4-acetylpiperazin-2-yl)methyl]-N-(4-chlorobenzyl)-3,4-dimethyl-7-oxo-4,7-dihydrothieno[3,2-b]pyridine-6-carboxamide | 487 | 2.23 |
| 30 | N-(4-chlorobenzyl)-2-[(4-hydroxypiperidin-1-yl)methyl]-3,4-dimethyl-7-oxo-4,7-dihydrothieno[3,2-b]pyridine-6-carboxamide | 460 | 2.18 |
| 31 | N-(4-chlorobenzyl)-2-{[(3-hydroxy-3-phenylpropyl)(methyl)amino]methyl}3,4-dimethyl-7-oxo-4,7-dihydrothieno[3,2-b]pyridine-6-carboxamide | 524 | 1.76 |
| 32 | N-(4-chlorobenzyl)-2-{[(3R)-3-hydroxypyrrolidin-1-yl]methyl}-3,4-dimethyl-7-oxo-4,7-dihydrothieno[3,2-b]pyridine-6-carboxamide | 446 | 2.19 |

TABLE 2-continued

Examples 29–51.

| Ex # | Compound Structure, Name | Observed Ion (M + H) | HPLC Rt (min) |
|---|---|---|---|
| 33 | 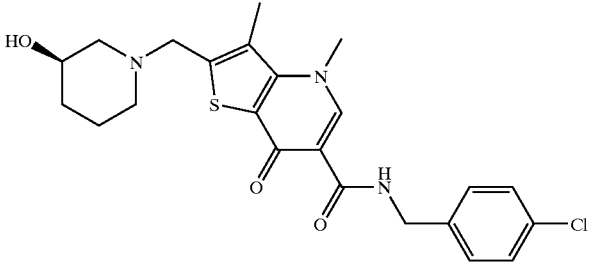<br>N-(4-chlorobenzyl)-2-{[(3R)-3-hydroxypiperidin-1-yl]methyl}-3,4-dimethyl-7-oxo-4,7-dihydrothieno[3,2-b]pyridine-6-carboxamide | 460 | 2.21 |
| 34 | 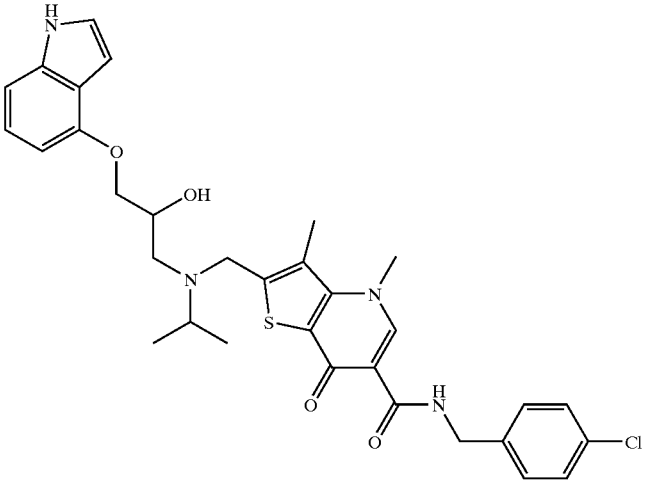<br>N-(4-chlorobenzyl)-2-{[[2-hydroxy-3-(1H-indol-4-yloxy)propyl](isopropyl)amino]methyl}-3,4-dimethyl-7-oxo-4,7-dihydrothieno[3,2-b]pyridine-6-carboxamide | 607 | 2.17 |
| 35 | 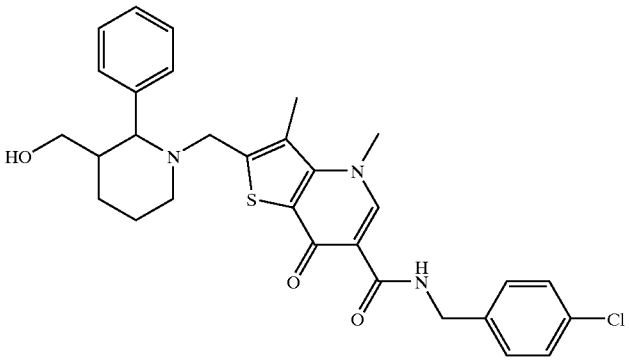<br>N-(4-chlorobenzyl)-2-{[(3-hydroxymethyl)-2-phenylpiperidin-1-yl]methyl}-3,4-dimethyl-7-oxo-4,7-dihydrothieno[3,2-b]pyridine-6-carboxamide | 550 | 2.04 |

TABLE 2-continued

Examples 29–51.

| Ex # | Compound Structure, Name | Observed Ion (M + H) | HPLC Rt (min) |
|---|---|---|---|
| 36 | 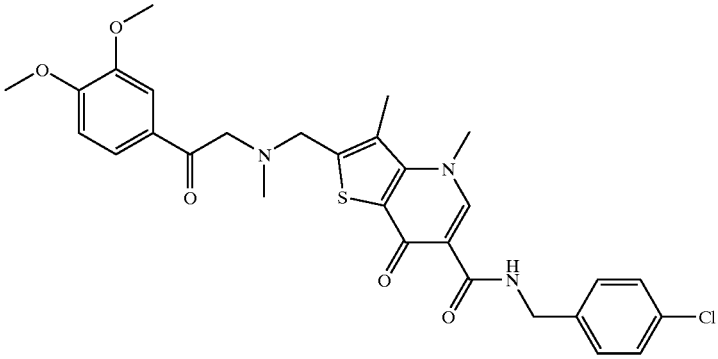<br>N-(4-chlorobenzyl)-2-{[[2-(3,4-dimethoxyphenyl)-2-oxoethyl](methyl)amino]-methyl}-3,4-dimethyl-7-oxo,4,7-dihydrothieno[3,2-b]pyridine-6-carboxamide | 568 | 2.73 |
| 37 | 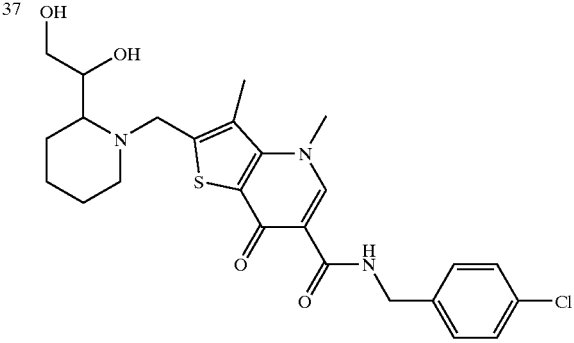<br>N-(4-chlorobenzyl)-2-{[2-(1,2-dihydroxyethyl)piperidin-1-yl]methyl}-3,4-dimethyl-7-oxo-4,7-dihydrothieno[3,2-b]pyridine-6-carboxamide | 504 | 1.22 |
| 38 | 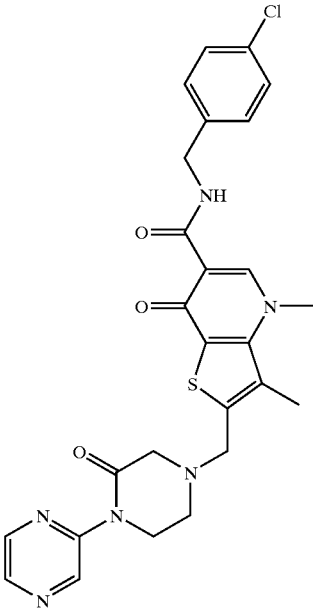<br>N-(4-chlorobenzyl)-3,4-dimethyl-7-oxo-2-[(4-pyrimidin-2-ylpiperazin-1-yl)methyl]-4,7-dihydrothieno[3,2-b]pyridine-6-carboxamide | 523 | 2.51 |

TABLE 2-continued

Examples 29–51.

| Ex # | Compound Structure, Name | Observed Ion (M + H) | HPLC Rt (min) |
|---|---|---|---|
| 39 | 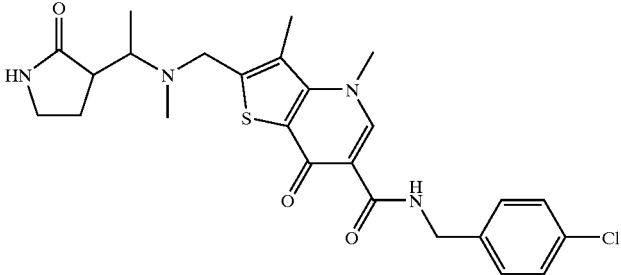<br>N-(4-chlorobenzyl)-3,4-dimethyl-2-[(methyl{(1S)-1-[(3S)-2-oxopyrrolidin-3-yl]ethyl}amino)methyl]-7-oxo-4,7-dihydrothieno[3,2-b]pyridine-6-carboxamide | 501 | 1.5 |
| 40 | 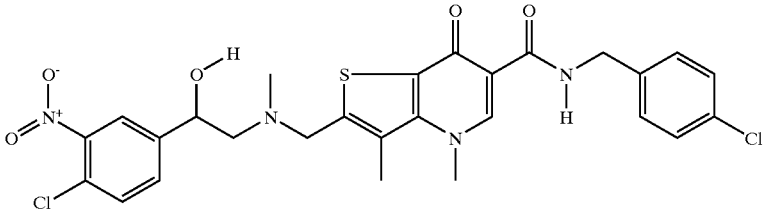<br>N-(4-chlorobenzyl)-2-{[[2-(4-chloro-3-nitrophenyl)-2-hydroxyethyl](methyl)amino]methyl}-3,4-dimethyl-7-oxo-4,7-dihydrothieno[3,2-b]pyridine-6-carboxamide | 589 | 2.34 |
| 41 | 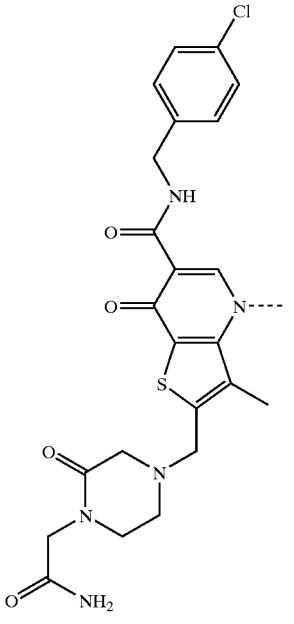<br>2-{[4-(2-amino-2-oxoethyl)-3-oxopiperazin-1-yl]methyl}-N-(4-chlorobenzyl)-3,4-dimethyl-7-oxo-4,7-dihydrothieno[3,2-b]pyridine-6-carboxamide | 516 | 1.73 |

TABLE 2-continued

Examples 29–51.

| Ex # | Compound Structure, Name | Observed Ion (M + H) | HPLC Rt (min) |
|---|---|---|---|
| 42 | 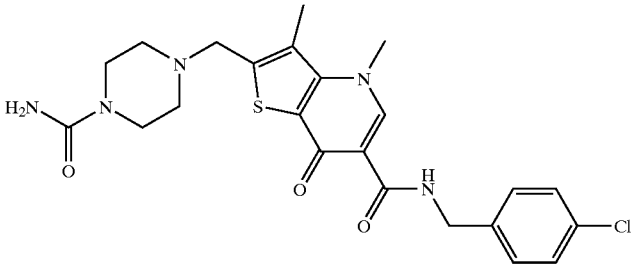<br>2-{[4-(aminocarbonyl)piperazin-1-yl]methyl}-N-(4-chlorobenzyl)-3,4-dimethyl-7-oxo-4,7-dihydrothieno[3,2-b]pyridine-6-carboxamide | 488 | 1.32 |
| 43 | 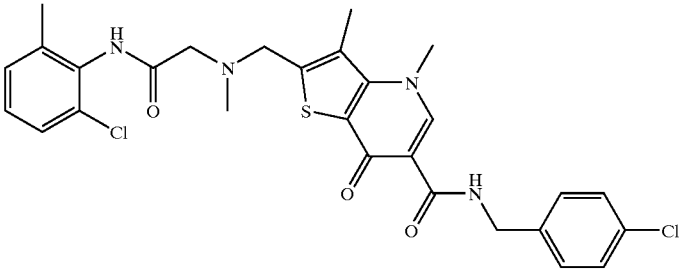<br>N-(4-chlorobenzyl)-2-{[{2-[(2-chloro-6-methylphenyl)amino]-2-oxoethyl}-(methyl)amino]methyl}-3,4-dimethyl-7-oxo-4,7-dihydrothieno[3,2-b]pyridine-6-carboxamide | 572 | 2.43 |
| 44 | 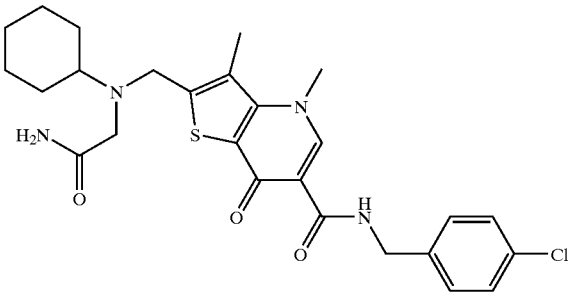<br>2-{[(2-amino-2-oxoethyl)(cyclohexyl)-amino]methyl}-N-(4-chlorobenzyl)-3,4-dimethyl-7-oxo-4,7-dihydrothieno[3,2-b]pyridine-6-carboxamide | 515 | 2.28) |

TABLE 2-continued

Examples 29–51.

| Ex # | Compound Structure, Name | Observed Ion (M + H) | HPLC Rt (min) |
|---|---|---|---|
| 45 | N-(4-chlorobenzyl)-2-[(8-methoxy-1,4,5,6-tetrahydroazepino[4,5-b]indol-3(2H)-yl)methyl]-3,4-dimethyl-7-oxo-4,7-dihydrothieno[3,2-b]pyridine-6-carboxamide | 575 | 2.27 |
| 46 | N-(4-chlorobenzyl)-2-({ethyl[2-(2-hydroxyphenoxy)-1-methylethyl]amino}methyl)-3,4-dimethyl-7-oxo-4,7-dihydrothieno[3,2-b]pyridine-6-carboxamide | 554 | 2.17 |
| 47 | N-(4-chlorobenzyl)-2-{[[2-hydroxy-2-(3-hydroxyphenyl)ethyl](methyl)amino]methyl}-3,4-dimethyl-7-oxo-4,7-dihydrothieno[3,2-b]pyridine-6-carboxamide | 526 | 1.72 |

TABLE 2-continued

Examples 29–51.

| Ex # | Compound Structure, Name | Observed Ion (M + H) | HPLC Rt (min) |
|---|---|---|---|
| 48 | 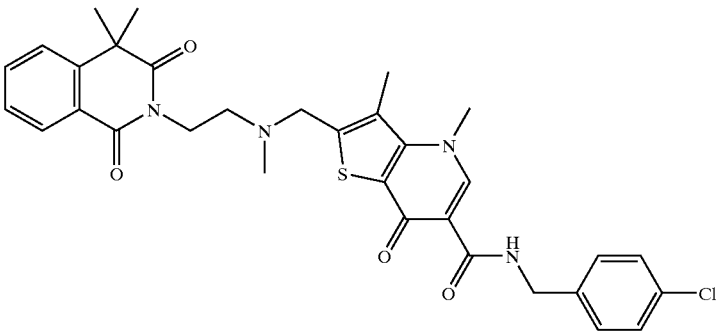<br>N-(4-chlorobenzyl)-2-{[[2-(4,4-dimethyl-1,3-dioxo-3,4-dihydroisoquinolin-2(1H)-yl)ethyl](methyl)amino]methyl}-3,4-dimethyl-7-oxo-4,7-dihydrothieno[3,2-b]pyridine-6-carboxamide | 605 | 2.69 |
| 49 | 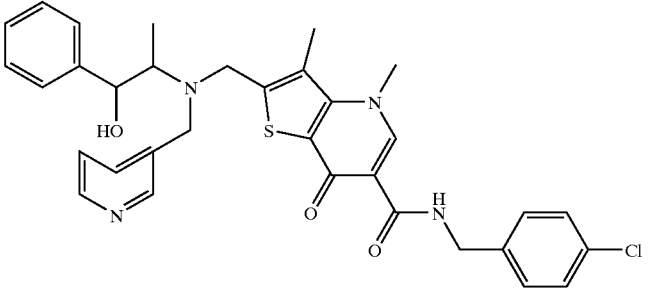<br>N-(4-chlorobenzyl)-2-{[(2-hydroxy-1-methyl-2-phenylethyl)(pyridin-3-ylmethyl)amino]methyl}-3,4-dimethyl-7-oxo-4,7-dihydrothieno[3,2-b]pyridine-6-carboxamide | 602 | 2.36 |
| 50 | 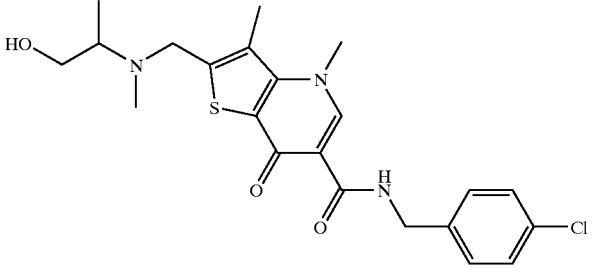<br>N-(4-chlorobenzyl)-2-{[(2-hydroxy-1-methylethyl)(methyl)amino]methyl}-3,4-dimethyl-7-oxo-4,7-dihydrothieno[3,2-b]pyridine-6-carboxamide | 448 | 1.44 |
| 51 | 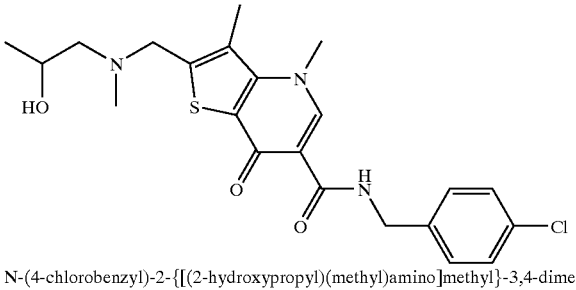<br>N-(4-chlorobenzyl)-2-{[(2-hydroxypropyl)(methyl)amino]methyl}-3,4-dimethyl-7-oxo-4,7-dihydrothieno[3,2-b]pyridine-6-carboxamide | 448 | 1.45 |

The starting amines for the preparation of Examples 29–51 are either commercially available, known in the literature, or can be prepared from available starting materials using procedures analogous to those described in the literature.

Preparation 15

N-(4-fluorobenzyl)-7-hydroxy-2-(hydroxymethyl)-3-methylthieno[3,2-b]pyridine-6-carboxamide A suspension of 140 mg (0.52 mmol) ethyl 7-hydroxy-2-(hydroxymethyl)-3-methylthieno[3,2-b]pyridine-6-carboxylate in 1.28 mL (11.2 mmol) 4-fluorobenzylamine was heated to 80° C. for 24 hours. The mixture was then cooled to room temperature and added to 10 mL of 1N HCl and then cooled in the refrigerator for three hours. The resulting mixture was then filtered and the obtained solid was washed with 1N HCl several times (50 mL total volume) and dried in a vacuum oven at 60° C. over night to provide 154 mg of the title compound as a tan solid.

Physical characteristics are as follows:

$^1$H NMR (400 MHz, DMSO-$d_6$) δ 13.0 (1 H), 10.45 (1 H), 8.52 (1 H), 7.38 (2 H), 7.17 (2 H), 4.72 (2 H), 4.52 (2 H), 2.27 (3 H); MS (ES) for $C_{17}H_{15}FN_2O_3S$ calc'd 346; found 345 m/z (ES−), 347 m/z (ES+). HPLC retention time=2.48 min.

Preparation 16

N-(4-fluorobenzyl)-2-(hydroxymethyl)-3,4-dimethyl-7-oxo-4,7-dihydrothieno[3,2-b]pyridine-6-carboxamide To a slurry of 3.34 g (9.64 mmol) N-(4-fluorobenzyl)-7-hydroxy-2-(hydroxymethyl)-3-methylthieno[3,2-b]pyridine-6-carboxamide and 1.99 g (14.4 mmol) potassium carbonate in 50 mL anhydrous DMF, was added 0.89 mL (14.3 mmol) iodomethane. The mixture was stirred at room temperature. After 40 minutes the slurry became homogeneous and then cloudy. After another 15 minutes the mixture became a thick slurry that stopped stirring. An additional 30 mL of anhydrous DMF was added and the thick slurry was stirred at room temperature over night. Then, 150 mL of water was added to the slurry and the solids were collected by vacuum filtration and dried in a vacuum oven at 60° C. to provide 3.30 g of title compound as a tan solid.

Physical characteristics are as follows:

$^1$H NMR (400 MHz, DMSO-$d_6$) δ 10.4 (1H), 8.59 (1H), 7.37 (2H), 7.16 (2H), 5.91 (1H), 4.72 (2H), 4.52 (2 H), 4.21 (3H), 2.47 (3 H). HRMS for $C_{18}H_{17}FN_2O_3S+H_1$ calc'd 361.1022; found 361.1037. HPLC retention time=2.60 min.

Preparation 17

N-(4-fluorobenzyl)-2-(chloromethyl)-3,4-dimethyl-7-oxo-4,7-dihydrothieno[3,2-b]pyridine-6-carboxamide To a slurry of 3.3 g (9.2 mmol) N-(4-fluorobenzyl)-2-(hydroxymethyl)-3,4-dimethyl-7-oxo-4,7-dihydrothieno[3,2-b]pyridine-6-carboxamide in 200 mL anhydrous DMF at 0° C., was added 3.0 mL (22.7 mmol) 2,4,6-collidine and 0.75 g (6.14 mmol) 4-(dimethylamino) pyridine. To this mixture, 1.8 mL (23.3 mmol) of methanesulfonyl chloride was added in two portions of 0.9 mL. The mixture was allowed to slowly warm to room temperature with stirring over night. After 19 hours, the homogeneous dark brown mixture was poured into 1.0 L of water. The resulting slurry was stirred for 2 hours at room temperature. The solids were then collected by vacuum filtration, washed with additional water, and dried in a vacuum oven at 60° C. over a weekend. This provided 2.91 g of the title compound as a tan solid.

Physical characteristics are as follows:

$^1$H NMR (400 MHz, DMSO-$d_6$) δ 10.3 (H), 8.65 (1H), 7.36 (2H), 7.16 (2H), 5.12 (2H), 4.52 (2 H), 4.24 (3H), 2.60 (3 H). MS (ES) for $C_{18}H_{16}ClFN_2O_2S$ calc'd 378; found 377 m/z (ES−), 379 m/z (ES+). HPLC retention time=3.51 min.

EXAMPLE 52

N-(4-fluorobenzyl)-2-{[[(2R)-2-hydroxy-2-pyrazin-2-ylethyl](methyl)amino]methyl}-3,4-dimethyl-7-oxo-4,7-dihydrothieno[3,2-b]pyridine-6-carboxamide

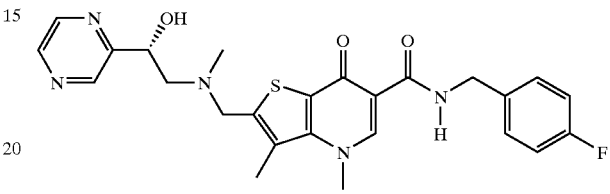

A mixture of N-(4-fluorobenzyl)-2-(chloromethyl)-3,4-dimethyl-7-oxo-4,7-dihydrothieno[3,2-b]pyridine-6-carboxamide (104 mg, 0.275 mmol), (1R)-2-(methylamino)-1-pyrazin-2-ylethanol (Preparation 80, 65 mg, 0.0.42 mmol) and diisopropylethylamine (72 μL, 0.0.41 mmol) in dry DMF (5.5 mL) was stirred at room temperature for 17 hours. The solution was then diluted with water (20 mL). The resulting precipitate was collected by filtration and the collected solid was dried in vacuo, providing a white solid. Attempted recrystallization from acetonitrile (20 mL, dissolved with warming and then cooled to room temperature) gave the title compound (31 mg) as a white solid upon concentrating the filtrate.

Physical characteristics are as follows:

$^1$H NMR (400 MHz, DMSO-$d_6$) δ 10.35 (1H), 8.71 (1H), 8.56 (1H), 8.52 (2H), 7.37 (2H), 7.16 (2H), 5.65 (1H), 4.88 (1H), 4.52 (2H), 4.18 (3H), 3.80 (2H), 2.92 (1H), 2.81 (1H), 2.42 (3H), 2.31 (3H). HRMS calc'd for $C_{25}H_{26}F_1N_5O_3S_1+H_1$=496.1818. Found 496.1831.

EXAMPLES 53–69

General Procedure for the Multiple Parallel Synthesis of Examples 53–69

In a capped 8 mL vial, a mixture of 0.25–0.40 mmol selected amine (prepared as described in related Examples herein), 3.0 mL of 0.05 M solution of N-(4-fluorobenzyl)-2-(chloromethyl)-3,4-dimethyl-7-oxo-4,7-dihydrothieno[3,2-b]pyridine-6-carboxamide (Preparation 17) in DMF, and 250 uL (1.4 mmol) diisopropyl ethyl amine was heated to 60° C. over night using a J-chem heating block on an orbital shaker. The reaction mixtures were then poured into 20 mL of water and the solids that formed were collected by vacuum filtration and dried at 60° C. in a vacuum oven over night. The Examples are presented in Table 4. HPLC Rt is defined in the procedure for Examples 29–51.

TABLE 4

Examples 53–69.

| Ex # | Compound No., Structure | Observed Ion (ESI) | HPLC Rt (min) |
|---|---|---|---|
| 53 | N-(4-fluorobenzyl)-2-{[[(2-hydroxy-2-pyrimidin-2-ylethyl)(methyl)amino]methyl}-3,4-dimethyl-7-oxo-4,7-dihydrothieno[3,2-b]pyridine-6-carboxamide | 518 (M + 23) | 2.01 |
| 54 | N-(4-fluorobenzyl)-2-{[[2-hydroxy-2-(1H-indol-3-yl)ethyl](methyl)amino]methyl}-3,4-dimethyl-7-oxo-4,7-dihydrothieno[3,2-b]pyridine-6-carboxamide | 533 (M + H) | 2.35 |
| 55 | N-(4-fluorobenzyl)-2-{[[(2R)-2-(2-furyl)-2-hydroxyethyl](methyl)amino]methyl}-3,4-dimethyl-7-oxo-4,7-dihydrothieno[3,2-b]pyridine-6-carboxamide | 506 (M + 23) | 2.23 |
| 56 | 2-{[{2-[4-(acetylamino)phenyl]-2-hydroxyethyl}(methyl)amino]methyl}-N-(4-fluorobenzyl)-3,4-dimethyl-7-oxo-4,7-dihydrothieno[3,2-b]pyridine-6-carboxamide | 549 (M − H) | 2.15 |

TABLE 4-continued

Examples 53–69.

| Ex # | Compound No., Structure | Observed Ion (ESI) | HPLC Rt (min) |
|---|---|---|---|
| 57 | 2-{[[2-(2,3-dihydro-1,4-benzodioxin-6-yl)-2-hydroxyethyl](methyl)amino]methyl}-N-(4-fluorobenzyl)-3,4-dimethyl-7-oxo-4,7-dihydrothieno[3,2-b]pyridine-6-carboxamide | 550 (M − H) | 2.44 |
| 58 | N-(4-fluorobenzyl)-2-{[[2-hydroxy-2-(1,3-thiazol-2-yl)ethyl](methyl)amino]methyl}-3,4-dimethyl-7-oxo-4,7-dihydrothieno[3,2-b]pyridine-6-carboxamide | 523 (M + H) | 2.17 |
| 59 | N-(4-fluorobenzyl)-2-{[(2-hydroxy-2-pyridin-3-ylethyl)(methyl)amino]methyl}-3,4-dimethyl-7-oxo-4,7-dihydrothieno[3,2-b]pyridine-6-carboxamide | 495 (M + H) | 1.72 |
| 60 | N-(4-fluorobenzyl)-2-{[{2-hydroxy-2-[4-(hydroxymethyl)phenyl]ethyl}(methyl)amino]methyl}-3,4-dimethyl-7-oxo-4,7-dihydrothieno[3,2-b]pyridine-6-carboxamide | 522 (M − H) | 2.13 |

TABLE 4-continued

Examples 53–69.

| Ex # | Compound No., Structure | Observed Ion (ESI) | HPLC Rt (min) |
|---|---|---|---|
| 61 | 2-{[[2-(3-aminophenyl)-2-hydroxyethyl](methyl)amino]methyl}-N-(4-fluorobenzyl)-3,4-dimethyl-7-oxo-4,7-dihydrothieno[3,2-b]pyridine-6-carboxamide | 507 (M − H) | 1.81 |
| 62 | N-(4-fluorobenzyl)-2-{[(2-hydroxy-2-quinolin-2-ylethyl)(methyl)amino]methyl}-3,4-dimethyl-7-oxo-4,7-dihydrothieno[3,2-b]pyridine-6-carboxamide | 545 (M + H) | 2.43 |
| 63 | N-(4-fluorobenzyl)-2-{[[2-hydroxy-2-(1H-pyrazol-5-yl)ethyl](methyl)amino]methyl}-3,4-dimethyl-7-oxo-4,7-dihydrothieno[3,2-b]pyridine-6-carboxamide | 484 (M + H) | 1.82 |
| 64 | N-(4-fluorobenzyl)-2-{[[(2S)-2-hydroxy-2-pyridin-3-ylethyl](methyl)amino]methyl}-3,4-dimethyl-7-oxo-4,7-dihydrothieno[3,2-b]pyridine-6-carboxamide | 495 (M + H) | 1.72 |

TABLE 4-continued

Examples 53–69.

| Ex # | Compound No., Structure | Observed Ion (ESI) | HPLC Rt (min) |
|---|---|---|---|
| 65 | 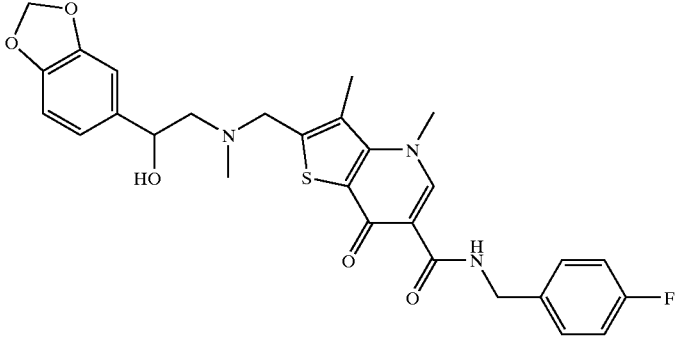<br>2-{[[2-(1,3-benzodioxol-5-yl)-2-hydroxyethyl](methyl)amino]methyl}-N-4-fluorobenzyl)-3,4-dimethyl-7-oxo-4,7-dihydrothieno[3,2-b]pyridine-6-carboxamide | 536 (M − H) | 2.45 |
| 66 | 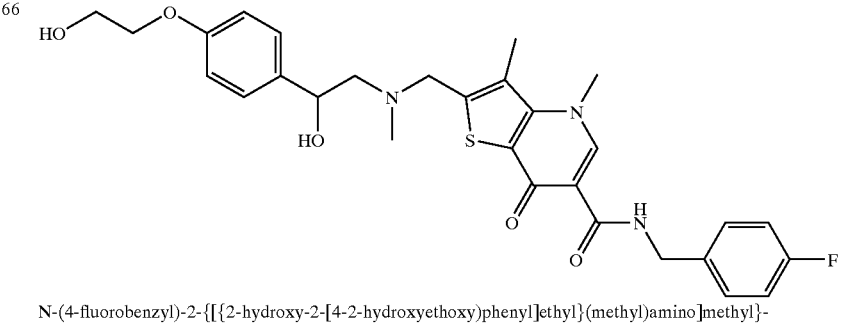<br>N-(4-fluorobenzyl)-2-{[{2-hydroxy-2-[4-2-hydroxyethoxy)phenyl]ethyl}(methyl)amino]methyl}-3,4-dimethyl-7-oxo-4,7-dihydrothieno[3,2-b]pyridine-6-carboxamide | 554 (M + H) | 2.17 |
| 67 | 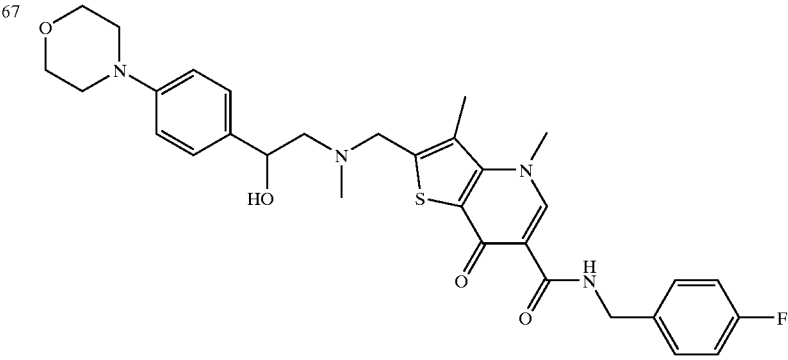<br>N-(4-fluorobenzyl)-2-{[[2-hydroxy-2-4-morpholin-4-ylphenyl)ethyl](methyl)amino]methyl}-3,4-dimethyl-7-oxo-4,7-dihydrothieno[3,2-b]pyridine-6-carboxamide | no ion | 1.78 |
| 68 | 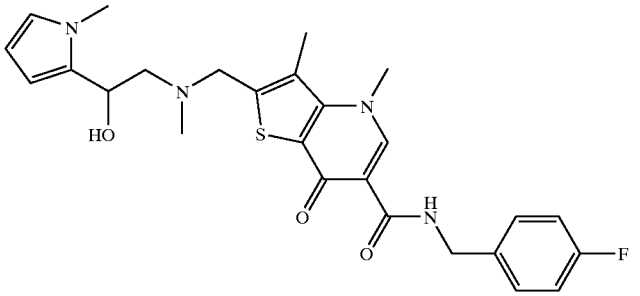<br>N-(4-fluorobenzyl)-2-{[[2-hydroxy-2-(1-methyl-1H-pyrrol-2-yl)ethyl](methyl)amino]methyl}-3,4-dimethyl-7-oxo-4,7-dihydrothieno[3,2-b]pyridine-6-carboxamide | 495 (M − H) | 2.30 |

TABLE 4-continued

Examples 53–69.

| Ex # | Compound No., Structure | Observed Ion (ESI) | HPLC Rt (min) |
|---|---|---|---|
| 69 | <br>N-(4-fluorobenzyl)-2-{[[2-(3-furyl)-2-hydroxyethyl](methyl)amino]methyl}-3,4-dimethyl-7-oxo-4,7-dihydrothieno[3,2-b]pyridine-6-carboxamide | 506 (M + Na) | 2.25 |

EXAMPLE 70

N-(4-chlorobenzyl)-2-{[(2-hydroxy-2-phenylethyl)amino]methyl}-3,4-dimethyl-7-oxo-4,7-dihydrothieno[3,2-b]pyridine-6-carboxamide

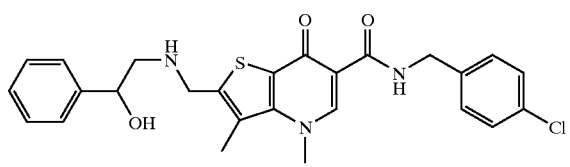

Prepared from 2-amino-1-phenylethanol (Aldrich) by the procedure described for Example 2. Recrystallization afforded 35 mg of the title compound as a white solid..

Physical characteristics are as follows:

$^1$H NMR (400 MHz, DMSO-d$_6$) δ 10.42 (1 H), 8.57 (1 H), 7.2–7.4 (9 H), 5.39 (1 H), 4.71 (1 H), 4.53 (2 H), 4.21 (3 H), 4.01, 3.96 (2 H), 2.72 (2 H), 2.51 (3 H); Anal Found: C, 61.52; H, 5.39; N, 8.22. MS (ESI+) for C$_{26}$H$_{26}$ClN$_3$O$_3$S m/z 496, 498 (M+H)$^+$.

EXAMPLE 71

2-({[(1S)-1-benzyl-2-hydroxyethyl]amino}methyl)-N-(4-chlorobenzyl)-3,4-dimethyl-7-oxo-4,7-dihydrothieno[3,2-b]pyridine-6-carboxamide

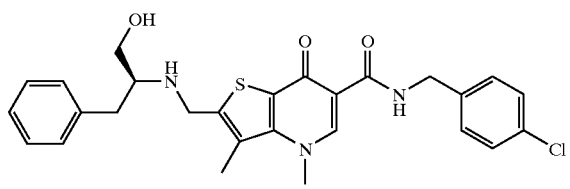

Prepared from (2S)-2-amino-3-phenylpropan-1-ol (Aldrich) by the procedure described for Example 2. Recrystallization afforded 56 mg of the title compound as a white solid.

Physical characteristics are as follows:

$^1$H NMR (400 MHz, DMSO-d$_6$) δ 10.45 (1 H), 8.56 (1 H), 7.39, 7.34 (4 H), 7.15–7.3 (5 H), 4.63 (1 H), 4.53 (2 H), 4.19 (3 H), 4.02, 3.91 (2 H), 3.36 (2 H), 2.78 (1 H), 2.71 (2 H), 2.44 (3 H); Anal. Found: C, 60.51; H, 5.49; N, 7.99. MS (ESI+) for C$_{27}$H$_{28}$ClN$_3$O$_3$S m/z 510, 512 (M+H)$^+$.

Preparation 18

Ethyl 3,4-dimethyl-7-oxo-4,7-dihydrothieno[3,2-b]pyridine-6-carboxylate

A 500 mL three-necked flask fitted with an overhead stirrer and argon inlet is charged with 21.9 g of ethyl 7-hydroxy-3-methylthieno[3,2-b]pyridine-6-carboxylate and 150 mL of DMF. The mixture is stirred while 25.5 g of powdered potassium carbonate is added in portions, then is cooled to 0° C. Iodomethane (15 mL) is added dropwise over 45 min, and the completed mixture is stirred vigorously and allowed to warm slowly as the ice in the bath melts. The following day, the mixture is diluted slowly with water to a final volume of 800 ml, and the resulting solid is filtered, washed well with water, and dried under vacuum to provide 17.2 g of the title compound as a brown crystalline solid. Flash chromatography of 12.2 g using 2–4% MeOH in CH$_2$Cl$_2$ affords 11.43 g of tan solid.

Physical properties are as follows:

$^1$H NMR (CDCl$_3$+CD$_3$OD) δ 1.40, 2.64, 4.14, 4.37, 7.39, 8.28 ppm. TLC R$_f$ 0.26 (5% MeOH in CH$_2$Cl$_2$).

Preparation 19

Ethyl 3-(bromomethyl)-4-methyl-7-oxo-4,7-dihydrothieno[3,2-b]pyridine-6-carboxylate A solution of 5.0 g of ethyl 3,4-dimethyl-7-oxo-4,7-dihydrothieno[3,2-b]pyridine-6-carboxylate and 4.8 g of NBS is prepared with the aid of heat in 200 mL of dichloroethane in a 500 mL round bottom flask. The flask is topped with an efficient reflux condenser and irradiated with a tungsten sunlamp at a distance of about 3". After 2.5 h the solution is cooled, washed with aqueous NaHCO$_3$, dried (Na$_2$SO$_4$), and concentrated under reduced pressure. Flash chromatography of the residue on silica using 3% MeOH in CH$_2$Cl$_2$ affords 5.8 g of cream colored solid. This is triturated with ether and dried in vacuo to provide 5.34 g of the title compound as an off-white solid.

Physical properties are as follows:

$^1$H NMR (CDCl$_3$) δ 1.40, 4.29, 4.38, 4.77, 7.71, 8.25 ppm. TLC R$_f$ 0.18 (5% MeOH in CH$_2$Cl$_2$).

Preparation 20

N-(4-Chlorobenzyl)-3-[(2-methoxyethoxy)methyl]-4-methyl-7-oxo-4,7-dihydrothieno[3,2-b]pyridine-6-carboxamide To a cold (−78° C.), stirred solution of 2.0 mL of 2-methoxyethanol in 15 mL of dry THF, under argon, is added 3.9 mL of butyllithium (2.5 M in hexanes). The solution is warmed briefly to ambient and then recooled to −78° C., and a solution of 2.67 g of ethyl 3-(bromomethyl)-4-methyl-7-oxo-4,7-dihydrothieno[3,2-b]pyridine-6-carboxylate in 10 mL of dry DMF is added via cannula. The mixture is allowed to warm to room temperature, giving a clear amber solution. After 30 min the mixture is partitioned between $CH_2Cl_2$ and dil HCl, and the aqueous phase is extracted with three additional portions of $CH_2Cl_2$. The combined organic phase is dried ($Na_2SO_4$) and concentrated under reduced pressure. Flash chromatography of the residue on silica using 5% MeOH in $CH_2Cl_2$ affords 2.59 g of intermediate mixed esters as a yellow solid. A mixture of this product and 5.8 g of p-chlorobenzylamine is heated at 150° C. for 18 h, then cooled and stirred well with 40 mL of 1N HCl. The solid is filtered, washed well with water, and dried in vacuo. Flash chromatography of the solid on silica using 2% MeOH in $CH_2Cl_2$ provides 2.47 g of white solid. Recrystallization from EtOAc (160 ml) furnishes 2.31 g of amide title compound as small white needles.

Physical properties are as follows:

Mp 158–159° C. $^1$H NMR ($CDCl_3$) δ 3.36, 3.56, 3.65, 4.25, 4.62, 4.74, 7.29, 7.71, 8.58, 10.41 ppm. TLC $R_f$ 0.30 (5% MeOH in $CH_2Cl_2$). IR (diffuse reflectance) 3046, 1656, 1601, 1551, 1525, 1511, 1491, 1218, 1099, 1092, 1080, 1055, 820, 809, 799 cm$^{-1}$; OAMS supporting ions at: ESI+ 421.2; HRMS (FAB) 421.0996; Anal. found: C, 57.12; H, 5.11; N, 6.62.

Preparation 21

N-(4-Chlorobenzyl)-2-formyl-3-[(2-methoxyethoxy)methyl]-4-methyl-7-oxo-4,7-dihydrothieno[3,2-b]pyridine-6-carboxamide A mixture of 210 mg of N-(4-chlorobenzyl)-3-[(2-methoxyethoxy)methyl]-4-methyl-7-oxo-4,7-dihydrothieno[3,2-b]pyridine-6-carboxamide and 5.0 mL of dry THF is heated to boiling under argon to dissolve the solid, then is cooled to −78° C. Into this mixture is cannulated a solution of LDA in THF, prepared in the usual manner from 0.35 mL of diisopropylamine and 0.80 mL of 2.5 M (in hexane) butyllithium in 4.0 mL of THF. The resulting deep blue mixture is stirred at −78° C. for 15 min, then 0.25 mL of dry DMF is added and the mixture allowed to warm to ambient temperature. The mixture is then partitioned between $CH_2Cl_2$ and dil HCl, and the organic phase dried ($Na_2SO_4$) and concentrated under reduced pressure. Flash chromatography on silica gel using 2% MeOH in $CH_2Cl_2$ provides 146 mg of the title compound as an orange solid. Recrystallization of a sample from EtOAc provides an analytical sample as a white solid.

Physical properties are as follows:

Mp 152–153° C. $^1$H NMR ($CDCl_3$) δ 3.37, 3.57, 3.73, 4.30, 4.61, 5.14, 7.29, 8.66, 10.18, 10.29 ppm. TLC $R_f$ 0.24 (5% MeOH in $CH_2Cl_2$). IR (diffuse reflectance) 1675, 1646, 1596, 1569, 1545, 1517, 1493, 1443, 1320, 1221, 1205, 1195, 1126, 1088, 798 cm$^{-1}$; OAMS supporting ions at: ESI+ 449.2; HRMS (FAB) 449.0933; Anal. found: C, 56.13; H, 4.64; N, 6.18.

Preparation 22

N-(4-Chlorobenzyl)-2-(hydroxymethyl)-3-[(2-methoxyethoxy)methyl]-4-methyl-7-oxo-4,7-dihydrothieno[3,2-b]pyridine-6-carboxamide To a cold (0° C.), stirred solution of 1.05 g of N-(4-chlorobenzyl)-2-formyl-3-[(2-methoxyethoxy)methyl]-4-methyl-7-oxo-4,7-dihydrothieno[3,2-b]pyridine-6-carboxamide in 20 mL of $CH_2Cl_2$ is added 0.67 mL of acetic acid and 1.5 g of sodium triacetoxyborohydride. The mixture is allowed to warm to room temperature and stirred for 2 h, then partitioned between $CH_2Cl_2$ and aqueous $NaHCO_3$. The organic phase is dried ($Na_2SO_4$) and concentrated under reduced pressure. Flash chromatography of the residue on silica using 2.5–4% MeOH in $CH_2Cl_2$ affords 1.08 g (100%) of the title compound as a yellow crystalline solid. Recrystallization from acetonitrile affords white spars.

Physical properties are as follows:

Mp 167.0–168.5° C. $^1$H NMR ($CDCl_3$+$CD_3OD$) δ 3.36, 3.55, 3.62, 4.24, 4.61, 4.86, 7.32, 8.42, 10.50 ppm. TLC $R_f$ 0.21 (5% MeOH in $CH_2Cl_2$). IR (diffuse reflectance) 3305, 1644, 1595, 1555, 1531, 1507, 1351, 1215, 1133, 1113, 1097, 1063, 1056, 853, 800 cm$^{-1}$; OAMS supporting ions at: ESI+ 451.2; HRMS (FAB) 451.1098; Anal. found: C, 55.86; H, 5.12; N, 6.23.

Preparation 23

N-(4-Chlorobenzyl)-2-(chloromethyl)-3-[(2-methoxyethoxy)methyl]-4-methyl-7-oxo-4,7-dihydrothieno[3,2-b]pyridine-6-carboxamide To a cold (0° C.), stirred solution of 932 mg of N-(4-chlorobenzyl)-2-(hydroxymethyl)-3-[(2-methoxyethoxy)methyl]-4-methyl-7-oxo-4,7-dihydrothieno[3,2-b]pyridine-6-carboxamide and 1.1 mL of 2,4,6-collidine in 11 mL of dry DMF is added 0.32 mL of methanesulfonyl chloride. The reaction temperature is allowed to rise slowly to ambient as the ice in the bath melts. The following day, the reaction mixture is diluted with water to a volume of 120 ml, and 15 mL of 1N HCl is added. The resulting solid is filtered, washed well with water, and dried in vacuo to afford 890 mg of the chloride as a brown solid.

Physical properties are as follows:

$^1$H NMR ($CDCl_3$) δ 3.38, 3.57, 3.71, 4.26, 4.62, 4.77, 4.85, 7.29, 8.58, 10.33 ppm. IR (diffuse reflectance) 3053, 2931, 1654, 1600, 1554, 1513, 1491, 1353, 1220, 1133, 1101, 1092, 796, 731, 685 cm$^{-1}$; OAMS supporting ions at: ESI+ 469.1; HRMS (FAB) 469.0732; Anal. found: C, 53.30; H, 4.68; N, 5.84.

EXAMPLE 72

N-(4-Chlorobenzyl)-2-{[(2-hydroxy-2-pyridin-3-ylethyl)(methyl)amino]methyl}-3-[(2-methoxyethoxy)methyl]-4-methyl-7-oxo-4,7-dihydrothieno[3,2-b]pyridine-6-carboxamide

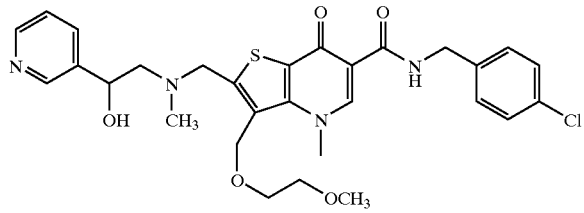

A mixture of 111 mg of N-(4-chlorobenzyl)-2-(chloromethyl)-3-[(2-methoxyethoxy)methyl]-4-methyl-7-oxo-4,7-dihydrothieno[3,2-b]pyridine-6-carboxamide, 54 mg of 2-(methylamino)-1-pyridin-3-ylethanol (Arch. Pharm. (1961), 294, 453), and 62 µL of diisopropylethylamine in 1.5 mL of DMF is heated at 50° C. for 18 h, then cooled and partitioned between EtOAc and water. The organic phase is washed with two additional portions of water and brine, dried ($Na_2SO_4$), and concentrated under reduced pressure. Flash chromatography of the residue on silica using 5% MeOH in $CH_2Cl_2$ affords 128 mg of the title compound as a white foam. Recrystallization of a sample from EtOAc provides white crystals.

Physical properties are as follows:

Mp 129–132° C. $^1$H NMR ($CDCl_3$) δ 2.49, 2.62, 2.69, 3.36, 3.56, 3.69, 3.85, 3.85, 4.01, 4.24, 4.62, 4.68, 4.81, 7.3, 7.70, 8.52, 8.53, 8.56, 10.43 ppm. TLC $R_f$ 0.36 (10% MeOH in $CH_2Cl_2$). IR (diffuse reflectance) 2893, 1645, 1596, 1569, 1542, 1523, 1489, 1428, 1352, 1344, 1215, 1132, 1088, 800, 717 $cm^{-1}$; OAMS supporting ions at: ESI+ 585.0; HRMS (FAB) 585.1946; Anal. found: C, 59.24; H, 5.73; N, 9.51.

EXAMPLE 73

N-(4-Chlorobenzyl)-2-{[[2-hydroxy-2-(3-methoxyphenyl)ethyl](methyl)amino]methyl}-3-[(2-methoxyethoxy)methyl]-4-methyl-7-oxo-4,7-dihydrothieno[3,2-b]pyridine-6-carboxamide

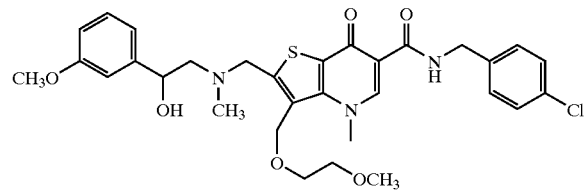

Prepared following the procedure for preparation of Example 72. Flash chromatography on silica using 2% MeOH in $CH_2Cl_2$ followed by recrystallization from EtOAc affords white granular crystals.

Physical properties are as follows:

Mp 135–138° C. $^1$H NMR ($CDCl_3$) δ 2.46, 2.63, 2.69, 3.36, 3.55, 3.66, 3.79, 3.83, 3.98, 4.23, 4.62, 4.66, 4.76, 6.80, 6.91, 7.24, 7.30, 8.51, 10.45 ppm. TLC $R_f$ 0.29 (5% MeOH in $CH_2Cl_2$). IR (diffuse reflectance) 1655, 1648, 1639, 1598, 1542, 1534, 1522, 1518, 1508, 1502, 1491, 1487, 1214, 1092, 804 $cm^{-1}$; OAMS supporting ions at: ESI+ 614.2; HRMS (FAB) 614.2111; Anal. found: C, 60.47; H, 5.95; N, 6.83.

EXAMPLE 74

N-(4-Chlorobenzyl)-2-{[[(2R)-2-(2-furyl)-2-hydroxyethyl](methyl)amino]methyl}-3-[(2-methoxyethoxy)methyl]-4-methyl-7-oxo-4,7-dihydrothieno[3,2-b]pyridine-6-carboxamide

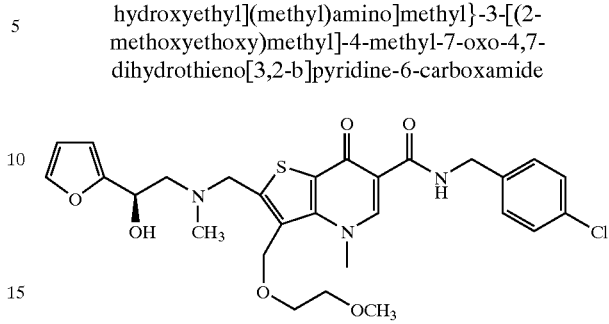

Prepared following the procedure for preparation of Example 72. Flash chromatography on silica using 2% MeOH in $CH_2Cl_2$ followed by recrystallization from EtOAc affords white crystals.

Physical properties are as follows:

Mp 146–147° C. $^1$H NMR ($CDCl_3$) δ 2.42, 2.74, 2.99, 3.36, 3.55, 3.65, 3.67, 3.83, 3.97, 4.22, 4.61, 4.69, 4.81, 6.29, 6.33, 7.30, 7.36, 8.50, 10.45 ppm. TLC $R_f$ 0.30 (5% MeOH in $CH_2Cl_2$). IR (diffuse reflectance) 1654, 1648, 1642, 1596, 1542, 1534, 1522, 1518, 1513, 1508, 1502, 1488, 1215, 1093, 801 $cm^{-1}$; OAMS supporting ions at: ESI+ 575.1; HRMS (FAB) 574.1799; Anal. found: C, 58.48; H, 5.56; N, 7.26.

EXAMPLE 75

N-(4-Chlorobenzyl)-2-{[[2-hydroxy-2-(1H-indol-3-yl)ethyl](methyl)amino]methyl}-3-[(2-methoxyethoxy)methyl]-4-methyl-7-oxo-4,7-dihydrothieno[3,2-b]pyridine-6-carboxamide

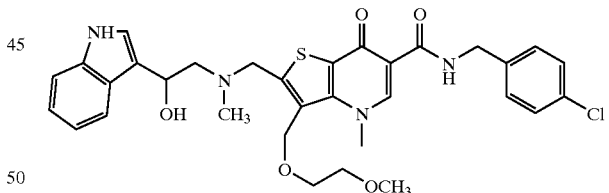

Prepared following the procedure for preparation of Example 72. Flash chromatography on silica using 3% MeOH in $CH_2Cl_2$ followed by recrystallization from EtOAc affords white crystals.

Physical properties are as follows:

Mp 167–169° C. $^1$H NMR ($CDCl_3$) δ 2.48, 2.84, 2.98, 3.35, 3.53, 3.56, 3.63, 3.83, 3.97, 4.17, 4.63, 5.14, 7.04, 7.14, 7.30, 7.59, 8.48, 8.50, 10.47 ppm. TLC $R_f$ 0.16 (5% MeOH in $CH_2Cl_2$). IR (diffuse reflectance) 3224, 1645, 1599, 1544, 1526, 1516, 1492, 1133, 1104, 1087, 800, 743, 736, 713, 706 $cm^{-1}$; OAMS supporting ions at: ESI+ 623.3; HRMS (FAB) 623.2087; Anal. found: C, 61.35; H, 5.68; N, 8.97.

EXAMPLE 76

N-(4-Chlorobenzyl)-2-{[(2-hydroxy-2-pyridin-2-ylethyl)(methyl)amino]methyl}-3-[(2-methoxyethoxy)methyl]-4-methyl-7-oxo-4,7-dihydrothieno[3,2-b]pyridine-6-carboxamide

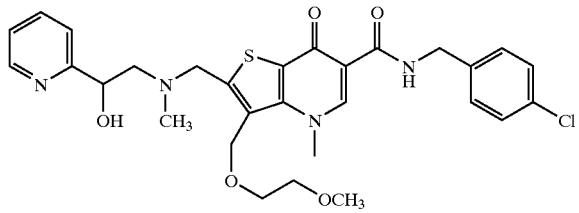

Prepared following the procedure for preparation of Example 72. Flash chromatography on silica using 4–5% MeOH in CH$_2$Cl$_2$ followed by recrystallization from EtOAc affords white crystals.

Physical properties are as follows:

Mp 150.5–152.0° C. $^1$H NMR (CDCl$_3$) δ 2.47, 2.76, 2.91, 3.36, 3.55, 3.67, 3.87, 4.02, 4.15, 4.24, 4.62, 4.68, 4.89, 7.20, 7.30, 7.49, 7.70, 8.52, 8.533, 10.46 ppm. TLC R$_f$ 0.14 (5% MeOH in CH$_2$Cl$_2$). IR (diffuse reflectance) 2888, 1645, 1594, 1542, 1520, 1487, 1351, 1343, 1214, 1132, 1105, 1093, 1082, 802, 770 cm$^{-1}$; OAMS supporting ions at: ESI+ 585.1; HRMS (FAB) 585.1961; Anal. found: C, 59.54; H, 5.72; N, 9.59.

EXAMPLE 77

N-(4-Chlorobenzyl)-2-{[(2-hydroxy-2-pyrimidin-2-ylethyl)(methyl)amino]methyl}-3-[(2-methoxyethoxy)methyl]-4-methyl-7-oxo-4,7-dihydrothieno[3,2-b]pyridine-6-carboxamide

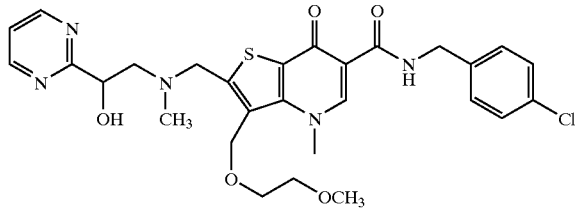

Prepared following the procedure for preparation of Example 72. Flash chromatography on silica using 5% MeOH in CH$_2$Cl$_2$ followed by recrystallization from EtOAc affords white crystals.

Physical properties are as follows:

Mp 146.5–147.5° C. $^1$H NMR (CDCl$_3$) δ 2.42, 3.01, 3.11, 3.36, 3.55, 3.66, 3.91, 4.11, 4.23, 4.32, 4.61, 4.70, 5.05, 7.30, 8.51, 8.74, 8.75, 10.47 ppm. TLC R$_f$ 0.13 (5% MeOH in CH$_2$Cl$_2$). IR (diffuse reflectance) 1645, 1597, 1568, 1542, 1520, 1487, 1428, 1423, 1352, 1346, 1213, 1130, 1105, 1092, 800 cm$^{-1}$; OAMS supporting ions at: ESI+ 586.3; HRMS (FAB) 586.1890; Anal. found: C, 57.41; H, 5.57; N, 11.94.

EXAMPLE 78

2-{[[2-(3-Aminophenyl)-2-hydroxyethyl](methyl)amino]methyl}-N-(4-chlorobenzyl)-3-[(2-methoxyethoxy)methyl]-4-methyl-7-oxo-4,7-dihydrothieno[3,2-b]pyridine-6-carboxamide

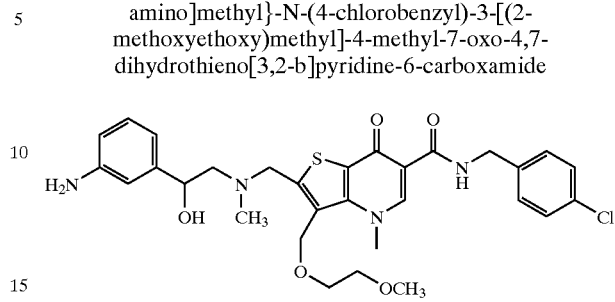

Prepared in 100% yield following the procedure for preparation of

Example 72. Flash chromatography on silica using 4% MeOH in CH$_2$Cl$_2$ followed by recrystallization from EtOAc affords white crystals.

Physical properties are as follows:

Mp 128.5–131.0° C. $^1$H NMR (CDCl$_3$) δ 2.45, 2.60, 2.67, 3.35, 3.55, 3.58, 3.66, 3.67, 3.82, 3.96, 4.23, 4.62, 4.67, 4.68, 6.57, 6.69, 7.09, 7.30, 8.52, 10.46 ppm. TLC R$_f$ 0.13 (5% MeOH in CH$_2$Cl$_2$). IR (diffuse reflectance) 1653, 1644, 1596, 1542, 1523, 1511, 1490, 1458, 1353, 1345, 1214, 1132, 1088, 799, 699 cm$^{-1}$; OAMS supporting ions at: ESI+ 599.3; HRMS (FAB) 599.2122; Anal. found: C, 59.99; H, 6.19; N, 9.21.

EXAMPLE 79

N-(4-Chlorobenzyl)-2-{[(2-hydroxy-2-{3-[2-(2-methoxyethoxy)ethoxy]phenyl}ethyl)(methyl)amino]methyl}-3-[(2-methoxyethoxy)methyl]-4-methyl-7-oxo-4,7-dihydrothieno[3,2-b]pyridine-6-carboxamide

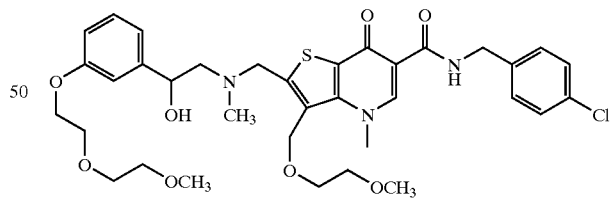

Prepared following the procedure for preparation of Example 72. Flash chromatography on silica using 3% MeOH in CH$_2$Cl$_2$ affords a yellow semisolid.

Physical properties are as follows:

$^1$H NMR (CDCl$_3$) δ 2.45, 2.61, 2.67, 3.35, 3.39, 3.56, 3.65, 3.71, 3.83, 3.98, 4.12, 4.23, 4.62, 4.66, 4.75, 6.81, 6.90, 6.94, 7.22, 7.30, 8.51, 10.45 ppm. TLC R$_f$ 0.17 (5% MeOH in CH$_2$Cl$_2$). OAMS supporting ions at: ESI+ 599.3.

EXAMPLE 80

N-(4-Chlorobenzyl)-2-{[[2-(5-cyanothien-2-yl)-2-hydroxyethyl](methyl)amino]methyl}-3-[(2-methoxyethoxy)methyl]-4-methyl-7-oxo-4,7-dihydrothieno[3,2-b]pyridine-6-carboxamide

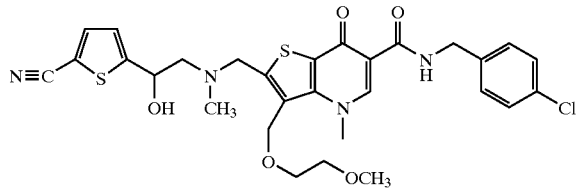

Prepared following the procedure for preparation of Example 72. Flash chromatography on silica using 2% MeOH in CH$_2$Cl$_2$ followed by recrystallization from EtOAc affords white crystals.

Physical properties are as follows:

Mp 163–164° C. $^1$H NMR (CDCl$_3$) δ 2.46, 2.75, 3.36, 3.56, 3.68, 3.86, 3.97, 4.22, 4.23, 4.61, 4.64, 5.00, 6.93, 7.30, 7.48, 8.48, 10.41 ppm. TLC R$_f$ 0.29 (5% MeOH in CH$_2$Cl$_2$). IR (diffuse reflectance) 2217, 1655, 1599, 1545, 1525, 1491, 1456, 1352, 1216, 1133, 1090, 1038, 1015, 811, 797 cm$^{-1}$; OAMS supporting ions at: ESI+ 615.2; HRMS (FAB) 615.1525; Anal. found: C, 56.47; H, 5.15; N, 9.04.

Preparation 24

3-[(Allyloxy)methyl]-N-(4-chlorobenzyl)-4-methyl-7-oxo-4,7-dihydrothieno[3,2-b]pyridine-6-carboxamide To a cold (0° C.), stirred solution of 0.82 mL of allyl alcohol in 12 mL of dry THF, under argon, is added 2.1 mL of a 2.5 M solution of butyllithium in hexanes. The solution is stirred for 5 min, then added via cannula to a cold (0° C.), stirred mixture of 1.25 g of ethyl 3-(bromomethyl)-4-methyl-7-oxo-4,7-dihydrothieno[3,2-b]pyridine-6-carboxylate (Preparation 19) in 8 mL of dry DMF. The resulting solution is stirred at 0° C. for 20 min, then quenched with dil. HCl. Aqueous workup (EtOAc/dil HCl) followed by flash chromatography on silica using 3% MeOH in CH$_2$Cl$_2$ affords a mixture of ethyl and allyl esters (873 mg). A mixture of 165 mg of the mixed esters and 580 mg of p-chlorobenzylamine is heated at 120° C. for 18 h, then cooled and diluted with ether. The resulting solid is filtered, washed well with ether, and dried in vacuo. Flash chromatography of the solid on silica using 2% MeOH in CH$_2$Cl$_2$ provides 922 mg of the title compound as a pale yellow solid. Recrystallization from EtOAc affords glistening yellow prisms.

Physical properties are as follows:

Mp 156–158° C. $^1$H NMR (CDCl$_3$) δ 4.04, 4.23, 4.62, 4.68, 5.28, 5.90, 7.30, 7.69, 8.57, 10.41 ppm. TLC R$_f$ 0.39 (5% McOH in CH$_2$Cl$_2$). IR (diffuse reflectance) 3055, 1655, 1603, 1545, 1509, 1484, 1091, 1084, 997, 932, 852, 797, 713, 659, 652 cm$^{-1}$; OAMS supporting ions at: ESI+ 403.3; HRMS (FAB) 403.0873; Anal. found: C, 59.43; H, 4.81; N, 6.96.

Preparation 25

N-(4-Chlorobenzyl)-4-methyl-7-oxo-3-{[2-(trimethylsilyl)ethoxy]methyl}-4,7-dihydrothieno[3,2-b]pyridine-6-carboxamide To a cold (−78° C.), stirred solution of 5.7 mL of 2-(trimethylsilyl)ethanol in 40 mL of dry THF is added dropwise 14.4 mL of a 2.5 M hexane solution of butyllithium. The solution is stirred for 10 min at −78° C., then 15 mL of dry DMF is added, followed by 2.64 g of ethyl 3-(bromomethyl)-4-methyl-7-oxo-4,7-dihydrothieno[3,2-b]pyridine-6-carboxylate (Preparation 19). The mixture is allowed to warm to 0° C., stirred at that temperature for 10 min, then quenched into 50 mL of 1N HCl. Aqueous workup (EtOAc, dil. HCl) and removal of solvent under reduced pressure affords the mixed esters as a waxy yellow solid. This material is heated neat with 5.7 g of p-chlorobenzylamine at 120° C. for 18 h. The reaction mixture is then cooled and subjected to aqueous workup (CHCl$_3$, dil. HCl). Flash chromatography of the crude material using 35–40% EtOAc in CH$_2$Cl$_2$ provides 2.03 g of the title compound as a pale yellow solid. Recrystallization from EtOAc-hexane provides white platelets.

Physical properties are as follows:

Mp 135–136° C. $^1$H NMR (CDCl$_3$) δ 0.00, 0.96, 3.57, 4.23, 4.61, 4.63, 7.29, 7.68, 8.56, 10.42 ppm. TLC R$_f$ 0.37 (1:1 EtOAc in CH$_2$Cl$_2$). IR (diffuse reflectance) 3056, 1656, 1603, 1543, 1509, 1487, 1249, 1086, 994, 863, 852, 834, 798, 713, 653 cm$^{-1}$; OAMS supporting ions at: ESI+ 463.3; HRMS (FAB) 463.1291; Anal. found: C, 56.77; H, 5.99; N, 6.00.

Preparation 26

3-[(Allyloxy)methyl]-N-(4-chlorobenzyl)-2-formyl-4-methyl-7-oxo-4,7-dihydrothieno[3,2-b]pyridine-6-carboxamide To a cold (−78° C.), stirred solution of 922 mg of 3-[(allyloxy)methyl]-N-(4-chlorobenzyl)-4-methyl-7-oxo-4,7-dihydrothieno[3,2-b]pyridine-6-carboxamide in 30 mL of dry THF, under argon, is added via cannula a THF solution of LDA, prepared in the usual manner from 1.3 mL of diisopropylamine and 2.7 mL of 2.5 M (hexanes) butyllithium in 20 mL of THF. The solution is stirred at −78° C. for 10 min, then 0.89 mL of dry DMF is added, and the mixture is allowed to warm to 0° C. After 10 min, aqueous workup (CHCl$_3$/dil. HCl) is performed and is followed by flash chromatography on silica using 1.5% MeOH in CH$_2$Cl$_2$ to provide 620 mg of the title compound as a yellow-orange solid. Recrystallization from EtOAc gives yellow crystals.

Physical properties are as follows:

Mp 144–147° C. $^1$H NMR (CDCl$_3$) δ 4.12, 4.28, 4.61, 5.04, 5.31, 5.92, 7.29, 8.64, 10.17, 10.24 ppm. TLC R$_f$ 0.39 (5% MeOH in CH$_2$Cl$_2$). IR (diffuse reflectance) 1677, 1647, 1595, 1569, 1549, 1545, 1518, 1490, 1442, 1426, 1343, 1206, 1070, 797, 723 cm$^{-1}$; OAMS supporting ions at: ESI+ 431.3; HRMS (EI) 430.0744; Anal. found: C, 58.30; H, 4.34; N, 6.50.

Preparation 27

N-(4-Chlorobenzyl)-2-formyl-4-methyl-7-oxo-3-{[2-(trimethylsilyl)ethoxy]methyl}4,7-dihydrothieno[3,2-b]pyridine-6-carboxamide To a cold (−78° C.), stirred mixture of 2.03 g of N-(4-chlorobenzyl)-4-methyl-7-oxo-3-{[2-(trimethylsilyl)ethoxy]methyl}-4,7-dihydrothieno[3,2-b]pyridine-6-carboxamide in 50 mL of dry TBF is added via cannula a solution of LDA, prepared as usual in 25 mL of dry THF from 2.5 mL of diisopropylamine and 5.3 mL of a 2.5 M solution of butyllithium in hexanes. The resulting deeply colored solution is stirred for 5 min at −78° C., then 1.7 mL of dry DMF is added, causing the mixture to solidify. The mixture is allowed to warm to 0° C. whereupon it becomes fluid, and is quenched with 50 mL of 1N HCl. Aqueous workup (CH$_2$Cl$_2$, dil. HCl) followed by flash chromatography on silica gel using 30–40% EtOAc in CH$_2$Cl$_2$ affords 1.56 g of the title compound as a yellow solid. Recrystallization from EtOAc provides pale yellow crystals.

Physical properties are as follows:

Mp 174–176° C. $^1$H NMR (CDCl$_3$) δ 0.02, 0.99, 3.66, 4.29, 4.61, 5.01, 7.30, 8.66, 10.19, 10.29 ppm. TLC R$_f$ 0.39 (1:1 EtOAc in CH$_2$Cl$_2$). IR (diffuse reflectance) 3253, 1664, 1595, 1563, 1526, 1506, 1486, 1441, 1348, 1249, 1218, 1191, 861, 835, 803 cm$^{-1}$; HRMS (FAB) 491.1231; Anal. found: C, 56.15; H, 5.55; N, 5.68.

Preparation 28

3-[(Allyloxy)methyl]-N-4-chlorobenzyl)-2-(hydroxymethyl)-4-methyl-7-oxo-4,7-dihydrothieno[3,2-b]pyridine-6-carboxamide To a cold (0° C.), stirred solution of 310 mg of 3-[(allyloxy)methyl]-N-(4-chlorobenzyl)-2-formyl-4-methyl-7-oxo-4,7-dihydrothieno[3,2-b]pyridine-6-carboxamide in 8 mL of CH$_2$Cl$_2$ is added 0.21 mL of acetic acid and 462 mg of sodium triacetoxyborohydride. The ice bath is removed and the resulting solution allowed to stir at room temperature for 2.5 h. Aqueous workup (CH$_2$Cl$_2$/aq. NaHCO$_3$) followed by flash chromatography on silica using 3% MeOH in CH$_2$Cl$_2$ affords 286 mg of the title compound as a pale yellow solid. Recrystallization from acetonitrile gives pale tan needles.

Physical properties are as follows:

Mp 184–185° C. $^1$H NMR (CDCl$_3$+CD$_3$OD) δ 4.01, 4.24, 4.55, 4.60, 4.85, 5.24–5.34, 5.90, 7.31, 8.42 ppm. TLC R$_f$ 0.23 (5% MeOH in CH$_2$Cl$_2$). IR (diffuse reflectance) 3234, 3181, 3058, 1659, 1607, 1555, 1541, 1513, 1494, 1350, 1346, 1068, 1056, 917, 794 cm$^{-1}$; OAMS supporting ions at: ESI+ 433.3; HRMS (FAB) 433.0981; Anal. found: C, 58.20; H, 4.94; N, 6.52.

Preparation 29

N-(4-Chlorobenzyl)-2-(hydroxymethyl)-4-methyl-7-oxo-3-{[2-(trimethylsilyl)ethoxy]methyl}-4,7-dihydrothieno[3,2-b]pyridine-6-carboxamide To a cold (0° C.), stirred solution of 1.56 g of N-(4-chlorobenzyl)-2-formyl-4-methyl-7-oxo-3-{[2-(trimethylsilyl)ethoxy]methyl}-4,7-dihydrothieno[3,2-b]pyridine-6-carboxamide And 0.91 mL of acetic acid in 32 mL of CH$_2$Cl$_2$ is added 1.7 g of sodium triacetoxyborohydride. The ice bath is removed and the reaction allowed to stir at room temperature for 4 h, then partitioned between chloroform and aq. NaHCO$_3$. The organic phase is dried (Na$_2$SO$_4$) and concentrated under reduced pressure, and the residue flash chromatographed on silica using 2% MeOH in CH$_2$Cl$_2$ to provide 1.53 g of the title compound as a pale yellow solid. Recrystallization from acetonitrile furnishes white platelets.

Physical properties are as follows:

Mp 193–194° C. $^1$H NMR (CDCl$_3$) δ 0.00, 0.88, 3.37, 4.14, 4.27, 4.59, 4.63, 4.72, 7.37, 8.01, 10.52 ppm. TLC R$_f$ 0.31 (5% MeOH in CH$_2$Cl$_2$). IR (diffuse reflectance) 2953, 1645, 1601, 1550, 1545, 1531, 1526, 1512, 1486, 1350, 1249, 1207, 1066, 835, 802 cm$^{-1}$; OAMS supporting ions at: ESI+ 493.3; HRMS (FAB) 493.1397; Anal. found: C, 55.92; H, 5.94; N, 5.59.

Preparation 30

3-[(Allyloxy)methyl]-N-4-chlorobenzyl)-2-(chloromethyl)-4-methyl-7-oxo-4,7-dihydrothieno[3,2-b]pyridine-6-carboxamide To a cold (0° C.), stirred solution of 436 mg of 3-[(allyloxy)methyl]-N-(4-chlorobenzyl)-2-(hydroxymethyl)-4-methyl-7-oxo-4,7-dihydrothieno[3,2-b]pyridine-6-carboxamide and 0.53 mL of 2,4,6-collidine in 5 mL of dry DMF is added 0.20 mL of methanesulfonyl chloride. The ice bath is removed and the mixture stirred at room temperature for 18 h, then diluted with water to a volume of 50 ml. The resulting solid is filtered, washed well with water, and dried in vacuo to afford 441 mg of the chloride as a tan solid.

Physical properties are as follows:

$^1$H NMR (CDCl$_3$) δ 4.11, 4.25, 4.62, 4.69, 4.82, 5.32, 5.94, 7.29, 8.58, 10.33 ppm. IR (diffuse reflectance) 3053, 1653, 1600, 1554, 1512, 1491, 1437, 1343, 1221, 1134, 1093, 1077, 1015, 796, 689 cm$^{-1}$; HRMS (FAB) 451.0649; Anal. found: C, 61.21; H, 5.54; N, 9.92.

Preparation 31

N-(4-Chlorobenzyl)-2-(chloromethyl)-4-methyl-7-oxo-3-{[2-(trimethylsilyl)ethoxy]methyl}-4,7-dihydrothieno[3,2-b]pyridine-6-carboxamide To a cold (0° C.), stirred solution of 426 mg of N-(4-chlorobenzyl)-2-(hydroxymethyl)-4-methyl-7-oxo-3-{[2-(trimethylsilyl)ethoxy]methyl}-4,7-dihydrothieno[3,2-b]pyridine-6-carboxamide and 0.46 mL of 2,4,6-collidine in 4 mL of dry DMF is added 0.17 mL of methanesulfonyl chloride. The ice bath is removed and the mixture is allowed to stir for 18 h, then is diluted slowly with water to a volume of 25 mL. The resulting solid is filtered, washed well with water, and dried in vacuo to furnish 429 mg of the title compound as a brown solid.

Physical properties are as follows:

$^1$H NMR (CDCl$_3$) δ 0.02, 0.99, 3.64, 4.25, 4.62, 4.65, 4.83, 7.29, 8.58, 10.34 ppm. TLC R$_f$ 0.38 (30% EtOAc in CH$_2$Cl$_2$).

EXAMPLE 81

3-[(Allyloxy)methyl]-N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide

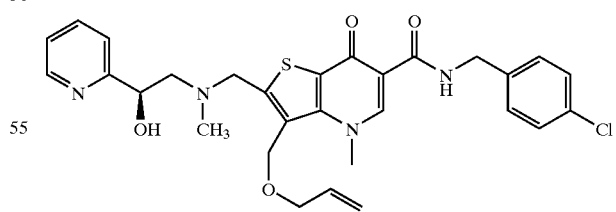

The title compound is prepared following the procedure for preparation of Example 72. Flash chromatography on silica using 3% MeOH in CH$_2$Cl$_2$ followed by recrystallization from EtOAc-hexane affords pale tan crystals.

Physical properties are as follows:

Mp 125–127° C. $^1$R NMR (CDCl$_3$) δ 2.46, 2.75, 2.91, 3.84, 4.00, 4.06, 4.15, 4.21, 4.60, 4.61, 4.89, 5.25–5.35, 5.92, 7.19, 7.29, 7.49, 7.69, 8.51, 8.52, 10.45 ppm. TLC $R_f$ 0.28 (5% MeOH in $CH_2Cl_2$). IR (diffuse reflectance) 3055, 1646, 1595, 1569, 1542, 1523, 1489, 1455, 1432, 1405, 1354, 1342, 1215, 1076, 801 $cm^{-1}$; OAMS supporting ions at: ESI+ 567.4; HRMS (FAB) 567.1853; Anal. found: C, 61.21; H, 5.54; N, 9.92.

EXAMPLE 82

N-(4-Chlorobenzyl)-2-{[(2-hydroxy-2-pyrazin-2-ylethyl)(methyl)amino]methyl}-4-methyl-7-oxo-3-{[2-(trimethylsilyl)ethoxy]methyl}-4,7-dihydrothieno[3,2-b]pyridine-6-carboxamide

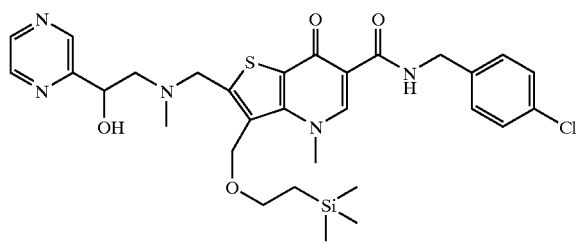

The title compound is prepared following the procedure for preparation of Example 72. Flash chromatography on silica using 3% MeOH in $CH_2Cl_2$ followed by recrystallization from EtOAc-hexane affords glistening white crystals.

Physical properties are as follows:

Mp 154.9–155.5° C. $^1$H NMR ($CDCl_3$) δ 0.02, 0.99, 2.50, 2.78, 2.92, 3.60, 3.85, 4.0, 4.03, 4.23, 4.56, 4.62, 4.93, 7.30, 8.48, 8.51, 8.52, 8.81, 10.44 ppm. TLC $R_f$ 0.30 (5% MeOH in $CH_2Cl_2$). IR (diffuse reflectance) 2950, 1645, 1598, 1519, 1491, 1474, 1347, 1249, 1220, 1091, 1071, 1014, 861, 836, 801 $cm^{-1}$; OAMS supporting ions at: ESI+ 628.3; HRMS (FAB) 628.2189; Anal. found: C, 57.18; H, 6.17; N, 11.12.

Preparation 32

N-(4-Chlorobenzyl)-2-{[[2-(5-cyanothien-2-yl)-2-hydroxyethyl](methyl)amino]methyl}-4-methyl-7-oxo-3-([2-(trimethylsilyl)ethoxy]methyl}-4,7-dihydrothieno[3,2-b]pyridine-6-carboxamide The title compound is prepared following the procedure for preparation of Example 72. Flash chromatography on silica using 2% MeOH in $CH_2Cl_2$ followed by recrystallization from EtOAc-hexane affords granular yellow crystals.

Physical properties are as follows:

Mp 152.5–154.5° C. $^1$H NMR ($CDCl_3$) δ 0.02, 0.99, 2.47, 2.75, 3.59, 3.84, 3.96, 4.21, 4.28, 4.51, 4.61, 5.01, 6.93, 7.30, 7.48, 8.46, 10.42 ppm. TLC $R_f$ 0.40 (5% MeOH in $CH_2Cl_2$). IR (diffuse reflectance) 1645, 1597, 1549, 1532, 1509, 1491, 1354, 1343, 1245, 1221, 1086, 957, 841, 799, 723 $cm^{-1}$; OAMS supporting ions at: ESI+ 657.3; HRMS (FAB) 657.1777; Anal. found: C, 56.58; H, 5.78; N, 8.36.

Preparation 33

N-(4-Chlorobenzyl)-2-{[[2-hydroxy-2-(3-methoxyphenyl)ethyl](methyl)amino]methyl}-4-methyl-7-oxo-3-{[2-(trimethylsilyl)ethoxy]methyl}-4,7-dihydrothieno[3,2-b]pyridine-6-carboxamide The title compound is prepared following the procedure for preparation of Example 72. Flash chromatography on silica using 2% MeOH in $CH_2Cl_2$ followed by recrystallization from EtOAc-hexane affords white needles.

Physical properties are as follows:

Mp 149.5–151.5° C. $^1$H NMR ($CDCl_3$) δ 0.03, 0.99, 2.48, 2.64, 2.71, 3.60, 3.70, 3.80, 3.83, 3.99, 4.24, 4.56, 4.63, 4.77, 6.81, 6.92, 7.30, 8.52, 10.47 ppm. TLC $R_f$ 0.46 (5% MeOH in $CH_2Cl_2$). IR (diffuse reflectance) 2950, 1638, 1589, 1532, 1507, 1489, 1456, 1352, 1280, 1248, 1218, 1090, 1078, 837, 805 $cm^{-1}$; OAMS supporting ions at: ESI+ 656.3; HRMS (FAB) 656.2396; Anal. found: C, 60.34; H, 6.22; N, 6.54.

Preparation 34

2-{[[2-(1-Benzofuran-2-yl)-2-hydroxyethyl](methyl)amino]methyl}-N-(4-chlorobenzyl)-4-methyl-7-oxo-3-{[2-(trimethylsilyl)ethoxy]methyl}-4,7-dihydrothieno[3,2-b]pyridine-6-carboxamide The title compound is prepared following the procedure for preparation of Example 72. Flash chromatography on silica using 0–2% MeOH in 1:1 EtOAc-$CH_2Cl_2$ followed by recrystallization from EtOAc affords white crystals.

Physical properties are as follows:

Mp 157–159° C. $^1$H NMR ($CDCl_3$) δ 0.02, 0.99, 2.48, 2.92, 3.05, 3.58, 3.85, 3.89, 3.97, 4.18, 4.49, 4.53, 4.63, 4.95, 6.69, 7.18–7.35, 7.42, 7.52, 8.48, 10.47 ppm. TLC $R_f$ 0.32 (1:1 EtOAc in $CH_2Cl_2$). IR (diffuse reflectance) 1643, 1596, 1536, 1524, 1509, 1483, 1353, 1249, 1215, 1038, 858, 838, 801, 756, 745 $cm^{-1}$; OAMS supporting ions at: ESI+ 666.3; HRMS (FAB) 666.2218; Anal. found: C, 61.15; H, 6.21; N, 6.26.

Preparation 35

N-(4-Chlorobenzyl)-2-{[[(2R)-2-(2-furyl)-2-hydroxyethyl](methyl)amino]methyl}-4-methyl-7-oxo-3-{[2-(trimethylsilyl)ethoxy]methyl}-4,7-dihydrothieno[3,2-b]pyridine-6-carboxamide The title compound is prepared following the procedure for preparation of Example 72. Flash chromatography on silica using 0–2% MeOH in 1:1 EtOAc-$CH_2Cl_2$ followed by recrystallization from EtOAc-hexane affords white crystals.

Physical properties are as follows:

Mp 110–113° C. $^1$H NMR ($CDCl_3$) δ 0.02, 0.99, 2.43, 2.74, 2.99, 3.59, 3.82, 3.97, 4.22, 4.56, 4.62, 4.81, 6.29, 6.32, 7.30, 7.36, 8.51, 10.45 ppm. TLC $R_f$ 0.25 (1:1 EtOAc in $CH_2Cl_2$). IR (diffuse reflectance) 2948, 1644, 1596, 1541, 1521, 1491, 1342, 1249, 1216, 1086, 1071, 1015, 860, 838, 800 $cm^{-1}$; OAMS supporting ions at: ESI+ 616.3; HRMS (FAB) 616.2065; Anal. Found: C, 58.20; H, 6.29; N, 6.74.

Preparation 36

N-(4-Chlorobenzyl)-2-{[(2-hydroxy-2-quinolin-2-ylethyl)(methyl)amino]methyl}-4-methyl-7-oxo-3-{[2-(trimethylsilyl)ethoxy]methyl}-4,7-dihydrothieno[3,2-b]pyridine-6-carboxamide The title compound is prepared following the procedure for preparation of Example 72. Flash chromatography on silica using 2% MeOH in $CH_2Cl_2$ followed by recrystallization from EtOAc-hexane affords pale yellow crystals.

Physical properties are as follows:

Mp 163–166° C. $^1$H NMR ($CDCl_3$) δ 0.02, 0.96, 2.52, 2.88, 3.02, 3.57, 3.93, 4.03, 4.18, 4.51, 4.55, 4.63, 4.69, 5.07, 7.30, 7.53, 7.58, 7.71, 7.82, 8.04, 8.15, 8.51, 10.49 ppm. TLC $R_f$ 0.39 (5% MeOH in $CH_2Cl_2$). IR (diffuse reflectance) 1652, 1600, 1549, 1545, 1530, 1527, 1507, 1247, 1215, 1093, 1086, 858, 837, 824, 799 $cm^{-1}$; OAMS supporting ions at: ESI+ 677.3; HRMS (FAB) 677.2354; Anal. found: C, 61.89; H, 6.21; N, 8.12.

EXAMPLE 83

N-(4-Chlorobenzyl)-3-(hydroxymethyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide

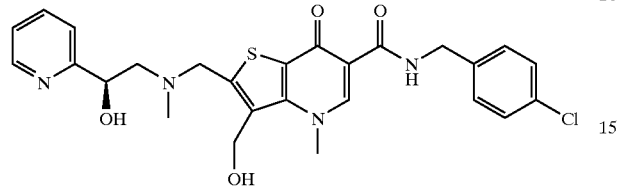

A mixture of 104 mg of 3-[(allyloxy)methyl]-N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide and 75 mg of 5% Pd/C in 5 mL of MeOH is stirred and heated at 100° C. in a sealed tube for 3 days, then cooled and filtered through Celite. The filtrate is concentrated under reduced pressure, and the residue flash chromatographed on silica gel using 5% MeOH in $CH_2Cl_2$ to afford 28 mg of the title compound as a pale yellow glass. Recrystallization from EtOAc-hexane provides 18 mg of white solid.

Physical properties are as follows:

$^1$H NMR (CDCl$_3$) δ 2.52, 2.59, 2.65, 3.74, 4.01, 4.32, 4.60, 4.77, 4.84, 4.92, 7.21, 7.28, 7.69, 8.46, 8.55, 10.42 ppm. TLC R$_f$ 0.33 (10% MeOH in $CH_2Cl_2$). IR (diffuse reflectance) 3176, 3053, 3030, 1649, 1599, 1550, 1517, 1488, 1435, 1322, 1216, 999, 798, 765, 747 cm$^{-1}$; OAMS supporting ions at: ESI+ 527.4; HRMS (FAB) 527.1536; Anal. found: C, 58.52; H, 5.35; N, 10.61.

EXAMPLE 84

N-(4-Chlorobenzyl)-3-(hydroxymethyl)-2-{[(2-hydroxy-2-pyrazin-2-ylethyl)(methyl)amino]methyl}-4-methyl-7-oxo-4,7-dihydrothieno[3,2-b]pyridine-6-carboxamide

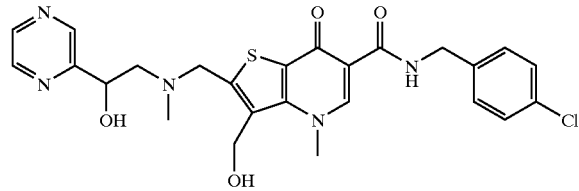

A solution of 144 mg of N-(4-chlorobenzyl)-2-{[(2-hydroxy-2-pyrazin-2-ylethyl)(methyl)amino]methyl}-4-methyl-7-oxo-3-{[2-(trimethylsilyl)ethoxy]methyl}-4,7-dihydrothieno[3,2-b]pyridine-6-carboxamide in 3 mL of 75% TFA in $CH_2Cl_2$ is stirred at room temperature for 3 h, then diluted with CHCl$_3$ and added to stirred aq. NaHCO$_3$. The aqueous phase is adjusted to pH 10–11 with added NaOH, then extracted with 6 portions of CHCl$_3$. The combined organic phase is dried (Na$_2$SO$_4$) and concentrated under reduced pressure. Flash chromatography of the residue on silica gel (compound pre-loaded onto silica gel using CHCl$_3$-MeOH) using 5–8% MeOH in $CH_2Cl_2$ provides 114 mg of the title compound as a white solid. Trituration with boiling acetonitrile affords white solid.

Physical properties are as follows:

Mp 211–213° C. $^1$H NMR (CDCl$_3$) δ 1.75, 2.48, 2.70, 3.70, 3.98, 4.29, 4.59, 4.75, 4.86, 4.92, 7.28, 8.46, 8.51, 8.68, 10.38 ppm. TLC R$_f$ 0.34 (10% MeOH in $CH_2Cl_2$). IR (diffuse reflectance) 3270, 1654, 1600, 1551, 1520, 1503, 1489, 1406, 1353, 1211, 1083, 1016, 1002, 801, 612 cm$^{-1}$; OAMS supporting ions at: ESI+ 528.2; HRMS (FAB) 528.1479; Anal. found: C, 55.75; H, 4.92; N, 12.93.

EXAMPLE 85

N-(4-Chlorobenzyl)-2-{[[2-(5-cyanothien-2-yl)-2-hydroxyethyl](methyl)amino]methyl}-3-(hydroxymethyl)-4-methyl-7-oxo-4,7-dihydrothieno[3,2-b]pyridine-6-carboxamide

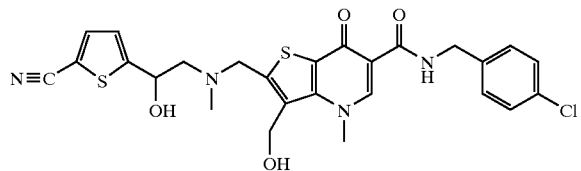

A solution of 170 mg of N-(4-chlorobenzyl)-2-{[[2-(5-cyanothien-2-yl)-2-hydroxyethyl](methyl)amino]methyl}-4-methyl-7-oxo-3-{[2-(trimethylsilyl)ethoxy]methyl}-4,7-dihydrothieno[3,2-b]pyridine-6-carboxamide in 3 mL of 75% TFA in $CH_2Cl_2$ is stirred at room temperature for 4 h, then diluted with CHCl$_3$ and added to stirred aq. NaHCO$_3$. The aqueous phase is extracted with 4 portions of $CH_2Cl_2$, and the combined organic phases dried (Na$_2$SO$_4$) and concentrated under reduced pressure. Flash chromatography of the residue on silica gel using 5% MeOH in $CH_2Cl_2$ provides 146 mg of the title compound as a white solid. Recrystallization from acetonitrile affords white needles.

Physical properties are as follows:

Mp 188–190° C. $^1$H NMR (CDCl$_3$) δ 2.35, 2.59, 2.71, 3.63, 3.82, 4.25, 4.56, 4.6, 4.71, 4.77, 4.99, 6.91, 7.29, 7.45, 8.40, 10.35 ppm. TLC R$_f$ 0.39 (10% MeOH in $CH_2Cl_2$). IR (diffuse reflectance) 2972, 2958, 2934, 2901, 1681, 1497, 1451, 1415, 1397, 1330, 1242, 1135, 1102, 1033, 765 cm$^{-1}$; OAMS supporting ions at: ESI+ 557.2; HRMS (FAB) 557.1098; Anal. found: C, 56.02; H, 4.52; N, 9.98.

EXAMPLE 86

N-(4-Chlorobenzyl)-2-{[[2-hydroxy-2-(3-methoxyphenyl)ethyl](methyl)amino]methyl}-3-(hydroxymethyl)-4-methyl-7-oxo-4,7-dihydrothieno[3,2-b]pyridine-6-carboxamide

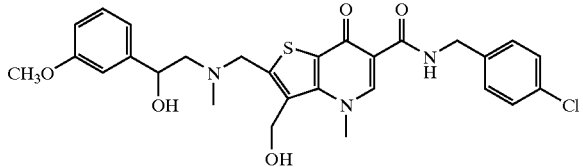

A solution of 157 mg of N-(4-chlorobenzyl)-2-{[[2-hydroxy-2-(3-methoxyphenyl)ethyl](methyl)amino]methyl}-4-methyl-7-oxo-3-{[2-(trimethylsilyl)ethoxy]methyl}-4,7-dihydrothieno[3,2-b]pyridine-6-carboxamide in 3 mL of 75% TFA in $CH_2Cl_2$ is stirred at room temperature for 4 h, then diluted with $CHCl_3$ and added to stirred aq. $NaHCO_3$. The aqueous phase is extracted with 4 portions of $CH_2Cl_2$, and the combined organic phases dried ($Na_2SO_4$) and concentrated under reduced pressure. Flash chromatography of the residue on silica gel using 3–6% MeOH in $CH_2Cl_2$ provides 140 mg of the title compound as a white solid. Recrystallization from acetonitrile affords white crystals.

Physical properties are as follows:

Mp 165–168° C. $^1$H NMR ($CDCl_3$) δ 2.39, 3.41, 2.67, 3.61, 3.75, 3.88, 4.20, 4.57, 4.70, 4.76, 4.82, 6.78, 6.83, 7.21, 7.28, 8.45, 10.39 ppm. TLC $R_f$ 0.40 (10% MeOH in $CH_2Cl_2$). IR (diffuse reflectance) 3082, 3043, 3012, 2980, 2950, 2917, 2887, 2840, 2666, 2560, 1685, 1316, 1265, 923, 747 $cm^{-1}$; OAMS supporting ions at: ESI+ 556.3; HRMS (FAB) 556.1674; Anal. found: C, 60.37; H, 5.53; N, 7.54.

EXAMPLE 87

2-{[[2-(1-Benzofuran-2-yl)-2-hydroxyethyl](methyl)amino]methyl}-N-(4-chlorobenzyl)-3-(hydroxymethyl)-4-methyl-7-oxo-4,7-dihydrothieno[3,2-b]pyridine-6-carboxamide

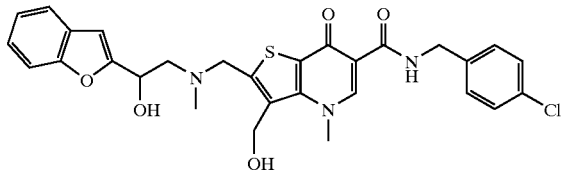

A solution of 154 mg of 2-{[[2-(1-benzofuran-2-yl)-2-hydroxyethyl](methyl)amino]methyl}-N-(4-chlorobenzyl)-4-methyl-7-oxo-3-{[2-(trimethylsilyl)ethoxy]methyl}-4,7-dihydrothieno[3,2-b]pyridine-6-carboxamide in 3 mL of 75% TFA in $CH_2Cl_2$ is stirred at room temperature for 4 h, then diluted with $CHCl_3$ and added to stirred aq. $NaHCO_3$. The aqueous phase is extracted with 4 portions of $CH_2Cl_2$, and the combined organic phases dried ($Na_2SO_4$) and concentrated under reduced pressure. Flash chromatography of the residue on silica gel using 4% MeOH in $CH_2Cl_2$ provides 103 mg of the title compound as a pale yellow solid. Recrystallization from acetonitrile affords white needles.

Physical properties are as follows: 4.79, 4.94, 6.59, 7.17, 7.22, 7.27, 7.35, 7.47, 8.38, 10.38 ppm. TLC $R_f$ 0.18 (5% MeOH in $CH_2Cl_2$). IR (diffuse reflectance) 3336, 1651, 1598, 1545, 1521, 1508, 1453, 1360, 1252, 1210, 1088, 1052, 1015, 799, 746 $cm^{-1}$; OAMS supporting ions at: ESI+ 566.2; HRMS (FAB) 566.1510; Anal. found: C, 61.53; H, 4.96; N, 7.42.

EXAMPLE 88

N-(4-Chlorobenzyl)-2-{[[(2R)-2-(2-furyl)-2-hydroxyethyl](methyl)amino]methyl}-3-(hydroxymethyl)-4-methyl-7-oxo-4,7-dihydrothieno[3,2-b]pyridine-6-carboxamide

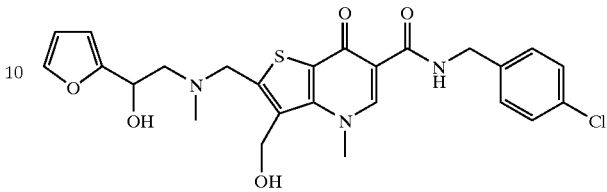

A solution of 121 mg of compound N-(4-chlorobenzyl)-2-{[[(2R)-2-(2-furyl)-2-hydroxyethyl](methyl)amino]methyl}-4-methyl-7-oxo-3-{[2-(trimethylsilyl)ethoxy]methyl}-4,7-dihydrothieno[3,2-b]pyridine-6-carboxamide in 3 mL of 75% TFA in $CH_2Cl_2$ is stirred at room temperature for 3 h, then diluted with $CHCl_3$ and added to stirred aq. $NaHCO_3$. The aqueous phase is extracted with 4 portions of $CH_2Cl_2$, and the combined organic phases dried ($Na_2SO_4$) and concentrated under reduced pressure. Flash chromatography of the residue on silica gel using 3% MeOH in $CH_2Cl_2$ provides 19 mg of the title compound as a brown solid. Recrystallization from EtOAc-hexane affords granular brown crystals.

Physical properties are as follows:

$^1$H NMR ($CDCl_3$) δ 2.40, 2.60, 2.95, 3.67, 3.95, 4.26, 4.61, 4.74, 4.86, 4.86, 6.25, 6.31, 7.29, 7.34, 8.51, 10.41 ppm. TLC $R_f$ 0.15 (5% MeOH in $CH_2Cl_2$). OAMS supporting ions at: ESI+ 516.2.

EXAMPLE 89

N-(4-Chlorobenzyl)-3-(hydroxymethyl)-2-{[(2-hydroxy-2-quinolin-2-ylethyl)(methyl)amino]methyl}-4-methyl-7-oxo-4,7-dihydrothieno[3,2-b]pyridine-6-carboxamide

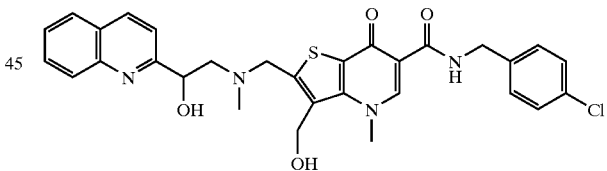

A solution of 174 mg of N-(4-chlorobenzyl)-2-{[(2-hydroxy-2-quinolin-2-ylethyl)(methyl)amino]methyl}-4-methyl-7-oxo-3-{[2-(trimethylsilyl)ethoxy]methyl}-4,7-dihydrothieno[3,2-b]pyridine-6-carboxamide in 3 mL of 75% TFA in $CH_2Cl_2$ is stirred at room temperature for 2.5 h, then diluted with $CHCl_3$ and added to stirred aq. $NaHCO_3$. The aqueous phase is extracted with 4 portions of $CH_2Cl_2$, and the combined organic phases dried ($Na_2SO_4$) and concentrated under reduced pressure. Flash chromatography of the residue on silica gel using 3% MeOH in $CH_2Cl_2$ provides 146 mg of the title compound as a white solid. Recrystallization from EtOAc-hexane affords white solid.

Physical properties are as follows:

Mp 196–198° C. $^1$H NMR ($CDCl_3$) δ 2.52, 2.64, 2.74, 3.69, 4.00, 4.25, 4.58, 4.72, 4.89, 4.98, 5.31, 7.26, 7.34, 7.52, 7.69, 7.78, 7.97, 8.11, 8.47, 10.40 ppm. TLC $R_f$ 0.21 (5%

Preparation 37

Ethyl 3-(azidomethyl)-4-methyl-7-oxo-4,7-dihydrothieno[3,2-b]pyridine-6-carboxylate A mixture of 1.14 g of ethyl 3-(bromomethyl)-4-methyl-7-oxo-4,7-dihydrothieno[3,2-b]pyridine-6-carboxylate (Preparation 19) and 337 mg of sodium azide in 6 mL of DMF is stirred at room temperature for 3 h, then diluted slowly with water to a volume of 50 ml. The resulting solid is filtered, washed well with water, and dried in vacuo to afford 759 mg of the title compound as a cream colored solid. Recrystallization of a sample from acetonitrile gives tan needles.

Physical properties are as follows:

Mp 218° C. (d). $^1$H NMR (CDCl$_3$+CD$_3$OD) δ 1.40, 4.19, 4.38, 4.62, 7.79, 8.36 ppm. TLC R$_f$ 0.22 (5% MeOH in CH$_2$Cl$_2$). IR (diffuse reflectance) 2113, 1717, 1608, 1579, 1496, 1450, 1426, 1306, 1242, 1215, 1165, 1126, 1089, 1046, 800 cm$^{-1}$; OAMS supporting ions at: ESI+ 292.5; HRMS (FAB) 293.0703; Anal. found: C, 49.43; H, 4.01; N, 17.56.

Preparation 38

3-(Azidomethyl)-N-(4-chlorobenzyl)-4-methyl-7-oxo-4,7-dihydrothieno[3,2-b]pyridine-6-carboxamide A mixture of 610 mg of ethyl 3-(azidomethyl)-4-methyl-7-oxo-4,7-dihydrothieno[3,2-b]pyridine-6-carboxylate and 1.89 g of p-chlorobenzylamine is heated at 120° C. for 18 h, then cooled and diluted with ether. The resulting solid is filtered, washed well with ether, and dried in vacuo to provide 782 mg of tan solid. The solid is adsorbed onto silica gel and then flash chromatographed on silica using 2% MeOH in CH$_2$Cl$_2$ to afford 596 mg of the title compound as a yellow solid. Recrystallization from acetonitrile provides off-white crystals.

Physical properties are as follows:

Mp 184.5–187.5° C. (d). $^1$H NMR (CDCl$_3$) δ 4.14, 4.52, 4.61, 7.29, 7.71, 8.54, 10.33 ppm. TLC R$_f$ 0.43 (5% MeOH in CH$_2$Cl$_2$). IR (diffuse reflectance) 2100, 1666, 1601, 1550, 1534, 1516, 1508, 1421, 1411, 1262, 1230, 1213, 1091, 807, 685 cm$^{-1}$; OAMS supporting ions at: ESI+ 388.2; HRMS (FAB) 388.0653; Anal. found: C, 52.95; H, 3.46; N, 17.33.

Preparation 39

3-(Azidomethyl)-N-(4-chlorobenzyl)-2-formyl-4-methyl-7-oxo-4,7-dihydrothieno[3,2-b]pyridine-6-carboxamide Into a cold (−78° C.), stirred mixture of 2.54 g of 3-(azidomethyl)-N-(4-chlorobenzyl)-4-methyl-7-oxo-4,7-dihydrothieno[3,2-b]pyridine-6-carboxamide in 100 mL of dry THF is added via cannula a solution of LDA in THF, prepared from 3.7 mL of diisopropylamine and 8.0 mL of 2.5 M (hexanes) butyllithium in 50 mL of THF. The mixture is stirred at −78° C. for 90 min, then 2.5 mL of dry DMF is added and the mixture is allowed to warm to 0° C. Aqueous workup (CHCl$_3$/dil. HCl) followed by flash chromatography on silica using 2% MeOH in CH$_2$Cl$_2$ affords 1.61 g of the title compound as an amber foam.

Physical properties are as follows:

$^1$H NMR (CDCl$_3$) δ 4.23, 4.61, 5.00, 7.30, 8.63, 10.10, 10.15 ppm. TLC R$_f$ 0.30 (5% MeOH in CH$_2$Cl$_2$). OAMS supporting ions at: ESI+ 416.2.

Preparation 40

3-(Azidomethyl)-N-(4-chlorobenzyl)-2-(hydroxymethyl)-4-methyl-7-oxo-4,7-dihydrothieno[3,2-b]pyridine-6-carboxamide To a cold (0° C.), stirred solution of 230 mg of 3-(azidomethyl)-N-(4-chlorobenzyl)-2-formyl-4-methyl-7-oxo-4,7-dihydrothieno[3,2-b]pyridine-6-carboxamide in 6 mL of CH$_2$Cl$_2$ is added 0.16 mL of acetic acid and 296 mg of sodium triacetoxyborohydride. The ice bath is removed and the solution allowed to stir at room temperature for 2 h. Aqueous workup (CHCl$_3$/aq. NaHCO$_3$) followed by flash chromatography on silica using 3% MeOH in CH$_2$Cl$_2$ affords 150 mg of the title compound as a white solid. Recrystallization from acetonitrile provides off-white crystals.

Physical properties are as follows:

Mp 215° C. (d). $^1$H NMR (CDCl$_3$+CD$_3$OD) δ 4.22, 4.58, 4.61, 5.32, 7.31, 8.51 ppm. TLC R$_f$ 0.26 (5% MeOH in CH$_2$Cl$_2$). IR (diffuse reflectance) 3266, 2107, 2090, 1650, 1598, 1544, 1527, 1502, 1451, 1343, 1337, 1215, 1076, 801, 791 cm$^{-1}$; OAMS supporting ions at: ESI+ 418.3; HRMS (FAB) 418.0745; Anal. found: C, 51.69; H, 3.74; N, 16.74.

Preparation 41

3-(Azidomethyl)-N-(4-chlorobenzyl)-2-(chloromethyl)-4-methyl-7-oxo-4,7-dihydrothieno[3,2-b]pyridine-6-carboxamide To a cold (0° C.), stirred solution of 810 mg of 3-(azidomethyl)-N-(4-chlorobenzyl)-2-(hydroxymethyl)-4-methyl-7-oxo-4,7-dihydrothieno[3,2-b]pyridine-6-carboxamide in 11 mL of dry DMF is added 1.05 mL of 2,4,6-collidine and 0.39 mL of methanesulfonyl chloride. The ice bath is later removed and the mixture stirred at room temperature for 18 h. Water is then added slowly to a volume of 100 ml, and the resulting solid is filtered, washed well with water, and dried in vacuo to afford 807 mg of the chloride as a brown solid.

Physical properties are as follows:

$^1$H NMR (CDCl$_3$) δ 4.22, 4.62, 4.67, 4.83, 7.29, 8.59, 10.25 ppm. TLC R$_f$ 0.42 (5% MeOH in CH$_2$Cl$_2$). OAMS supporting ions at: ESI+ 436.3.

EXAMPLE 90

3-(Azidomethyl)-N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide

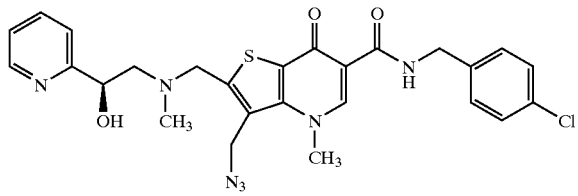

The title compound is prepared following the procedure for preparation of Example 72. Flash chromatography on silica using 3% MeOH in $CH_2Cl_2$ followed by recrystallization from EtOAc-hexane affords white crystals.

Physical properties are as follows:

$^1$H NMR (CDCl$_3$) δ 2.43, 2.82, 2.96, 3.92, 4.03, 4.16, 4.2, 4.53, 4.59, 4.61, 4.97, 7.22, 7.30, 7.46, 7.71, 8.50, 8.54, 10.39 ppm. TLC R$_f$ 0.23 (5% MeOH in $CH_2Cl_2$). IR (diffuse reflectance) 2111, 2092, 1640, 1594, 1532, 1506, 1471, 1337, 1247, 1221, 860, 804, 761, 745, 727 cm$^{-1}$; OAMS supporting ions at: ESI+ 552.4; HRMS (FAB) 552.1592; Anal. found: C, 56.35; H, 4.89; N, 17.45.

EXAMPLE 91

3-(Aminomethyl)-N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide

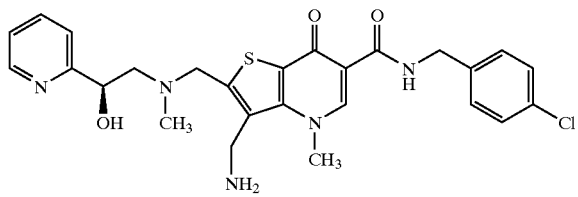

A solution of 111 mg of 3-(azidomethyl)-N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide and 58 mg of triphenylphosphine in 2 mL of THF containing 5 drops of water is stirred overnight, then concentrated under reduced pressure with $CHCl_3$/MeOH azeotrope. Flash chromatography on silica gel using 4–10% methanolic ammonia in $CH_2Cl_2$ provides 83.1 mg of the amine as a white solid. Recrystallization from acetonitrile furnishes white solid.

Physical properties are as follows:

Mp 144–148° C. $^1$H NMR (CDCl$_3$) δ 2.42, 2.4, 2.76, 2.88, 3.81, 3.97, 4.04, 4.37, 4.61, 4.91, 7.20, 7.29, 7.45, 7.69, 8.50, 8.52, 10.47 ppm. TLC R$_f$ 0.23 (6% methanolic ammonia in $CH_2Cl_2$). IR (diffuse reflectance) 3052, 1648, 1600, 1568, 1544, 1525, 1491, 1433, 1351, 1339, 1324, 1216, 799, 760, 753 cm$^{-1}$; OAMS supporting ions at: ESI+ 526.3; HRMS (FAB) 526.1678; Anal. found: C, 59.10; H, 5.41; N, 12.94.

EXAMPLE 92

N-(4-Chlorobenzyl)-2-{[[(2R)-2-hydroxy-2-pyridin-2-ylethyl](methyl)amino]methyl}-4-methyl-3-{[(methylsulfonyl)amino]methyl}-7-oxo-4,7-dihydrothieno[3,2-b]pyridine-6-carboxamide

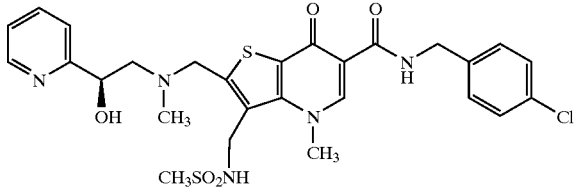

To a cold (0° C.), stirred solution of 96 mg of 3-(aminomethyl)-N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide and 40 μL of diisopropylethylamine in 2 mL of $CH_2Cl_2$ is added 15 μL of methanesulfonyl chloride. The solution is stirred at 0° C. for 20 min, then quenched with dil. HCl and aqueous NaHCO$_3$ to pH 7.0. The mixture is extracted three times with CHCl$_3$, and the combined extracts dried (Na$_2$SO$_4$) and concentrated under reduced pressure. Flash chromatography of the residue on silica using 3–4% MeOH in $CH_2Cl_2$ furnishes 114 mg of the title compound as a white foam. Recrystallization from EtOAc provides white crystals.

Physical properties are as follows:

Mp 171–177° C. (darkening). $^1$H NMR (CDCl$_3$) δ 2.41, 2.55, 2.61, 3.13, 3.53, 4.07, 4.19, 4.38, 4.45, 4.57, 4.94, 5.4, 7.2, 7.66, 8.47, 8.67, 10.32 ppm. TLC R$_f$ 0.21 (5% MeOH in $CH_2Cl_2$). IR (diffuse reflectance) 1651, 1599, 1549, 1510, 1488, 1434, 1417, 1346, 1322, 1213, 1146, 1011, 823, 798, 774 cm$^{-1}$; OAMS supporting ions at: ESI+ 604.3; HRMS (FAB) 604.1472; Anal. found: C, 53.60; H, 5.06; N, 11.47.

Preparation 42

3-[2-(2-Methoxyethoxy)ethoxy]benzaldehyde

A mixture of 3.66 g of 3-hydroxybenzaldehyde, 4.6 g of powdered potassium carbonate, and 5.5 g of 1-bromo-2-(2-methoxyethoxy)ethane in 40 ml of acetone is stirred and refluxed under nitrogen for 18 h, then cooled and filtered. The filtrate is concentrated under reduced pressure, and the residue partitioned between $CH_2Cl_2$ and 1N NaOH. The aqueous phase is extracted with two additional portions of $CH_2Cl_2$, and the combined organic extracts dried (MgSO$_4$) and concentrated under reduced pressure. Flash chromatography of the residue on silica using 20% EtOAc in $CH_2Cl_2$ affords 1.32 g of the title compound as a pale yellow oil.

Physical properties are as follows:

$^1$H NMR (CDCl$_3$) δ 3.40, 3.59, 3.73, 3.89, 4.21, 7.21, 7.4–7.5, 9.97 ppm. TLC R$_f$ 0.38 (25% EtOAc in $CH_2Cl_2$). OAMS supporting ions at: ESI+ 225.0.

Preparation 43

2-{3-[2-(2-Methoxyethoxy)ethoxy]phenyl}oxirane

To a stirred solution of 1.32 g of 3-[2-(2-methoxyethoxy)ethoxy]benzaldehyde and 15 mg of tetra-n-butylammonium bromide in 15 ml of $CH_2Cl_2$ is added a solution of 2.4 g of trimethylsulfonium methylsulfate in 4 ml of water, followed by 10 ml of 50% NaOH. The mixture is stirred and refluxed for 4 h, then cooled, diluted with ether and brine, and filtered. The organic phase is washed with brine, dried (MgSO$_4$), and concentrated under reduced pressure to provide 1.78 g of the title compound as a pale yellow oil.

Physical properties are as follows:

$^1$H NMR (CDCl$_3$) δ 2.77, 3.13, 3.40, 3.58, 3.72, 3.83, 3.86, 4.14, 6.86, 7.25 ppm. OAMS supporting ions at: ESI+ 239.2.

Preparation 44

1-{3-[2-(2-Methoxyethoxy)ethoxy]phenyl}-2-(methylamino)ethanol. {36824-SRT-3}

A solution of 1.78 g of 2-{3-[2-(2-methoxyethoxy)ethoxy]phenyl}oxirane in 30 ml of 2.0 M methylamine in methanol is stirred at room temperature overnight, then concentrated under reduced pressure. Flash chromatography of the residue on silica using 5–7% methanolic ammonia in CH$_2$Cl$_2$ affords 809 mg of the title compound as a colorless oil.

Physical properties are as follows:

$^1$H NMR (CDCl$_3$) δ 2.3, 2.47, 2.71, 2.82, 3.39, 3.58, 3.73, 3.86, 4.15, 4.70, 6.82, 6.95, 7.24 ppm. TLC R$_f$ 0.2$^7$ (8% methanolic ammonia in CH$_2$Cl$_2$). OAMS supporting ions at: ESI+ 239.2.270.3.

EXAMPLE 93

N-(4-chlorobenzyl)-2-{[[2-(2,6-dimethoxyphenyl)-2-hydroxyethyl](methyl)amino]methyl}-3,4-dimethyl-7-oxo-4,7-dihydrothieno[3,2-b]pyridine-6-carboxamide

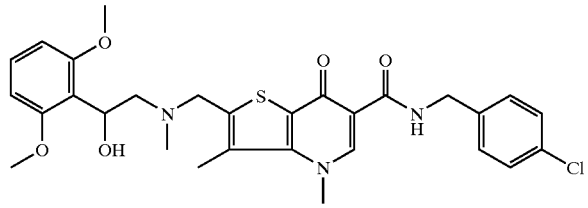

A mixture of N-(4-chlorobenzyl)-2-(chloromethyl)-3,4-dimethyl-7-oxo-4,7-dihydrothieno[3,2-b]pyridine-6-carboxamide (50 mg, 0.13 mmol), 1-(2,6-dimethoxyphenyl)-2-(methylamino)ethanol (PNU-149291, Arch. Intern. Pharmacodyn. 1965, 154, 26–39) (42 mg, 0.20 mmol) and diisopropylethylamine (34 μL, 0.20 mmol) in dry DMF (2.7 mL) was heated to 60° C., becoming a solution. The reaction was stirred for 7 hours at that temperature. After cooling to room temperature, the solution was diluted with water (7 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (39 mg) as a white solid.

Physical characteristics are as follows:

$^1$H NMR (400 MHz, DMSO-d$_6$) δ 10.43 (1 H), 8.57 (1 H), 7.38 (4 H), 7.17 (1 H), 6.59 (2 H), 5.26 (1 H), 4.53 (2 H), 4.28 (1 H), 4.19 (3 H), 3.82 (1 H), 3.68 (7 H), 2.86 (2 H), 2.41 (3 H), 2.28 (3 H); Anal. Found: C, 60.80; H, 5.70; N, 7.43. MS (ESI+) for C$_{29}$H$_{32}$ClN$_3$O$_5$S m/z 570 (M+H)$^+$; HRMS (ESI+) calcd. for C$_{29}$H$_{32}$ClN$_3$O$_5$S+H 570.1829, found 570.1840.

EXAMPLE 94

2-{[(1-benzyl-2-hydroxyethyl)(methyl)amino]methyl}-N-(4-chlorobenzyl)-3,4-dimethyl-7-oxo-4,7-dihydrothieno[3,2-b]pyridine-6-carboxamide

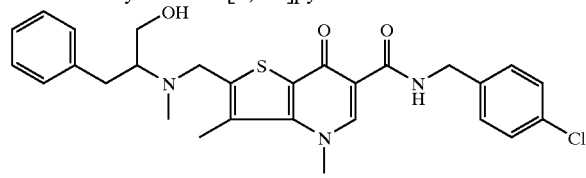

A mixture of N-(4-chlorobenzyl)-2-(chloromethyl)-3,4-dimethyl-7-oxo-4,7-dihydrothieno[3,2-b]pyridine-6-carboxamide (50 mg, 0.13 mmol), 2-(methylamino)-3-phenylpropan-1-ol (Tetrahedron 2001, 57, 3425)(33 mg, 0.20 mmol) and diisopropylethylamine (35 μL, 0.20 mmol) in dry DMF (2.7 mL) was heated to 60° C., becoming a solution. The reaction was stirred for 10 hours at that temperature. After cooling to room temperature, the solution was diluted with water (7 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (5 mL, dissolved with warming and then cooled to 0° C. overnight) gave the title compound (52 mg) as a white solid.

Physical characteristics are as follows:

$^1$H NMR (400 MHz, DMSO-d$_6$) δ 10.45 (1 H), 8.55 (1 H), 7.41, 7.33 (4 H), 7.28, 7.16 (5 H), 4.52 (3 H), 4.19 (3 H), 3.94 (2 H), 3.60 (1 H), 3.47 (1 H), 2.95 (1 H), 2.80, 2.68 (2 H), 2.42 (3 H), 2.34 (3 H); Anal. Found: C, 63.61; H, 5.76; N, 7.95. MS (ESI+) for C$_{28}$H$_{30}$ClN$_3$O$_3$S m/z 524 (M+H)$^+$; HRMS (ESI+) calcd for C$_{28}$H$_{30}$ClN$_3$O$_3$S+H 524.1774, found 524.1781.

EXAMPLE 95

2-{[(2-[4-(acetylamino)phenyl]-2-hydroxyethyl}(methyl)amino]methyl}-N-(4-chlorobenzyl)-3,4-dimethyl-7-oxo-4,7-dihydrothieno[3,2-b]pyridine-6-carboxamide

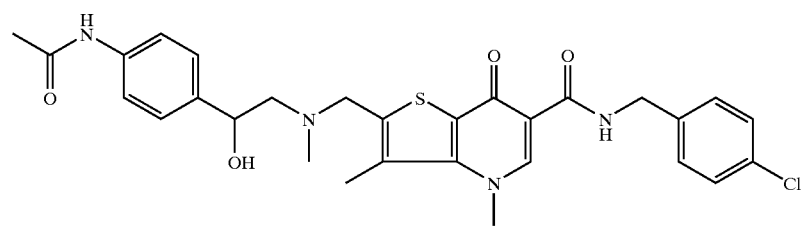

A mixture of N-(4-chlorobenzyl)-2-(chloromethyl)-3,4-dimethyl-7-oxo-4,7-dihydrothieno[3,2-b]pyridine-6-carboxamide (50 mg, 0.13 mmol), N-{4-[1-hydroxy-2-(methylamino)ethyl]phenyl}acetamide (Preparation 56)(42 mg, 0.20 mmol) and diisopropylethylamine (35 μL, 0.20 mmol) in dry DMF (2.7 mL) was heated to 60° C., becoming a solution. The reaction was stirred for 7 hours at that temperature. After cooling to room temperature, the solution was diluted with water (7 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile/DMF/water (5 mL/2 drops/1 mL, dissolved with warming, added water and then cooled to 0° C. overnight) gave the title compound (58 mg) as a white solid.

Physical characteristics are as follows:

$^1$H NMR (400 MHz, DMSO-d$_6$), δ 0.44 (1 H), 9.87 (1 H), 8.57 (1 H), 7.48 (2 H), 7.36 (4 H), 7.22 (2 H), 5.06 (1 H), 4.71 (1 H), 4.53 (2 H), 4.20 (3 H), 3.82 (2 H), 2.6 (2 H), 2.46 (3 H), 2.31 (3 H); Anal. Found: C, 60.61; H, 5.59; N, 9.72. HRMS (ESI+) calcd for C$_{29}$H$_{31}$ClN$_4$O$_4$S+H 567.1832, found 567.1822.

EXAMPLE 96

N-(4-chlorobenzyl)-2-{[(2-hydroxy-2-{3-[2-(2-methoxyethoxy)ethoxy]phenyl}ethyl)(methyl)amino]methyl}-3,4-dimethyl-7-oxo-4,7-dihydrothieno[3,2-b]pyridine-6-carboxamide

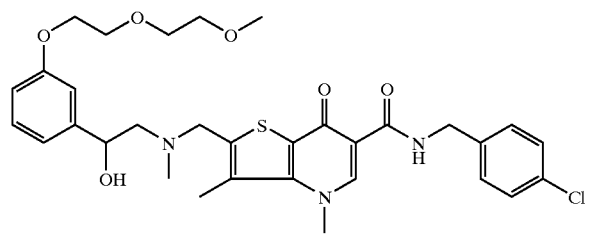

A mixture of N-(4-chlorobenzyl)-2-(chloromethyl)-3,4-dimethyl-7-oxo-4,7-dihydrothieno[3,2-b]pyridine-6-carboxamide (85 mg, 0.21 mmol), 1-{3-[2-(2-methoxyethoxy)ethoxy]phenyl}-2-(methylamino)ethanol (Preparation 44) (85 mg, 0.32 mmol) and diisopropylethylamine (56 μL, 0.32 mmol) in dry DMF (4.4 mL) was heated to 60° C., becoming a solution. The reaction was stirred for 5 hours at that temperature. After cooling to room temperature, the solution was diluted with ice (6 g). The resulting milky suspension was stirred vigorously for 30 minutes, and then left standing overnight at room temp. The mixture was filtered, and the collected solid was washed with water and dried in vacuo, leaving a white solid. Recrystallization from acetonitrile/water (10 mL, 1:1, v/v, dissolved with warming acetonitrile, diluted with water and then cooled to 0° C. overnight) gave the title compound (107 mg) as a white solid.

Physical characteristics are as follows:

$^1$H NMR (400 MHz, DMSO-d$_6$) δ 10.44 (1 H), 8.58 (1 H), 7.38 (4 H), 7.19 (1 H), 6.90 (2 H), 6.78 (1 H), 5.15 (1 H), 4.73 (1 H), 4.54 (2 H), 4.20 (3 H), 4.02 (2 H), 3.82 (2H), 3.69 (2 H), 3.55 (2H), 3.43 (2 H), 3.23 (3 H), 2.63 (2 H), 2.45 (3 H), 2.33 (3 H); Anal. Found: C, 60.79; H, 6.22; N, 6.65. MS (CI) for C$_{32}$H$_{38}$ClN$_3$O$_6$S m/z 628 (M+H)$^+$, 628, 404, 392, 390, 363, 362, 361, 242, 142, 140.

EXAMPLE 97

2-{[[2-(3-aminophenyl)-2-hydroxyethyl](methyl)amino]methyl}-N-(4-chlorobenzyl)-3,4-dimethyl-7-oxo-4,7-dihydrothieno[3,2-b]pyridine-6-carboxamide

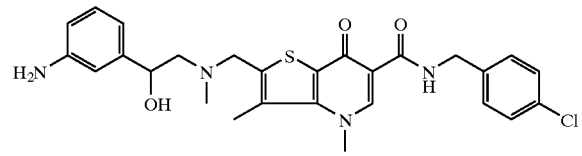

A mixture of N-(4-chlorobenzyl)-2-(chloromethyl)-3,4-dimethyl-7-oxo-4,7-dihydrothieno[3,2-b]pyridine-6-carboxamide (90 mg, 0.23 mmol), 1-(3-aminophenyl)-2-(methylamino)ethanol (*Khim.-Farm. Zh* 1983, 17, 1093)(69 mg, 0.42 mmol) and diisopropylethylamine (60 μL, 0.34 mmol) in dry DMF (4.6 mL) was heated to 60° C., becoming a solution. The reaction was stirred for 5 hours at that temperature. After cooling to room temperature, the solution was diluted with ice (6 g). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the tide compound (79 mg) as a white solid.

Physical characteristics are as follows:

$^1$H NMR (400 MHz, DMSO-d$_6$) δ 10.44 (1 H), 8.58 (1 H), 7.37 (4 H), 6.91 (1 H), 6.54 (1 H), 6.42 (2 H), 4.96 (2 H), 4.93 (1 H), 4.61 (1 H), 4.53 (2 H), 4.21 (3 H), 3.83 (2 H), 2.5 (2 H), 2.48 (3 H), 2.34 (3 H); Anal. Found: C, 61.19; H, 5.59; N, 10.46; MS (CI) for C$_{27}$H$_{29}$ClN$_4$O$_3$S m/z 525 (M+H)$^+$, 364, 363, 362, 361, 347, 327, 167, 153, 139, 120; HRMS (ESI+) calcd for C$_{27}$H$_{29}$ClN$_4$O$_3$S+H 525.1727, found 525.1718.

Preparation 45

N-{3-[1-hydroxy-2-(methylamino)ethyl]phenyl}acetamide

The title compound was synthesized following procedures analogous to that described for the preparation of N-{4-[1-hydroxy-2-methylamino)ethyl]phenyl}acetamide (Preparations 54–56), starting with 3-acetamidoacetophenone instead of 4-acetamidoacetophenone.

Physical characteristics are as follows:

$^1$H NMR (400 MHz, DMSO-d$_6$) δ 9.91 (1 H), 7.53 (1 H), 7.49 (1 H), 7.21 (1 H), 4.58 (1 H), 2.5 (2 H), 2.30 (3 H), 2.02 (3 H).

EXAMPLE 98

2-{[{2-[3-(acetylamino)phenyl]-2-hydroxyethyl}(methyl)amino]methyl}-N-(4-chlorobenzyl)-3,4-dimethyl-7-oxo-4,7-dihydrothieno[3,2-b]pyridine-6-carboxamide

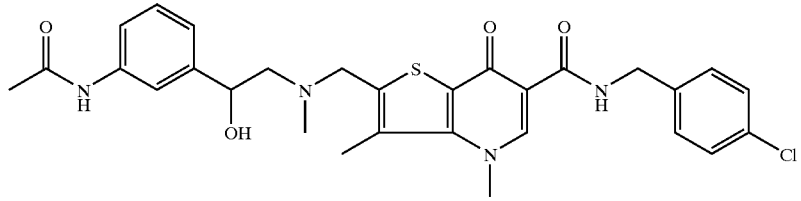

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), N-{3-[1-hydroxy-2-(methylamino)ethyl]phenyl}acetamide (Preparation 45) (79 mg, 0.38 mmol) and diisopropylethylamine (67 μL, 0.38 mmol) in dry DMF (5 mL) was heated to 60° C., becoming a solution. The reaction was stirred for 6 hours at that temperature. After cooling to room temperature, the solution was concentrated under high vacuum. The oil residue was purified with a silica gel chromatotron plate to give the title compound (62 mg) as a white solid.

Physical characteristics are as follows:

$^1$H NMR (400 MHz, DMSO-$d_6$) δ 10.42 (1 H), 9.89 (1 H), 8.57 (1 H), 7.48 (2 H), 7.36 (4 H), 7.19 (1 H), 6.97 (1 H), 5.15 (1 H), 4.71 (1 H), 4.54 (2 H), 4.19 (3 H), 3.81 (2 H), 2.5 (2 H), 2.43 (3 H), 2.34 (3 H), 1.99 (3 H); MS (CI) for $C_{29}H_{31}ClN_4O_4S$ m/z 567 (M+H)$^+$, 570, 568, 567, 361, 209, 195, 181, 153, 96, 61; HRMS (ESI+) calcd for $C_{29}H_{31}ClN_4O_4S$ 567.1832, found 567.1835.

EXAMPLE 99

N-(4-chlorobenzyl)-2-{[[2-hydroxy-2-(3,4,5-trifluorophenyl)ethyl](methyl)amino]methyl}-3,4-dimethyl-7-oxo-4,7-dihydrothieno[3,2-b]pyridine-6-carboxamide

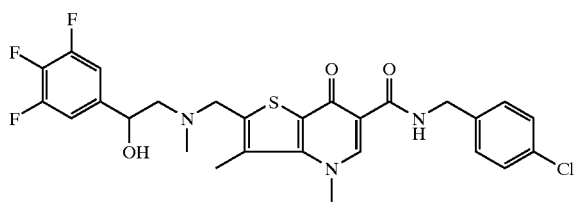

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 2-(methylamino)-1-(3,4,5-trifluorophenyl)ethanol (Preparation 46)(77 mg, 0.38 mmol) and diisopropylethylamine (67 μL, 0.38 mmol) in dry DMF (5 mL) was heated to 60° C., becoming a solution. The reaction was stirred for 6 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (30 mL, dissolved with warming and then cooled to 0° C. overnight) gave the title compound (71 mg) as a white solid.

Physical characteristics are as follows:

$^1$H NMR (400 MHz, DMSO-$d_6$) δ 10.42 (1 H), 8.57 (1 H), 7.41, 7.33 (4 H), 7.26 (2 H), 5.54 (1 H), 4.76 (1 H), 4.53 (2 H), 4.20 (3 H), 3.80 (2 H), 2.6 (2 H), 2.46 (3 H), 2.30 (3 H);

Anal. Found: C, 57.11; H, 4.65; N, 7.45. MS (CI) for $C_{27}H_{25}ClF_3N_3O_3S$ m/z 564 (M+H)$^+$, 566, 564, 363, 362, 361, 347, 206, 204, 188, 61; HRMS (ESI+) calcd for $C_{27}H_{25}ClF_3N_3O_3S$+H 564.1335, found 564.1356.

Preparation 46

2-(methylamino)-1-(3,4,5-trifluorophenyl)ethanol

To a solution of methylamine (20 mL, 2.0 M in methanol, 40 mmol) was added 2-(3,4,5-trifluorophenyl)oxirane (0.17 g, 0.98 mmol) at room temperature. The reaction mixture was stirred at that temperature for 24 hours. Solvent and excessive methylamine were evaporated, leaving a solid. The solid was dissolved in dichloromethane (5 mL). To the resulting clear solution was added hexanes (15 mL), standing overnight. The solid precipitant was collected by filtration to yield the title compound (0.14 g) as a white solid.

Physical characteristics are as follows:

$^1$H NMR (400 MHz, CDCl$_3$) δ 7.04 (2 H), 4.82 (1 H), 2.92 (1 H), 2.71 (1 H), 2.56 (3 H); Anal. Found: C, 52.66; H, 4.92; N, 6.82. MS (CI) m/z for $C_9H_{10}F_3NO$ 206 (M+H)$^+$, 207, 206, 204, 190, 189, 188, 160, 96, 79, 61; HRMS (ESI+) calcd for $C_9H_{10}F_3NO$+H 206.0793, found 206.0795.

Preparation 47

2-(3,4,5-Trifluorophenyl)oxirane

A mixture of trifluorobenzyladehyde (3.2 g, 0.02 mol) and tetrabutylammonium bromide (16.2 g, 0.05 mol) in dichloromethane (70 mL), sodium hydroxide (28 g, 0.7 mol in 60 mL of water), trimethylsulfonium methyl sulfate (9.4 g, 0.05 mol, in 30 mL of water) was refluxed for 5 hours. After cooling to room temperature, the mixture was diluted with diethyl ether (70 mL). The organic phase was separated. The aqueous phase was extracted with diethyl ether (3×50 mL). The organic phases were combined, washed with water (150 mL) and brine (150 mL), and dried over sodium sulfate (20 g). After removing the drying agent, the diethyl ether solution was concentrated to give a crude yellow oil. A fast Kugelrohr distillation yield a colorless oil (1.6 g). The oil was further purified with a silica gel column to give the title compound (1.12 g) as a colorless oil.

Physical characteristics are as follows:

$^1$H NMR (400 MHz, CDCl$_3$) δ 6.94 (2 H), 3.82 (1 H), 3.16 (1 H), 2.70 (1 H); MS (ES−) m/z for $C_8H_5F_3O$ 173 (M−H)$^-$.

EXAMPLE 100

N-(4-chlorobenzyl)-2-{[(2-hydroxy-2-pyrimidin-2-ylethyl)(methyl)amino]methyl}-3,4-dimethyl-7-oxo-4,7-dihydrothieno[3,2-b]pyridine-6-carboxamide

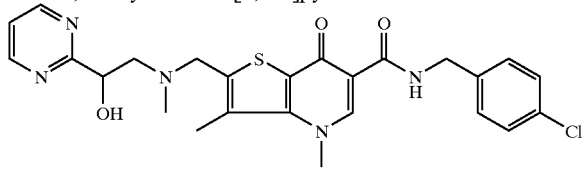

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 2-(methylamino)-1-pyrimidin-2-ylethanol (Preparation 61)(59 mg, 0.38 mmol) and diisopropylethylamine (67 µL, 0.38 mmol) in dry DMF (5 mL) was stirred for 72 hours at room temperature. The solution was diluted with water (7 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (5 mL, dissolved with warming and then cooled to 0° C. overnight) gave the title compound (110 mg) as a white solid.

Physical characteristics are as follows:

$^1$H NMR (400 MHz, DMSO-d$_6$) δ 10.42 (1 H), 8.76 (2 H), 8.56 (1 H), 7.42, 7.33 (5 H), 5.35 (1 H), 4.85 (1 H), 4.53 (2 H), 4.19 (3 H), 3.79 (2 H), 3.01 (1 H), 2.82 (1 H), 2.42 (3 H), 2.28 (3 H); Anal. Found: C, 58.56; H, 5.17; N, 13.75. MS (CI) for C$_{25}$H$_{26}$ClN$_5$O$_3$S m/z 512 (M+H)$^+$, 512, 361, 142, 140, 136, 123, 109, 108, 107, 96; HRMS (ESI+) calcd for C$_{25}$H$_{26}$ClN$_5$O$_3$S+H 512.1523, found 512.1525.

EXAMPLE 101

N-(4-chlorobenzyl)-2-{[[2-(3-furyl)-2-hydroxyethyl](methyl)amino]methyl}-3,4-dimethyl-7-oxo-4,7-dihydrothieno[3,2-b]pyridine-6-carboxamide

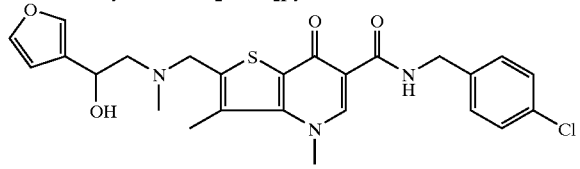

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 1-(3-furyl)-2-(methylamino)ethanol (Preparation 64) (54 mg, 0.38 mmol) and diisopropylethylamine (67 µL, 0.38 mmol) in dry DMF (5.0 mL) was stirred at room temperature for 24 hours. The solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (5 mL, dissolved with warming and then cooled to 0° C. overnight) gave the title compound (102 mg) as a white solid.

Physical characteristics are as follows:

$^1$H NMR (400 MHz, DMSO-d$_6$) δ 10.44 (1 H), 8.58 (1 H), 7.55 (2 H), 7.41, 7.33 (4 H), 6.45 (1 H), 5.02 (1 H), 4.72 (1 H), 4.53 (2 H), 4.21 (3 H), 3.84 (2 H), 2.6 (2 H), 2.50 (DMSO+3 H), 2.31 (3 H); Anal. Found: C, 59.36; H, 5.25; N, 8.32. MS (CI) for C$_{25}$H$_{26}$ClN$_3$O$_4$S m/z 500 (M+H)$^+$, 503, 502, 501, 500, 486, 363, 361, 142, 69, 61; HRMS (ESI+) calcd for C$_{25}$H$_{26}$ClN$_3$O$_4$S+H 500.1411, found 500.1409.

EXAMPLE 102

N-(4-chlorobenzyl)-2-{[(2-hydroxy-2-pyridin-4-ylethyl)(methyl)amino]methyl}-3,4-dimethyl-7-oxo-4,7-dihydrothieno[3,2-b]pyridine-6-carboxamide

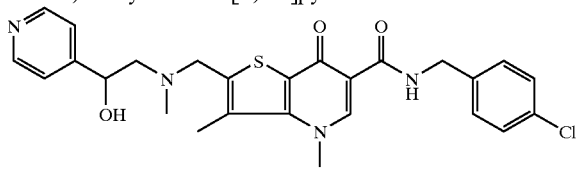

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 2-(methylamino)-1-pyridin-4-ylethanol (Arch. Pharm. Ber. Deut. Pharm. Ges. 1972, 305, 248–53) (58 mg, 0.38 mmol) and diisopropylethylamine (67 µL, 0.38 mmol) in dry DMF (5.0 mL) was stirred for 48 hours at room temperature. The solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (5 mL, dissolved with warming and then cooled to 0° C. overnight) gave the title compound (83 mg) as a white solid.

Physical characteristics are as follows:

$^1$H NMR (400 MHz, DMSO-d$_6$) δ 10.42 (1 H), 8.57 (1 H), 8.48 (2 H), 7.40 (2 H), 7.35 (4 H), 5.46 (1 H), 4.80 (1 H), 4.53 (2 H), 4.20 (3 H), 3.84 (2 H), 2.68 (2 H), 2.44 (3 H), 2.32 (3 H); MS (CI) for C$_{26}$H$_{27}$ClN$_4$O$_3$S m/z 511 (M+H)$^+$, 511, 363, 361, 153, 135, 122, 108, 106, 96, 94; HRMS (ESI+) calcd for C$_{26}$H$_{27}$ClN$_4$O$_3$S+H 511.1570, found 511.1567.

EXAMPLE 103

N-(4-chlorobenzyl)-2-{[[2-hydroxy-2-(4-morpholin-4-ylphenyl)ethyl](methyl)amino]methyl}-3,4-dimethyl-7-oxo-4,7-dihydrothieno[3,2-b]pyridine-6-carboxamide

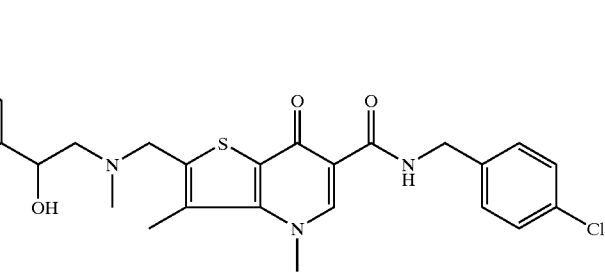

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 2-(methylamino)-1-(4-morpholin-4-ylphenyl)ethanol dihydrochloride (Preparation 89) (118 mg, 0.38 mmol) and diisopropylethylamine (180 μL, 1.0 mmol) in dry DMF (5.0 mL) was stirred for 48 hours at room temperature. The solution was diluted with water (10 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (76 mg) as a white solid.

Physical characteristics are as follows:

$^1$H NMR (400 MHz, DMSO-d$_6$) δ 10.44 (1 H), 8.58 (1 H), 7.41, 7.34 (4 H), 7.17 (2 H), 6.86 (2 H), 4.95 (1 H), 4.67 (1 H), 4.53 (2 H), 4.20 (3 H), 3.85, 3.78 (2 H), 3.72 (4 H), 3.05 (4 H), 2.6 (2 H), 2.46 (3 H), 2.31 (3 H); Anal. Found: C, 62.09; H, 5.94; N, 9.61. MS (CI) for C$_{31}$H$_{35}$ClN$_4$O$_4$S m/z 595 (M+H)$^+$, 363, 361, 220, 219, 206, 192, 190, 142, 96, 88; HRMS (ESI+) calcd for C$_{31}$H$_{35}$ClN$_4$O$_4$S+H 595.2145, found 595.2161.

EXAMPLE 104

N-(4-chlorobenzyl)-2-{[(2-hydroxy-3-phenylpropyl)(methyl)amino]methyl}-3,4-dimethyl-7-oxo-4,7-dihydrothieno[3,2-b]pyridine-6-carboxamide

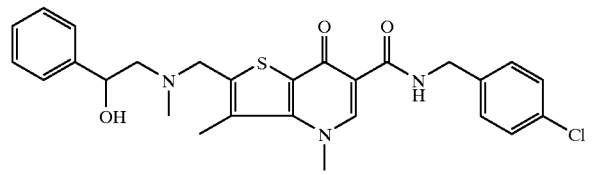

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 1-(methylamino)-3-phenylpropan-2-ol (Eur. J Med. Chem.—Chim. Ther. 1979, 14, 165–70)(63 mg, 0.38 mmol) and diisopropylethylamine (67 μL, 0.38 mmol) in dry DMF (5.0 mL) was stirred for 24 hours at room temperature. The solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (94 mg) as a white solid.

Physical characteristics are as follows:

$^1$H NMR (400 MHz, DMSO-d$_6$) δ 10.44 (1 H), 8.59 (1 H), 7.41, 7.33 (4 H), 7.2 (4 H), 7.15 (1 H), 4.54 (3 H), 4.22 (3 H), 3.8 (1 H), 3.79 (2 H), 2.88 (1 H), 2.6 (2 H), 2.5 (DMSO+3 H), 2.43 (2 H), 2.28 (3 H); Anal. Found: C, 63.80; H, 5.75; N, 8.01. MS (CI) for C$_{28}$H$_{30}$ClN$_3$O$_3$S m/z 524 (M+H)$^+$, 526, 524, 363, 362, 361, 166, 164, 152, 148, 96; HRMS (ESI+) calcd for C$_{28}$H$_{30}$ClN$_3$O$_3$S+H 524.1774, found 524.1777.

EXAMPLE 105

N-(4-chlorobenzyl)-2-{[(2-hydroxy-2-pyridin-3-ylethyl)(methyl)amino]methyl}-3,4-dimethyl-7-oxo-4,7-dihydrothieno[3,2-b]pyridine-6-carboxamide

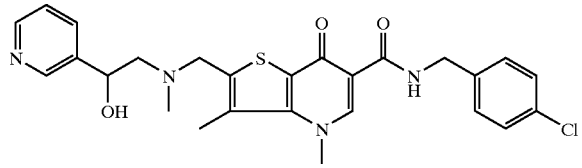

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 2-(methylamino)-1-pyridin-3-ylethanol hydrobromide (Arch. Pharm. 1961, 294 453–68)(89 mg, 0.38 mmol) and diisopropylethylamine (134 μL, 0.76 mmol) in dry DMF (5.0 mL) was stirred for 30 hours at room temperature. The solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (87 mg) as a white solid.

Physical characteristics are as follows:

$^1$H NMR (400 MHz, DMSO-d$_6$) δ 10.43 (1 H), 8.57 (1 H), 8.53 (1 H), 8.44 (1 H), 7.70 (1 H), 7.41, 7.34 (4 H), 7.31 (1 H), 5.38 (1 H), 4.82 (1 H), 4.53 (2 H), 4.20 (3 H), 3.8 (2 H), 2.7 (2 H), 2.43 (3 H), 2.31 (3 H); Anal. Found: C, 59.31; H, 5.13; N, 10.40. MS (CI) for C$_{26}$H$_{27}$ClN$_4$O$_3$S m/z 511 (M+H)$^+$, 361, 153, 135, 125, 122, 109, 108, 106, 94, 80; HRMS (ESI+) calcd for C$_{26}$H$_{27}$ClN$_4$O$_3$S+H 511.1570, found 511.1570.

EXAMPLE 106

N-(4-chlorobenzyl)-2-{[[2-hydroxy-2-(1H-indol-3-yl)ethyl](methyl)amino]methyl}-3,4-dimethyl-7-oxo-4,7-dihydrothieno[3,2-b]pyridine-6-carboxamide

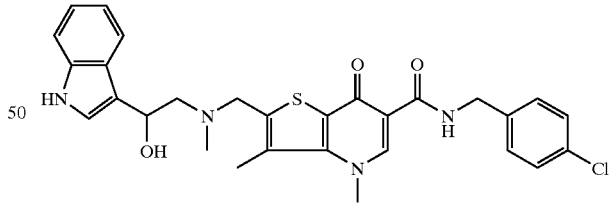

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 1-(1H-indol-3-yl)-2-(methylamino)ethanol (Khim.-Farm. Zh. 1970, 4, 5–9)(73 mg, 0.38 mmol) and diisopropylethylamine (67 μL, 0.38 mmol) in dry DMF (5.0 mL) was stirred for 48 hours at room temperature. The solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (112 mg) as a white solid.

Physical characteristics are as follows:

$^1$H NMR (400 MHz, DMSO-d$_6$) δ 10.85 (1 H), 10.45 (1 H), 8.57 (1 H), 7.51 (1 H), 7.41, 7.34 (4 H), 7.31 (1 H), 7.21 (1 H), 7.01 (1 H), 6.86 (1 H), 5.05 (1 H), 4.82 (1 H), 4.54 (2 H), 4.18 (3 H), 3.8 (2 H), 2.83 (2 H), 2.43 (3 H), 2.37 (3 H); Anal. Found: C, 62.33; H, 5.31; N, 10.05. MS (CI) for C$_{29}$H$_{29}$ClN$_4$O$_3$S m/z 549 (M+H)$^+$, 390, 363, 361, 173, 156, 146, 144, 142, 132, 118; HRMS (ESI+) calcd for C$_{29}$H$_{29}$ClN$_4$O$_3$S+H 549.1727, found 549.1730.

EXAMPLE 107

2-{[(2-[4-(aminosulfonyl)phenyl]-2-hydroxyethyl}(methyl)amino]methyl}-N-(4-chlorobenzyl)-3,4-dimethyl-7-oxo-4,7-dihydrothieno[3,2-b]pyridine-6-carboxamide

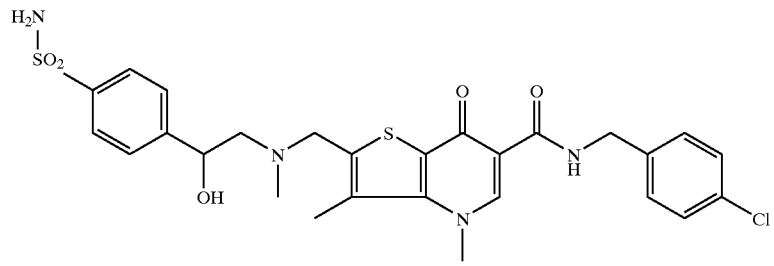

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 4-[1-hydroxy-2-(methylamino)ethyl]benzenesulfonamide (Preparation 48) (60 mg, 0.26 mmol) and diisopropylethylamine (67 μL, 0.38 mmol) in dry DMF (5.0 mL) was stirred for 72 hours at room temperature. The solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (5 mL, dissolved with warming and then cooled to 0° C. overnight) gave the title compound (69 mg) as a white solid.

Physical characteristics are as follows:

$^1$H NMR (400 MHz, DMSO-d$_6$) δ 10.42 (1 H), 8.58 (1 H), 7.75 (2 H), 7.51 (2 H), 7.40, 7.34 (4 H), 7.30 (2 H), 5.40 (1 H), 4.85 (1 H), 4.54 (2 H), 4.20 (3 H), 3.88, 3.78 (2 H), 2.7 (2 H), 2.46 (3 H), 2.32 (3 H); MS (EI+) for C$_{27}$H$_{29}$ClN$_4$O$_5$S$_2$, m/z 588 (M+), 222, 220, 193, 192, 164, 140, 106, 94, 77, 76; HRMS (ESI+) calcd for C$_{27}$H$_{29}$ClN$_4$O$_5$S$_2$+H 589.1346, found 589.1357.

Preparation 48

4-[1-Hydroxy-2-(methylamino)ethyl]benzenesulfonamide

To a solution of methyl amine (20 mL, 40 mmol, 2.0 M in methanol) was added 4-oxiran-2-ylbenzenesulfonamide (Preparation 49)(0.52 g, 2.6 mmol) at 0° C. The clear solution was warmed to room temperature and stirred overnight. The solvent and excess of methyl amine was evaporated to yield an oil. The crude oil was dissolved in methanol (5 mL), and stirred with resin (BioRad 50W×2, 1 g) for 4 hours. The resin was collected by filtration and washed with methanol (3×15 mL). The product on the resin was washed off with NH$_4$OH/CH$_3$OH (20 mL, 10% ammonium hydroxide aqueous solution (Aldrich, 29.4% NH$_3$) in methanol). The solution was concentrated to dryness, and treated with high vacuum to give the title compound (0.19 g) as a white solid.

Physical characteristics are as follows:

$^1$H NMR (400 MHz, DMSO-d$_6$) δ 7.77 (2 H), 7.53 (2 H), 4.74 (1 H), 2.64 (2 H), 2.32 (3 H); MS (ES+) for C$_9$H$_{14}$N$_2$O$_3$S, m/z 231 (M+H)$^+$, 213.

Preparation 49

4-Oxiran-2-ylbenzenesulfonamide

To a suspension of 4-sulfonamidostyrene (1.83 g, 0.01 mmol) and ammonium hydrogencarbonate (1.6 g, 0.02 mol) in acetonitrile/water (60 mL/30 mL) was added hydrogen peroxide (30% solution, 10 mL, 0.09). The mixture was kept in dark without stirring for 72 hours during which two portion of hydrogen peroxide (5 mL each) were introduced slowly. While HPLC showed all of the starting 4-sulfonamidostyrene was consumed, sodium thiosulfate solution (10%, 60 mL) was added slowly and stirred for 15 minutes. The mixture was extracted with dichloromethane (3×80 mL). The organic phases were combined, washed with brine and dried over magnesium sulfate. The solution was concentrated to give the crude title compound (0.52 g) as an oil.

Physical characteristics are as follows:

$^1$H NMR (400 MHz, DMSO-d$_6$) δ 7.78 (2 H), 7.31 (2 H), 3.84 (1 H), 3.12 (1 H), 2.69 (3 H).

EXAMPLE 108

N-(4-chlorobenzyl)-2-{[(3-hydroxy-2-phenylpropyl)(methyl)amino]methyl}-3,4-dimethyl-7-oxo-4,7-dihydrothieno[3,2-b]pyridine-6-carboxamide

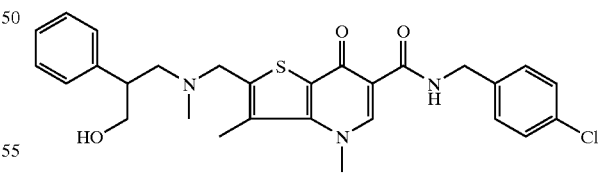

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 3-(methylamino)-2-phenylpropan-1-ol (DE 1261862 19680229 CAN 69:35694) (74 mg, 0.38 mmol) and diisopropylethylamine (67 μL, 0.38 mmol) in dry DMF (5 mL) was heated to 60° C., becoming a solution. The reaction was stirred for 7 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (86 mg) as a white solid.

Physical characteristics are as follows:

$^1$H NMR (400 MHz, DMSO-d$_6$) δ 10.43 (1 H), 8.57 (1 H), 7.41, 7.33 (4 H), 7.2 (5 H), 4.62 (1 H), 4.53 (2 H), 4.19 (3 H), 3.79 (3 H), 3.58 (1 H), 2.99 (1 H), 2.81 (1 H), 2.66 (1 H), 2.42 (3 H), 2.20 (3 H); Anal. Found: C, 63.68; H, 5.76; N, 7.98. MS (CI) for C$_{28}$H$_{30}$ClN$_3$O$_3$S m/z 524 (M+H)$^+$, 526, 524, 361, 166, 164, 134, 96, 61, 59, 58; HRMS (ESI+) calcd for C$_{28}$H$_{30}$ClN$_3$O$_3$S+H 524.1774, found 524.1768.

EXAMPLE 109

N-(4-chlorobenzyl)-2-{[[2-hydroxy-2-(1 H-pyrazol-5-yl)ethyl](methyl)amino]methyl}-3,4-dimethyl-7-oxo-4,7-dihydrothieno[3,2-b]pyridine-6-carboxamide

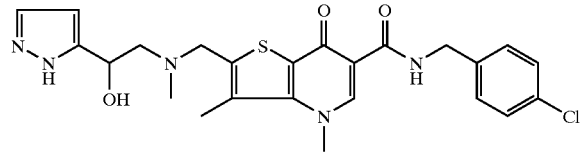

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 2-(methylamino)-1-(1H-pyrazol-5-yl)ethanol dihydrochloride Preparation 97) (67 mg, 0.38 mmol) and diisopropylethylamine (201 µL, 1.14 mmol) in dry DMF (5 mL) was heated to 60° C., becoming a solution. The reaction was stirred for 48 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (5 mL, dissolved with warming and then cooled to 0° C. overnight) gave the title compound (63 mg) as a white solid.

Physical characteristics are as follows:

$^1$H NMR (400 MHz, DMSO-d$_6$) δ 12.5 (1 H), 10.44 (1 H), 8.57 (1 H), 7.5 (1 H), 7.41, 7.33 (4 H), 6.16 (1 H), 4.85 (1 H), 4.53 (2 H), 4.21 (3 H), 3.84 (2 H), 2.75 (2 H), 2.49 (3 H), 2.32 (3 H); Anal. Found: C, 55.56; H, 5.43; N, 13.33. MS (CI) for C$_{24}$H$_{26}$ClN$_5$O$_3$S m/z 500 (M+H)$^+$, 502, 501, 500, 361, 142, 140, 128, 114, 96, 61; HRMS (ESI+) calcd for C$_{24}$H$_{26}$ClN$_5$O$_3$S+H 500.1523, found 500.1523.

EXAMPLE 110

N-(4-chlorobenzyl)-2-{[[2-hydroxy-2-(1-methyl-1H-pyrrol-2-yl)ethyl](methyl)amino]methyl}-3,4-dimethyl-7-oxo-4,7-dihydrothieno[3,2-b]pyridine-6-carboxamide

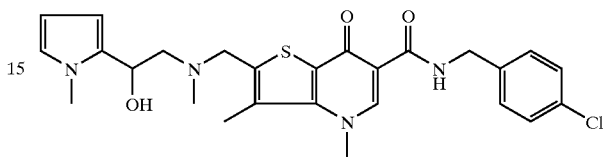

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 2-(methylamino)-1-pyrimidin-2-ylethanol (Preparation 62)(63 mg, 0.38 mmol) and diisopropylethylamine (67 µL, 0.3.8 mmol) in dry DMF (5 mL) was heated to 60° C., becoming a solution. The reaction was stirred for 24 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (86 mg) as a white solid.

Physical characteristics are as follows:

$^1$H NMR (400 MHz, DMSO-d$_6$) δ 10.43 (1 H), 8.58 (1 H), 7.41, 7.33 (4 H), 6.62 (1 H), 5.90 (1 H), 5.86 (1 H), 4.88 (1 H), 4.79 (1 H), 4.53 (2 H), 4.21 (3 H), 3.85 (2 H), 3.58 (3 H), 2.81 (1 H), 2.50 (DMSO+3 H), 2.31 (3 H); Anal. Found: C, 59.78; H, 5.80; N, 10.69. MS (CI) for C$_{26}$H$_{29}$ClN$_4$O$_3$S m/z 513 (M+H)$^+$, 513, 361, 137, 127, 124, 110, 108, 96, 82, 61; HRMS (ESI+) calcd for C$_{26}$H$_{29}$ClN$_4$O$_3$S+H 513.1727, found 513.1721.

EXAMPLE 111

N-(4-chlorobenzyl)-2-{[{2-hydroxy-2-[4-(hydroxymethyl)phenyl]ethyl}(methyl)amino]methyl}-3,4-dimethyl-7-oxo-4,7-dihydrothieno[3,2-b]pyridine-6-carboxamide

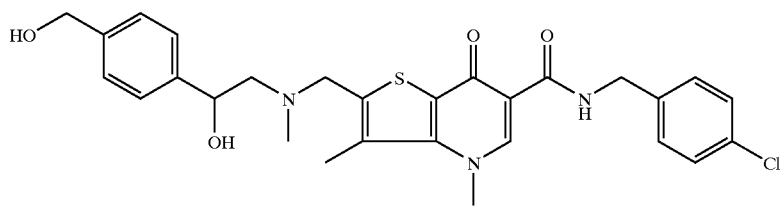

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 1-[4-(hydroxymethyl)phenyl]-2-(methylamino)ethanol (Preparation 93) (69 mg, 0.38 mmol) and diisopropylethylamine (67 µL, 0.38 mmol) in dry DMF (5 mL) was heated to 60° C., becoming a solution. The reaction was stirred for 5 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile/DMF (15 mL/1 mL, dissolved with warming DMF, added with acetonitrile, and then cooled to 0° C. overnight) gave the title compound (92 mg) as a white solid.

Physical characteristics are as follows:

$^1$H NMR (400 MHz, DMSO-d$_6$) δ 10.44 (1 H), 8.58 (1 H), 7.41, 7.34 (4 H), 7.28, 7.22 (4 H), 5.10 (2 H), 4.75 (1 H), 4.53 (2 H), 4.46 (2 H), 4.20 (3 H), 3.84 (2 H), 2.6 (2 H), 2.47 (3 H), 2.32 (3 H); Anal. Found: C, 61.89; H, 5.60; N, 7.96. MS (CI) for C$_{28}$H$_{30}$ClN$_3$O$_4$S m/z 540 (M+H)$^+$, 361, 148, 142, 140, 136, 122, 120, 108, 106, 59; HRMS (ESI+) calcd for C$_{28}$H$_{30}$ClN$_3$O$_4$S+H 540.1724, found 540.1710.

EXAMPLE 112

N-(4-chlorobenzyl)-2-{[{2-hydroxy-2-[4-(2-hydroxyethoxy)phenyl]ethyl}(methyl)amino]methyl}-3,4-dimethyl-7-oxo-4,7-dihydrothieno[3,2-b]pyridine-6-carboxamide

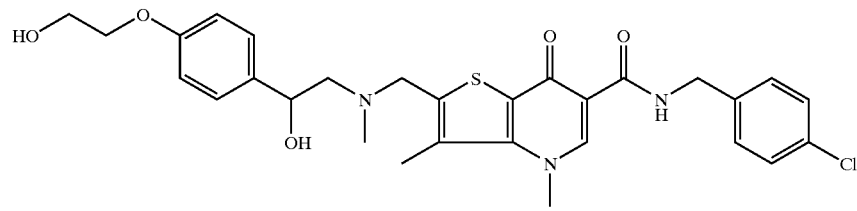

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 1-[4-(2-hydroxyethoxy)phenyl]-2-(methylamino)ethanol (Preparation 83) (70 mg, 0.38 mmol) and diisopropylethylamine (67 µL, 0.38 mmol) in dry DMF (5 mL) was heated to 60° C., becoming a solution. The reaction was stirred for 4 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (5 mL, dissolved with warming and then cooled to 0° C. overnight) gave the title compound (82 mg) as a white solid.

Physical characteristics are as follows:

$^1$H NMR (400 MHz, DMSO-d$_6$) δ 10.44 (1 H), 8.58 (1 H), 7.41, 7.34 (4 H), 7.21 (2 H), 6.85 (2 H), 5.03 (1 H), 4.85 (1 H), 4.70 (1 H), 4.53 (2 H), 4.20 (3 H), 3.94 (2 H), 3.82 (2 H), 3.69 (2 H), 2.6 (2 H), 2.46 (3 H), 2.31 (3 H); Anal. Found: C, 60.20; H, 5.71; N, 7.24. MS (FAB) for C$_{29}$H$_{32}$ClN$_3$O$_5$S m/z 570 (M+H)$^+$, 573, 572, 571, 570, 568, 402, 361, 360, 220, 192; HRMS (FAB) calcd for C$_{29}$H$_{32}$ClN$_3$O$_5$S+H 570.1829, found 570.1838.

EXAMPLE 113

2-{[[2-(1,3-benzodioxol-5-yl)-2-hydroxyethyl](methyl)amino]methyl}-N-(4-chlorobenzyl)-3,4-dimethyl-7-oxo-4,7-dihydrothieno[3,2-b]pyridine-6-carboxamide

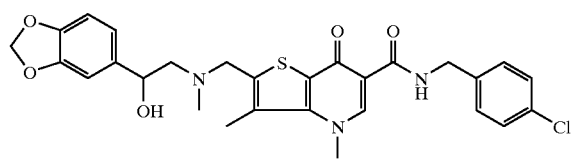

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 1-(1,3-benzodioxol-5-yl)-2-(methylamino)ethanol (*Journal of Organometallic Chemistry*, 1998, 339, 267–75) (74 mg, 0.38 mmol) and diisopropylethylamine (67 µL, 0.38 mmol) in dry DMF (5 mL) was heated to 60° C., becoming a solution. The reaction was stirred for 7 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (101 mg) as a white solid.

Physical characteristics are as follows:

$^1$H NMR (400 MHz, DMSO-d$_6$) δ 10.44 (1 H), 8.57 (1 H), 7.41, 7.34 (4 H), 6.86 (1 H), 6.81 (2 H), 5.96 (2 H), 5.09 (1 H), 4.67 (1 H), 4.53 (2 H), 4.20 (3 H), 3.81 (2 H), 2.6 (2 H), 2.47 (3 H), 2.30 (3 H); Anal. Found: C, 60.00; H, 5.13; N, 7.44. MS (FAB) for C$_{28}$H$_{28}$ClN$_3$O$_5$S m/z 554 (M+H)$^+$, 556, 555, 554, 552, 402, 361, 360, 359, 220, 192; HRMS (ESI+) calcd for C$_{28}$H$_{28}$ClN$_3$O$_5$S+H 554.1516, found 554.1501.

EXAMPLE 114

N-(4-chlorobenzyl)-2-{[(2-{4-[(dimethylamino)methyl]phenyl}-2-hydroxyethyl)(methyl)amino]methyl}-3,4-dimethyl-7-oxo-4,7-dihydrothieno[3,2-b]pyridine-6-carboxamide

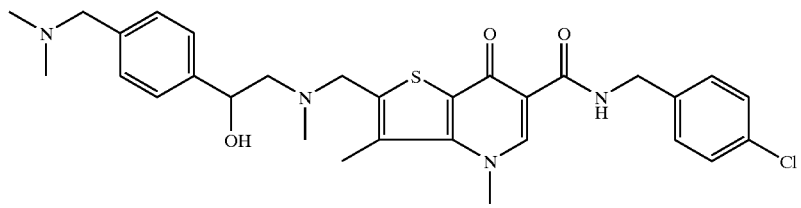

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 1-{4-[(dimethylamino)methyl]phenyl}-2-(methylamino)ethanol (Preparation 50) (89 mg, 0.43 mmol) and diisopropylethylamine (67 μL, 0.38 mmol) in dry DMF (5 mL) was heated to 60° C., becoming a solution. The reaction was stirred for 7 hours at that temperature. After cooling to room temperature, the solution was diluted with water (7 mL). The resulting milky mixture was concentrated to dryness. The residue was purified with a silica gel chromatotron plate to yield the title compound (36 mg) as a white solid.

Physical characteristics are as follows:
$^1$H NMR (400 MHz, DMSO-d$_6$) δ 10.44 (1 H), 8.57 (1 H), 7.41, 7.34 (4, H), 7.29, 7.21 (4 H), 5.13 (1 H), 4.77 (1 H), 4.53 (2 H), 4.20 (3 H), 3.83 (2 H), 3.4 (2 H), 2.6 (2 H), 2.46 (3 H), 2.32 (3 H), 2.16 (6 H); Anal. Found: C, 61.66; H, 6.26; N, 9.48. MS (CI) for C$_{30}$H$_{35}$ClN$_4$O$_3$S m/z 567 (M+H)$^+$, 363, 361, 209, 165, 164, 74, 63, 61, 60, 58; HRMS (ESI+) calcd for C$_{30}$H$_{35}$ClN$_4$O$_3$S+H 567.2197, found 567.2202.

Preparation 50

1-{4-[(Dimethylamino)methyl]phenyl}-2-(methylamino)ethanol

To a solution of HCl-dioxane (20 mL, 4.0 M HCl in dioxane) was added tert-butyl 2-{4-[(dimethylamino)methyl]phenyl}-2-hydroxyethyl(methyl)carbamate (124 mg, 0.40 mmol). The mixture was stirred at room temperature for 16 hours. The solvent and HCl was evaporated. After treated with high vacuum for 15 minutes, the residue was dissolved in methanol (2 mL) and treated with resin (BioRad 50w×2, 0.20 g) for 3 hours. The resin was collected by filtration and washed with methanol. The product on the resin was washed off with NH$_4$OH/CH$_3$OH (20 mL, 10% ammonium hydroxide aqueous solution (Aldrich, 29.4% NH$_3$) in methanol). The solution was concentrated to dryness, and treated with high vacuum to give the title compound (89 mg) as an oil.

Physical characteristics are as follows:
$^1$H NMR (400 MHz, MeOH-d$_4$) δ 7.35 (4, H), 4.80 (1 H), 3.48 (2 H), 2.76 (2 H), 2.45 (3 H), 2.25 (6 H); MS (ES+) for C$_{12}$H$_{20}$N$_2$O m/z 209 (M+H)$^+$.

Preparation 51 tert-Butyl 2-{4-[(dimethylamino)methyl]phenyl}-2-hydroxyethyl(methyl)carbamate

To a solution of tert-butyl dimethylcarbamate (350 mg, 2.4 mmol) and tetramethylethylenediamine (511 mg, 4.4 mmol) in THF (anhydrous, 10 mL) was added sec-butyllithium (1.4 M in cyclohexane, 2.2 mL, 3.1 mmol) at −78° C. The mixture was stirred at that temperature for 1 hour before 4-[(dimethylamino)methyl]benzaldehyde (J.Heterocycl.Chem.; 26; 1989; 1325–1330)(280 mg, 1.7 mmol) was introduced. The reaction mixture was stirred for 2 hours, warmed to room temperature and stirred for 1 hour. Saturated ammonium chloride aqueous solution (10 mL) was added to quench the reaction after the reaction mixture was cooled to −78° C. The organic phase was separated and the aqueous phase was extracted with dichloromethane. The organic phases were combined, washed with brine and dried over sodium sulfate and concentrated. The residue was purified with a silica gel column to give the title compound (0.40 g) as a white solid.

Physical characteristics are as follows: MS (ES+) for C$_{17}$H$_{28}$N$_2$O$_3$ m/z 309 (M+H)$^+$.

EXAMPLE 115

N-(4-chlorobenzyl)-2-{[(2-hydroxy-2-quinolin-2-ylethyl)(methyl)amino]methyl}-3,4-dimethyl-7-oxo-4,7-dihydrothieno[3,2-b]pyridine-6-carboxamide A mixture of N-(4-chlorobenzyl)-2-(chloromethyl)-3,4-dimethyl-7-oxo-4,7-dihydrothieno[3,2-b]pyridine-6-carboxamide (150 mg, 0.38 mmol), 2-(methylamino)-1-quinolin-2-ylethanol (Preparation 63)(150 mg, 0.74 mmol) and diisopropylethylamine (134 μL, 0.76 mmol) in dry DMF (5 mL) was heated to 60° C., becoming a solution. The reaction was stirred for 6 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (126 mg) as a white solid.

Physical characteristics are as follows:
$^1$H NMR (400 MHz, DMSO-d$_6$) δ 10.42 (1 H), 8.56 (1 H), 8.31 (1 H), 7.93 (2 H), 7.70 (1 H), 7.64 (1 H), 7.55 (1 H), 7.41, 7.34 (4 H), 5.57 (1 H), 4.98 (1 H), 4.53 (2 H), 4.12 (3 H), 3.85 (2 H), 2.98, 2.82 (2 H), 2.39 (3 H), 2.36 (3 H); Anal. Found: C, 64.14; H, 5.35; N, 9.94. MS (CI) for C$_{30}$H$_{29}$ClN$_4$O$_3$S m/z 561 (M+H)$^+$, 563, 562, 561, 172, 158, 144, 130, 96, 69, 61; HRMS (ESI+) calcd for C$_{30}$H$_{29}$ClN$_4$O$_3$S+H 561.1727, found 561.1711.

EXAMPLE 116

N-(4-chlorobenzyl)-2-{[[2-hydroxy-2-(6-methoxypyridin-3-yl)ethyl](methyl)amino]methyl}-3,4-dimethyl-7-oxo-4,7-dihydrothieno[3,2-b]pyridine-6-carboxamide

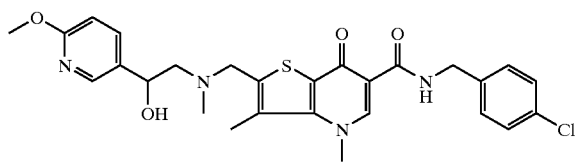

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 1-(6-methoxypyridin-3-yl)-2-(methylamino)ethanol dihydrochloride (Preparation 52) (97 mg, 0.38 mmol) and diisopropylethylamine (199 µL, 1.2 mmol) in dry DMF (5 mL) was heated to 60° C., becoming a solution. The reaction was stirred for 6 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (86 mg) as a white solid.

Physical characteristics are as follows:

$^1$H NMR (400 MHz, DMSO-d$_6$) δ 10.43 (1 H), 8.57 (1 H), 8.08 (1 H), 7.63 (1 H), 7.41, 7.33 (4 H), 6.73 (1 H), 5.22 (1 H), 4.73 (1 H), 4.53 (2 H), 4.20 (3 H), 3.80 (5 H), 2.72, 2.60 (2 H), 2.45 (3 H), 2.30 (3 H); MS (CI) for C$_{27}$H$_{29}$ClN$_4$O$_4$S m/z 541 (M+H)$^+$, 152, 142, 140, 138, 136, 110, 108, 96, 61, 58; HRMS (ESI+) calcd for C$_{27}$H$_{29}$ClN$_4$O$_4$S+H 541.1676, found 541.1685.

Preparation 52

1-(6-Methoxypyridin-3-yl)-2-(methylamino)ethanol dihydrochloride

To a solution of HCl-dioxane (4.0 M, 50 mL) was added tert-butyl 2-hydroxy-2-(6-methoxypyridin-3-yl)ethyl (methyl)carbamate (1.0 g, 3.5 mmol). The suspension was stirred at room temperature for 16 hours. The solvent and excess HCl was evaporated, leaving a white solid. The solid was dissolved in methanol and purified with a silica gel column, diluting with 1% NH$_4$OH/5% Methanol/dichloromethane, to yield the title compound (0.63 g) as a colorless oil.

Physical characteristics are as follows:

$^1$H NMR (400 MHz, DMSO-d$_6$) δ 8.10 (1 H), 7.66 (1 H), 6.77 (1 H), 4.65 (1 H), 3.83 (3 H), 2.65 (2 H), 2.32 (3 H); MS (CI) for C$_9$H$_{14}$N$_2$O$_2$ m/z 183 (M+H)$^+$, 183, 167, 165, 152, 139, 138, 136, 110, 96, 61; HRMS (ESI+) calcd for C$_9$H$_{14}$N$_2$O$_{2+H}$ 183.1133, found 183.1139.

Preparation 53 tert-Butyl 2-hydroxy-2-(6-methoxypyridin-3-yl) ethyl(methyl)carbamate

To a solution of tert-butyl dimethylcarbamate (1.8 g, 0.012 mol) and tetramethylethylenediamine (2.6 g, 0.022 mol) in THF (anhydrous, 30 mL) was added sec-butyllithium (1.4 M in cyclohexane, 11 mL, 0.015 mmol) at −78° C. The mixture was stirred at that temperature for 30 minutes before a solution of 6-methoxy-3-pyridinecarboxaldehyde (J.Org.Chem. 55; 1; 1990; 69–73) (1.4 g, 0.01 mol, in 5 mL of dry THF) was introduced. The reaction mixture was stirred for 30 minutes, warmed to room temperature and stirred for 3 hours. Saturated ammonium chloride aqueous solution (20 mL) was added to quench the reaction after the reaction mixture was cooled to −78° C. The organic phase was separated and the aqueous phase was extracted with dichloromethane. The organic phases were combined, washed with brine and dried over sodium sulfate and concentrated. The residue was purified with a silica gel column to give the title compound (1.2 g) as a white solid.

Physical characteristics are as follows:

$^1$H NMR (400 MHz, DMSO-d$_6$) δ 8.03 (1 H), 7.62 (1 H), 6.80 (1 H), 5.50 (1 H), 4.71 (1 H), 3.82 (3 H), 3.3 (2 H), 2.78 (3 H), 1.3 (9 H).

EXAMPLE 117

N-(4-chlorobenzyl)-2-{[[2-hydroxy-2-(1H-imidazol-2-yl)ethyl](methyl)amino]methyl}-3,4-dimethyl-7-oxo-4,7-dihydrothieno[3,2-b]pyridine-6-carboxamide

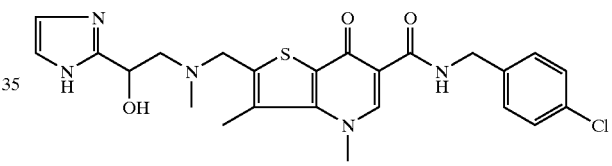

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 1-(1H-imidazol-2-yl)-2-(methylamino)ethanol dihydrochloride (Preparation 99) (82 mg, 0.38 mmol) and diisopropylethylamine (230 µL, 1.3 mmol) in dry DMF (5 mL) was heated to 60° C., becoming a solution. The reaction was stirred for 5 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (61 mg) as a white solid.

Physical characteristics are as follows:

$^1$H NMR (400 MHz, DMSO-d$_d$) δ 11.88 (1 H), 10.44 (1 H), 8.57 (1 H), 7.41, 7.33 (4 H), 6.89 (2 H), 5.44 (1 H), 4.81 (1 H), 4.53 (2 H), 4.21 (3 H), 3.82 (2 H), 2.90, 2.75 (2 H), 2.48 (3 H), 2.31 (3 H); MS (EI+) for C$_{24}$H$_{26}$ClN$_5$O$_3$S m/z 499 (M$^+$), 402, 362, 360, 359, 222, 220, 193, 140, 77, 68; HRMS (ESI+) calcd for C$_{24}$H$_{26}$ClN$_5$O$_3$S+H 500.1523, found 500.1513.

EXAMPLE 118

N-(4-chlorobenzyl)-2-{[[2-hydroxy-2-(4-methoxyphenyl)ethyl](methyl)amino]methyl}-3,4-dimethyl-7-oxo-4,7-dihydrothieno[3,2-b]pyridine-6-carboxamide

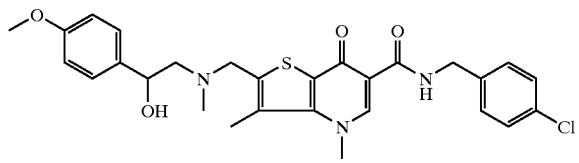

A mixture of N-(4-chlorobenzyl)-2-(chloromethyl)-3,4-dimethyl-7-oxo-4,7-dihydrothieno[3,2-b]pyridine-6-carboxamide (80 mg, 0.20 mmol), 1-(4-methoxyphenyl)-2-(methylamino)ethanol (*Tetrahedron* 1999, 55, 4831–4842) (58 mg, 0.32 mmol) and diisopropylethylamine (67 µL, 0.38 mmol) in dry DMF (5 mL) was heated to 60° C., becoming a solution. The reaction was stirred for 16 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving a white solid. Recrystallization from acetonitrile (10 mL, dissolved with warming and then cooled to 0° C. overnight) gave the title compound (49 mg) as a white solid.

Physical characteristics are as follows:
$^1$H NMR (400 MHz, DMSO-d$_6$) δ 10.44 (1 H), 8.58 (1 H), 7.42, 7.34 (4 H), 7.24 (2 H), 6.85 (2 H), 5.03 (1 H), 4.72 (1 H), 4.54 (2 H), 4.21 (3 H), 3.83 (2 H), 3.72 (3 H), 2.68, 2.54 (2 H), 2.47 (3 H), 2.31 (3 H); Anal. Found: C, 61.72; H, 5.71; N, 7.74. MS (CI) for C$_{28}$H$_{30}$ClN$_3$O$_4$S m/z 540 (M+H)$^+$, 542, 540, 363, 361, 182, 168, 164, 154, 151, 137; HRMS (ESI+) calcd for C$_{28}$H$_{30}$ClN$_3$O$_4$S+H 540.1724, found 540.1743.

EXAMPLE 119

N-(4-chlorobenzyl)-2-{[(2-hydroxyethyl)(methyl)amino]methyl}-3,4-dimethyl-7-oxo-4,7-dihydrothieno[3,2-b]pyridine-6-carboxamide

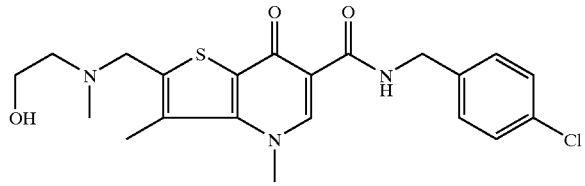

A mixture of N-(4-chlorobenzyl)-2-(chloromethyl)-3,4-dimethyl-7-oxo-4,7-dihydrothieno[3,2-b]pyridine-6-carboxamide (100 mg, 0.25 mmol), 2-(methylamino)ethanol (40 mg, 0.53 mmol) and diisopropylethylamine (67 µL, 0.38 mmol) in dry DMF (5 mL) was heated to 60° C., becoming a solution. The reaction was stirred for 7 hours at that temperature. After cooling to room temperature, the solution was diluted with water (15 mL). The resulting milky suspension was stirred vigorously for 30 minutes, and then left standing overnight at room temp. The mixture was filtered, and the collected solid was washed with water and dried in vacuo, leaving the title compound (106 mg) as a white solid.

Physical characteristics are as follows:
$^1$H NMR (400 MHz, DMSO-d$_6$) δ 10.44 (1 H), 8.58 (1 H), 7.41, 7.34 (4 H), 4.54 (2 H), 4.49 (1 H), 4.22 (3 H), 3.78 (2 H), 3.54 (2 H), 2.5 (DMSO+5 H), 2.29 (3 H); Anal. Found: C, 57.58; H, 5.74; N, 9.33. MS (EI) m/z for C$_{21}$H$_{24}$ClN$_3$O$_3$S 433 (M$^+$), 435, 433, 402, 361, 359, 266, 220, 193, 192, 86; HRMS (ESI+) calcd for C$_{21}$H$_{24}$ClN$_3$O$_3$S+H 434.1305, found 434.1283.

Preparation 54

N-[4-(2-bromoacetyl)phenyl]acetamide

To a suspension of 4-acetamidoacetophenone (Lancaster, 5.32 g, 0.03 mol) in 1,4-dioxane/diethyl ether (100 mL, 1:2, v/v) was added bromine (1.53 mL, 0.03 mol) via a syringe. The reaction mixture was stirred at room temperature for 4 hours until the color of the mixture was changed from brown to white. The solid was collected by filtration, washed with diethyl ether, and dried under high vacuum to give the title compound as a white solid (4.8 g).

Physical characteristics are as follows:
$^1$H NMR (400 MHz, DMSO-d$_6$) δ 10.36 (1 H), 7.96 (2 H), 7.73 (2 H), 4.85 (2 H), 2.10 (3 H); MS (ESI+) for C$_{10}$H$_{10}$BrNO$_2$ m/z 256 (M+H)$^+$, 258.

Preparation 55

N-[4-(2-bromo-1-hydroxyethyl)phenyl]acetamide

To a solution of N-[4-(2-bromoacetyl)phenyl]acetamide (2.1 g, 0.0082 mol, in 30 mL of methanol) was introduced solid NaBH$_4$ (1.0 g, 0.026 mol) at 0° C. and stirred at that temperature for 15 minutes. The mixture was diluted with diethyl ether (20 mL) and water (20 mL). The ether phase was separated and the aqueous phase was extracted with diethyl ether. The ether phases were combined and washed with brine, dried. Purification on a silica gel column gave the title compound as a white solid (0.40 g).

Physical characteristics are as follows:
$^1$H NMR (400 MHz, DMSO-d$_6$) δ 9.92 (1 H), 7.52 (2 H), 7.29 (2 H), 5.73 (1 H), 4.72 (1 H), 3.61 (1 H), 3.53 (1 H), 2.02 (3 H); MS (ESI+) for C$_{10}$H$_{12}$BrNO$_2$ m/z 258 (M+H)$^+$, 260.

Preparation 56

N-{4-[1-hydroxy-2-(methylamino)ethyl]phenyl}acetamide

To a solution of N-[4-(2-bromo-1-hydroxyethyl)phenyl]acetamide (0.40 g, in 10 mL of methanol) was introduced methylamine (10 mL, 2.0 M in methanol) at 0° C. The reaction mixture was warmed to room temperature after 30 minutes, and stirred at that temperature for 2 hours. The solvent and excess methylamine was evaporated. The residue was dissolved in methanol (5 mL) and stirred with resin (BioRad 50W×2, 0.5 g) overnight. The resin was collected by filtration, washed with methanol. The product on the resin was washed off with NH$_4$OH/CH$_3$OH (10% NH$_4$OH aqueous solution (Aldrich, 29.4% NH$_3$) in methanol, v/v). The solution was concentrated to give the title compound as a white solid (0.16 g).

Physical characteristics are as follows:
$^1$H NMR (400 MHz, DMSO-d$_6$) δ 9.89 (1 H), 7.50 (2 H), 7.23 (2 H), 5.15 (1 H), 4.56 (1 H), 2.59, 2.53 (2 H), 2.29 (3 H), 2.02 (3 H); MS (ESI+) for C$_{11}$H$_{16}$N$_2$O$_2$ m/z 209 (M+H)$^+$, 191.

Preparation 57

2-{1-[(Triisopropylsilyl)oxy]vinyl}pyrimidine

2-Acetylpyrimidine (Khim. Geterotsikl. Soedin., (7), 958–62; 1981)(7.37 g, 60.4 mmol) and DIEA (23.4 g, 181.2 mmol) were dissolved in dry $CH_2Cl_2$ under $N_2$ then cooled in an ice bath. TIPS-triflate (17.9 ml, 20.4 g, 66.4 mmol) was added over 2–3 min and stirred over night. The solvent was evaporated and the residue treated with ether (200 ml), filtered and washed with sat. sodium bicarbonate solution (2×50 ml). Evaporation gave a quantitative yield of the silyl ether as a red oil.

Physical characteristics are as follows: HRMS (FAB) calcd for $C_{15}H_{26}N_2OSi+H$ 279.1892, found 279.1898. $^1H$ NMR (300 MHz, $CDCl_3$) δ 1.15 (18 H), 1.31 (3 H), 4.90 (1 H), 5.82 (1 H), 7.16 (1 H), 8.74 (2 H).

Preparation 58

2-{2-Chloro-1-[(triisopropylsilyl)oxy]ethenyl}pyrimidine. 737980

N-chlorosuccinimide (9.97 g, 74.7 mmol) was added to a solution of 2-{1-[(Triisopropylsilyl)oxy]vinyl}pyrimidine (17.3 g, 62.2 mmol) in dry THF (120 ml) under $N_2$ then heated at 65° for 5 hr. After cooling, ether (275 ml) was added and then washed with sat sodium bicarbonate solution (2×100 ml). The organic layer was dried over sodium sulfate, filtered and evaporated to leave an amber oil. This oil was dissolved in hexane (250 ml), treated with $MgSO_4$ and filtered. Evaporation afforded the product as a yellow oil in quantitative yield.

Physical characteristics are as follows: HRMS (FAB) calcd for $C_{15}H_{25}ClN_2OSi+H$ 313.1503, found 313.1509. $^1H$ NMR (300 MHz, $CDCl_3$) δ 1.13 (18 H), 1.33 (3 H), 6.97 (1 H), 7.17 (1 H), 8.68 (2 H).

Preparation 59

2-Chloro-1-pyrimidin-2-ylethanone

2-{2-Chloro-1-[(triisopropylsilyl)oxy]ethenyl}pyrimidine (19.4 g, 62.2 mmol) was dissolved in acetonitrile (90 ml) and treated with 48% HF (10 ml) for 4 hr. Sat. sodium bicarbonate solution (ca. 250 ml) was then added carefully to pH7 and the mixture extracted with $CH_2Cl_2$ (3×200 ml). After drying ($Na_2SO_4$), filtration and evaporation two oils were obtained, the upper colorless oil was decanted off and discarded and the lower oil crystallized to an oily solid. Chromatography over silica gel (500 g) eluting with 2.5% MeOH—$CHCl_3$ gave the product as a pale yellow solid (6.50 g) mp:73–80°.

Physical characteristics are as follows: Anal. Found: C, 46.05; H, 3.09; N, 17.93.

Preparation 60

2-Chloro-1-pyrimidin-2-ylethanol

2-Chloro-1-pyrimidin-2-ylethanone (6.15 g, 39.3 mmol) was dissolved in ethanol (125 ml) and $CeCl_3.7H_2O$ (14.64 g, 39.3 mmol) was added. Stirring was continued for 10 min then sodium borohydride (1.49 g, 39.3 mmol) was added over 2 min. After 1 hr the solid was filtered and the filtrate evaporated. Sat. ammonium chloride solution (25 ml) was added followed by brine (250 ml) and the mixture adjusted to pH3–4 with 1N.HCl. Extraction with ethyl acetate (3×250 ml) afforded an amber oil which was chromatographed over silica gel (150 g) to give the product as a pale yellow oil (3.85 g) Physical characteristics are as follows: Anal. Found: C, 45.08; H, 4.47; N, 17.46.

Preparation 61

2-(Methylamino)-1-pyrimidin-2-ylethanol

In a pressure bottle was placed 2-chloro-1-pyrimidin-2-ylethanol (3.525 g, 22.24 mmol), sodium iodide (0.344 g, 2.29 mmol) and a 2M. methylamine solution (160 ml, 320 mmol) in methanol. The bottle was sealed and heated at 62° for 17 hr. The solvent was evaporated and the residue stirred with 10% MeOH—$CHCl_3$. Filtration and evaporation gave a dark oil that was chromatographed over silica gel (90 g) eluting with 5–10% MeOH—$CH_2Cl_2$ containing 1% triethylamine The product was obtained as an amber oil (1.625 g).

Physical characteristics are as follows:

$^1H$ NMR (400 MHz, $CDCl_3$) δ 2.53 (3 H), 3.03 (1 H), 3.21 (1 H), 3.66 (2 H), 5.03 (1 H), 7.26 (1 H), 8.77 (2H); HRMS (ESI) calcd for $C_7H_{11}N_3O+H$ 154.0980, found 154.0979.

Preparation 62

2-(methylamino)-1-(1-methyl-1H-pyrrol-2-yl)ethanol 2-chloro-1-(1-methyl-1H-pyrrol-2-yl)ethanol (Croce, P. D.; Ferraccioli, R.; Ritieni, A. *Synthesis*, 1990, 212–213) (2.05 g) is dissolved in methanol (40 mL) and added dropwise to a 2.0 M solution of methylamine in methanol (65 mL) at 0° C. The reaction mixture is stirred at 0° C. for 1 h and then allowed to warm to room temperature. The reaction mixture is stirred at room temperature for 18 h and then cooled to 0° C. Sodium borohydride (0.738 g) in $H_2O$ (40 mL) is added dropwise. The reaction mixture is stirred at 0° C. for 30 min and then allowed to warm to room temperature. The reaction mixture is stirred at room temperature for 18 h. An additional 0.738 g (19.5 mmol) of sodium borohydride is added and the reaction mixture is stirred at room temperature for 18 h. The reaction is quenched with a 1 N HCl solution and then concentrated in vacuo to remove methanol. The aqueous layer is adjusted to pH 12 with a 2 N NaOH solution and extracted with $CH_2Cl_2$ (4×100 mL). The combined organic layers are dried ($MgSO_4$), filtered, and concentrated in vacuo. The resulting yellow oil is crystallized from ethyl acetate to yield 0.772 g of the title compound as a white solid.

Physical characteristics are as follows:

Mp 64–66° C.; $^1H$ NMR (400 MHz, DMSO-$d_6$) δ 6.63–6.62, 5.99–5.86, 5.00, 4.62–4.59, 3.59, 2.81–2.68, 2.32. MS (ESI+) m/z 155 $(M+H)^+$.

Preparation 63

2-(methylamino)-1-quinolin-2-ylethanol

Potassium hydroxide (3.21 g) and $H_2O$ (0.13 mL) are added to acetonitrile (50 mL). Trimethylsulfonium iodide (5.84 g) and 2-quinoline carboxaldehyde (4.50 g) are then added. The reaction mixture is heated to 60° C. for 4 h. The reaction mixture is allowed to cool to room temperature and is diluted with $Et_2O$ (25 mL) The precipitate is filtered off. $^1H$ NMR of an aliquot of the filtrate showed mostly starting material and a small amount of the desired epoxide. The filtrate is concentrated in vacuo and the residue is re-subjected to the reaction conditions above and heated to 60° C. for 1 h. The reaction mixture is allowed to cool to room temperature and is diluted with Et2O (25 mL). The precipitate is filtered off and the filtrate is concentrated in vacuo. The resulting crude epoxide (5.5 g) is dissolved in methanol (20 mL) and added to a 2.0 M solution of methylamine in methanol (100 mL). The reaction mixture is heated to reflux for 1 h. The reaction mixture is allowed to cool to room temperature and concentrated in vacuo. The resulting brown oil is purified via column chromatography ($CHCl_3$/methanol, 95/5, 90/10; $CHCl_3$/methanol/$NH_4OH$, 90/10/1) to yield 1.191 g of the title compound as a yellow-green oil.

Physical characteristics are as follows:

$^1$H NMR (400 MHz, DMSO-$d_6$) δ 8.36–8.33, 7.98–7.94, 7.76–7.67, 7.59–7.54, 5.63, 4.88–4.84, 2.89–2.72, 2.32. MS (ESI+) m/z 203 (M+H)$^+$.

Preparation 64

1-(3-Furyl)-2-(methylamino)ethanol [35966-MMC-019-2A]

Trimethylsulfonium iodide (20.4 g) and 3-furaldehyde (8.65 mL) are added to potassium hydroxide (11.2 g) and $H_2O$ (0.45 mL) in acetonitrile (150 mL). The reaction mixture is heated to 60° C. for 2.5 h. The reaction mixture is allowed to cool to room temperature. The precipitate is filtered off, and the filtrate is concentrated in vacuo. The resulting crude epoxide (10.747 g) is dissolved in methanol (50 mL) and added to a 2.0 M solution of methylamine in methanol (100 mL). The reaction mixture is stirred at room temperature for 3 d and then heated to reflux for 30 min. The reaction mixture is allowed to cool to room temperature and is concentrated in vacuo. The resulting brown oil was purified via column chromatography ($CHCl_3$/methanol, 95/5, 90/10; $CHCl_3$/methanol/$NH_4OH$, 90/10/1) to yield 2.703 g (19%) of the title compound as a yellow oil.

Physical characteristics are as follows:

$^1$H NMR (400 MHz, DMSO-$d_6$) δ 7.56–7.55, 7.51, 6.44, 5.07, 4.58–4.55, 2.62–2.56, 2.30. MS (ESI+) m/z 142 (M+H)$^+$.

Preparation 65

2-{1-[(triisopropylsilyl)oxy]vinyl}pyridine

2-Acetylpyridine (50 g, 0.413 mol) is placed in a 2 L 1N round bottom flask and anhydrous $CH_2Cl_2$ (Aldrich Sure Seal®, 0.65 L) is added, followed by the addition of i-$Pr_2$NEt (160.27 g, 1.24 mol, 3 eq., 216 mL). The flask is equipped with a 125 mL pressure equalized dropping funnel, and the mixture is placed under nitrogen and cooled in an ice-water bath. To the chilled ketone/amine mixture is added TIPSOTf (139.7 g, 0.456 mol, 1.1 eq., 122.6 mL) over 1.5 hours. The mixture is allowed to warm to room temperature overnight. The reaction mixture is concentrated in vacuo on a rotary evaporator (T≦25° C.) to give a yellow oil and a white solid. The flask contents are transferred to a 2 L separatory funnel with ether (1.2 L) resulting in the formation of additional white solid material (likely $iPr_2$(Et)$NH^+$ $^-$OTf which might be removed by filtration but is not in this experiment) and the mixture is washed with saturated aq. $NaHCO_3$ (2×0.65 L). The organic phase is separated, dried over $Na_2SO_4$, then is concentrated in vacuo to furnish the crude 2-[1-Tri-isopropylsilyloxy-vinyl]-pyridine (131.5 g) as a yellow-orange oil. This crude material is not further purified, but is immediately carried to the next step.

Physical characteristics are as follows:

$^1$H-NMR (400 MHz, $CDCl_3$): δ=8.57, 7.71, 7.21, 5.65, 4.58, 1.36, 1.15.

Preparation 66

2-{2-chloro-1-[(triisopropylsilyl)oxy]ethenyl}pyridine

Crude 2-{1-[(triisopropylsilyl)oxy]vinyl}pyridine (131.5 g, assumed 0.413 mmol) is placed in a 2 L, 1N round bottom flask and dissolved in anhydrous THF (Aldrich Sure Seal, 0.6 L). The flask is equipped with a reflux condenser and the apparatus is placed under nitrogen. NCS (60.66 g, 0.454 mol, 1.1 eq.) is added and the mixture is heated to reflux and maintained at reflux for 2 hours. The reaction mixture is cooled to room temperature, poured into a 4 L separatory funnel containing ether (1.5 L), and is washed with saturated aq. $NaHCO_3$ (2×0.7 L). The organic phase is separated, dried ($Na_2SO_4$), and concentrated in vacuo affords the target (117.5 g, 91%) as a yellow-orange oil. The crude material is not further purified, but is immediately carried into the next step.

Physical characteristics are as follows:

$^1$H-NMR (400 MHz, $CDCl_3$):δ=8.53, 7.71, 7.52, 7.22, 6.58, 1.21, 1.13.

Preparation 67

2-chloro-1-pyridin-2-ylethanone

Crude 2-{2-chloro-1-[(triisopropylsilyl)oxy]ethenyl}pyridine (117.3 g, 0.376 mol) is placed in a 4 L plastic bottle and is dissolved in acetonitrile (0.4 L). To the stirring solution is added 48% aqueous HF (170 mL, 0.45 mL/mmol) and the progress of the reaction is monitored by reverse phase analytical HPLC. After. Ca. 2 hours the reaction is judged to be complete, and the pH of the solution is carefully adjusted to ca. 8 with saturated aq. $NaHCO_3$. The mixture is poured into a separatory funnel containing $CH_2Cl_2$ (1.5 L). The organic phase is removed and the aq. layer is extracted with $CH_2Cl_2$ (2×1.0 L). The combined organic layers are dried ($Na_2SO_4$), and concentration in vacuo affords the title compound (49.5 g, 85%) as a tan solid (after cooling). The crude material is judged to be quite pure by $^1$H-NMR and HPLC and is used as is in the Noyori asymmetric reduction.

Physical characteristics are as follows:

$^1$H-NMR (400 MHz, $CDCl_3$): δ=8.66, 8.09, 7.88, 7.54, 5.12.

Preparation 68

(1S)-2-chloro-1-pyridin-2-ylethanol

[$RuCl_2(\eta^6$-p-cymene)]$_2$ (0.84 g, 1.37 mmol), $Et_3$N (0.67 g, 6.66 mmol, 0.93 mL), and (1R,2R)-N-p-toluenesulfonyl-1,2-diphenylethylenediamine (1.0 g, 2.72 mmol, 1.78 mol % based upon ketone) are combined in a 500 mL 1N round bottom flask. i-PrOH is added, a reflux condenser is attached and the mixture is warmed under reflux, and maintained, for 1 hour. Cool to room temperature and concentrate in vacuo (rotovapor followed by vacuum pump) to furnish the catalyst as a brown powdery solid. To the catalyst is added anhydrous DMF (Aldrich Sure Seal, 225 mL), followed in order by 2-chloro-1-pyridin-2-ylethanone (23.88 g, 0.153 mol) and HCOOH/$Et_3$N (5:2, Fluka, 55 mL). After ca. 2–3 minutes of stirring (room temperature) bubbles (presumed to be $CO_2$) are apparent, emanating from the stirring vortex of the red-black solution. Reaction progress is monitored by reverse phase analytical HPLC, and after 65 minutes of stirring, the starting material is consumed (95:5 $NaH_2PO_4$/

$H_3PO_4$ buffered water/$CH_3CN$ to 5:95, 17 minutes; retention time of starting chloroketone: 7.39 minutes, retention time of halohydrin 2.66 minutes). Quench the reaction by adding MeOH (25 mL), stir 5 minutes and then the DMF, etc is removed in vacuo (cold finger rotovapor, vacuum pump) to give a red-black viscous oil. The crude material is taken up in $Et_2O/CH_2Cl_2$ (4:1, 1.25 L), placed in a 3 L separatory funnel, washed with saturated aq. $NaHCO_3$ (1.0 L), brine (1.0 L), and dried ($Na_2SO_4$). Filtration and concentration in vacuo affords the crude product as a red-orange oil which is purified by chromatography on a column of silica gel (70 mm OD, 250 g 230–400 mesh, packed hexanes; compound applied in $CH_2Cl_2$/hexanes 60:40; eluted with hexanes/$Et_2O$ (75:25 2 L; 65:35 2 L; 55:45 2 L; 350 mL fractions) using the flash technique. Fractions 11–17 are combined to afford 16.41 g (68%) of the target as a pale yellow solid.

Physical characteristics are as follows:

MP: 49–50° C.; $^1$H-NMR (400 MHz, $CDCl_3$): δ=8.60, 7.77, 7.58, 7.30, 5.00, 4.20, 3.85; EI-MS (70EV): 160($M^+$, 35), 158($M^+$, 90), 122(90), 106(base); Anal. Found: C, 53.27; H, 5.19; N, 8.81; Cl, 22.29. Specific Rotation $[α]^D_{25}$= 62 (c 0.94, methanol).

Preparation 69

(1R)-2-(methylamino)-1-pyridin-2-ylethanol (1S)-2-chloro-1-pyridin-2-ylethanol (6.0 g, 38 mmol) and NaI (0.57 g, 3.8 mmol) are combined in a 500 mL, plastic coated, thick walled bottle and are covered with 2M $MeNH_2$ in MeOH (0.19 L). The Teflon stopper is wrapped in Teflon tape, the bottle is sealed. Stirring is started, and the bottle is immersed in a 60° C. oil bath for 16 hours. The yellow-brown mixture is cooled to room temperature and analyzed by analytical reverse phase HPLC, which indicated that the reaction is complete (retention time starting material=2.44 minutes; retention time product=1.24 minutes). Concentration in vacuo affords the crude product as a yellow oil, which is treated with $CH_2Cl_2$-THF (0.25 L, 10:90) to give a yellow solution and a white precipitate. The precipitate is removed by filtration, is rinsed with $CH_2Cl_2$-THF (10:90) and the combined filtrated are concentrated in vacuo to give a yellow-brown oil. The crude product is purified by chromatography on a column of silica gel (70 mm OD, 250 g, 230–400 mesh; packed with $CH_2Cl_2$-MeOH 90:10; eluted with $CH_2Cl_2$-MeOH 90:10, 2 L, 500 mL fractions; $CH_2Cl_2$-MeOH—$NH_4OH$ 89:10:1, 8 L, 350 mL fractions) using the flash technique. Fractions 14–30 are combined to provide 3.18 g (54%) of the target as an amber oil.

Physical characteristics are as follows:

$^1$H-NMR (400 MHz, DMSO-$d_6$): δ=8.49, 7.79, 7.52, 7.25, 4.75, 2.90, 2.67, 2.32; EI-MS (70EV): 153($M^+$, base), 135(18), 122(20), 108(62); HRMS (FAB): Found 153.1009; Specific Rotation $[α]^D_{25}$=49 (c 0.36, $CH_2Cl_2$).

Preparation 70

(1S)-2-(methylamino)-1-pyridin-2-ylethanol

As described for the preparation of (1R)-2-(methylamino)-1-pyridin-2-ylethanol (Preparations 65–69), using (1S,2S)-N-p-toluenesulfonyl-1,2-diphenylethylenediamine in place of (1R,2R)-N-p-toluenesulfonyl-1,2-diphenylethylenediamine, 2-acetylpyridine was converted to the title compound, isolated as an amber oil.

Physical characteristics are as follows:

$^1$H-NMR (400 MHz, DMSO-$d_6$): δ=8.48, 7.78, 7.50, 7.25, 4.70, 2.85, 2.67, 2.34. MS (CI) m/z (rel. intensity) 153 (MH+, 99), 153 (99), 151 (18), 137 (23), 135 (13), 122 (27), 110 (15), 108 (37), 106 (25), 80 (20), 52 (49); HRMS (ESI) Found 153.1046; Specific Rotation $[α]^{25}_D$=46 (c 0.37, methylene chloride).

Preparation 76

(1S)-2-(methylamino)-1-pyridin-3-ylethanol

As described for the preparation of (1R)-2-(methylamino)-1-pyridin-2-ylethanol (Preparations 68–69), 3-chloroacetylpyridine (*Chem. Ber.* 1951, 84, 147–149) is converted to the title compound, isolated as a pale yellow amorphous solid.

Physical characteristics are as follows:

OAMS supporting ions at: ESI+ 153.1 ESI− 151.1; HRMS (ESI) Found 153.1017; Specific Rotation $[α]^{25}_D$= 70° (c 1.03, methylene chloride); Anal. Found: C, 62.39; H, 7.93; N, 18.00.

Preparation 77

(1S)-2-chloro-1-(2-furyl)ethanol

As described for the preparation of (1S)-2-chloro-1-pyridin-2-ylethanol, 2-acetylfuran is converted to the title compound, isolated as an oil.

Physical characteristics are as follows:

$^1$H-NMR (400 MHz, $CDCl_3$):δ=7.41, 6.37, 4.95, 3.85, 2.58. MS (EI) m/z (rel. intensity) 146 (M+, 17), 129 (2), 98 (6), 97 (base), 95 (3), 94 (1), 69 (3), 41 (2); HRMS (EI) Found 146.0136; Specific Rotation $[α]^D_{25}$=17 (c 0.97, methanol).

Preparation 78

(5R)-5-(2-furyl)-3-methyl-1,3-oxazolidin-2-one

To (1S)-2-chloro-1-(2-furyl)ethanol (5.0 g, 34.2 mmol) in dry $CH_2Cl_2$ (Aldrich Sure Seal®, 75 mL), cooled in an ice-water bath under nitrogen, is added $Et_3N$ (1.38 g, 13.7 mmol, 0.4 eq., 1.9 mL). Stir 5 minutes, then methylisocyanate (3.32 g, 58.21 mmol, 1.7 eq., 3.46 mL) is added via syringe over 2 minutes. Allow the ice to melt and the mixture to warm toward room temperature while monitoring the reaction by HPLC. At 45 minutes the reaction is ca. 35% complete (halohydrin retention time=6.355 min.; product RT=7.826 min.). Allow to stir overnight, HPLC at 16 hours indicated that the reaction is complete. The mixture is cast into $Et_2O$ (0.3 L) and brine (0.3 L). The organic phase is reserved, the aq. layer is extracted with $Et_2O$ (2×0.2 L), the combined organic phases are washed with brine (0.4 L), and dried ($Na_2SO_4$). Concentration in vacuo affords the crude carbamate as a brown viscous oil, which is purified by chromatography (Biotage® 40 g column, EtOAc/hexanes 10:90 1 L, EtOAc/hexanes 20:80 1 L, 50 mL fractions). Fractions 25–42 affords 4.56 g (65%) of the target carbamate, S-1-(2-furyl)-2-chloroethanol-N-methylcarbamate, as a clear, pale yellow oil which solidified to an ivory solid upon cooling.

The crude carbamate, from 95.88 mmol of (1S)-2-chloro-1-(2-furyl)ethanol, is dissolved in dry THF (0.2 L, Aldrich Sure Seal®) and the solution is cooled in an ice-water bath under nitrogen. To the chilled carbamate solution is added KOtBu (1.0 M in THF, 97 mL, 97 mmol, 1.01 eq.) over 15 minutes. The mixture is allowed to stir after the addition is complete and HPLC analysis suggested that the reaction is complete within 15 minutes. The mixture is cast into $Et_2O$ (1.25 L) and brine (1.0 L) containing 1N aq. HCl (50 mL). The organic phase is separated, the aqueous layer is extracted with Et$_2$O (1.0 L). The combined organic phases are washed with saturated aq. NaHCO$_3$ (1.0 L) and dried (Na$_2$SO$_4$). Concentration in vacuo affords the crude oxazolidinone as a red-black oil which is triturated with pentane-Et$_2$O (2:1; 3×0.2 L). The pentane-Et$_2$O aliquots are concentrated in vacuo to give a red solid which is purified by chromatography on a 120 g Biotage® column (introduced as a solution in CH$_2$Cl$_2$, eluted with EtOAc/hexanes, 35:65, 1.0 L; EtOAc/hexanes, 50:50, 2.0 L, 50 mL fractions). Fractions 21–45 are combined to afford 8.75 g (55% from halohydrin) of the target oxazolidinone as a pale yellow oil, which solidified to furnish an ivory solid upon cooling.

Physical characteristics are as follows:

MP: 54–55° C.; $^1$H-NMR (400 MHz, CDCl$_3$):δ=7.47, 6.49, 6.41, 5.46, 3.78, 2.97; $^{13}$C-NMR (100 MHz, CDCl$_3$): δ=155.9, 148.1, 142.1, 109.0, 108.4, 65.9, 48.8, 29.4. MS (EI) m/z (rel. intensity): 167 (M+, 71), 167 (71), 123 (base), 108 (76), 95 (43), 94 (59), 86 (45), 84 (64), 81 (70), 53 (28), 51 (50); KF Moisture: 0.07%; Anal. Found: C, 57.46; H, 5.39; N, 8.36; Specific Rotation $[\alpha]^D_{25}$=–106 (c 1.01, CH$_2$Cl$_2$).

Preparation 79

(1R)-1-(2-furyl)-2-(methylamino)ethanol

To (5R)-5-(2-furyl)-3-methyl-1,3-oxazolidin-2-one (8.0 g, 47.8 mmol) in a 500 mL 1N RB flask is added 1N aq. KOH (240 mL, 0.24 mol, 5 eq.). The flask is equipped with a reflux condenser, placed under nitrogen, then is immersed in a preheated (50° C.) oil bath. The mixture is allowed to stir and the suspension slowly gave way to a clear solution. After stirring for 3 hours at 50° C. HPLC analysis indicated that the reaction is complete. The mixture is cooled to room temperature and is cast into a separatory funnel, the flask is rinsed into the separatory funnel with Et$_2$O/CH$_2$Cl$_2$ (95:5, 0.5 L) and the aq. layer is saturated with salt. The organic phase is removed, the aq. phase is extracted with Et$_2$O/CH$_2$Cl$_2$ (95:5, 2×0.5 L) and the combined organic phases are dried (Na$_2$SO$_4$). Concentration in vacuo affords the desired aminoethanol (6.50 g, 96%) as a pale orange oil which solidifies at freezer (–20° C.) temperatures.

Physical characteristics are as follows:

$^1$H-NMR (400 MHz, DMSO-d$_6$):δ=7.55, 6.37, 6.25, 4.59, 2.70, 2.25; $^{13}$C-NMR (100 MHz, DMSO-d$_6$): δ=157.3, 141.9, 110.5, 105.9, 65.5, 56.5, 36.5. MS (CI) m/z (rel. intensity): 159 (M+NH4$^+$, 14), 142 (M+H, base), 126 (15), 124 (8), 112 (4), 74 (7), 69 (6), 61 (18); KF Moisture: 0.83%; Anal. Found: C, 59.90; H, 7.83; N, 9.68; Specific Rotation $[\alpha]^D_{25}$=32 (c 0.96, EtOH).

Preparation 80

(1R)-2-(methylamino)-1-pyrazin-2-ylethanol

As described for the preparation of (1R)-2-(methylamino)-1-pyridin-2-ylethanol, 2-acetylpyrazine is converted to the title compound, isolated as a light orange liquid that solidified on standing.

Physical characteristics are as follows:

MP: 78–81° C.; $^1$H NMR (400 MHz, CD$_3$OD) δ 8.79, 8.58, 8.53, 5.00, 3.15, 3.05, 2.55; $^{13}$C NMR (75 MHz, CD$_3$OD) δ 159.1, 145.1, 144.6, 143.9, 71.5, 57.5, 35.6. MS (CI) m/z (rel. intensity) 154 (MH$^+$, 73), 154 (73), 138 (62), 136 (57), 124 (24), 111 (32), 109 (31), 107 (87), 95 (56), 61 (41), 52 (99); HRMS (FAB) Found 154.0973; Specific Rotation $[\alpha]_D^{25}$ +58 (c 1.02, methanol).

The optical purity is upgraded as follows: Carbonyldiimidazole (4.26 g, 1.1 equiv., 26.2 mmol) is dissolved in dichloromethane (80 mL). To this solution is slowly added, via cannula addition, (1R)-2-(methylamino)-1-pyrazin-2-ylethanol (3.66 g, 23.9 mmol) dissolved in dichloromethane (60 mL). The reaction is stirred at room temperature for 16 h. The solvent in vacuo and purification is accomplished by silica gel column chromatography (98:2 dichloromethane-methanol, sample and silica gel loaded in dichloromethane). Any uncyclized carbamate collected off the column is dissolved in methanol, to which is added a catalytic amount of 1 M NaOH and the solution is refluxed until completely cyclized. This freshly cyclized material is then purified by column chromatography as above. The combined pure oxazolidinone fractions are then concentrated in vacuo producing an 88% yield of (5R)-3-methyl-5-pyrazin-2-yl-1,3-oxazolidin-2-one (3.77 g, 21.0 mmol) as a white solid. This material is upgraded by chiral preparative HPLC to give material with >95% ee. MP: 113.5–114.1°; $^1$H NMR (400 MHz, CDCl$_3$) δ 8.84, 8.62, 8.58, 5.62, 4.02, 3.80, 2.94; $^{13}$C NMR (100 MHz, CDCl$_3$) δ 157.4, 153.2, 144.8, 144.1, 142.7, 72.2, 51.6, 31.1. MS (CI) m/z (rel. intensity) 180 (MH$^+$, 12), 197 (45), 180 (12), 138 (35), 137 (17), 136 (99), 122 (11), 107 (24), 96 (14), 95 (10), 58 (11); HRMS (FAB) Found 180.0781; Specific Rotation $[\alpha]_D^{25}$ +20 (c 0.95, methylene chloride); Anal. Found: C, 53.38; H, 5.03; N, 23.35.

As described for the preparation of (1R)-1-(2-furyl)-2-(methylamino)ethanol, the oxazolidinone (1.51 g, 8.43 mmol) is treated with 1N aq. KOH (42.1 mL, 5 equiv., 42.1 mmol) to give (1R)-2-(methylamino)-1-pyrazin-2-ylethanol (1.02 g, 6.65 mmol) in 79% yield as a white solid. MP: 84–85° C.; Specific Rotation $[\alpha]_D^{25}$+66 (c 0.94, methanol).

Preparation 81

4-(2-{[tert-butyl(dimethyl)silyl]oxy}ethoxy) benzaldehyde

To 4-(2-hydroxyethoxy)benzaldehyde (commercial, 0.5 g, 3 mmol) dissolved in DMF (10 mL) is added imidazole (0.4 g, 6 mmol) and tert-butyldimethylsilylchloride (0.53 g, 3.5 mmol). Reaction mixture is stirred for 20 h. at room temperature. TLC analysis (hexane:ethyl acetate,7:3) shows small amounts of unreacted starting material. Additional tert-butyldimethylsilylchloride (0.25 g, 1 mmol) is added and stirring continued for 16 h. The reaction is quenched with saturated aqueous ammonium chloride (20 mL) and diluted further with ethyl ether (20 mL). Aqueous layer is separated and extracted thrice with ether (10 mL). Combined organics dried over anhydrous magnesium sulfate, filtered and concentrated under reduced pressure. The residue is purified by flash chromatography on silica gel using a gradient of 2% to 5% ethyl acetate in hexanes to provide 0.42 g of the title compound.

Physical characteristics are as follows:

$^1$H NMR (400 MHz, CDCl$_3$) δ 9.78, 7.73, 6.92, 4.03, 3.90, 0.81, 0.00.

Preparation 82

5-[4-(2-{[tert-butyl(dimethyl)silyl]oxy}ethoxy) phenyl]-3-methyl-1,3-oxazolidin-2-one To a solution of tert-butyl dimethylcarbamate (1.36 g, 9.4 mmol) in tetrahydrofuran (40 mL) and N,N,N,N- tetramethylethylenediamine (3 mL, 20.7 mmol) is added s-BuLi (1.3 M in cyclohexane, 9 mL, 11.8 mmol) at −78° C. dropwise. The resultant yellow solution is stirred at this temperature for 75 minutes. 4-(2-{[tert-butyl(dimethyl)silyl]oxy}-ethoxy)benzaldehyde (2.0 g, 7.2 mmol) dissolved in tetrahydrofuran (10 mL) is then added dropwise at −78° C. and this mixture is stirred for 2 h. Warmed to 0° C. and after stirring for 15 minutes, the reaction mixture is quenched with saturated aqueous ammonium chloride (30 mL). The mixture is diluted with ether (50 mL), the organic layer is separated and aqueous layer is extracted thrice with ether (30 mL). The combined organic layers are dried over anhydrous magnesium sulfate, filtered and concentrated under reduced pressure to provide a crude mixture (1.4 g) containing tert-butyl-2-[4-(2-{[tert-butyl(dimethyl)silyl]oxy}ethoxy)phenyl]-2-hydroxyethyl(methyl)carbamate. The crude is used as is in the next step.

To the crude (1.4 g, 3.29 mmol) dissolved in tetrahydrofuran (10 mL) is added sodium hydride (0.27 g, 6.6 mmol, 60% dispersion in oil). The resultant suspension is stirred at room temperature for 2 h and then carefully quenched with water. The mixture is diluted with ether, the organic layer is separated and aqueous layer is extracted twice with ether. Combined organics washed once with water, dried over magnesium sulfate, filtered and concentrated under reduced pressure. The residue is purified by flash chromatography on silica gel using a gradient of 10% to 30% ethyl acetate in hexanes to provide 0.76 g of the title compound.

The physical characteristics are as follows:
$^1$H NMR (400 MHz, CDCl$_3$) δ 7.18, 6.83, 5.30, 3.95, 3.87, 3.76, 3.34, 2.84, 0.81, 0.00. MS (CI) m/z 352 (MH$^+$), 370, 369, 352, 310, 308, 194, 159, 132, 96, 61. HRMS (ESI) calcd for $C_{18}H_{29}NO_4SI+H_1$ 352.1944, found 352.1933.

Preparation 83

1-[4-(2-hydroxyethoxy)phenyl]-2-(methylamino) ethanol

5-[4-(2-{[tert-butyl(dimethyl)silyl]oxy}ethoxy)phenyl]-3-methyl-1,3-oxazolidin-2-one (0.66 g, 1.87 mmol) and potassium hydroxide (4M aqueous solution, 1.4 mL, 5.61 mmol) dissolved in ethanol (8 mL) is refluxed for 2.5 h and then stirred at room temperature for 16 h. Reaction mixture is concentrated under reduced pressure, water (5 mL) is added and the mixture is extracted with chloroform:methanol (9:1) (5×10 mL). The combined organic layers are dried over magnesium sulfate and concentrated to provide a residual oil. This oil is triturated with ether to provide a white solid (0.28 g).

Physical characteristics are as follows:
$^1$H NMR (400 MHz, MeOH-d$_4$) δ 7.31, 6.95, 4.74, 4.05, 3.88, 2.75, 2.44. MS (CI) m/z 212 (MH$^+$), 212, 157, 113, 110, 98, 97, 96, 81, 80, 79. HRMS (ESI) calcd for $C_{11}H_{17}NO_3+H_1$ 212.1287, found 212.1290.

Preparation 84

3-Oxiran-2-ylpyridine {37134-PMG-24b}

To a solution of 2.59 g of 3-pyridinecarboxaldehyde and 62 mg of tetra-n-butylammonium bromide in 60 mL CH$_2$Cl$_2$ at room temperature is added a solution of 10.0 g of trimethylsulfonium methylsulfate in 15 mL H$_2$O. The resulting solution is set stirring and cooled to 0° C. Aqueous NaOH (50% w/w; 40 mL) is added in portions while stirring and the mixture subsequently refluxed for 1 h. After cooling to room temperature, the mixture is filtered and the filtrate extracted with CH$_2$Cl$_2$. The combined extracts are dried over MgSO$_4$, filtered, and concentrated to yield a red oil, which is subjected to Kugelrohr distillation under high vacuum at 150° C. to yield 838 mg of the title compound as a clear, light yellow oil.

Physical properties are as follows:
$^1$HMR (CDCl$_3$) δ 2.82–2.84, 3.29–3.22, 3.99–3.91, 7.28–7.32, 7.53–7.56, 8.54–8.60 ppm.

Preparation 85

3-Oxiran-2-ylpyridine 1-oxide {37134-PMG-25b}

A solution of 2.33 g of 77% m-chloroperbenzoic acid and 1.05 g of NaHCO$_3$ in 50 mL CH$_2$Cl$_2$ is stirred for 3 min. at room temperature. To the stirring solution is added 838 mg of 3-oxiran-2-ylpyridine dissolved in a minimum of CH$_2$Cl$_2$. The resulting solution is stirred overnight at room temperature. A solution of 0.851 g of Na$_2$S$_2$O$_3$ and 1.05 g of NaHCO$_3$ in 25 mL H$_2$O is then added and the resulting solution stirred for 20 min. at room temperature. The biphasic mixture is extracted with CH$_2$Cl$_2$ (6×25 mL) and the combined extracts dried over MgSO$_4$, filtered, and concentrated to yield a viscous, yellow gel (398 mg). The gel is subjected to silica gel flash column chromatography (3% MeOH/CH$_2$Cl$_2$) to yield 198 mg of the title compound.

Physical properties are as follows:
$^1$HMR (CDCl$_3$) δ 2.81–2.83, 3.22–3.24, 3.91–3.93, 7.32–7.40, 8.18–8.27 ppm. OAMS supporting ions at: ESI+ 138.01.

Preparation 86

2-(Methylamino)-1-{1-oxidopyridin-3-yl}ethanol {37134-PMG-27c}

Methylamine (7.22 mL, 2.0M in MeOH) is added to 198 mg of 3-oxiran-2-ylpyridine 1-oxide, and the resulting solution is stirred for 3 d at room temperature. The mixture is then concentrated by rotary evaporation to yield a viscous, orange oil (230 mg). The oil is subjected to flash column chromatography on alumina (Ak. Grad I) with 5% MeOH/CH$_2$Cl$_2$ (MeOH saturated with ammonia) to yield 54 mg of the title compound.

Physical properties are as follows:
$^1$HMR (CDCl$_3$) δ 2.48, 2.67–2.72, 2.83–2.87, 4.72–4.75, 7.22–7.27, 7.30–7.32, 8.08–8.10, 8.26 ppm. OAMS supporting ions at ESI+ 169.08.

Preparation 87 tert-Butyl 2-oxo-2-(4-morpholin-4-ylphenyl)ethyl (methyl)carbamate

2-Bromo-1-(4-morpholin-4-ylphenyl)ethanone (Tetrahedron Letters; 39, (1998), 4987–4990)(3.40 g, 11.97 mmol) was dissolved in dry THF (30 ml) under N$_2$ and cooled in ice. A 2M solution of methylamine in THF (12 ml, 24 mmol) was added and the reaction stirred for 1 hr. The mixture was filtered and the filtrate treated with di-t-butyl carbonate (2.61 g, 12 mmol) at ice temperature. Stirring was continued for 24 hr then the solvent evaporated. Chromatography of the residue over silica gel (500 g) eluting with 1% MeOH-1% Et$_3$N-EtOAc gave the product as a pale yellow solid (1.53 g, 38%): mp87–89°.

Physical characteristics are as follows:
$^1$H NMR (400 MHz, CDCl$_3$) (1:1 mixture of rotamers) δ 1.40, 1.51, 2.95, 2.97, 3.33, 3.88, 4.54, 4.63, 6.89, 7.90. MS (ESI+) 335.0 Anal. Found: C, 64.45; H, 7.75; N, 8.33.

Preparation 88 tert-Butyl 2-hydroxy-2-(4-morpholin-4-ylphenyl) ethyl(methyl)carbamate tert-Butyl 2-oxo-2-(4-morpholin-4-ylphenyl)ethyl (methyl)carbamate (1.41 g, 4.22 mmol) was stirred under $N_2$ in dry THF (25 ml) and absolute ethanol (2 ml). Sodium borohydride (0.16 g, 4.23 mmol) was added and the reaction stirred for 18 hr then the solvents evaporated. The residue was chromatographed over silica gel (90 g) eluting with 50% ethyl acetate-hexane. The product was obtained (1.0 g, 71%) as a clear gum which slowly crystallized to give a white solid.

Physical characteristics are as follows:

mp99–92°. $^1$H NMR (400 MHz, DMSO-$d_6$) (2:1 mixture of rotamers) δ 1.31, 1.38, 2.76, 3.06, 3.22, 3.73, 4.63, 5.23, 6.90, 7.15; Anal. Found: C, 64.18; H, 8.48; N, 8.31.

Preparation 89

2-(Methylamino)-1-(4-morpholin-4-ylphenyl)ethanol dihydrochloride tert-Butyl 2-hydroxy-2-(4-morpholin-4-ylphenyl)ethyl (methyl)carbamate (1.04 g, 3.095 mmol) was stirred in a mixture of methanol (4 ml) and ether (40 ml). HCl gas was bubbled in for 2–3 min and the mixture stirred for 30 min. Evaporation gave the product as a tan solid.

Physical characteristics are as follows:

mp151° dec. $^1$H NMR (400 MHz, DMSO-$d_6$) δ 2.56, 3.00, 3.25, 3.86, 4.90, 7.29, 8.72, 9.10; Anal. Found: C, 49.72; H, 7.36; N, 8.72; Cl, 22.42.

Preparation 90 tert-Butyl 2-(4-bromophenyl)-2-hydroxyethyl (methyl)carbamate

As described for the preparation of tert-Butyl 2-hydroxy-2-(4-morpholin-4-ylphenyl)ethyl(methyl)carbamate (Preparations 87–88), 2,4'-dibromoacetophenone was converted to the title compound, isolated as a pale yellow solid.

Physical characteristics are as follows:

mp80–82°. $^1$H NMR (400 MHz, DMSO-$d_6$) (2:1 mix of rotamers) δ 1.26, 1.36, 2.78, 2.79, 3.26, 4.70, 5.53, 7.26, 7.52. Anal. Found: C, 50.91; H, 6.09; N, 4.27.

Preparation 91 tert-Butyl 2-(4-formylphenyl)-2-hydroxyethyl (methyl)carbamate tert-Butyl 2-(4-bromophenyl)-2-hydroxyethyl(methyl) carbamate (36.7 g, 111.2 mmol) was dissolved in dry THF (600 ml) under $N_2$ and tetramethyl ethylenediamine (42.2 ml, 32.5 g, 280.1 mmol) was added. The stirred mixture was cooled in an ice bath and a 3M ether solution of MeMgBr (46.4 ml, 139.3 mmol). After stirring for 1 hr a 1.6M hexane solution of nBuLi (150 ml, 240 mmol) was added and stirred for an additional 1 hr at which time dry DMF (50 ml, 47.2 g, 647 mmol) was added. After 1 hr a satd. solution (100 ml) of ammonium chloride was added. Most of the organic solvent was evaporated and the residual mass was extracted with ethyl acetate (3×500 ml), washed with water (300 ml) and brine (100 ml) then dried over magnesium sulfate. Filtration and evaporation gave a viscous oil that was chromatographed over silica gel (500 g). Elution with 25–40% ethyl acetate-hexane gave the product as a pale yellow gum (21.3 g) which very slowly crystallized to a yellow solid.

Physical characteristics are as follows:

mp37–39°. $^1$H NMR (400 MHz, CDCl$_3$) δ 1.49, 2.77, 3.51, 4.66, 5.04, 7.57, 7.90, 10.04. MS (FAB) m/z 280 (MH+), 280, 225, 224, 207, 206, 178, 162, 144, 57, 44.

Preparation 92 tert-Butyl 2-hydroxy-2-[4-(hydroxymethyl)phenyl] ethyl(methyl)carbamate tert-Butyl 2-(4-formylphenyl)-2-hydroxyethyl(methyl) carbamate (1.808 g, 6.48 mmol) was dissolved in dry THF (50 ml) and absolute ethanol (10 ml) then cooled in an ice bath. Sodium borohydride (0.25 g, 6.61 mmol) was added then after 1 hr the solvent was evaporated. The residue was treated with satd. ammonium chloride solution (15 ml), water (35 ml) and chloroform (50 ml). The aqueous layer was extracted with additional chloroform (2×50 ml). The combined organics were washed with brine (30 ml), dried (magnesium sulfate), filtered and evaporated to afford the product as a white gum (1.82 g).

Physical characteristics are as follows:

$^1$H NMR (400 MHz, CDCl$_3$) δ 1.49, 2.83, 3.40, 3.54, 4.72, 4.96, 7.38.

Preparation 93

1-[4-(Hydroxymethyl)phenyl]-2-methylamino) ethanol tert-Butyl 2-hydroxy-2-[4-(hydroxymethyl)phenyl]ethyl (methyl)carbamate (1.804 g, 6.42 mmol) was stirred in 4N.HCl in dioxane (10 ml) for 3 hr at which time the solvent was evaporated. The residue was dissolved in methanol (35 ml) and stirred with MP-carbonate resin (3.1 mmol) for 15 hr. The resin was filtered and the solvent evaporated. The residue was chromatographed over silica gel(90 g) eluting with 1.5% ammonium hydroxide-15% methanol-chloroform to afford ethanolamine product as a white gum (0.462 g) which slowly formed crystals.

Physical characteristics are as follows:

mp80–81°. $^1$H NMR (400 MHz, DMSO-$d_6$) δ 2.30, 2.57, 3.32, 4.46, 4.61, 5.13, 7.24, 7.28. HRMS (ESI) calcd for $C_{10}H_{15}NO_2$+H 182.1181, found 182.1182.

Preparation 94

2-[methyl(trityl)amino]ethanol

A mixture of 2-methylamino-ethanol (5.0 gr, 66.6 mmol) and triphenylmethyl chloride (18.6 g, 66.6 mmol) in 150 mL of $CH_2Cl_2$ was treated with triethylamine (9.3 mL, 66.6 mmol) and stirred at room temperature for 2 h. The solvent was removed in vacuum and the residue was dissolved in EtOAc (200 mL). The organic solution was washed with water (100 mL) and brine (50 mL), dried over MgSO$_4$, filtered and concentrated in vacuo. The residue was chromatographed on a Flash 40M silica gel (90 g, 32–63 μm) cartridge, eluting with 20% EtOAc in n-heptane, and those fractions with $R_f$=0.5 by TLC (EtOAc/hexane, 3/7) were combined and concentrated in vacuo to give 18.7 g of the product as a white solid.

Physical characteristics are as follows:

$^1$H NMR (400 MHz, DMSO-$d_6$) δ 7.45–7.14 (15 H), 4.56 (1 H), 3.65 (2 H), 2.12 (2 H), 1.99 (3 H).

Preparation 95

[Methyl(trityl)amino]acetaldehyde

A solution of DMSO (1.47 mL, 20.8 mmol) in 60 mL of $CH_2Cl_2$ was cooled to −78° C. and treated with oxalyl chloride dropwise under N₂ atmosphere for 10 min. The resulting mixture was treated with a solution of 2-[methyl(trityl)amino]ethanol (3.0 g, 9.45 mmol) in 10 mL of CH₂Cl₂ dropwise and stirred for additional 15 min. Triethylamine (6.6 mL, 47.3 mmole) was added to the mixture and warmed up to room temperature. The reaction was quenched by adding water and diluted with 100 mL of CH₂Cl₂. The organic phase was washed with water and brine, dried over Na₂SO₄, filtered and concentrated in vacuo. The residue was triturated with ether to give the product as white solid.

Physical characteristics are as follows:
¹H NMR (400 MHz, DMSO-d₆) δ) δ 7.44–7.15 (15 H), 4.55 (1 H), 3.66–3.62 (2 H), 2.11 (2 H), 1.99 (3 H).

Preparation 96

2-[methyl(trityl)amino]-1-(1-{[2-(trimethylsilyl)ethoxy]methyl}-1H-pyrazol-5-yl)ethanol A solution of 1-{[2-(trimethylsilyl)ethoxy]methyl}-1H-pyrazole (Heterocycles (1992), 34(2), 303–14)(0.80 g, 4.03 mmol) in 50 mL of THF/ether (3/2) was cooled to −78° C. and treated with 2.5M solution of n-BuLi (1.8 mL, 4.43 mmol) dropwise under N₂ atmosphere. The resulting mixture was stirred for 30 min. [Methyl(trityl)amino] acetaldehyde (1.27 g, 4.04 mmol) in 5 mL of the THF/ether solution was added to reaction mixture and stirred for 1 h at −79° C. and warmed up to room temperature. The reaction was quenched by adding NH₄Cl (sat. aq.) and water dropwise and the resulting suspension was extrcted into EtOAc (2×100 mL). The organic phase was washed with water (100 mL) and brine (50 mL), dried over Na₂SO₄, filtered and concentrated in vacuo. The residue was chromatographed on a Flash 40M silica gel (90 g, 32–63 μm) cartridge, eluting with 20% EtOAc in n-heptane, and those fractions with R$_f$=0.3 by TLC(EtOAc/hexane, 3/7) were combined and concentrated in vacuo to give 0.7 g of the product as a white solid.

Physical characteristics are as follows:
¹H NMR (400 MHz, DMSO-d₆) δ 7.58–7.49 (6 H), 7.45–7.43 (1 H), 7.36–7.32 (6 H), 7.24–7.21 (3 H), 6.21 (1 H), 5.76 (1 H), 5.56–5.46 (2 H), 5.22–5.20 (2 H), 3.59–3.45 (2 H), 2.99–2.80 (1 H), 2.15 (3 H), 2.09–1.98 (1 H), 0.74–0.70 (2 H), 0.00 (9 H).

Preparation 97

2-(methylamino)-1-(1 H-pyrazol-5-yl)ethanol dihydrochloride

A solution of 2-[methyl(trityl)amino]-1-(1-{[2-(trimethylsilyl)ethoxy]methyl}-1H-pyrazol-5-yl)ethanol (0.7 g, 1.36 mmol) in 20 mL of MeOH was treated with a solution of 4N HCl in dioxane (20 mL) and refluxed overnight. After cooling to room temperature, the solvent was removed by evaporation in vacuum and the residue was suspended in EtOAc. The solid was collected by filtration and washed with hot EtOAc. A white solid 0.23 g was obtained after drying under vacuum.

Physical characteristics are as follows:
mp 186.1–187.3° C. ¹H NMR (400 MHz, DMSO-d₆) δ 9.26 (br. s, 1 H), 8.83 (br. s, 1 H), 7.77 (d, J=2.28 Hz, 1 H), 6.36 (d, J=2.28 Hz, 1 H), 5.04 (dd, J=9.43, 3.63 Hz, 1 H), 3.25–3.09 (m, 2 H), 2.58 (t, J=5.39 Hz, 3 H). ¹³C NMR (DMSO-d₆) δ 149.94, 131.05, 102.60, 62.58, 52.98, 32.69.

Preparation 98

2-[methyl(trityl)amino]-1-(1-trityl-1H-imidazol-2-yl)ethanol

A solution of 1-trityl imidazole (1.67 g, 5.38 mmol) in 60 mL of THF was cooled to −78° C. and treated with 2.5M solution of n-BuLi (2.15 mL, 5.38 mmol) dropwise under N₂ atmosphere. The resulting mixture was stirred for 30 min. 2-n-tritylmethylamino-acetaldehyde (1.0 g, 3.17 mmol) in 10 mL of the THF solution was added to reaction mixture and stirred for 1 h at −79° C. and warmed up to room temperature. The reaction was quenched by adding NH₄Cl (sat. aq.) and water dropwise and the resulting suspension was extracted into EtOAc (2×100 mL). The organic phase was washed with water (100 mL) and brine (50 mL), dried over Na₂SO₄, filtered and concentrated in vacuo. The residue was chromatographed on a Flash 40M silica gel (90 g, 32–63 μm) cartridge, eluting with 10% EtOAc in CH₂Cl₂, and those fractions with R$_f$ 0.3 by TLC(EtOAc/hexane, 3/7) were combined and concentrated in vacuo to give 0.93 g of the product as a white solid.

Physical characteristics are as follows:
¹H NMR (400 MHz, CDCl₃) δ 7.38–6.99 (31 H), 6.61 (1 H), 4.28–4.24 (1 H), 3.51 (1 H), 3.39–3.24 (1 H), 1.33 (3 H).

Preparation 99

1-(1H-imidazol-2-yl)-2-(methylamino)ethanol dihydrochloride

A solution of 2-[methyl(trityl)amino]-1-(1-trityl-1H-imidazol-2-yl)ethanol (3.4 g, 5.43 mmol) in 70 mL of acetone was treated with a solution of 4N HCl in dioxane (5 mL) and stirred for 4 h at room temperature. The solvent was removed by evaporation in vacuum and the residue was suspended in EtOAc. The solid was collected by filtration and washed with hot EtOAc. A white solid, 0.92 g (79%) was obtained after drying under vacuum. mp 176.4–177.3° C.

Physical characteristics are as follows:
¹H NMR (400 MHz, DMSO-d₆) δ 7.65 (2 H), 7.40 (1 H), 5.42 (1 H), 3.64–3.39 (3 H), 2.61 (3 H). ¹³C NMR (DMSO-d₆) δ 146.2, 119.9, 61.4, 51.34, 33.16.

EXAMPLE 120

N-(4-fluorobenzyl)-2-{[[(2R)-2-hydroxy-2-pyrimidin-2-ylethyl](methyl)amino]methyl}-3,4-dimethyl-7-oxo-4,7-dihydrothieno[3,2-b]pyridine-6-carboxamide

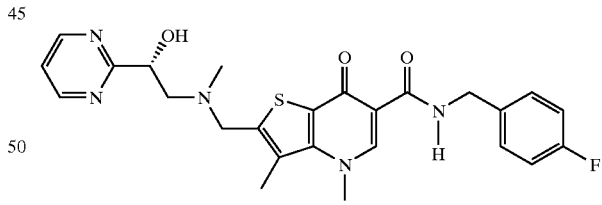

A mixture of N-(4-fluorobenzyl)-2-(chloromethyl)-3,4-dimethyl-7-oxo-4,7-dihydrothieno[3,2-b]pyridine-6-carboxamide (216 mg, 0.570 mmol), (1R)-2-(methylamino)-1-pyrimidin-2-ylethanol dihydrochloride (Preparation 104, 155 mg, 0.686 mmol) and diisopropylethylamine (600 μL, 3.44 mmol) in dry DMF (10.0 mL) was stirred at 60° C. for 20 hours. The solution was then diluted with water (75 mL). The resulting precipitate was collected by filtration and the collected solid was dried at 60° C. in vacuo, providing 209 mg of a tan solid.

Physical characteristics are as follows:
¹H NMR (400 MHz, DMSO₆) δ 10.35 (1H), 8.76 (2H), 8.56 (1H), 7.37 (3H), 7.16 (2H), 5.35 (1H), 4.86 (1H), 4.51

(2H), 4.18 (3H), 3.78 (2H), 3.00 (1H), 2.81 (1H), 2.41 (3H), 2.281 (3H). HRMS calc'd for $C_{25}H_{26}F_1N_5O_3S_1+H_1$= 496.1818. Found 496.1812.

Preparation 100

Sodium pyrimidine-2-carboxylate

To a slurry of 2-cyanopyrimidine (50 g) in water (100 ml) at 2° C. was added a solution of sodium hydroxide (50 wt %, 45.6 g) in water (30 ml) with an exotherm to 50° C. The mixture was stirred at 55° C. for 2 h, ethanol (500 ml) was added and the mixture concentrated in vacuo to an oil. Ethanol (250 ml) was added and the mixture concentrated to a paste. Ethanol (250 ml) was added and the mixture stirred at 15–20° C. for 30 min. The precipitate was collected by vacuum filtration, washed with ethanol (100 ml) and dried in a 75° C. vacuum oven to afford 67.57 g of the title compound as a white solid.

Physical characteristics are as follows:

$^1$H NMR (400 MHz, $CD_3OD$) δ 7.53, 8.84; $^{13}$C NMR (100 MHz, $CD_3OD$) δ 123.7, 159.2, 163.6, 171.5.

Preparation 101

N-Methoxy-N-methylpyrimidine-2-carboxamide

Sodium pyrimidine-2-carboxylate (154.05 g), imidazole hydrochloride (119.3 g), and 1,1-carbonyldiimidazole (195 g) was slurried in acetonitrile (700 ml). The mixture was warmed from 15° C. to 52° C. over 0.5 h. Carbon dioxide was vigorously evolved between 30 and 50° C. The mixture was stirred 1 h at 52° C. then cooled to 15° C. and N,O-dimethylhydroxylamine hydrochloride (131.90 g) was added with an exotherm to 34° C. The mixture was cooled to 14° C. and methylene chloride (300 ml) and water (500 ml) was added. The pH was adjusted from 7.6 to 1.6 with aqueous sulfuric acid (6.13 M, 226 ml). The phases were separated and the lower aqueous phase washed with methylene chloride (500 ml). To the combined organics was added water (300 ml) and the pH adjusted to 1.18 with aqueous sulfuric acid (6.13 M, 5.1 ml). The phases were separated and the organics washed with saturated aq. sodium bicarbonate (300 ml). All three aqueous phases were serial back extracted with methylene chloride (500 ml). The bicarbonate wash was back extracted with methylene chloride (500 ml). The combined organics were dried ($MgSO_4$) and concentrated in vacuo to a thin slurry. The residue was slurried in methylene chloride (200 ml) and the solids filtered off. The filtrate was concentrated to afford 160.7 g of the title compound as an oil.

Physical characteristics are as follows:

$^1$H NMR (400 MHz, $CDCl_3$) δ 3.38, 3.69, 7.39, 8.82; $^{13}$C NMR (100 MHz, $CDCl_3$) δ 32.05, 61.62, 121.34, 157.

Preparation 102 tert-Butyl (1-(pyrimidin-2-yl)ethanon-2-yl)(methyl) carbamate

To a solution of tert-butyl dimethylcarbamate (57.8 g) in N,N,N',N'-tetramethylethylenediamine (70 ml) and MTBE (485 g) was added sec-butyl lithium (1.4 M in cyclohexane, 300 ml) over 0.5 h while maintaining the temperature below −65° C. The mixture was stirred at −65° C. for 0.5 h, then magnesium bromide diethyl etherate (111.07 g) was added with an exotherm to −60° C. The resultant slurry was allowed to warm to −11° C. over 0.5 h then cooled to −72° C. The slurry was cannulated into a −72° C. solution of N-methoxy-N-methylpyrimidine-2-carboxamide (27.2 g) in methylene chloride (400 ml) with an exotherm to −60° C. and rinsed in with MTBE (25 ml). The mixture was warmed to 0° C. over 45 min then cooled to −27° C. Acetone (30.5 ml) was added. The mixture was cooled to −29° C., then a solution of acetic acid (63.7 g) in water (303 ml) was added with an exotherm to 11° C. The mixture was warmed to 20° C. and the phases separated. The organic layer was washed with saturated aq. sodium bicarbonate (250 ml) and the aqueous phases serial back extracted with MTBE (350 ml). The combined organics were dried ($MgSO_4$) and concentrated in vacuo to a net weight of 85 g. Toluene (200 ml) was added and the mixture concentrated to 128 g net weight. Branched octanes (205 g) was added to the cloud point, the mixture seeded and the product allowed to precipitate for 15 minutes with stirring. The slurry was cooled to −19° C. and the precipitate collected by vacuum filtration, washed with branched octanes (82 g) and dried in a nitrogen stream to afford 29.27 g of the title compound as a solid. Physical characteristics are as follows: $^1$H NMR (400 MHz, $CDCl_3$) δ 1.38, 1.49, 3.00, 4.83, 4.92, 7.50, 8.94; $^{13}$C NMR (100 MHz, $CDCl_3$) δ 28.11, 28.30, 35.57, 35.71, 56.11, 56.61, 79.96, 123.25, 123.36, 157.56, 157.65.

Preparation 103 tert-Butyl (2R)-2-hydroxy-2-pyrimidin-2-ylethyl (methyl)carbamate

In a glove box, triethylamine (6.6 g) was added carefully with stirring to formic acid (4.6 g) in a glass vial and stirring was continued until the mixture had cooled to room temperature. A 50 mL Schlenk flask was charged with [($\eta^6C_6H_6$)$RuCl_2$]$_2$ (200 mg), (R)(R)-TsDPEN (350 mg), anhydrous i-PrOH (10 mL), and triethylamine (0.35 mL). The Schlenk flask was removed from the glove box and placed on a Schlenk line, a reflux condenser attached, and the reaction mixture was heated to 75° C. for 1 h under nitrogen. The reaction was then cooled to 0° C. giving a solid which was collected by filtration. The solid was washed with diethyl ether and air-dried giving 228 mg of ($\eta^6C_6H_6$)Ru[(R,R)-TsDPEN]Cl. To a 50 mL RB flask in a glove box was added ($\beta^6C_6H_6$)Ru[(R,R)-TsDPEN]Cl (17 mg) followed by the mixture of the triethylamine/formic acid solution prepared above. The mixture was allowed to stir at room temperature for 20 min and tert-butyl 2-oxo-2-pyrimidin-2-ylethyl(methyl)carbamate (1.33 g) was added. The mixture was stirred at room temperature for 17 h, poured into water (75 mL), and extracted with EtOAc (3×100 mL). The combined organic layers were washed with 1 M aq. $NaHCO_3$ (50 mL) and brine (50 mL). The organic layer was dried ($MgSO_4$), filtered, and concentrated to afford 1.17 g of the title compound as an oil.

Physical characteristics are as follows:

$^1$H NMR ($CDCl_3$) 8.66, 7.20, 4.95, 3.69, 3.45, 2.88, 1.30. MS m/z 276 (MNa$^+$).

Preparation 104

(1R)-2-(Methylamino)-1-pyrimidin-2-ylethanol Dihydrochloride

A 6 N solution of aq. HCl (5 mL) was added to tert-butyl (2R)-2-hydroxy-2-pyrimidin-2-ylethyl(methyl)carbamate (1.17 g) at room temperature. After 2.5 h, reaction mixture was concentrated in vacuo using 3×10 mL portions of ethanol to assist in water removal. The oil was dissolved in ethanol, heated to ca. 50° C. and THF was added until slightly turbid at this temperature. The solution was allowed to cool to room temperature. The resulting solid was collected by filtration and washed with ethanol/THF (50/50) followed by diethyl ether to afford 0.78 g of the title compound.

Physical characteristics are as follows:

$^1$H NMR (D$_2$O) 8.85, 7.62, 5.17, 3.45, 3.30, 2.63. $^{13}$C NMR (D$_2$O) 165.1, 158.3, 122.3, 68.4, 52.5, 33.6.

All cited publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

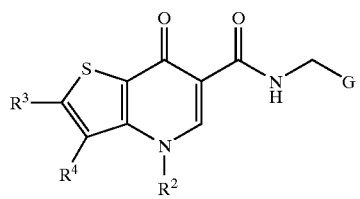

wherein
G is phenyl substituted with from one to five $R^1$ substituents, where
each $R^1$ is independently
- (a) Cl,
- (b) Br,
- (c) F,
- (b) cyano,
- (c) C$_{1-7}$alkyl, or
- (a) NO$_2$;

$R^2$ is
- (a) H,
- (b) $R^5$,
- (c) NR$^7$R$^8$,
- (d) SO$_2$R$^9$, or
- (e) OR$^6$;

$R^3$ is
- (a) halo,
- (b) aryl,
- (c) S(O)$_m$R$^6$,
- (d) (C=O)R$^6$,
- (e) (C=O)OH,
- (f) (C=O)OR$^9$,
- (g) cyano,
- (h) het, wherein the het is bound via a carbon atom or a nitrogen atom,
- (i) OR$^{14}$,
- (j) NR$^7$R$^8$,
- (k) SR$^{14}$,
- (l) NHSO$_2$R$^{12}$,
- (m) C$_{1-7}$alkyl which is optionally partially unsaturated and optionally substituted by one or more R$^{11}$ substituents, or
- (o) C$_{3-8}$cycloalkyl which is optionally partially unsaturated and optionally substituted by one or more R$^{11}$, or substituted by one or more C$_{1-7}$alkyl which C$_{1-7}$alkyl is optionally substituted by one or more R$^{11}$;

$R^4$ is
- (a) halo,
- (b) C$_{1-7}$alkyl which is optionally partially unsaturated and optionally substituted by one or more R$^{11}$ substituents,
- (c) NR$^7$R$^8$, or
- (d) S(O)$_m$R$^9$;

or $R^4$ together with $R^3$ may form a saturated carbocyclic or heterocyclic ring which is optionally substituted by OR$^{14}$, SR$^{14}$, NR$^7$R$^8$, or substituted by one or more C$_{1-7}$alkyl which C$_{1-7}$alkyl is optionally substituted by one or more R$^{11}$;

$R^5$ is
- (a) (CH$_2$CH$_2$O)$_i$R$^{10}$,
- (b) het, wherein the het is bound via a carbon atom,
- (c) aryl,
- (d) C$_{1-7}$alkyl which is optionally partially unsaturated and is optionally substituted with one or more R$^{11}$ substituents, or
- (e) C$_{3-8}$cycloalkyl which is optionally partially unsaturated and optionally substituted with one or more R$^{11}$, or substituted by one or more C$_{1-7}$alkyl which C$_{1-7}$alkyl is optionally substituted by one or more R$^{11}$;

$R^6$ is
- (a) C$_{1-7}$alkyl optionally substituted by aryl, het, OR$^{13}$, SR$^{13}$, NR$^{13}$R$^{13}$, halo, or C$_{3-8}$cycloalkyl, which C$_{3-8}$cycloalkyl is optionally substituted by OR$^{13}$,
- (b) C$_{3-8}$cycloalkyl which is optionally partially unsaturated and is optionally substituted by one or more halo, OR$^{13}$, SR$^{13}$, or NR$^{13}$R$^{13}$ substituents,
- (c) NR$^7$R$^8$,
- (d) aryl, or
- (e) het, wherein the het is bound via a carbon atom;

$R^7$ and $R^8$ are independently
- (a) H,
- (b)) aryl,
- (c) C$_{1-7}$alkyl which is optionally partially unsaturated and is optionally substituted by one or more NR$^{13}$R$^{13}$, OR$^{14}$, SR$^{14}$, S(O)$_m$R$^9$, P(=O)(OR$^{14}$)(R$^{14}$), CONR$^{14}$R$^{14}$, CO$_2$R$^{13}$, (C=O)R$^9$, het, aryl, cyano, or halo substituents,
- (d) C$_{3-8}$cycloalkyl which is optionally partially unsaturated and is optionally substituted by one or more halo, OR$^{13}$, SR$^{13}$, oxo, or NR$^{13}$R$^{13}$,
- (e) (C=O)R$^9$, or
- (f) R$^7$ and R$^8$ together with the nitrogen to which they are attached form a het;

$R^9$ is
- (a) aryl,
- (b) het,
- (c) C$_{3-8}$cycloalkyl, or
- (d) C$_{1-7}$alkyl which is optionally unsaturated and is optionally substituted with one or more NR$^{13}$R$^{13}$, OR$^{14}$, SR$^{14}$, halo, CONR$^{13}$R$^{13}$, CO$_2$R$^{13}$, het, or aryl substituents;

$R^{10}$ is
- (a) H, or
- (b) C$_{1-7}$alkyl optionally substituted with OH;

$R^{11}$ is
- (a) OR$^{14}$,
- (b) SR$^{14}$,
- (c) NR$^7$R$^8$,
- (d) halo,
- (e) CONH$_2$,
- (f) CONHR$^9$, (g) $CONR^9R^9$,
(h) $CO_2H$,
(i) $CO_2R^9$,
(j) het,
(k) aryl,
(l) cyano,
(m) oxo, or
(n) $SO_mR^6$, or
(o) $P(=O)(OR^{14})(R^{14})$;
(p) $NHSO_mR^6$;
(q) $N_3$;

$R^{12}$ is
(a) H,
(b) het,
(c) aryl,
(d) $C_{3-8}$cycloalkyl optionally substituted with $R^{11}$, or
(e) $C_{1-7}$alkyl optionally substituted with $R^{11}$;

$R^{13}$ is
(a) H, or
(b) $C_{1-7}$alkyl;

$R^{14}$ is
(a) H,
(b) aryl,
(c) het,
(d) $C_{1-7}$alkyl which is optionally partially unsaturated and optionally substituted by aryl, het, $OR^{13}$, $Si(R^{13})_3$, $SR^{13}$, $NR^{13}R^{13}$, halo, or $C_{3-8}$cycloalkyl which $C_{3-8}$cycloalkyl is optionally substituted by one or more $OR^{13}$, or
(e) $C_{3-8}$cycloalkyl which is optionally partially unsaturated and optionally substituted with one or more substituents halo, $OR^{13}$, $SR^{13}$, or $NR^{13}R^{13}$;

$R^{15}$ is
(a) H,
(b) halo,
(c) $OR^{13}$,
(d) $SR^{13}$,
(e) $NR^{13}R^{13}$,
(f) $O(CH_2CH_2O)_nR^{10}$,
(g) phenyl,
(h) cyano,
(i) nitro,
(j) $CONR^{13}R^{13}$,
(k) $CO_2R^{13}$,
(l) $S(O)_mNR^{13}R^{13}$,
(m) $C_{1-7}$alkyl which is optionally partially unsaturated and optionally substituted with one or more oxo, phenyl, 4-morpholine, $OR^{13}$, $SR^{13}$, $NR^{13}R^{13}$, halo, $CO_2R^{13}$, $CONR^{13}R^{13}$, or $C_{3-8}$cycloalkyl which $C_{3-8}$cycloalkyl is optionally substituted by one or more $OR^{13}$,
(n) $C_{3-8}$cycloalkyl which is optionally partially unsaturated and optionally substituted by one or more oxo, halo, $OR^{13}$, $SR^{13}$, $C_{1-7}$alkyl, or $NR^{13}R^{13}$ substituents,
(o) pyrimidinyl, pyridyl, pyrrolyl, pyrazinyl, pyridazinyl, imidazolyl, or pyrazolyl,
(p) morpholino, or
(q) $NR^{13}COR^{13}$, each i is independently 2, 3, or 4;
each n is independently 1, 2, 3, 4 or 5;
each m is independently 1 or 2;
wherein any aryl other than G is optionally substituted with one or more $R^{15}$ substituents; and wherein any het is a 4–16 membered saturated or unsaturated monocyclic, bicyclic, or tricyclic ring system having 1, 2, 3, or 4 heteroatoms selected from oxygen, sulfur, sulfinyl, sulfonyl, nitrogen, and an N-oxide and is optionally substituted with one or more $=O$, $=N-OR^{13}$, or $R^{15}$ substituents;

or a pharmaceutically acceptable salt thereof.

2. The compound of claim 1 wherein $R^1$ is F, Cl or Br.
3. The compound of claim 2 wherein $R^1$ is Cl.
4. The compound of claim 1 wherein $R^1$ is methyl.
5. The compound of claim 1 wherein $R^2$ is H.
6. The compound of claim 1 wherein $R^2$ is $C_{1-7}$alkyl which is optionally partially unsaturated and is optionally substituted with one or more $R^{11}$ substituents.
7. The compound of claim 6 wherein $R^2$ is methyl.
8. The compound of claim 6 wherein $R^2$ is ethyl.
9. The compound of claim 1 wherein $R^3$ is halo, aryl, $S(O)_mR^6$, $(C=O)R^6$, $(C=O)OH$, $(C=O)OR^9$, cyano, $OR^{14}$, $NR^7R^8SR^{14}$, or $NHSO_2R^{12}$.
10. The compound of claim 1 wherein $R^3$ is $C_{1-7}$alkyl which is optionally partially unsaturated and optionally substituted by one or more $R^{11}$ substituents, or $C_{3-8}$cycloalkyl which is optionally partially unsaturated and optionally substituted by one or more $R^{11}$ or $C_{1-7}$alkyl substituents.
11. The compound of claim 10 wherein $R^3$ is hydroxymethyl.
12. The compound of claim 10 wherein $R^3$ is $C_{1-7}$alkyl which comprises one double bond and is optionally substituted by one or more $R^{11}$ substituents.
13. The compound of claim 10 wherein $R^3$ is $C_{1-7}$alkyl which comprises one triple bond and is optionally substituted by one or more $R^{11}$ substituents.
14. The compound of claim 1 wherein $R^3$ is $CH_2NR^7R^8$ where $R^7$ is $C_{1-7}$alkyl, and $R^8$ is $C_{1-7}$alkyl which is optionally partially unsaturated and is optionally substituted by one or more $NR^{13}R^{13}$, $OR^{14}$, $SR^{14}$, $S(O)_mR^9$, $P(=O)(OR^{14})(R^{14})$, $CONR^{13}R^{13}$, $CO_2R^{13}$, $(C=O)R^9$, het, aryl, cyano, or halo substituents.
15. The compound of claim 14 wherein $R^3$ is $CH_2NR^7R^8$ where $R^7$ is methyl, and $R^8$ is ethyl substituted with aryl or het, and an $OR^{14}$.
16. The compound of claim 1 wherein $R^3$ is N-methyl-N-{2-(4-hydroxyphenyl)-2-hydroxy-ethyl}aminomethyl.
17. The compound of claim 1 wherein $R^3$ is N-methyl-N-(2-phenyl-2-hydroxy-ethyl)aminomethyl.
18. The compound of claim 1 wherein $R^3$ is N-methyl-N-(2-furan-2-yl-2-hydroxy-ethyl)aminomethyl.
19. The compound of claim 1 wherein $R^3$ is N-methyl-N-[2-(3-methoxyphenyl)-2-hydroxy-ethyl]aminomethyl.
20. The compound of claim 1 wherein $R^3$ is N-[2-phenyl-2-hydroxy-ethyl]aminomethyl.
21. The compound of claim 1 wherein $R^3$ is N-(2-hydroxy-1-benzylethyl)aminomethyl.
22. The compound of claim 1 wherein $R^3$ is N-(phenylphosphinylmethyl)-N-(methyl)aminomethyl.
23. The compound of claim 1 wherein $R^3$ is N-methyl-N-[2-(pyridin-2-yl)-2-hydroxy-ethyl]aminomethyl.
24. The compound of claim 1 wherein $R^3$ is N-methyl-N-[2-(pyridin-2-yl)-2-hydroxyethyl]aminomethyl; N-methyl-N-{2-(1,3-thiazol-2-yl)ethyl)aminomethyl; N-methyl-N-[2-(4-methylsulfonylphenyl)-2-hydroxyethyl]aminomethyl; N-methyl-N-(2-pyrazin-2-yl-2-hydroxyethyl)aminomethyl; N-methyl-N-[2-(5-cyanothien-2-yl)-2-hydroxyethyl]aminomethyl; N-methyl-N-[2-(4-acetylaminophenyl)-2-hydroxyethyl]aminomethyl; (R)-N-methyl-N-(2-pyridin-2-yl-2-hydroxyethyl)aminomethyl; (S)-N-methyl-N-(2-pyridin-2-yl-2-hydroxyethyl)aminomethyl; N-methyl-N-[2-(4-[2-(2-methoxyethoxy)

ethoxy]phenyl)-2-hydroxyethyl]aminomethyl; N-methyl-N-[2-(3-acetylaminophenyl)-2-hydroxyethyl]aminomethyl; N-methyl-N-[2-(3,4,5-trifluorophenyl)-2-hydroxyethyl]aminomethyl; N-methyl-N-(2-pyrimidin-2-yl-2-hydroxyethyl)aminomethyl; (S)-N-methyl-N-(2-furan-2-yl-2-hydroxyethyl)aminomethyl; N-methyl-N-(2-furan-3-yl-2-hydroxyethyl)aminomethyl; N-methyl-N-[2-(4-morpholinophenyl)-2-hydroxyethyl]aminomethyl; N-methyl-N-[2-(4-aminosulfonylphenyl)-2-hydroxyethyl]aminomethyl; N-methyl-N-(2-pyrazol-5-yl-2-hydroxyethyl)aminomethyl; N-methyl-N-[2-(1-methylpyrrol-2-yl)-2-hydroxyethyl]aminomethyl; N-methyl-N-[2-(4-(2-hydroxyethoxy)phenyl)-2-hydroxyethyl]aminomethyl; N-methyl-N-[2-(4-(N,N-dimethylaminomethyl)phenyl)-2-hydroxyethyl]aminomethyl; N-methyl-N-[2-(3-oxo-3,4-dihydro-2H-benzo[1,4]oxazin-7-yl)-2-hydroxyethyl]aminomethyl; N-methyl-N-(2-pyridin-2-yl-2-hydroxyethyl)aminomethyl(pyridyl-N-oxide); N-methyl-N-(2-quinol-2-yl-2-hydroxyethyl)aminomethyl; N-methyl-N-(2-imidazol-2-yl-2-hydroxyethyl)aminomethyl; (R)-N-methyl-N-(2-pyridin-3-yl-2-hydroxyethyl)aminomethyl; (R)-N-methyl-N-(2-pyrimidin-2-yl-2-hydroxyethyl)aminomethyl; or N-methyl-N-[2-(4-(hydroxymethyl)phenyl)-2-hydroxyethyl]aminomethyl.

25. The compound of claim 1 wherein $R^3$ is het, wherein the het is bound to the thieno ring via a carbon atom of het.

26. The compound of claim 1 wherein $R^3$ is het, wherein the het is bound to the thieno ring via a nitrogen atom.

27. The compound of claim 1 wherein $R^3$ is morpholinomethyl.

28. The compound of claim 1 wherein $R^3$ is Cl, F, or cyano.

29. The compound of claim 1 wherein $R^4$ is halo.

30. The compound of claim 1 wherein $R^4$ is $C_{1-7}$alkyl which is optionally partially unsaturated and optionally substituted by one or more $R^{11}$ substituents.

31. The compound of claim 1 wherein $R^4$ is methyl.

32. The compound of claim 1 wherein $R^4$ is $NR^7R^8$.

33. The compound of claim 1 wherein $R^4$ is $S(O)_mR^9$.

34. The compound of claim 1 wherein $R^4$ is propylsulfonyl.

35. The compound of claim 1 wherein $R^3$ and $R^4$ together form a saturated carbocyclic ring which is optionally substituted by $OR^{14}$, $SR^{14}$, $NR^7R^8$, or $C_{1-7}$alkyl which $C_{1-7}$alkyl is optionally substituted by one or more $R^{11}$ substituents.

36. The compound of claim 1 wherein $R^3$ and $R^4$ together form a saturated heterocyclic ring which is optionally substituted by $OR^{14}$, $SR^{14}$, $NR^7R^8$, or $C_{1-7}$alkyl which $C_{1-7}$alkyl is optionally substituted by one or more $R^{11}$ substituents.

37. The compound of claim 1 which is a compound of formula IV:

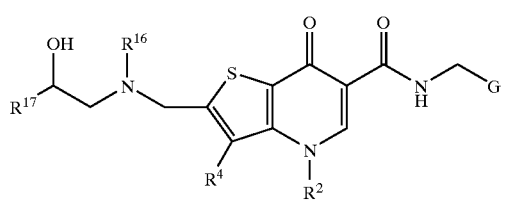

wherein:
$R^{16}$ is
(a) H,
(b) aryl,
(c) $C_{1-7}$alkyl which is optionally partially unsaturated and is optionally substituted by one or more $NR^{13}R^{13}$, $OR^{14}$, or $SR^{14}$, $S(O)_mR^9$, $CONR^{14}R^{14}$, $CO_2R^{13}$, $(C=O)R^9$, het, aryl, cyano, or halo substituents,
(d) $C_{3-8}$cycloalkyl which is optionally partially unsaturated and is optionally substituted by one or more halo, $OR^{13}$, $SR^{13}$, oxo, or $NR^{13}R^{13}$ substituents, or
(e) $(C=O)R^9$; and
$R^{17}$ is
(a) aryl, or
(b) het; and
or a pharmaceutically acceptable salt thereof.

38. The compound of claim 37 which is a compound of formula V:

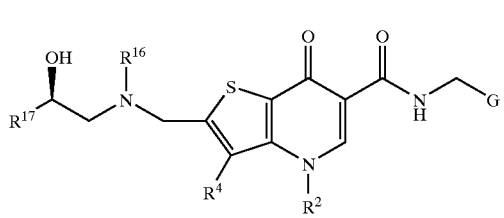

or a pharmaceutically acceptable salt thereof.

39. The compound of claim 37 which is a compound of formula VI:

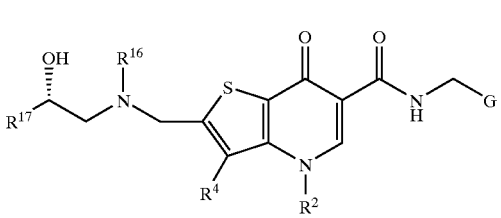

or a pharmaceutically acceptable salt thereof.

40. The compound of claim 1, 37, 38, or 39 wherein G is phenyl substituted with one, two, or three $R^1$ groups.

41. The compound of claim 1, 37, 38, or 39 wherein G is 4-chlorophenyl, 4-fluorophenyl, 3,4-dichlorophenyl, 3,4-difluorophenyl, 2,4-dichlorophenyl, 2,4-difluorophenyl, 4-chloro-2-fluorophenyl, 2-chloro-4-fluorophenyl, 3,4,5-trifluorophenyl, 4-bromophenyl, 4-methylphenyl, 4-cyanophenyl, or 4-nitrophenyl.

42. The compound of claim 1, 37, 38, or 39 wherein G is phenyl substituted with one or two $R^1$, and $R^2$, $R^3$ and $R^4$ are $C_{1-7}$alkyl which are optionally partially unsaturated and optionally substituted with one or more $R^{11}$ substituents.

43. The compound of claim 1, 37, 38, or 39 wherein G is phenyl substituted at the 4-position with $R^1$; $R^3$ is $C_{1-7}$alkyl optionally substituted by $NR^7R^8$; and $R^2$ and $R^4$ are $CH_3$.

44. The compound of claim 1, 37, 38, or 39 wherein G is 4-chlorophenyl; $R^3$ is $CH_2N(CH_3)CH_2CH(OH)$aryl or $CH_2N(CH_3)CH_2CH(OH)$het; and $R^2$ and $R^4$ are $CH_3$.

45. The compound of claim 1, which is N-(4-chlorobenzyl)-2-(hydroxymethyl)-3,4-dimethyl-7-oxo-4,7-dihydrothieno[3,2-b]pyridine-6-carboxamide; N-(4-chlorobenzyl)-2-{[[2-hydroxy-2-(4-hydroxyphenyl)ethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-phenylethyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(3-methoxyphenyl)ethyl](methyl)amino]methyl}-3,4-dimethyl-7-oxo-4,7-dihydrothieno[3,2-b]

pyridine-6-carboxamide; N-(4-chlorobenzyl)-2-{[[2-(2-furyl)-2-hydroxyethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyridin-2-ylethyl)(methyl)amino]methyl}-3,4-dimethyl-7-oxo-4,7-dihydrothieno[3,2-b]pyridine-6-carboxamide; N-(4-chlorobenzyl)-3,4-dimethyl-2-(morpholin-4-ylmethyl)-7-oxo-4,7-dihydrothieno[3,2-b]pyridine-6-carboxamide; [[(6-{[(4-chlorobenzyl)amino]carbonyl}-3,4-dimethyl-7-oxo-4,7-dihydrothieno[3,2-b]pyridin-2-yl)methyl](methyl)amino]methyl(phenyl)phosphinic acid; N-(4-chlorobenzyl)-2-{[[2-hydroxy-2-(1,3-thiazol-2-yl)ethyl](methyl)amino]methyl}-3,4-dimethyl-7-oxo-4,7-dihydrothieno[3,2-b]pyridine-6-carboxamide; N-(4-chlorobenzyl)-2-{[[2-(5-cyanothien-2-yl)-2-hydroxyethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyrazin-2-ylethyl)(methyl)amino]methyl}-3,4-dimethyl-7-oxo-4,7-dihydrothieno[3,2-b]pyridine-6-carboxamide; N-(4-chlorobenzyl)-2-{[{2-hydroxy-2-[4-(methylsulfonyl)phenyl]ethyl}(methyl)amino]methyl}-3,4-dimethyl-7-oxo-4,7-dihydrothieno[3,2-b]pyridine-6-carboxamide; N-(4-chlorobenzyl)-2-{[[2-hydroxy-1-(3-oxo-3,4-dihydro-2H-1,4-benzoxazin-6-yl)ethyl]amino]methyl}-3,4-dimethyl-7-oxo-4,7-dihydrothieno[3,2-b]pyridine-6-carboxamide; 4-(2-amino-2-oxoethyl)-N-(4-chlorobenzyl)-2-{[[2-(2-furyl)-2-hydroxyethyl](methyl)amino]methyl}-3-methyl-7-oxo-4,7-dihydrothieno[3,2-b]pyridine-6-carboxamide; N-(4-chlorobenzyl)-4-(cyanomethyl)-2-{[[2-(2-furyl)-2-hydroxyethyl](methyl)amino]methyl}-3-methyl-7-oxo-4,7-dihydrothieno[3,2-b]pyridine-6-carboxamide; N-(4-fluorobenzyl)-2-{[(2-hydroxy-2-pyridin-2-ylethyl)(methyl)amino]methyl}-3,4-dimethyl-7-oxo-4,7-dihydrothieno[3,2-b]pyridine-6-carboxamide; N-(4-chlorobenzyl)-2-{[[(2R)-2-hydroxy-2-pyrimidin-2-ylethyl](methyl)amino]methyl}-3,4-dimethyl-7-oxo-4,7-dihydrothieno[3,2-b]pyridine-6-carboxamide; 2-{[(2-hydroxy-2-pyridin-2-ylethyl)(methyl)amino]methyl}-3,4-dimethyl-7-oxo-N-(3,4,5-trifluorobenzyl)-4,7-dihydrothieno[3,2-b]pyridine-6-carboxamide; N-(4-fluorobenzyl)-2-{[[(2R)-2-hydroxy-2-pyridin-2-ylethyl](methyl)amino]methyl}-3,4-dimethyl-7-oxo-4,7-dihydrothieno[3,2-b]pyridine-6-carboxamide; N-(4-chlorobenzyl)-2-{[[(2R)-2-hydroxy-2-pyridin-2-ylethyl](methyl)amino]methyl}-3,4-dimethyl-7-oxo-4,7-dihydrothieno[3,2-b]pyridine-6-carboxamide; N-(4-chlorobenzyl)-2-{[[(2S)-2-hydroxy-2-pyridin-2-ylethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyrazin-2-ylethyl)(methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyrazin-2-ylethyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(1-oxidopyridin-3-yl)ethyl](methyl)amino]methyl}-3,4-dimethyl-7-oxo-4,7-dihydrothieno[3,2-b]pyridine-6-carboxamide; N-(4-chlorobenzyl)-2-{[hydroxy(2-hydroxy-2-phenylethyl)amino]methyl}-3,4-dimethyl-7-oxo-4,7-dihydrothieno[3,2-b]pyridine-6-carboxamide; N-(4-chlorobenzyl)-2-{[(2-hydroxyethyl)(2-hydroxy-2-phenylethyl)amino]methyl}-3,4-dimethyl-7-oxo 4,7-dihydrothieno[3,2-b]pyridine-6-carboxamide; N-(4-chlorobenzyl)-2-{[[2-(2,3-dihydro-1,4-benzodioxin-6-yl)-2-hydroxyethyl](methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(3-oxo-3,4-dihydro-2H-1,4-benzoxazin-6-yl)ethyl](methyl)amino]methyl}-3,4-dimethyl-7-oxo-4,7-dihydrothieno[3,2-b]pyridine-6-carboxamide; 2-[(4-acetylpiperazin-1-yl)methyl]-N-(4-chlorobenzyl)-3,4-dimethyl-7-oxo-4,7-dihydrothieno[3,2-b]pyridine-6-carboxamide; N-(4-chlorobenzyl)-2-[(4-hydroxypiperidin-1-yl)methyl]-3,4-dimethyl-7-oxo-4,7-dihydrothieno[3,2-b]pyridine-6-carboxamide; N-(4-chlorobenzyl)-2-{[(3-hydroxy-3-phenylpropyl)(methyl)amino]methyl}-3,4-dimethyl-7-oxo-4,7-dihydrothieno[3,2-b]pyridine-6-carboxamide; N-(4-chlorobenzyl)-2-{[(3R)-3-hydroxypyrrolidin-1-yl]methyl}-3,4-dimethyl-7-oxo-4,7-dihydrothieno[3,2-b]pyridine-6-carboxamide; N-(4-chlorobenzyl)-2-{[(3R)-3-hydroxypiperidin-1-yl]methyl}-3,4-dimethyl-7-oxo-4,7-dihydrothieno[3,2-b]pyridine-6-carboxamide; N-(4-chlorobenzyl)-2-{[[2-hydroxy-3-(1H-indol-4-yloxy)propyl](isopropyl)amino]methyl}-3,4-dimethyl-7-oxo-4,7-dihydrothieno[3,2-b]pyridine-6-carboxamide; N-(4-chlorobenzyl)-2-{[3-(hydroxymethyl)-2-phenylpiperidin-1-yl]methyl}-3,4-dimethyl-7-oxo-4,7-dihydrothieno[3,2-b]pyridine-6-carboxamide; N-(4-chlorobenzyl)-2-{[[2-(3,4-dimethoxy-phenyl)-2-oxoethyl](methyl)amino]-methyl}-3,4-dimethyl-7-oxo-4,7-dihydrothieno[3,2-b]pyridine-6-carboxamide; N-(4-chlorobenzyl)-2-{[2-(1,2-dihydroxyethyl)piperidin-1-yl]methyl}-3,4-dimethyl-7-oxo-4,7-dihydrothieno[3,2-b]pyridine-6-carboxamide; N-(4-chlorobenzyl)-3,4-dimethyl-7-oxo-2-[(4-pyrimidin-2-ylpiperazin-1-yl)methyl]-4,7-dihydrothieno[3,2-b]pyridine-6-carboxamide; N-(4-chlorobenzyl)-3,4-dimethyl-2-[(methyl{(1S)-1-[(3S)-2-oxopyrrolidin-3-yl]ethyl}amino)methyl]-7-oxo-4,7-dihydrothieno[3,2-b]pyridine-6-carboxamide; N-(4-chlorobenzyl)-2-{[[2-(4-chloro-3-nitrophenyl)-2-hydroxyethyl](methyl)amino]methyl}-3,4-dimethyl-7-oxo-4,7-dihydrothieno[3,2-b]pyridine-6-carboxamide; 2-{[4-(2-amino-2-oxoethyl)-3-oxopiperazin-1-yl]methyl}-N-(4-chlorobenzyl)-3,4-dimethyl-7-oxo-4,7-dihydrothieno[3,2-b]pyridine-6-carboxamide; 2-{[4-(aminocarbonyl)piperazin-1-yl]methyl}-N-(4-chlorobenzyl)-3,4-dimethyl-7-oxo-4,7-dihydrothieno[3,2-b]pyridine-6-carboxamide; N-(4-chlorobenzyl)-2-{[(2-[(2-chloro-6-methylphenyl)amino]-2-oxoethyl}-(methyl)amino]methyl}-3,4-dimethyl-7-oxo-4,7-dihydrothieno[3,2-b]pyridine-6-carboxamide; 2-{[(2-amino-2-oxoethyl)(cyclohexyl)amino]methyl}-N-(4-chlorobenzyl)-3,4-dimethyl-7-oxo-4,7-dihydrothieno[3,2-b]pyridine-6-carboxamide; N-(4-chlorobenzyl)-2-[(8-methoxy-1,4,5,6-tetrahydroazepino[4,5-b]indol-3(2H)-yl)methyl]-3,4-dimethyl-7-oxo-4,7-dihydrothieno[3,2-b]pyridine-6-carboxamide; N-(4-chlorobenzyl)-2-({ethyl[2-(2-hydroxyphenoxy)-1-methylethyl]amino}methyl)-3,4-dimethyl-7-oxo-4,7-dihydrothieno[3,2-b]pyridine-6-carboxamide; N-(4-chlorobenzyl)-2-{[[2-hydroxy-2-(3-hydroxyphenyl)ethyl](methyl)amino]methyl}-3,4-dimethyl-7-oxo-4,7-dihydrothieno[3,2-b]pyridine-6-carboxamide; N-(4-chlorobenzyl)-2-{[[2-(4,4-dimethyl-1,3-dioxo-3,4-dihydroisoquinolin-2(1H)-yl)ethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-1-methyl-2-phenylethyl)(pyridin-3-ylmethyl)amino]methyl}-3,4-dimethyl-7-oxo-4,7-dihydrothieno[3,2-b]pyridine-6-carboxamide; N-(4-chlorobenzyl)-2-{[(2-hydroxy-1-methylethyl)(methyl)amino]methyl}-3,4-dimethyl-7-oxo-4,7-dihydrothieno[3,2-b]pyridine-6-carboxamide; N-(4-chlorobenzyl)-2-{[(2-hydroxypropyl)(methyl)amino]methyl}-3,4-dimethyl-7-oxo-4,7-dihydrothieno[3,2-b]pyridine-6-carboxamide; N-(4-fluorobenzyl)-2-{[[(2R)-2-hydroxy-2-pyrazin-2-ylethyl](methyl)amino]methyl}-3,4-dimethyl-7-oxo-4,7- dihydrothieno[3,2-b]pyridine-6-carboxamide; N-(4-fluorobenzyl)-2-{[(2-hydroxy-2-pyrimidin-2-ylethyl)(methyl)amino]methyl}-3,4-dimethyl-7-oxo-4,7-dihydrothieno[3,2-b]pyridine-6-carboxamide; N-(4-fluorobenzyl)-2-{[[(2-hydroxy-2-(1H-indol-3-yl)ethyl](methyl)amino]methyl}-3,4-dimethyl-7-oxo-4,7-dihydrothieno[3,2-b]pyridine-6-carboxamide; N-(4-fluorobenzyl)-2-{[[(2R)-2-(2-furyl)-2-hydroxyethyl](methyl)amino]methyl}-3,4-dimethyl-7-oxo-4,7-dihydrothieno[3,2-b]pyridine-6-carboxamide; 2-{[{2-[4-(acetylamino)phenyl]-2-hydroxyethyl}(methyl)amino]methyl}-N-(4-fluorobenzyl)-3,4-dimethyl-7-oxo-4,7-dihydrothieno[3,2-b]pyridine-6-carboxamide; 2-{[[2-(2,3-dihydro-1,4-benzodioxin-6-yl)-2-hydroxyethyl](methyl)amino]methyl}-N-(4-fluorobenzyl)-3,4-dimethyl-7-oxo-4,7-dihydrothieno[3,2-b]pyridine-6-carboxamide; N-(4-fluorobenzyl)-2-{[[2-hydroxy-2-(1,3-thiazol-2-yl)ethyl](methyl)amino]methyl}-3,4-dimethyl-7-oxo-4,7-dihydrothieno[3,2-b]pyridine-6-carboxamide; N-(4-fluorobenzyl)-2-{[(2-hydroxy-2-pyridin-3-ylethyl)(methyl)amino]methyl}-3,4-dimethyl-7-oxo-4,7-dihydrothieno[3,2-b]pyridine-6-carboxamide; N-(4-fluorobenzyl)-2-{[{2-hydroxy-2-[4-(hydroxymethyl)phenyl]ethyl}(methyl)amino]methyl}-3,4-dimethyl-7-oxo-4,7-dihydrothieno[3,2-b]pyridine-6-carboxamide; 2-{[[2-(3-aminophenyl)-2-hydroxyethyl](methyl)amino]methyl}-N-(4-fluorobenzyl)-3,4-dimethyl-7-oxo-4,7-dihydrothieno[3,2-b]pyridine-6-carboxamide; N-(4-fluorobenzyl)-2-{[(2-hydroxy-2-quinolin-2-ylethyl)(methyl)amino]methyl}-3,4-dimethyl-7-oxo-4,7-dihydrothieno[3,2-b]pyridine-6-carboxamide; N-(4-fluorobenzyl)-2-{[[2-hydroxy-2-(1H-pyrazol-5-yl)ethyl](methyl)amino]methyl}-3,4-dimethyl-7-oxo-4,7-dihydrothieno[3,2-b]pyridine-6-carboxamide; N-(4-fluorobenzyl)-2-{[[(2S)-2-hydroxy-2-pyridin-3-ylethyl](methyl)amino]methyl}-3,4-dimethyl-7-oxo-4,7-dihydrothieno[3,2-b]pyridine-6-carboxamide; 2-{[[2-(1,3-benzodioxol-5-yl)-2-hydroxyethyl](methyl)amino]methyl}-N-(4-fluorobenzyl)-3,4-dimethyl-7-oxo-4,7-dihydrothieno[3,2-b]pyridine-6-carboxamide; N-(4-fluorobenzyl)-2-{[{2-hydroxy-2-[4-(2-hydroxyethoxy)phenyl]ethyl}(methyl)amino]methyl}-3,4-dimethyl-7-oxo-4,7-dihydrothieno[3,2-b]pyridine-6-carboxamide; N-(4-fluorobenzyl)-2-{[[2-hydroxy-2-(4-morpholin-4-ylphenyl)ethyl](methyl)amino]methyl}-3,4-dimethyl-7-oxo-4,7-dihydrothieno[3,2-b]pyridine-6-carboxamide; N-(4-fluorobenzyl)-2-{[[2-hydroxy-2-(1-methyl-1H-pyrrol-2-yl)ethyl](methyl)amino]methyl}-3,4-dimethyl-7-oxo-4,7-dihydrothieno[3,2-b]pyridine-6-carboxamide; N-(4-fluorobenzyl)-2-{[[2-(3-furyl)-2-hydroxyethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-phenylethyl)amino]methyl}-3,4-dimethyl-7-oxo-4,7-dihydrothieno[3,2-b]pyridine-6carboxamide; 2-({[(1S)-1-benzyl-2-hydroxyethyl]amino}methyl)-N-(4-chlorobenzyl)-3,4-dimethyl-7-oxo-4,7-dihydrothieno[3,2-b]pyridine-6-carboxamide; N-(4-Chlorobenzyl)-2-{[(2-hydroxy-2-pyridin-3-ylethyl)(methyl)amino]methyl}-3-[(2-methoxyethoxy)methyl]-4-methyl-7-oxo-4,7-dihydrothieno[3,2-b]pyridine-6-carboxamide; N-(4-Chlorobenzyl)-2-{[[2-hydroxy-2-(3-methoxyphenyl)ethyl](methyl)amino]methyl}-3-[(2-methoxyethoxy)methyl]-4-methyl-7-oxo-4,7-dihydrothieno[3,2-b]pyridine-6-carboxamide; N-(4-Chlorobenzyl)-2-{[[(2R)-2-(2-furyl)-2-hydroxyethyl](methyl)amino]methyl}-3-[(2-methoxyethoxy)methyl]-4-methyl-7-oxo-4,7-dihydrothieno[3,2-b]pyridine-6-carboxamide; N-(4-Chlorobenzyl)-2-{[[2-hydroxy-2-(1H-indol-3-yl)ethyl](methyl)amino]methyl}-3-[(2-methoxyethoxy)methyl]-4-methyl-7-oxo-4,7-dihydrothieno[3,2-b]pyridine-6-carboxamide; N-(4-Chlorobenzyl)-2-{[(2-hydroxy-2-pyridin-2-ylethyl)(methyl)amino]methyl}-3-[(2-methoxyethoxy)methyl]-4-methyl-7-oxo-4,7-dihydrothieno[3,2-b]pyridine-6-carboxamide; N-(4-Chlorobenzyl)-2-{[(2-hydroxy-2-pyrimidin-2-ylethyl)(methyl)amino]methyl}-3-[(2-methoxyethoxy)methyl]-4-methyl-7-oxo-4,7-dihydrothieno[3,2-b]pyridine-6-carboxamide; 2-{[[2-(3-Aminophenyl)-2-hydroxyethyl](methyl)amino]methyl}-N-(4-chlorobenzyl)-3-[(2-methoxyethoxy)methyl]-4-methyl-7-oxo-4,7-dihydrothieno[3,2-b]pyridine-6-carboxamide; N-(4-Chlorobenzyl)-2-{[(2-hydroxy-2-{3-[2-(2-methoxyethoxy)ethoxy]phenyl}ethyl)(methyl)amino]methyl}-3-[(2-methoxyethoxy)methyl]-4-methyl-7-oxo-4,7-dihydrothieno[3,2-b]pyridine-6-carboxamide; N-(4-Chlorobenzyl)-2-{[[2-(5-cyanothien-2-yl)-2-hydroxyethyl](methyl)amino]methyl}-3-[(2-methoxyethoxy)methyl]-4-methyl-7-oxo-4,7-dihydrothieno[3,2-b]pyridine-6-carboxamide; 3-[(Allyloxy)methyl]-N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide; N-(4-Chlorobenzyl)-2-{[(2-hydroxy-2-pyrazin-2-ylethyl)(methyl)amino]methyl}-4-methyl-7-oxo-3-{[2-(trimethylsilyl)ethoxy]methyl}-4,7-dihydrothieno[3,2-b]pyridine-6-carboxamide; N-(4-Chlorobenzyl)-3-(hydroxymethyl)-2-{[[(2R)-2-hydroxy-2-pyridin-2-ylethyl](methyl)amino]methyl}4-methyl-7-oxo-4,7-dihydrothieno[3,2-b]pyridine-6carboxamide; N-(4-Chlorobenzyl)-3-(hydroxymethyl)-2-{[(2-hydroxy-2-pyrazin-2-ylethyl)(methyl)amino]methyl}-4-methyl-7-oxo-4,7-dihydrothieno[3,2-b]pyridine-6-carboxamide; N-(4-Chlorobenzyl)-2-{[[2-(5-cyanothien-2-yl)-2-hydroxyethyl](methyl)amino]methyl}-3-(hydroxymethyl)-4-methyl-7-oxo-4,7-dihydrothieno[3,2-b]pyridine-6-carboxamide; N-(4-Chlorobenzyl)-2-{[[2-hydroxy-2-(3-methoxyphenyl)ethyl](methyl)amino]methyl}-3-(hydroxymethyl)-4-methyl-7-oxo-4,7-dihydrothieno[3,2-b]pyridine-6-carboxamide; 2-{[[2-(1-Benzofuran-2-yl)-2-hydroxyethyl](methyl)amino]methyl}-N-(4-chlorobenzyl)-3-(hydroxymethyl)-4-methyl-7-oxo-4,7-dihydrothieno[3,2-b]pyridine-6-carboxamide; N-(4-Chlorobenzyl)-2-{[[(2R)-2-(2-furyl)-2-hydroxyethyl](methyl)amino]methyl}-3-(hydroxymethyl)-4-methyl-7-oxo-4,7-dihydrothieno[3,2-b]pyridine-6-carboxamide; N-(4-Chlorobenzyl)-3-(hydroxymethyl)-2-{[(2-hydroxy-2-quinolin-2-ylethyl)(methyl)amino]methyl}-4-methyl-7-oxo-4,7-dihydrothieno[3,2-b]pyridine-6-carboxamide; 3-(Azidomethyl)-N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide; 3-(Aminomethyl)-N-(4-chlorobenzyl)-2-{[[(2R)-2-hydroxy-2-pyridin-2-ylethyl](methyl)amino]methyl}-4-methyl-7-oxo-4,7-dihydrothieno[3,2-b]pyridine-6-carboxamide; N-(4-Chlorobenzyl)-2-{[[(2R)-2-hydroxy-2-pyridin-2-ylethyl](methyl)amino]methyl}-4-methyl-3-{[(methylsulfonyl)amino]methyl}-7-oxo-4,7-dihydrothieno[3,2-b]pyridine-6-carboxamide; N-(4-chlorobenzyl)-2-{[[2-(2,6-dimethoxyphenyl)-2-hydroxyethyl](methyl)amino]methyl}-3,4-dimethyl-7-oxo-4,7-dihydrothieno[3,2-b]pyridine-6-carboxamide; 2-{[[(1-benzyl-2-hydroxyethyl)(methyl)amino]methyl}-N-(4-chlorobenzyl)-3,4-dimethyl-7-oxo-4,7-dihydrothieno[3,2-b]pyridine-6-carboxamide; 2-{[{2-[4-(acetylamino)phenyl]-2-hydroxyethyl}(methyl)amino]methyl}-N-(4-chlorobenzyl)-3,4-dimethyl-7-oxo-4,7-dihydrothieno[3,2-b]pyridine-6-carboxamide; N-(4-chlorobenzyl)-2-{[[(2-hydroxy-2-{3-[2-(2-methoxyethoxy)ethoxy]phenyl}ethyl)(methyl)amino]methyl}-3,4-dimethyl- 7-oxo-4,7-dihydrothieno[3,2-b]pyridine-6-carboxamide; 2-{[[2-(3-aminophenyl)-2-hydroxyethyl](methyl)amino]methyl}-N-(4-chlorobenzyl)-3,4-dimethyl-7-oxo-4,7-dihydrothieno[3,2-b]pyridine-6-carboxamide; 2-{[{2-[3-(acetylamino)phenyl]-2-hydroxyethyl}(methyl)amino]methyl}-N-(4-chlorobenzyl)-3,4-dimethyl-7-oxo-4,7-dihydrothieno[3,2-b]pyridine-6-carboxamide; N-(4-chlorobenzyl)-2-{[[2-hydroxy-2-(3,4,5-trifluorophenyl)ethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyrimidin-2-ylethyl)(methyl)amino]methyl}-3,4-dimethyl-7-oxo-4,7-dihydrothieno[3,2-b]pyridine-6-carboxamide; N-(4-chlorobenzyl)-2-{[[2-(3-furyl)-2-hydroxyethyl](methyl)amino]methyl}-3,4-dimethyl-7-oxo-4,7-dihydrothieno[3,2-b]pyridine-6-carboxamide; N(4-chlorobenzyl)-2-{[(2-hydroxy-2-pyridin-4-ylethyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(4-morpholin-4-ylphenyl)ethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-3-phenylpropyl)(methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyridin-3-ylethyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(1H-indol-3-yl)ethyl](methyl)amino]methyl}-3,4-dimethyl-7-oxo-4,7-dihydrothieno[3,2-b]pyridine-6-carboxamide; 2-{[{2-[4-(aminosulfonyl)phenyl]-2-hydroxyethyl}(methyl)amino]methyl}-N-(4-chlorobenzyl)-3,4-dimethyl-7-oxo-4,7-dihydrothieno[3,2-b]pyridine-6-carboxamide; N-(4-chlorobenzyl)-2-{[(3-hydroxy-2-phenylpropyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(1H-pyrazol-5-yl)ethyl](methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(1-methyl-1H-pyrrol-2-yl)ethyl](methyl)amino]methyl}-3,4-dimethyl-7-oxo-4,7-dihydrothieno[3,2-b]pyridine-6-carboxamide; N-(4-chlorobenzyl-2-{[{2-hydroxy-2-[4-(hydroxymethyl)phenyl]ethyl}(methyl)amino]methyl}-3,4-dimethyl-7-oxo-4,7-dihydrothieno[3,2-b]pyridine-6-carboxamide; N-(4-chlorobenzyl)-2-{[{2-hydroxy-2-[4-(2-hydroxyethoxy)phenyl]ethyl}(methyl)amino]methyl}-3,4-dimethyl-7-oxo-4,7-dihydrothieno[3,2-b]pyridine-6-carboxamide; 2-{[[2-(1,3-benzodioxol-5-yl)-2-hydroxyethyl](methyl)amino]methyl}-N-(4-chlorobenzyl)-3,4-dimethyl-7-oxo-4,7-dihydrothieno[3,2-b]pyridine-6-carboxamide; N-(4-chlorobenzyl)-2-{[(2-{4-[(dimethylamino)methyl]phenyl}-2-hydroxyethyl)(methyl)amino]methyl}-3,4-dimethyl-7-oxo-4,7-dihydrothieno[3,2-b]pyridine-6-carboxamide; N-(4-chlorobenzyl)-2-{[(2-hydroxy-2-quinolin-2-ylethyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(6-methoxypyridin-3-yl)ethyl](methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(1H-imidazol-2-yl)ethyl](methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(4-methoxyphenyl)ethyl](methyl)amino]methyl}-3,4-dimethyl-7-oxo-4,7-dihydrothieno[3,2-b]pyridine-6-carboxamide; N-(4-chlorobenzyl)-2-{[(2-hydroxyethyl)(methyl)-amino]methyl}-3,4-dimethyl-7-oxo-4,7-dihydrothieno[3,2-b]pyridine-6-carboxamide; N-(4-fluorobenzyl)-2-{[[(2R)-2-hydroxy-2-pyrimidin-2-ylethyl](methyl)amino]methyl}-3,4-dimethyl-7-oxo-4,7-dihydrothieno[3,2-b]pyridine-6-carboxamide; or a pharmaceutically acceptable salt thereof.

46. The compound of claim 1, which is: N-(4-chlorobenzyl)-2-{[[2-hydroxy-2-(4-hydroxyphenyl)ethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-phenylethyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(3-methoxyphenyl)ethyl](methyl)amino]methyl}-3,4-dimethyl-7-oxo-4,7-dihydrothieno[3,2-b]pyridine-6-carboxamide; N-(4-chlorobenzyl)-2-{[[2-(2-furyl)-2-hydroxyethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyridin-2-ylethyl)(methyl)amino]methyl}-3,4-dimethyl-7-oxo-4,7-dihydrothieno[3,2-b]pyridine-6carboxamide; N-(4-chlorobenzyl)-2-{[[2-(5-cyanothien-2-yl)-2-hydroxyethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyrazin-2-ylethyl)(methyl)amino]methyl}-3,4-dimethyl-7-oxo-4,7-dihydrothieno[3,2-b]pyridine-6-carboxamide; N-(4-chlorobenzyl)-2-{[[(2R)-2-hydroxy-2-pyridin-2-ylethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyrazin-2-ylethyl)(methyl)amino]methyl}-3,4-dimethyl-7-oxo-4,7-dihydrothieno[3,2-b]pyridine-6-carboxamide; N-(4-fluorobenzyl)-2-{[[(2R)-2-hydroxy-2-pyrazin-2-ylethyl](methyl)amino]methyl}-3,4-dimethyl-7-oxo-4,7-dihydrothieno[3,2-b]pyridine-6-carboxamide; 2-{[[2-(1-Benzofuran-2-yl)-2-hydroxyethyl](methyl)amino]methyl}-N-(4-chlorobenzyl)-3-(hydroxymethyl)-4-methyl-7-oxo-4,7-dihydrothieno[3,2-b]pyridine-6-carboxamide; 2-{[[2-(3-aminophenyl)-2-hydroxyethyl](methyl)amino]methyl}-N-(4-chlorobenzyl)-3,4-dimethyl-7-oxo-4,7-dihydrothieno[3,2-b]pyridine-6-carboxamide; 2-{[{2-[3-(acetylamino)phenyl]-2-hydroxyethyl}(methyl)amino]methyl}-N-(4-chlorobenzyl)-3,4-dimethyl-7-oxo-4,7-dihydrothieno[3,2-b]pyridine-6-carboxamide; N-(4-chlorobenzyl)-2-{[(2-hydroxy-2-pyrimidin-2-ylethyl)(methyl)amino]methyl}-3,4-dimethyl-7-oxo-4,7-dihydrothieno[3,2-b]pyridine-6-carboxamide; N-(4-chlorobenzyl)-2-{[[2-(3-furyl)-2-hydroxyethyl](methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(4-morpholin-4-ylphenyl)ethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyridin-3-ylethyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(1H-indol-3-yl)ethyl](methyl)amino]methyl}-3,4-dimethyl-7-oxo-4,7-dihydrothieno[3,2-b]pyridine-6-carboxamide; 2-{[{2-[4-(aminosulfonyl)phenyl]-2-hydroxyethyl}(methyl)amino]methyl}-N-(4-chlorobenzyl)-3,4-dimethyl-7-oxo-4,7-dihydrothieno[3,2-b]pyridine-6carboxamide; N-(4-chlorobenzyl)-2-{[[2-hydroxy-2-(1H-pyrazol-5-yl)ethyl](methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(1-methyl-1H-pyrrol-2-yl)ethyl](methyl)amino]methyl}-3,4-dimethyl-7-oxo-4,7-dihydrothieno[3,2-b]pyridine-6-carboxamide; N-(4-chlorobenzyl)-2-{[{2-hydroxy-2-[4-(hydroxymethyl)phenyl]ethyl}(methyl)amino]methyl}-3,4-dimethyl-7-oxo-4,7-dihydrothieno[3,2-b]pyridine-6-carboxamide; N-(4- chlorobenzyl)-2-{[{2-hydroxy-2-[4-(2-hydroxyethoxy) phenyl]ethyl}-(methyl)amino]methyl}-3,4-dimethyl-7-oxo-4,7-dihydrothieno[3,2-b]pyridine-6-carboxamide; 2-{[[2-(1, 3-benzodioxol-5-yl)-2-hydroxyethyl](methyl)amino]methyl}-N-(4-chlorobenzyl)-3,4-dimethyl-7-oxo-4,7-dihydrothieno[3,2-b]pyridine-6-carboxamide; N-(4-chlorobenzyl)-2-{[(2-hydroxy-2-quinolin-2-ylethyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(6-methoxypyridin-3-yl)ethyl](methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(1H-imidazol-2-yl)ethyl](methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(4-methoxyphenyl)ethyl](methyl)amino]methyl}-3,4-dimethyl-7-oxo-4,7-dihydrothieno[3,2-b]pyridine-6-carboxamide; N-(4-fluorobenzyl)-2-{[[(2R)-2-hydroxy-2-pyrimidin-2-ylethyl](methyl)amino]methyl}-3,4-dimethyl-7-oxo-4,7-dihydrothieno[3,2-b]pyridine-6-carboxamide; N-(4-chlorobenzyl)-2-{[[(2R)-2-hydroxy-2-pyrimidin-2-ylethyl](methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(1,3-thiazol-2-yl)ethyl](methyl)amino]methyl}-3,4-dimethyl-7-oxo-4,7-dihydrothieno[3,2-b]pyridine-6-carboxamide; N-(4-chlorobenzyl)-4-(cyanomethyl)-2-{[[2-(2-furyl)-2-hydroxyethyl](methyl)amino]methyl}-3-methyl-7-oxo-4,7-dihydrothieno[3,2-b]pyridine-6-carboxamide; N-(4-fluorobenzyl)-2-{[[(2R)2-hydroxy-2-pyridin-2-ylethyl](methyl)amino]methyl}-3,4-dimethyl-7-oxo-4,7-dihydrothieno[3,2-b]pyridine-6-carboxamide; N-(4-chlorobenzyl)-2-{[hydroxy(2-hydroxy-2-phenylethyl)amino]methyl}-3,4-dimethyl-7-oxo-4,7-dihydrothieno[3,2-b]pyridine-6-carboxamide; N-(4-chlorobenzyl)-2-{[[2-(2,3-dihydro-1,4-benzodioxin-6-yl)-2-hydroxyethyl](methyl)amino]methyl}-3,4-dimethyl-7-oxo-4,7-dihydrothieno[3,2-b]pyridine-6-carboxamide; N-(4-chlorobenzyl)-2-{[[2-(4-chloro-3-nitrophenyl)-2-hydroxyethyl](methyl)amino]methyl}-3,4-dimethyl-7-oxo-4,7-dihydrothieno[3,2-b]pyridine-6-carboxamide; N-(4-fluorobenzyl)-2-{[(2-hydroxy-2-pyrimidin-2-ylethyl)(methyl)amino]methyl}-3,4-dimethyl-7-oxo-4,7-dihydrothieno[3,2-b]pyridine-6-carboxamide; N-(4-fluorobenzyl)-2-{[[2-hydroxy-2-(1H-indol-3-yl)ethyl](methyl)amino]methyl}-3,4-dimethyl-7-oxo-4,7-dihydrothieno[3,2-b]pyridine-6-carboxamide; N-(4-fluorobenzyl)-2-{[[(2R)-2-(2-furyl)-2-hydroxyethyl](methyl)amino]methyl}-3,4-dimethyl-7-oxo-4,7-dihydrothieno[3,2-b]pyridine-6-carboxamide; 2-{[{2-[4-(acetylamino)phenyl]-2-hydroxyethyl}(methyl)amino]methyl}-N-(4-fluorobenzyl)-3,4-dimethyl-7-oxo-4,7-dihydrothieno[3,2-b]pyridine-6-carboxamide; N-(4-fluorobenzyl)-2-{[{2-hydroxy-2-[4-(hydroxymethyl)phenyl]ethyl}(methyl)amino]methyl}-3,4-dimethyl-7-oxo-4,7-dihydrothieno[3,2-b]pyridine-6-carboxamide; 2-{[[2-(3-aminophenyl)-2-hydroxyethyl](methyl)amino]methyl}-N-(4-fluorobenzyl)-3,4-dimethyl-7-oxo-4,7-dihydrothieno[3,2-b]pyridine-6-carboxamide; N-(4-fluorobenzyl)-2-{[(2-hydroxy-2-quinolin-2-ylethyl)(methyl)amino]methyl}-3,4-dimethyl-7-oxo-4,7-dihydrothieno[3,2-b]pyridine-6-carboxamide; N-(4-Chlorobenzyl)-2-{[[(2R)-2-(2-furyl)-2-hydroxyethyl](methyl)amino]methyl}-3-(hydroxymethyl)-4-methyl-7-oxo-4,7-dihydrothieno[3,2-b]pyridine-6-carboxamide; or 2-{[{2-[4-(acetylamino)phenyl]-2-hydroxyethyl}(methyl)amino]methyl}-N-(4-chlorobenzyl)-3,4-dimethyl-7-oxo-4,7-dihydrothieno[3,2-b]pyridine-6-carboxamide; or a pharmaceutically acceptable salt thereof.

47. The compound of claim 1, which is: N-(4-chlorobenzyl)-2-{[[2-hydroxy-2-(4-hydroxyphenyl)ethyl](methyl)amino]methyl}-3,4-dimethyl-7-oxo-4,7-dihydrothieno[3,2-b]pyridine-6-carboxamide; N-(4-chlorobenzyl)-2-{[2-hydroxy-2-phenylethyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(3-methoxyphenyl)ethyl](methyl)amino]methyl}-3,4-dimethyl-7-oxo-4,7-dihydrothieno[3,2-b]pyridine-6-carboxamide; N-(4-chlorobenzyl)-2-{[[2-(2-furyl)-2-hydroxyethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyridin-2-ylethyl)(methyl)amino]methyl}-3,4-dimethyl-7-oxo-4,7-dihydrothieno[3,2-b]pyridine-6-carboxamide; N-(4-chlorobenzyl)-2-{[[2-(5-cyanothien-2-yl)-2-hydroxyethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyrazin-2-ylethyl)(methyl)amino]methyl}-3,4-dimethyl-7-oxo-4,7-dihydrothieno[3,2-b]pyridine-6-carboxamide; N-(4-chlorobenzyl)-2-{[[(2R)-2-hydroxy-2-pyridin-2-ylethyl](methyl)amino]methyl}-3,4-dimethyl-7-oxo-4,7-dihydrothieno[3,2-b]pyridine-6-carboxamide; N-(4-chlorobenzyl)-2-{[(2-hydroxy-2-pyrazin-2-ylethyl)(methyl)amino]methyl}-3,4-dimethyl-7-oxo-4,7-dihydrothieno[3,2-b]pyridine-6-carboxamide; N-(4-fluorobenzyl)-2-{[[(2R)-2-hydroxy-2-pyrazin-2-ylethyl](methyl)amino]methyl}-3,4-dimethyl-7-oxo-4,7-dihydrothieno[3,2-b]pyridine-6-carboxamide; 2-{[[2-(1-Benzofuran-2-yl)-2-hydroxyethyl](methyl)amino]methyl}-N-(4-chlorobenzyl)-3-(hydroxymethyl)-4-methyl-7-oxo-4,7-dihydrothieno[3,2-b]pyridine-6-carboxamide; 2-{[[2-(3-aminophenyl)-2-hydroxyethyl](methyl)amino]-methyl}-N-(4-chlorobenzyl)-3,4-dimethyl-7-oxo-4,7-dihydrothieno[3,2-b]pyridine-6-carboxamide; N-(4-chlorobenzyl)-2-{[(2-hydroxy-2-pyrimidin-2-ylethyl)(methyl)amino]methyl}-3,4-dimethyl-7-oxo-4,7-dihydrothieno[3,2-b]pyridine-6-carboxamide; N-(4-chlorobenzyl)-2-{[[2-hydroxy-2-(1H-indol-3-yl)ethyl](methyl)amino]methyl}-3,4-dimethyl-7-oxo-4,7-dihydrothieno[3,2-b]pyridine-6-carboxamide; N-(4-chlorobenzyl)-2-{[{2-hydroxy-2-[4-(2-hydroxyethoxy)phenyl]ethyl}-(methyl)amino]methyl}-3,4-dimethyl-7-oxo-4,7-dihydrothieno[3,2-b]pyridine-6-carboxamide; 2-{[[2-(1,3-benzodioxol-5-yl)-2-hydroxyethyl](methyl)amino]-methyl}-N-(4-chlorobenzyl)-3,4-dimethyl-7-oxo-4,7-dihydrothieno[3,2-b]pyridine-6-carboxamide; N-(4-chlorobenzyl)-2-{[(2-hydroxy-2-quinolin-2-ylethyl)(methyl)amino]methyl}-3,4-dimethyl-7-oxo-4,7-dihydrothieno[3,2-b]pyridine-6-carboxamide; or {[[(2R)-2-hydroxy-2-pyrimidin-2-ylethyl](methyl)amino]methyl}-3,4-dimethyl-7-oxo-4,7-dihydrothieno[3,2-b]pyridine-6-carboxamide; or a pharmaceutically acceptable salt thereof.

48. The compound of claim 1 wherein $R^{15}$ is NH—C (=O)—$R^{13}$.

49. A pharmaceutical composition comprising a compound of claim 1 and a pharmaceutically acceptable excipient.

50. A method of treating a herpesviral infection in a mammal, comprising: administering to a mammal in need of such treatment an effective amount of a compound of claim 1.

51. The method of claim 50 wherein the mammal is a human or an animal.

52. The method of claim 50 wherein the mammal is a human.

53. The method of claim 50 wherein the mammal is an animal.

54. The method of claim 50 wherein the compound is administered in an amount of from about 0.1 to about 300 mg/kg of body weight.

55. The method of claim 50 wherein the compound is administered in an amount of from about 1 to about 30 mg/kg of body weight.

56. The method of claim 50 wherein the herpesviral infection is herpes simplex virus type 1, herpes simplex virus type 2, varicella zoster virus, human cytomegalovirus, Epstein-Barr virus, human herpes virus 6, human herpes virus 7, or human herpes virus 8.

57. The method of claim 50 wherein the herpesviral infection is human cytomegalovirus.

58. The method of claim 50 wherein the compound is administered orally, parenterally or topically.

59. A method of treating atherosclerosis or restenosis comprising administering to a mammal in need thereof a compound of claim 1.

60. A method for inhibiting a viral DNA polymerase, comprising contacting the polymerase with an effective inhibitory amount of a compound of claim 1.

61. A method for preparing a compound of formula I:

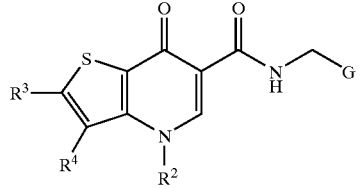

I wherein G, $R^1$–$R^4$ have the values described in claim 1, comprising: reacting a requisite nucleophile with a compound of the formula I where $R^3$ is $CH_2$—X wherein X is a leaving group.

62. The method of claim 61 wherein the nucleophile is of the formula $NHR^7R^8$ where $R^7$ is $C_{1-7}$alkyl, and $R^8$ is $C_{1-7}$alkyl which is optionally partially unsaturated and is optionally substituted by one or more $NR^{13}R^{13}$, $OR^{14}$, $SR^{14}$, $S(O)_mR^9$, $P(=O)(OR^{14})(R^{14})$, $CONR^{13}R^{13}$, $CO_2R^{13}$, $(C=O)R^9$, het, aryl, cyano, or halo substituents, and the leaving group is halo.

63. A method for preparing a compound of formula I:

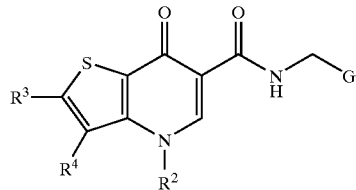

I wherein G, $R^2$, $R^3$, and $R^4$ have the values described in claim 1 comprising: reacting a nucleophile of the formula $NH_2CH_2G$ with a compound of the formula II:

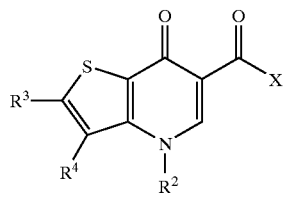

II where X is a leaving group.

64. A method for preparing a compound of formula A-4:

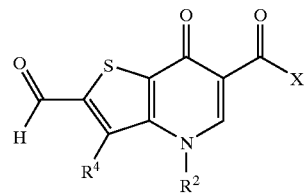

A-4 wherein $R^2$ is H, $R^4$ is as defined in claim 1, and X is a blocking group, comprising: treating a compound of formula A-3:

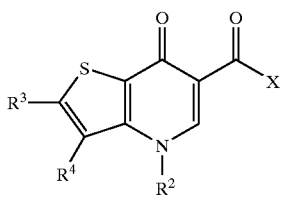

A-3 wherein $R^3$ is H, with a strong aprotic base and then reacting the resulting intermediate with a formulating agent.

* * * * *